(12) United States Patent
Sato et al.

(10) Patent No.: US 9,752,124 B2
(45) Date of Patent: Sep. 5, 2017

(54) CULTURE MEDIUM FOR EPITHELIAL STEM CELLS AND ORGANOIDS COMPRISING THE STEM CELLS

(75) Inventors: Toshiro Sato, Hilversum (NL); Johannes C. Clevers, Huis ter Heide (NL); Meritxell Huch Ortega, Utrecht (NL)

(73) Assignee: Koninklijke Nederlandse Akademie van Wetenschappen, Utrecht (NL)

( * ) Notice: Subject to any disclaimer, the term of this patent is extended or adjusted under 35 U.S.C. 154(b) by 300 days.

(21) Appl. No.: 13/194,866

(22) Filed: Jul. 29, 2011

(65) Prior Publication Data

US 2012/0196312 A1    Aug. 2, 2012

Related U.S. Application Data

(63) Continuation-in-part of application No. 13/147,163, filed as application No. PCT/NL2010/000017 on Feb. 3, 2010, now Pat. No. 8,642,339.

(60) Provisional application No. 61/149,622, filed on Feb. 3, 2009, provisional application No. 61/368,736, filed on Jul. 29, 2010, provisional application No. 61/520,569, filed on Jun. 10, 2011, provisional application No. 61/571,663, filed on Jun. 30, 2011.

(30) Foreign Application Priority Data

| Feb. 3, 2009 | (EP) | ................. 09151970 |
| Sep. 30, 2009 | (EP) | ................. 09171831 |
| Jul. 29, 2010 | (EP) | ................. 10171265 |
| Jun. 30, 2011 | (GB) | ................. 1111244.8 |

(51) Int. Cl.
  *C12Q 1/02*   (2006.01)
  *C12N 5/02*   (2006.01)
  *C12N 5/071*  (2010.01)

(52) U.S. Cl.
  CPC ......... *C12N 5/0671* (2013.01); *C12N 5/068* (2013.01); *C12N 5/0677* (2013.01); *C12N 5/0679* (2013.01); *C12N 2500/32* (2013.01); *C12N 2500/38* (2013.01); *C12N 2501/11* (2013.01); *C12N 2501/117* (2013.01); *C12N 2501/119* (2013.01); *C12N 2501/12* (2013.01); *C12N 2501/13* (2013.01); *C12N 2501/15* (2013.01); *C12N 2501/155* (2013.01); *C12N 2501/335* (2013.01); *C12N 2501/345* (2013.01); *C12N 2501/415* (2013.01); *C12N 2501/998* (2013.01); *C12N 2533/90* (2013.01)

(58) Field of Classification Search
  None
  See application file for complete search history.

(56) References Cited

U.S. PATENT DOCUMENTS

| 5,464,758 | A | 11/1995 | Gossen et al. |
| 6,165,782 | A | 12/2000 | Naldini et al. |
| 6,207,455 | B1 | 3/2001 | Chang |
| 6,218,181 | B1 | 4/2001 | Verma et al. |
| 6,277,633 | B1 | 8/2001 | Olsen |
| 6,323,031 | B1 | 11/2001 | Cichutek |
| 6,432,705 | B1 | 8/2002 | Yee et al. |
| 6,743,626 | B2 * | 6/2004 | Baum et al. ............ 435/325 |
| 7,411,052 | B2 | 8/2008 | Tang |
| 7,439,927 | B2 | 10/2008 | Lenart et al. |
| 7,541,431 | B2 | 6/2009 | Yoon |
| 8,642,339 | B2 | 2/2014 | Clevers et al. |
| 8,906,631 | B2 | 12/2014 | Clevers et al. |
| 2003/0003088 | A1 | 1/2003 | Tsao et al. |
| 2003/0032034 | A1 | 2/2003 | Tang |
| 2004/0191902 | A1 | 9/2004 | Hambor et al. |
| 2005/0054829 | A1 | 3/2005 | Wiley et al. |
| 2005/0058687 | A1 | 3/2005 | Guarino et al. |
| 2007/0010008 | A1 | 1/2007 | Tseng et al. |
| 2007/0020637 | A1 | 1/2007 | Isogai et al. |
| 2007/0036769 | A9 | 2/2007 | Li et al. |

(Continued)

FOREIGN PATENT DOCUMENTS

| EA | 7611 B1 | 12/2006 |
| EP | 1347046 A1 | 9/2003 |

(Continued)

OTHER PUBLICATIONS

Semler et al., "Mechanochemical Manipulation of hepatocyte Aggregation Can Selectively Induce or Repress Liver-Specific Function", Biotechnology and Bioengineering, 2000, vol. 69, No. 4, pp. 359-369.*

(Continued)

*Primary Examiner* — Laura Schuberg

(74) *Attorney, Agent, or Firm* — Wolf, Greenfield & Sacks, P.C.

(57) ABSTRACT

The invention relates to a method for culturing epithelial stem cells, isolated tissue fragments comprising the epithelial stem cells, or adenoma cells, and culturing the cells or fragments in the presence of a Bone Morphogenetic Protein (BMP) inhibitor, a mitogenic growth factor, and a Wnt agonist when culturing epithelial stem cells and isolated tissue fragments. The invention further relates to a cell culture medium comprising a BMP inhibitor, a mitogenic growth factor, and a Wnt agonist, to the use of the culture medium, and to crypt-villus organoids, gastric organoids, pancreatic organoids, liver organoids, colon organoids, Barrett's Esophagus organoids, adenocarcinoma organoids and colon carcinoma organoids that are formed in the culture medium.

13 Claims, 120 Drawing Sheets

(56) References Cited

U.S. PATENT DOCUMENTS

| | | |
|---|---|---|
| 2007/0122903 A1 | 5/2007 | Rezania et al. |
| 2007/0244061 A1 | 10/2007 | Niehrs et al. |
| 2007/0254359 A1 | 11/2007 | Rezania et al. |
| 2008/0113433 A1 | 5/2008 | Robins et al. |
| 2008/0166327 A1 | 7/2008 | Asahara et al. |
| 2008/0182328 A1* | 7/2008 | Snyder et al. ............... 435/353 |
| 2008/0233088 A1 | 9/2008 | Guha et al. |
| 2008/0242594 A1 | 10/2008 | McKay et al. |
| 2009/0275067 A1 | 11/2009 | Taniguchi et al. |
| 2009/0311748 A1 | 12/2009 | Isogai et al. |
| 2010/0047853 A1 | 2/2010 | Kuo et al. |
| 2010/0071078 A1 | 3/2010 | Niehrs |
| 2010/0137210 A1 | 6/2010 | Funk et al. |
| 2010/0166713 A1 | 7/2010 | Dalton et al. |
| 2010/0247648 A1 | 9/2010 | Grubb et al. |
| 2010/0275280 A1 | 10/2010 | Clevers et al. |
| 2010/0278800 A1 | 11/2010 | Boyle et al. |
| 2011/0002897 A1 | 1/2011 | Snyder et al. |
| 2012/0028355 A1 | 2/2012 | Sato et al. |
| 2013/0089562 A1 | 4/2013 | French et al. |
| 2013/0189327 A1 | 7/2013 | Ortega et al. |
| 2014/0044713 A1 | 2/2014 | De Lau et al. |
| 2014/0243227 A1 | 8/2014 | Clevers et al. |
| 2014/0256037 A1 | 9/2014 | Sato et al. |
| 2015/0011420 A1 | 1/2015 | Beekman et al. |
| 2015/0231201 A1 | 8/2015 | Clevers et al. |

FOREIGN PATENT DOCUMENTS

| | | |
|---|---|---|
| EP | 1440981 A2 | 7/2004 |
| EP | 1 792 979 A1 | 6/2007 |
| EP | 2157192 A1 | 2/2010 |
| EP | 1673475 B1 | 4/2010 |
| EP | 2228443 A1 | 9/2010 |
| EP | 1427747 B1 | 4/2012 |
| EP | 1727560 B1 | 9/2012 |
| JP | 2007-504823 A | 3/2007 |
| JP | 2009-520474 A | 5/2009 |
| RU | 2465323 C2 | 10/2012 |
| WO | WO 01/23528 A1 | 4/2001 |
| WO | WO 01/77169 A2 | 10/2001 |
| WO | WO 02/18544 A2 | 3/2002 |
| WO | WO 03/029405 A2 | 4/2003 |
| WO | WO 03/029437 A2 | 4/2003 |
| WO | WO 03/054152 A2 | 7/2003 |
| WO | WO 03/055911 A2 | 7/2003 |
| WO | WO 2004/087896 A2 | 10/2004 |
| WO | WO 2005/034625 A1 | 4/2005 |
| WO | WO 2005/040418 A2 | 5/2005 |
| WO | WO 2005/072419 A2 | 8/2005 |
| WO | WO 2005/110009 A2 | 11/2005 |
| WO | WO 2005/117994 A2 | 12/2005 |
| WO | WO 2006/104536 A2 | 10/2006 |
| WO | WO 2007/013666 A2 | 2/2007 |
| WO | WO 2007/030290 A2 | 3/2007 |
| WO | WO 2007/050043 A2 | 5/2007 |
| WO | WO 2007/071339 A1 | 6/2007 |
| WO | WO 2007/127454 | 8/2007 |
| WO | WO 2007/100357 A2 | 9/2007 |
| WO | WO 2007/149182 A2 | 12/2007 |
| WO | WO 2008/020942 A2 | 2/2008 |
| WO | WO 2008/046649 A1 | 4/2008 |
| WO | WO 2008/075796 A1 | 6/2008 |
| WO | WO 2008/088524 A2 | 7/2008 |
| WO | WO 2008/101215 | 8/2008 |
| WO | WO 2008/101215 A | 8/2008 |
| WO | WO 2008/120218 A2 | 10/2008 |
| WO | WO 2008/155120 A2 | 12/2008 |
| WO | WO 2009/005809 A2 | 1/2009 |
| WO | WO 2009/012428 A2 | 1/2009 |
| WO | WO 2009/022907 | 2/2009 |
| WO | WO 2010/011352 A2 | 1/2010 |
| WO | WO 2010/016766 | 2/2010 |
| WO | WO 2010/077681 A1 | 7/2010 |
| WO | WO 2010/077955 A1 | 7/2010 |
| WO | WO 2010/090513 A2 | 8/2010 |
| WO | WO 2010/108001 A2 | 9/2010 |
| WO | WO 2010/121923 A1 | 10/2010 |
| WO | WO 2012/014076 A2 | 2/2012 |
| WO | WO 2012/087965 A2 | 6/2012 |
| WO | WO 2012/140274 A2 | 10/2012 |
| WO | WO 2012/168930 A1 | 12/2012 |
| WO | WO 2013/093812 A2 | 6/2013 |

OTHER PUBLICATIONS

Kemp et al., "The Roles of Wnt Signaling in Early Mouse Development and Embryonic Stem Cells", Functional Development and Embryology, 2007, pp. 1-13.*
MediLexicon Dictionary, http://www.medilexicon.com/medicaldictionary.php?t=63274 , "Organoid", 2006, p. 1.*
Vincan et al., "Frizzled-7 dictates three-dimensional organization of colorectal cancer cell carcinoids", Oncogene, 2007, vol. 26, pp. 2340-2352.*
Martin-Belmonte et al., "Cell-Polarity Dynamics Controls the Mechanism of Lumen Formation in Epithelial Morphogenesis", Current Biology, 2008, vol. 18, pp. 507-513.*
Capaccio et al, "Modern management of obstructive salivary diseases", Acta Otorhinolaryngologica Italica 2007, vol. 27, pp. 161-172.*
Naftalin et al, "Progesterone stimulation of fluid absorption by the rat uterine gland", Reproduction, 2002, vol. 123, pp. 633-638.*
Cambridge Dictionary, definition for "sealed", http://dictionary.cambridge.org/us/dictionary/english/sealed , Sep. 24, 2016, p. 1.*
Visco et al., Differential Response to Keratinocyte Growth Factor Receptor and Epidermal Growth Factor Receptor Ligands of Proliferating and Differentiating Intestinal Epithelial Cells, J. Cell. Physiol. 200, 31-44 (2004).
Chapman et al., Analysis of Spatial and Temporal Gene Expression Patterns in Blastula and Gastrula Stage, Dev. Biol. 245, 187-199 (2002).
Kadesch et al., Notch Signaling: A Dance of Proteins Changing Partners, Exp. Cell. Res. 260, 1-8 (2000).
Abud et al., Growth of intestinal epithelium in organ culture is dependent on EGF signalling, Experimental Cell Research, Feb. 15, 2005, pp. 252-262, vol. 303, No. 2, Academic Press, US.
Bjerknes, et al., Intestinal epithelial stem cells and progenitors, Methods in Enzymology, Jan. 1, 2006, pp. 337-383, vol. 419, Academic Press Inc., San Diego, CA, US.
Booth et al., Maintenance of functional stem cells in isolated and cultured adult intestinal epithelium, Experimental Cell Research, Jun. 15, 1999, pp. 359-366, vol. 249, No. 2, Academic Press, US.
Haramis et al., De novo crypt formation and juvenile polyposis on BMP inhibition in mouse intestine, Science, Mar. 12, 2004, pp. 1684-1686, vol. 303, No. 5664, Washington, DC.
Kim et al., Mitogenic Influence of Human R-Spondinl on the Intestinal Epithelium. Science, Aug. 19, 2005, pp. 1256-1259, American Association for the Advancement of Science, US, Washington, DC.
Barker et al., Identification of stem cells in small intestine and colon by marker gene Lgr5, Nature. Oct. 25, 2007, pp. 1003-1008, vol. 449, Nature Publishing Group, London, GB.
Sato et al., Single Lgr5 stem cells build crypt-villus structures in vitro without a mesenchymal niche, Nature, May 14, 2009, pp. 262-265, vol. 459, No. 7244.
PCT International Search Report, PCT/NL2010/000017, dated Oct. 8, 2010.
Booth et al., The isolation and Culture of Adult Mouse Colonic Epithelium, Epithelial Cell Biology. Jan. I, 1995, pp. 76-86, vol. 4, No. 2, Springer International, Berlin, DE.
Partial European Search Report for 09151970.2-2403 dated Jun. 12, 2009.
U.S. Appl. No. 60/339,739, filed Dec. 10, 2001, Tang et al.
Notice of Rejection for Japanese Application No. 2011-547839 mailed Sep. 3, 2012. Full translation.
Gastroenterology. 2005;128(4):Suppl. 2, A702.
[No Author Listed] An open label dose-escalation study of a self-complementary adeno-associated viral vector (scAAV2/8-LP1-

(56) References Cited

OTHER PUBLICATIONS hFIXco) for gene transfer in hemophilia B. ClinicalTrials.gov Archive. Jun. 29, 2010. Identifier NCT00979238. http://clinicaltrials.gov/archive/NTC00979238/2010_06_29. 3 pages.

[No Author Listed] The Wnt family of secreted proteins. R&D Systems. Jan. 1, 2004. http://www.rndsystems.com/mini_review_detail_objectname_MR04_WntFamily.aspx. 7 pages.

Amado et al., Lentiviral vectors—the promise of gene therapy within reach? Science. Jul. 30, 1999;285(5428):674-6.

Anderson, Human gene therapy. Nature. Apr. 30, 1998;392(6679 Suppl):25-30.

Bainbridge et al., Effect of gene therapy on visual function in Leber's congenital amaurosis. N Engl J Med. May 22, 2008;358(21):2231-9. doi: 10.1056/NEJMoa0802268. Epub Apr. 27, 2008.

Biotechnology Journal. 2007;11-12:701-5.

Brewer et al., Optimized survival of hippocampal neurons in B27-supplemented Neurobasal, a new serum-free medium combination. J Neurosci Res. Aug. 1, 1993;35(5):567-76.

Brinster et al., Regulation of metallothionein-thymidine kinase fusion plasmids injected into mouse eggs. Nature. Mar. 4, 1982;296(5852):39-42.

Caplen et al., Specific inhibition of gene expression by small double-stranded RNAs in invertebrate and vertebrate systems. Proc Natl Acad Sci U S A. Aug. 14, 2001;98(17):9742-7. Epub Jul. 31, 2001.

Crosnier et al., Organizing cell renewal in the intestine: stem cells, signals and combinatorial control. Nat Rev Genet. May 2006;7(5):349-59.

De Gouville et al., Inhibition of TGF-β signaling by an ALK5 inhibitor protects rats from dimethylnitrosamine-induced liver fibrosis. Br J Pharmacol May 2005;145(2):166-77.

Elbashir et al., Duplexes of 21-nucleotide RNAs mediate RNA interference in cultured mammalian cells. Nature. May 24, 2001;411(6836):494-8.

Federico, Lentiviruses as gene delivery vectors. Curr Opin Biotechnol. Oct. 1999;10(5):448-53.

Fuchs, Inhibition of TGF-β signaling for the treatment of tumor metastasis and fibrotic diseases. Curr Signal Transduction Ther. 2011;6:39-43.

Furth et al., Temporal control of gene expression in transgenic mice by a tetracycline-responsive promoter. Proc Natl Acad Sci U S A. Sep. 27, 1994;91(20):9302-6.

G.I Research. 2004;12(2):3-10.

Gao et al., Biology of AAV serotype vectors in liver-directed gene transfer to nonhuman primates. Mol Ther. Jan. 2006;13(1):77-87. Epub Oct. 10, 2005.

Geiduschek et al., Transcription by RNA polymerase III. Annu Rev Biochem. 1988;57:873-914.

Gonçalves et al., Adeno-associated virus: from defective virus to effective vector. Virol J. 2005;2:43. 17 pages.

Gossen et al., Tight control of gene expression in mammalian cells by tetracycline-responsive promoters. Proc Natl Acad Sci U S A. Jun. 15, 1992;89(12):5547-51.

Gupta et al., Compilation of small RNA sequences. Nucleic Acids Res. Apr. 25, 1991;19 Suppl:2073-5.

Herbst, Review of epidermal growth factor receptor biology. Int J Radiat Oncol Biol Phys. 2004;59(2 Suppl):21-6.

Hernandez, Small nuclear RNA genes: a model system to study fundamental mechanisms of transcription. J Biol Chem. Jul. 20, 2001;276(29):26733-6. Epub Jun. 4, 2001.

Horikoshi et al., Functional analyses of secreted proteins by high-speed knock-in (HSKI) system II: intestinotrophic activities of R-spondin family proteins. Seikagaku. 2007:3P-1232.

Howe et al., The responsiveness of a tetracycline-sensitive expression system differs in different cell lines. J Biol Chem. Jun. 9, 1995;270(23):14168-74.

Igarashi et al., Characterization of recombinant human fibroblast growth factor (FGF)-10 reveals functional similarities with keratinocyte growth factor (FGF-7). J Biol Chem. May 22, 1998;273(21):13230-5.

Kaplitt et al., Safety and tolerability of gene therapy with an adeno-associated virus (AAV) borne GAD gene for Parkinson's disease: an open label, phase I trial. Lancet. Jun. 23, 2007;369(9579):2097-105.

Kay et al., Viral vectors for gene therapy: the art of turning infectious agents into vehicles of therapeutics. Nat Med. Jan. 2001;7(1):33-40.

Lemaigre, Mechanisms of liver development: concepts for understanding liver disorders and design of novel therapies. Gastroenterology. Jul. 2009;137(1):62-79.

Mader et al., A steroid-inducible promoter for the controlled overexpression of cloned genes in eukaryotic cells. Proc Natl Acad Sci U S A. Jun. 15, 1993;90(12):5603-7.

Maguire et al., Safety and efficacy of gene transfer for Leber's congenital amaurosis. N Engl J Med. May 22, 2008;358(21):2240-8. Epub Apr. 27, 2008. Author manuscript available in PMC Mar. 1, 2010.

Malorni et al., The antioxidant N-acetyl-cysteine protects cultured epithelial cells from menadione-induced cytopathology. Chem Biol Interact. May 19, 1995;96(2):113-23.

Manno et al., Successful transduction of liver in hemophilia by AAV-Factor IX and limitations imposed by the host immune response. Nat Med. Mar. 2006;12(3):342-7. Epub Feb. 12, 2006. Erratum in: Nat Med. May 2006;12(5):592. Rasko, John [corrected to Rasko, John JE]; Rustagi, Pradip K [added].

Marin et al., Towards efficient cell targeting by recombinant retroviruses. Mol Med Today. Sep. 1997;3(9):396-403.

Mattaj et al., Changing the RNA polymerase specificity of U snRNA gene promoters. Cell. Nov. 4, 1988;55(3):435-42.

Mayo et al., The mouse metallothionein-I gene is transcriptionally regulated by cadmium following transfection into human or mouse cells. Cell. May 1982;29(1):99-108.

McEwen et al., Regulation of the fibroblast growth factor receptor 3 promoter and intron I enhancer by Sp1 family transcription factors. J Biol Chem. Feb. 27, 1998;273(9):5349-57.

Metzger et al., The human oestrogen receptor functions in yeast. Nature. Jul. 7, 1988;334(6177):31-6.

Mitaka, Reconstruction of hepatic organoid by hepatic stem cells. J Hepatobiliary Pancreat Surg. 2002;9(6):697-703.

Mori et al., Micropatterned organoid culture of rathepatocytes and HepG2 cells. J Biosci Bioeng. Sep. 2008;106(3):237-42.

Myslinski et al., An unusually compact external promoter for RNA polymerase III transcription of the human H1RNA gene. Nucleic Acids Res. Jun. 15, 2001;29(12):2502-9.

Peng et al., Viral vector targeting. Curr Opin Biotechnol. Oct. 1999;10(5):454-7.

Reiser, Production and concentration of pseudotyped HIV-1-based gene transfer vectors. Gene Ther. Jun. 2000;7(11):910-3.

Resnitzky et al., Acceleration of the G1/S phase transition by expression of cyclins D1 and E with an inducible system. Mol Cell Biol. Mar. 1994;14(3):1669-79.

Rokutan et al., Epidermal growth factor-induced mitogen signals in cultured intestinal epithelial cells. J Gastroenterol. Jul. 1994;29 Suppl 7:59-62.

Russell, Update on adenovirus and its vectors. J Gen Virol. Nov. 2000;81(Pt 11):2573-604.

Sato et al., Long-term expansion of epithelial organoids from human colon, adenoma, adenocarcinoma, and Barrett's epithelium. Gastroenterology. Nov. 2011;141(5):1762-72.

Schroter et al., Detection of myosin light chain phosphorylation—a cell-based assay for screening Rho-kinase inhibitors. Biochem Biophys Res Commun. Sep. 19, 2008;374(2):356-60. Epub Jul. 16, 2008.

Shockett et al., A modified tetracycline-regulated system provides autoregulatory, inducible gene expression in cultured cells and transgenic mice. Proc Natl Acad Sci U S A. Jul. 3, 1995;92(14):6522-6.

Snykers et al., Differentiation of neonatal rat epithelial cells from biliary origin into immature hepatic cells by sequential exposure to

(56) References Cited

OTHER PUBLICATIONS hepatogenic cytokines and growth factors reflecting liver development. Toxicol In Vitro. Oct. 2007;21(7):1325-31. Epub Apr. 4, 2007.
Sommerfelt, Retrovirus receptors. J Gen Virol. Dec. 1999;80 ( Pt 12):3049-64.
St Clair et al., Inhibition by ganciclovir of cell growth and DNA synthesis of cells biochemically transformed with herpesvirus genetic information. Antimicrob Agents Chemother. Jun. 1987;31(6):844-9.
Stroes et al., Intramuscular administration of AAV1-lipoprotein lipase S447X lowers triglycerides in lipoprotein lipase-deficient patients. Arterioscler Thromb Vasc Biol. Dec. 2008;28(12):2303-4. Supplementary Tables and Figures 8 pages.
Trautmann et al., Isolation, culture, and characterization of human pancreatic duct cells. Pancreas. Mar. 1993;8(2):248-54.
Vigna et al., Lentiviral vectors: excellent tools for experimental gene transfer and promising candidates for gene therapy. J Gene Med. Sep.-Oct. 2000;2(5):308-16.
Walther et al., Viral vectors for gene transfer: a review of their use in the treatment of human diseases. Drugs. Aug. 2000;60(2):249-71.
Wang et al., A regulatory system for new use in gene transfer. Proc. Natl. Acad. Sci. USA. 1994;91:8180-4.
Wang et al., Regulation of TRAIL expression by the phosphatidylinositol 3-kinase/Akt/GSK-3 pathway in human colon cancer cells. J Biol Chem. Sep. 27, 2002;277(39):36602-10.
Williams et al., The role of the Wnt family of secreted proteins in rat oval "stem" cell-based liver regeneration: Wnt1 drives differentiation. Am J Pathol. Jun. 2010;176(6):2732-42. Epub Apr. 22, 2010.
Willis, RNA polymerase III. Genes, factors and transcriptional specificity. Eur J Biochem. Feb. 15, 1993;212(1):1-11.
Zhu et al., Chemical strategies for stem cell biology and regenerative medicine. Annu Rev Biomed Eng. Aug. 15, 2011;13:73-90.
Zilberberg et al., A rapid and sensitive bioassay to measure bone morphogenetic protein activity. BMC Cell Biol. Sep. 19, 2007;8:41.
Abe K, Watanabe S. (1995) Apoptosis of mouse pancreatic acinar cells after duct ligation.Arch Histol Cytol. 58:221-9.
Apelqvist A, Li H, Sommer L, Beatus P, Anderson DJ, Honjo T, Hrabe de Angelis M, Lendahl U, Edlund H. (1999) Notch signalling controls pancreatic cell differentiation. Nature 400:877-81.
Barker et al., Tissue-Resident Adult Stem Cell Populations of Rapidly Self-Renewing Organs, Cell Stem Cell, 2010, pp. 656-670, vol. 7.
Barker N, van Es JH, Kuipers J, Kujala P, van den Born M, Cozijnsen M, Haegebarth A, Korving J, Begthel H, Peters PJ, Clevers H. (2007) Identification of stem cells in small intestine and colon by marker gene Lgr5. Nature. 449:1003-7.
Barker, N., van de Wetering, M. & Clevers, H. The intestinal stem cell. Genes Dev 22, 1856-64 (2008).
Batlle, E. et al., Beta-catenin and TCF mediate cell positioning in the intestinal epithelium by controlling the expression of EphB/ephrinB. Cell 111, 251-63 (2002).
Binnerts ME et al, R-Spondin1 regulates Wnt signaling by inhibiting internalization of LRP6, PNAS, 104:14700-5 (2007).
Bjerknes and Cheng, Rapid Communications, Gastroenterology, 1999, 116, 7-14.
Bjerknes and Cheng, Multipotential stem cells in adult mouse gastric epithelium, Am J Physiol Gastrointest Liver Physiol. Sep. 2002;283(3):G767-77.
Bjerknes, M. & Cheng, H. Intestinal epithelial stem cells and progenitors. Methods Enzymol 419, 337-83 (2006).
Bonner-Weir, S., Taneja, M., Weir, G.C., Tatarkiewicz, K., Song, K.H., Sharma, A., and O'Neil, J.J. (2000). In vitro cultivation of human islets from expanded ductal tissue. Proc. Natl. Acad. Sci. USA 97, 7999-8004.
Bonner-Weir, S., and Weir, G.C. (2005). New sources of pancreatic beta-cells. Nat. Biotechnol. 23, 857-861.
Bouwens, L., and Rooman, I. (2005). Regulation of pancreatic beta-cell mass. Physiol. Rev. 85, 1255-1270.

Chen et al, Small molecule-mediated disruption of Wnt-dependent signaling in tissue regeneration and cancer, Nat Chem Biol., Feb. 2009;5(2):100-7.
Cheng, H. & Leblond, C. P. Origin, differentiation and renewal of the four main epithelial cell types in the mouse small intestine. I. Columnar cell. Am J Anat 141, 461-79 (1974).
Dignass, A. U. & Sturm, A. Peptide growth factors in the intestine. Eur J Gastroenterol Hepatol 13, 763-70 (2001).
Dontu et al., Role of Notch signaling in cell-fate determination of human mammary stem/progenitor cells, Breast Cancer Res, 2004, 6: R605-R615.
Dor, Y., Brown, J., Martinez, O.I., and Melton, D.A. (2004). Adult pancreatic beta-cells are formed by self-duplication rather than stem-cell differentiation. Nature 429, 41-46.
Evans, G. S., Flint, N., Somers, A. S., Eyden, B. & Potten, C. S. The development of a method for the preparation of rat intestinal epithelial cell primary cultures. J Cell Sci 101 ( Pt 1), 219-31 (1992).
Fukamachi, H. Proliferation and differentiation of fetal rat intestinal epithelial cells in primary serum-free culture. J Cell Sci 103 ( Pt 2), 511-9 (1992).
Githens S, Schexnayder JA, Desai K, Patke CL. (1989) Rat pancreatic interlobular duct epithelium: isolation and culture in collagen gel. In Vitro Cell Dev Biol. 25:679-88.
Gradwohl, G., Dierich, A., LeMeur, M., and Guillemot, F. (2000). neurogenin3 is required for the development of the four endocrine cell lineages of the pancreas. Proc. Natl. Acad. Sci. USA 97, 1607-1611.
Gregorieff and Clevers, Wnt signaling in the intestinal epithelium: from endoderm to cancer, Genes Dev, 2005, 19, 877-90.
Gu, G., Dubauskaite, J., and Melton, D.A. (2002). Direct evidence for the pancreatic lineage: NGN3+ cells are islet progenitors and are distinct from duct progenitors. Development 129, 2447-2457.
Hao, E., Tyrberg, B., Itkin-Ansari, P., Lakey, J.R., Geron, I., Monosov, E.Z., Barcova, M., Mercola, M., and Levine, F. (2006). Beta-cell differentiation from nonendocrine epithelial cells of the adult human pancreas. Nat. Med. 12, 310-316.
Haramis, A. P. et al., De novo crypt foil iation and juvenile polyposis on BMP inhibition in mouse intestine. Science 303, 1684-6 (2004).
Hofmann, C. et al., Cell-cell contacts prevent anoikis in primary human colonic epithelial cells. Gastroenterology 132, 587-600 (2007).
Hsieh et al., Truncated Mammalian Notch1 Activates CBF1;RBPJk-Represeed Genes by a Mechanism Resembling That of Epstein-Barr Virus EBNA2, Mol. Cell. Biol., 1996, 16, 952-959.
Huch et al., Urokinase-Type Plasminogen Activator Receptor Transcriptionally Controlled Adenoviruses Eradicate Pancreatic Tumors and Live Metastasis in Mouse Models, Neoplasia, 2009, pp. 518-528, vol. 11, No. 6.
Jaks V, Barker N, Kasper M, van Es JH, Snippert HJ, Clevers H, Toftgard R. (2008) Lgr5 marks cycling, yet long-lived, hair follicle stem cells. Nat Genet. 40:1291-9.
Jensen, T-box Genes in Early Embryogenesis, Developmental Dynamics, 2004, pp. 201-218, vol. 229.
Kedinger, M. et al., Intestinal epithelial-mesenchymal cell interactions. Ann N Y Acad Sci 859, 1-17 (1998).
Planutis, Kestutis et al., Regulation of norrin receptor frizzled-4 by Wnt2 in colon-derived cells, BMC Cell Biol. (2007) 8: 12.
Kim, K. A. et al., Mitogenic influence of human R-spondin1 on the intestinal epithelium. Science 309, 1256-9 (2005).
Kirikoshi H et al., WNT10A and WNT6, Clustered in Human Chromosome 2q35 Region with Head-to-Tail Manner, Are Strongly Coexpressed in SW480 Cells, Biochem Biophys Res Com, 2001, 283: 798-805.
Korinek et al., Constitutive Transcriptional Activation by a β-Catenin-Tef Complex in APC$^{-/-}$ Colon Carcinoma, Science, 1997, 275:1784-1787.
Korinek, V. et al., Depletion of epithelial stem-cell compartments in the small intestine of mice lacking Tcf-4. Nat Genet 19, 379-83 (1998).
Kuhnert, F. et al., Essential requirement for Wnt signaling in proliferation of adult small intestine and colon revealed by adenoviral expression of Dickkopf-1. Proc Natl Acad Sci U S A 101, 266-71 (2004).

(56) References Cited

OTHER PUBLICATIONS

Lefebvre VH, Otonkoski T, Ustinov J, Huotari MA, Pipeleers DG, Bouwens L.(1998) Culture of adult human islet preparations with hepatocyte growth factor and 804G matrix is mitogenic for duct cells but not for beta-cells. Diabetes. 47:134-7.
Leost, M. et al., Paullones are potent inhibitors of glycogen synthase kinase-3β and cyclin-dependent kinase 5/p25, Eur. J. Biochem. (2000) 267, 5983-5994.
Li, L. et al., The human homolog of rat Jagged1 expressed by marrow stroma inhibits differentiation of 32D cells through interaction with Notch1. Immunity 8, 43-55 (1998).
Li, L. & Xie, T. Stem cell niche: structure and function. Annu Rev Cell Dev Biol 21, 605-31 (2005).
Liao et al Glycogen Synthase Kinase-3β Activity Is Required for Androgen-Stimulated Gene Expression in Prostate Cancer, Endocrinology, 2004, 145(6): 2941-9.
Little et al., Engineering Biomaterials for Synthetic Neural Stem Cell Microenvironments, Chem. Rev, 2008, 108, 1787-1796.
Liu et al., A Small-Molecule Agonist of the Wnt Signaling Pathway, Angew Chem Int Ed Engl. (2005) 44, 1987-90.
Lustig B, Jerchow B, Sachs M, Weiler S, Pietsch T, Karsten U, van de Wetering M, Clevers H, Schlag PM, Birchmeier W, Behrens J. (2002) Negative feedback loop of Wnt signaling through upregulation of conductin/axin2 in colorectal and liver tumors, J. Mol Cell Biol.1184-93.
Meijer, L. et al., GSK-3-Selective Inhibitors Derived from Tyrian Purple Indirubins, Chem. Biol. (2003) 10, 1255-1266.
Meijer et al., Pharmacological inhibitors of glycogen synthase kinase 3, Trends in Pharmacological Sciences (2004) 25, 471-480.
Miralles F, Czernichow P, Ozaki K, Itoh N, Scharfmann R. (1999) Signaling through fibroblast growth factor receptor 2b plays a key role in the development of the exocrine pancreas. Proc Natl Acad Sci U S A. 96:6267-72.
Ootani A, Toda S, Fujimoto K, Sugihara H. Foveolar Differentiation of Mouse Gastric Mucosa in Vitro, Am J Pathol. Jun. 2003;162(6):1905-12.
Perreault, N. & Jean-Francois, B. Use of the dissociating enzyme thermolysin to generate viable human normal intestinal epithelial cell cultures. Exp Cell Res 224, 354-64 (1996).
Pinto, D., Gregorieff, A., Begthel, H. & Clevers, H. Canonical Wnt signals are essential for homeostasis of the intestinal epithelium. Genes Dev 17, 1709-13 (2003).
Powell, D. W. et al., Myofibroblasts. II. Intestinal subepithelial myofibroblasts. Am J Physiol 277, C183-201 (1999).
Ramiya, V.K., Maraist, M., Arfors, K.E., Schatz, D.A., Peck, A.B., and Cornelius, J.G. (2000). Reversal of insulin-dependent diabetes using islets generated in vitro from pancreatic stem cells. Nat. Med. 6, 278-282.
Rooman I, Heremans Y, Heimberg H, Bouwens L. Modulation of rat pancreatic acinoductal transdifferentiation and expression of PDX-1 in vitro. Diabetologia, Jul. 2000;43(7):907-14.
Rooman I, Lardon J, Flamez D, Schuit F, Bouwens L. (2001) Mitogenic effect of gastrin and expression of gastrin receptors in duct-like cells of rat pancreas. Gastroenterology 121:940-9.
Saha et al., Designing synthetic materials to control stem cell phenotype, Curr Opin Chem Biol., 2007, 11(4): 381-387.
Saha et al., Substrate Modulus Directs Neural Stem Cell Behavior, Biophysical Journal, 2008, 95: 4426-4438.
Sasaki, T., Giltay, R., Talts, U., Timpl, R. & Talts, J. F. Expression and distribution of laminin alpha1 and alpha2 chains in embryonic and adult mouse tissues: an immunochemical approach. Exp Cell Res 275, 185-99 (2002).
Sato T, Vries RG, Snippert HJ, van de Wetering M, Barker N, Stange DE, van Es JH, Abo A, Kujala P, Peters PJ, Clevers H. (2009) Single Lgr5 stem cells build crypt-villus structures in vitro without a mesenchymal niche. Nature 459:262-5.
Sawada et al., Selective killing of Paneth cells by intravenous administration of dithizone in rats, Int J Exp Pathol;72:407-21 (1991).
Schwitzgebel, V.M., Scheel, D.W., Conners, J.R., Kalamaras, J., Lee, J.E., Anderson, D.J., Sussel, L., Johnson, J.D., and German, M.S. (2000). Expression of neurogenin3 reveals an islet cell precursor population in the pancreas. Development 127, 3533-3542.
Seaberg, R.M., Smukler, S.R., Kieffer, T.J., Enikolopov, G., Asghar, Z., Wheeler, M.B., Korbutt, G., and van der Kooy, D. (2004). Clonal identification of multipotent precursors from adult mouse pancreas that generate neural and pancreatic lineages. Nat. Biotechnol. 22, 1115-1124.
Soriano, P. Generalized lacZ expression with the ROSA26 Cre reporter strain. Nat Genet 21, 70-1 (1999).
Spradling, A., Drummond-Barbosa, D. & Kai, T. Stem cells find their niche. Nature 414, 98-104 (2001).
Srinivas, S. et al., Cre reporter strains produced by targeted insertion of EYFP and ECFP into the ROSA26 locus. BMC Dev Biol 1, 4 (2001).
St Clair, W. H. & Osborne, J. W. Crypt fission and crypt number in the small and large bowel of postnatal rats. Cell Tissue Kinet 18, 255-62 (1985).
Stingl, J., Eaves, C. J., Zandieh, I. & Emerman, J. T. Characterization of bipotent mammary epithelial progenitor cells in normal adult human breast tissue. Breast Cancer Res Treat 67, 93-109 (2001).
Stingl, J. et al., Purification and unique properties of mammary epithelial stem cells. Nature 439, 993-7 (2006).
Suzuki, A., Nakauchi, H., and Taniguchi, H. (2004). Prospective isolation of multipotent pancreatic progenitors using flow-cytometric cell sorting. Diabetes 53, 2143-2152.
Teta, M., Rankin, M.M., Long, S.Y., Stein, G.M., and Kushner, J.A. (2007). Growth and regeneration of adult beta cells does not involve specialized progenitors. Dev. Cell 12, 817-826.
Trautmann B, Schlitt HJ, Hahn EG, Löhr M. (1993) Isolation, culture, and characterization of human pancreatic duct cells. Pancreas 8:248-54.
van de Wetering et al., Mutant E-cadherin Breast Cancer Cells Do Not Display Constitutive Wnt Signaling, Cancer Res., Jan. 1, 2001;61(1):278-84.
van Es, J. H. et al., Notch/gamma-secretase inhibition turns proliferative cells in intestinal crypts and adenomas into goblet cells. Nature 435, 959-63 (2005).
Wang, R.N., Kloppel, G., and Bouwens, L. (1995). Duct- to islet-cell differentiation and islet growth in the pancreas of duct-ligated adult rats. Diabetologia 38, 1405-1411.
Watanabe, K. et al., A ROCK inhibitor permits survival of dissociated human embryonic stem cells. Nat Biotechnol 25, 681-6 (2007).
Whitehead, R. H., Demmler, K., Rodman, S. P. & Watson, N. K. Clonogenic growth of epithelial cells from normal colonic mucosa from both mice and humans. Gastroenterology 117, 858-65 (1999).
Willert K, Brown JD, Danenberg E, Duncan AW, Weissman IL, Reya T, Yates JR 3rd, Nusse R. Wnt proteins are lipid-modified and can act as stem cell growth factors, Nature. May 22, 2003;423(6938):448-52.
Xu X, D'Hoker J, Stangé G, Bonné S, De Leu N, Xiao X, Van de Casteele M, Mellitzer G, Ling Z, Pipeleers D, Bouwens L, Scharfmann R, Gradwohl G, Heimberg H. (2008) Beta cells can be generated from endogenous progenitors in injured adult mouse pancreas. Cell. 132(2):197-207.
Yen, T. H. & Wright, N. A. The gastrointestinal tract stem cell niche. Stem Cell Rev 2, 203-12 (2006).
Partial European search report for Application No. 09151970.2 dated Dec. 6, 2009.
Abud HE et al., "Growth of intestinal epithelium in organ culture is dependent on EGF signalling." Experimental cell research 303, 252-262 (2005).
Booth C et al., "The isolation and Culture of adult mouse colonic epithelium" Epithelial cell biology, Springer International 4, 76-86 (1995).
Booth C et al., "Maintenance of functional stem cells in isolated and cultured adult intestinal epithelium." Experimental cell research 249, 359-366 (1999).
van der Flier, L.G., van Gijn, M.E., .., and Clevers H. Transcription factor Achaete scute-like 2 (Asc12) controls intestinal stem cell fate Cell 136: 903-12 (2009).

(56) References Cited

OTHER PUBLICATIONS

Barker, N, Huch, M., . . . , and Hans Clevers. Lgr5+ve stem cells drive self-renewal in the stomach and build long-lived gastric units in vitro Cell Stem Cell, 6: 25-36 (2010).
van de Wetering M et al., The β-Catenin/TCF-4 Complex Imposes a Crypt Progenitor Phenotype on Colorectal Cancer Cells, Cell 2002;111:241-50.
Clarke et al., Cancer Stem Cells—Perspectives on Current Status and Future Directions: AACR Workshop on Cancer Stem Cells, Cancer Res. 2006, 66:9339-44.
Chun et al., A New Selective and Potent Inhibitor of Human Cytochrome P450 1B1 and Its Application to Antimutagenesis, Cancer Res, 2001, 61: 8164-8170.
Partial European Search Report for Application EP 10 17 1265 dated Oct. 5, 2010.
Snykers S et al., In vitro differentiation of embryonic and adult stem cells into hepatocytes: State of the art. Stem Cells, 27(3) 577-605, 2009.
Snykers S et al., Differentiation of neonatal rat epithelial cells from biliary origin into immature hepatic cells by sequential exposure to hepatogenic cytokines and growth factors reflecting liver development. Toxicology in vitro. 30, 1-7 (2007).
Search Report for GB1111244.8 dated Sep. 27, 2011.
Peng et al., In Vitro Cellular & Developmental Biology—Animal 45 (2009) 'Inhibition of p38 MAPK facilitates ex vivo expansion of skin epithelial progenitor cells' 558-565.
Zhou et al., Biochemical and Biophysical Research Communications 350 (2006), 'Oxidative stress-induced intestinal epithelial cell apoptosis is mediated by p38 MAPK' 860-865.
Bjerknes and Cheng, Methods in Enzymology 419 (2006), 'Intestinal epithelial stem cells and progenitors' 337-383.
Booth et al., Experimental Cell Research 249 (1999); Maintenance of functional stem cells in isolated and cultured adult intestinal epithelium 359-366.
Snippert, H.J., Haegebarth, A., Kasper, M., Jaks, V., van Es, J.H., Barker, N., van de Wetering, M., van den Born, M., Begthel, H., Vries, R.G., Stange, D.E., Toftgård, R., Clevers H. Lgr6 marks stem cells in the hair follicle that generate all cell lineages of the skin. Science 327: 1385-1389 (2010).
Sato, T., van Es, J.H., Snippert, H.J., Stange, D.E., Vries, R.G., van den Born, M., Barker, N., Shroyer, N.F., van de Wetering, M., Clevers, H. Paneth cells constitute the niche for Lgr5 stem cells in intestinal crypts. Nature 469: 415-418 (2011).
Snippert, .J., van der Flier, L.G., Sato, T., van Es, J.H., van den Born, M., Kroon-Veenboer, C., Barker, N.,Klein, A.M., van Rheenen, J. Benjamin D. Simons, B.D. and Clevers, H. Intestinal Crypt Homeostasis results from Neutral Competition between Symmetrically Dividing Lgr5 Stem Cells. Cell 143:134-44 (2010).
Azuma et al., Robust expansion of human hepatocytes in Fah$^{-/-}$ /Rag2$^{-/-}$ /Il2rg$^{-/-}$ mice, Nature Biotech, 2007, 25(8), 903-910.
Buset M et al., In vitro cellular & developmental biology: journal of the Tissue Culture Association 1987;23:403-12.
Clotman F. Control of liver cell fate decision by a gradient of TGFβ signaling modulated by Onecut transcription factors, Genes and Development, 2005, pp. 1849-1854, vol. 19.
Denu JM. Vitamin B$_3$ and sirtuin function, Trends Biochem Sci 2005;30:479-83.
Deveney CW et al., Establishment of Human Colonic Epithelial Cells in Long-Term Culture, The Journal of surgical research 1996;64:161-9.
Dey D et al., Phenotypic and Functional Characterization of Human Mammary Stem/Progenitor Cells in Long Term Culture, PloS one 2009;4:e5329.
Dignass AU & Sturm A., Peptide growth factors in the intestine, Eur J Gastroenterol Hepatol 2001;13:763-70.
Furuyama K et al., Continuous cell supply from a Sox9-expressing progenitor zone in adult liver, exocrine pancreas and intestine, Nat Genetics, 43, 34-41, 2001.

Garraway IP et al., Human Prostate Sphere-Forming Cells Represent a Subset of Basal Epithelial Cells Capable of Glandular Regeneration In Vivo, The Prostate, 2010;70:491-501.
Gregorieff A et al., Expression Pattern of Wnt Signaling Components in the Adult Intestine, Gastroenterology 2005;129:626-38.
Grossmann J et al., Progress on isolation and short-term ex-vivo culture of highly purified non-apoptotic human intestinal epithelial cells (IEC), European journal of cell biology, 2003;82:262-70.
Haramis AP et al., De Novo Crypt Formation and Juvenile Polyposis on BMP Inhibition in Mouse Intestine, Science 2004;303:1684-6.
Hu et al., Basic-Liver, Pancreas, and Biliary Tract: Wnt/β-Catenin Signaling in Murine Hepatic Transit Amplifying Progenitor Cells, Gastroenterology, 2007, 133(5): 1579-91.
Huch et al., Urokinase-Type Plasminogen Activator Receptor Transcriptionally Controlled Adenoviruses Eradicate Pancreatic Tumors and Liver Metastasis in Mouse Models, Neoplasia, 2009, pp. 518-528, vol. 11, No. 6.
Latella G et al., Characterizaton of the mucins produced by normal human colonocytes in primary culture, International journal of colorectal disease 1996;11:76-83.
Menke V et al., Conversion of metaplastic Barrett's epithelium into post-mitotic goblet cells by γ-secretase inhibition, Disease models & mechanisms 2010;3:104-10.
Odze RD, Barrett esophagus: histology and pathology for the clinician, Nat Rev Gastroenterol Hepatol 2009;6:478-90.
Ootani A et al., Sustained in vitro intestinal epithelial culture within a Wnt-dependent stem cell niche, Nat Med 2009;15:701-6.
Otsuka M et al., Distinct Effects of p38α Deletion in Myeloid Lineage and Gut Epithelia in Mouse Models of Inflammatory Bowel Disease, Gastroenterology 2010;138:1255-65, 1265 e1-9.
Overturf et al., Hepatocytes corrected by gene therapy are selected in vivo in a murine model of hereditary tyrosinaemia type I, Nature, 1996, pp. 266-273, vol. 12.
Pang G et al. Alimentary Tract: Immunologic, Functional, and Morphological Characterization of Three New Human Small Intestinal Epithelial Cell Lines, Gastroenterology 1996;111:8-18.
Panja A. Brief Methods: A Novel Method for the Establishment of a Pure Population of Nontransformed Human Intestinal Primary Epithelial Cell (HIPEC) Lines in Long Teim Culture, Laboratory investigation; a journal of technical methods and pathology, 2000;80:1473-5.
Rogler G et al., Differential Activation of Cytokine Secretion in Primary Human Colonic Fibroblast/Myofibroblast Cultures, Scandinavian journal of gastroenterology, 2001;36:389-98.
Shay et al., Telomerase therapeutics for cancer: challenges and new directions, 2006, pp. 1-8.
van Es JH et al., Notch/γ-secretase inhibition turns proliferative cells in intestinal crypts and adenomas into giblet cells, Nature 2005;435:959-63.
Walen KH, Spontaneous Cell Transormation: Karyoplasts Derived From Multinucleated Cells Produce New Cell Growth in Senescent Human Epithelial Cell Cultures, In vitro cellular & developmental biology. Animal, 2004;40:150-8, Society for In Vitro Biology.
Whitehead RH et al., A Method for the Isolation and Culture of Human Colonic Crypts in Collagen Gels, In vitro cellular & developmental biology: journal of the Tissue Culture Association, 1987;23:436-42.
Zong Y. et al., Notch signaling controls liver development by regulating biliary differentiation, Development, 2009, pp. 1727-1739, vol. 136.
de Lau, W., Barker, N., . . . and Clevers, H. Lgr5 homologues associate with Wnt receptors and mediate R-spondin signalling Nature 476: 293-297 (2011).
[No Author Listed] Purified Human Pancreatic Islets, In Vivo Islets Function. Document No. 3104, A04, Effective Date Jul. 7, 2008. DAIT, NIAID, NIH.
Bakkebø et al., TGF-β-induced growth inhibition in B-cell lymphoma correlates with Smad1/5 signalling and constitutively active p38 MAPK. BMC Immunol. Nov. 23, 2010;11:57. doi: 10.1186/1471-2172-11-57.

(56) References Cited

OTHER PUBLICATIONS

Bodnar et al., Characterization of human islet-like structures generated from pancreatic precursor cells in culture. Biotechnol Bioeng. Apr. 5, 2006;93(5):980-8.
Bottenstein et al., Growth of a rat neuroblastoma cell line in serum-free supplemented medium. Proc Natl Acad Sci U S A. Jan. 1979;76(1):514-7.
Drew et al., Comparison of 2 cell-based phosphoprotein assays to support screening and development of an ALK inhibitor. J Biomol Screen. Feb. 2011;16(2):164-73. doi: 10.1177/1087057110394657.
Hayflick., The cell biology of aging. J Invest Dermatol. Jul. 1979;73(1):8-14.
Hodin et al., Immediate-early gene expression in EGF-stimulated intestinal epithelial cells. J Surg Res. Jun. 1994;56(6):500-4.
Hong et al., Proteomic analysis of differential protein expression in response to epidermal growth factor in neonatal porcine pancreatic cell monolayers. J Cell Biochem. Jul. 1, 2005;95(4):769-81.
Liu et al., A novel chemical-defined medium with bFGF and N2B27 supplements supports undifferentiated growth in human embryonic stem cells. Biochem Biophys Res Commun. Jul. 21, 2006;346(1):131-9. Epub May 24, 2006.
Macchiarini et al., Clinical transplantation of a tissue-engineered airway. Lancet. Dec. 13, 2008;372(9655):2023-30. doi: 10.1016/S0140-6736(08)61598-6. Epub Nov. 18, 2008.
Mason et al., Entrapped collagen type 1 promotes differentiation of embryonic pancreatic precursor cells into glucose-responsive beta-cells when cultured in three-dimensional PEG hydrogels. Tissue Eng Part A. Dec. 2009;15(12):3799-808. doi: 10.1089/ten.TEA.2009.0148.
Mirochnik et al., Androgen receptor drives cellular senescence. PLoS One. 2012;7(3):e31052. doi: 10.1371/journal.pone.0031052. Epub Mar. 5, 2012.
Nasonkin et al., Nonhuman sialic acid NeuSGc is very low in human embryonic stem cell-derived neural precursors differentiated with B27/N2 and noggin: implications for transplantation. Exp Neurol. Oct. 2006;201(2):525-9.
Niu et al., Differential androgen receptor signals in different cells explain why androgen-deprivation therapy of prostate cancer fails. Oncogene. Jun. 24, 2010;29(25):3593-604. doi: 10.1038/onc.2010.121. Epub May 3, 2010. Review.
Petersen et al., Interaction with basement membrane serves to rapidly distinguish growth and differentiation pattern of normal and malignant human breast epithelial cells. Proc Natl Acad Sci U.S.A. Oct. 1, 1992;89(19):9064-8.
Pettipher et al., Antagonism of the prostaglandin D2 receptors DP1 and CRTH2 as an approach to treat allergic diseases. Nat Rev Drug Discov. Apr. 2007;6(4):313-25. Review.
Robinton et al., The promise of induced pluripotent stem cells in research and therapy. Nature. Jan. 18, 2012;481(7381):295-305. doi: 10.1038/nature10761. Review.
Sansom et al., Loss of Apc in vivo immediately perturbs Wnt signaling, differentiation, and migration. Genes Dev. Jun. 15, 2004;18(12):1385-90.
Segev et al., Differentiation of human embryonic stem cells into insulin-producing clusters. Stem Cells. 2004;22(3):265-74.
Touhami et al., The role of NGF signaling in human limbal epithelium expanded by amniotic membrane culture. Invest Ophthalmol Vis Sci. Apr. 2002;43(4):987-94.
[No Author Listed] Infection, inflammation and immunity. 2004;34(2):40-52. Japanese.
Bonaguidi et al., LIF and BMP signaling generate separate and discrete types of GFAP-expressing cells. Development. Dec. 2005;132(24):5503-14.
Bonaguidi et al., Noggin expands neural stem cells in the adult hippocampus. J Neurosci. Sep. 10, 2008;28(37):9194-204. doi: 10.1523/JNEUROSCI.3314-07.2008.
Cheng et al., Origin, differentiation and renewal of the four main epithelial cell types in the mouse small intestine. I. Columnar cell. Am J Anat. Dec. 1974;141(4):461-79.
Clevers et al. Cell Technology. 2009; 28(7):702-03. Japanese.
Dong et al.,The epithelial-mesenchymal transition promotes transdifferentiation of subcutaneously implanted hepatic oval cells into mesenchymal tumor tissue. Stem Cells Dev. Nov. 2009;18(9):1293-8. doi: 10.1089/scd.2008.0321.
Egan et al., Notch receptors, partners and regulators—from conserved domains to powerful functions. Experimental Med. 1998;16(3):200-229. Japanese.
Lee et al., the role of gremlin, a BMP antagonist, and epithelial-to-mesenchymal transition in proliferative vitreoretinopathy. Invest Ophthalmol Vis Sci. Sep. 2007;48(9):4291-9.
Zaret, Genetic programming of liver and pancreas progenitors: lessons for stem-cell differentiation. Nat Rev Genet. May 2008;9(5):329-40. doi:10.1038/nrg2318.
Apte et al., Wnt/beta-catenin signaling mediates oval cell response in rodents. Hepatology. Jan. 2008;47(1):288-95.
Hirata et al., Establishment and characterization of hepatic stem-like cell lines from normal adult rat liver. J Biochem. Jan. 2009;145(1):51-8. doi: 10.1093/jb/mvn146. Epub Oct. 30, 2008.
Huch et al., Long-term culture of genome-stable bipotent stem cells from adult human liver. Cell. Jan. 15, 2015;160(1-2):299-312.doi: 10.1016/j.cell.2014.11.050. Epub Dec. 18, 2014.
Itoh et al., Inducible expression of Wnt genes during adult hepatic stem/progenitor cell response. FEBS Lett. Feb. 18, 2009;583(4):777-81. doi: 10.1016/j.febslet.2009.01.022. Epub Jan. 25, 2009.
Kawasaki et al., Effects of growth factors on the growth and differentiation of mouse fetal liver epithelial cells in primary cultures. J Gastroenterol Hepatol. Jun. 2005;20(6):857-64.
Kerr-Conte et al., Ductal cyst formation in collagen-embedded adult human islet preparations. A means to the reproduction of nesidioblastosis in vitro. Diabetes. Aug. 1996;45(8):1108-14.
Kim et al., In vivo functioning and transplantable mature pancreatic islet-like cell clusters differentiated from embryonic stem cell. Pancreas. Aug. 2003;27(2):e34-41.
Kitisin et al., Hepatocellular stem cells. Cancer Biomark. 2007;3(4-5):251-62.
Lee et al., In vitro hepatic differentiation of human mesenchymal stem cells. Hepatology. Dec. 2004;40(6):1275-84.
Lowes et al., Oval cell-mediated liver regeneration: Role of cytokines and growth factors. J Gastroenterol Hepatol. Jan. 2003;18(1):4-12.
Montesano et al., Collagen matrix promotes reorganization of pancreatic endocrine cell monolayers into islet-like organoids. J Cell Biol. Sep. 1983;97(3):935-9.
Sen Majumdar et al., Generation of insulin-producing islet-like clusters from human embryonic stem cells. Diabetologia. 2007;50(1):S222-223, Abstract 0530.
Suzuki et al., Role for growth factors and extracellular matrix in controlling differentiation of prospectively isolated hepatic stem cells. Development. Jun. 2003;130(11):2513-24.
Thenappan et al., Role of transforming growth factor beta signaling and expansion of progenitor cells in regenerating liver. Hepatology. Apr. 2010;51(4):1373-82. doi: 10.1002/hep.23449.
Partial European Search Report for EP16151949.1, mailed May 19, 2016.
Jiang et al., Generation of insulin-producing islet-like clusters from human embryonic stem cells, Stem Cells. Aug. 2007;25(8):1940-53.
Huch et al., In vitro expansion of single Lgr5+ liver stem cells induced by Wnt-driven regeneration. Nature. Feb. 14, 2013;494(7436):247-50. doi: 10.1038/nature11826. Epub Jan. 27, 2013.
Yaswen et al., Isolation of oval cells by centrifugal elutriation and comparison with other cell types purified from normal and preneoplastic livers. Cancer Res. Jan. 1984;44(1):324-31.

* cited by examiner

Freshly isolated colon crypts

Colon crypt organoid Day 4

Colon crypt organoid Day 14

FIG. 19
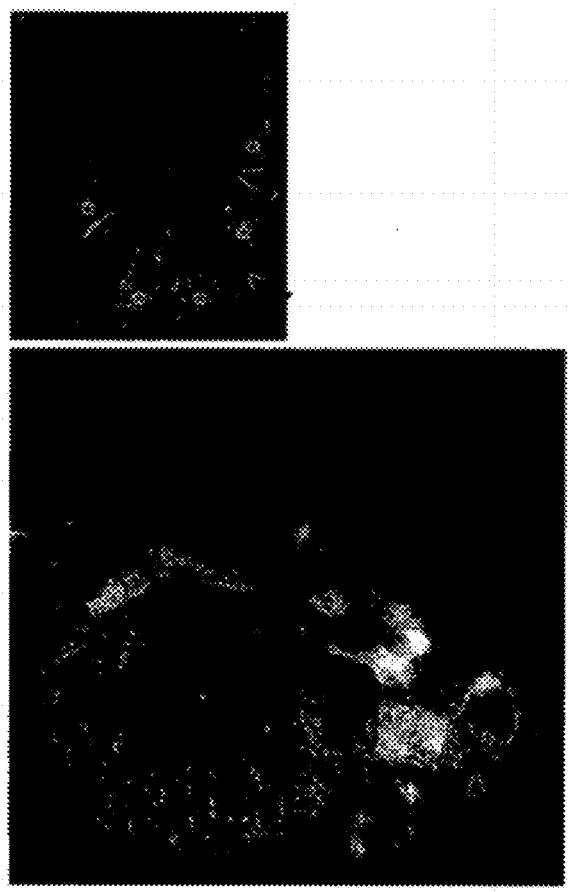
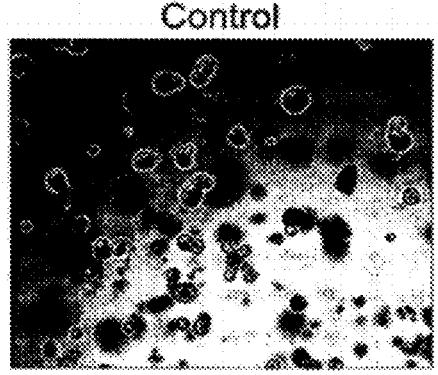
Control
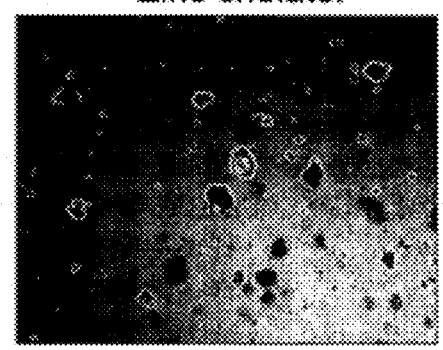
Zinc chelator
FIG. 20

Pancreatic duct organoid with islet like structures (arrows) Day 21

Islet like structure (high magnification)

Pancreatic islet-like structure

Day
0 
1 
3 
5 
7 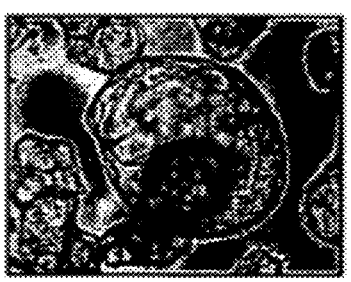
10
Passage 1 
FIG. 30

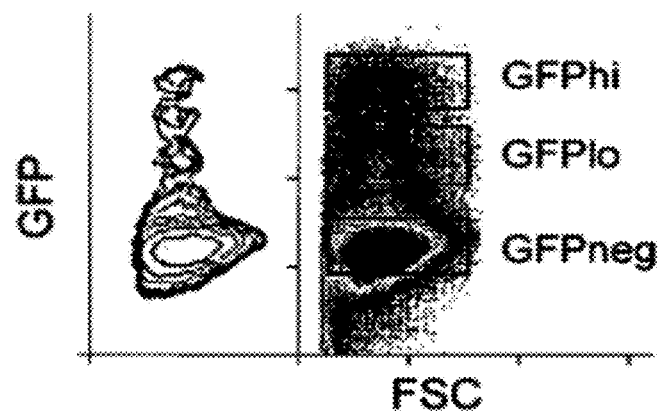
FIG. 34A  FIG. 34B
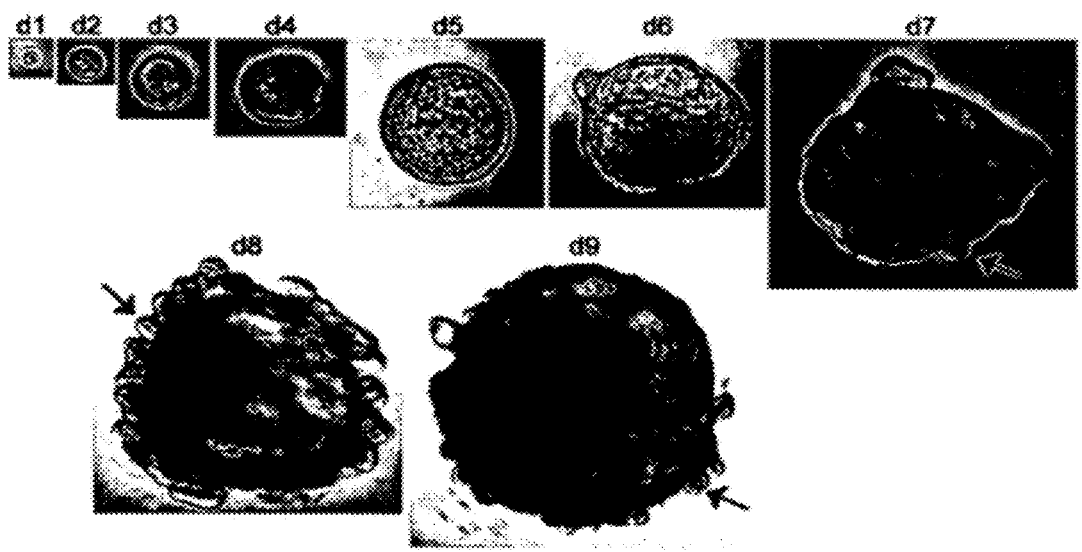
FIG. 34C

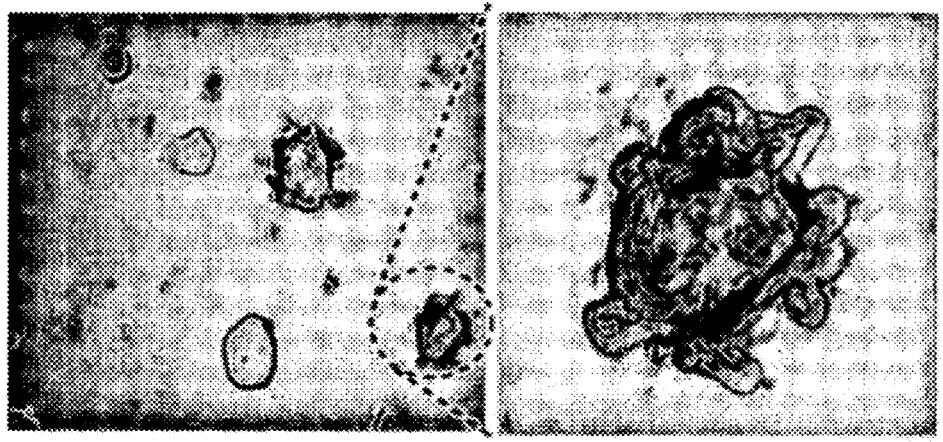
FIG. 34D
 
FIG. 34E  FIG. 34F

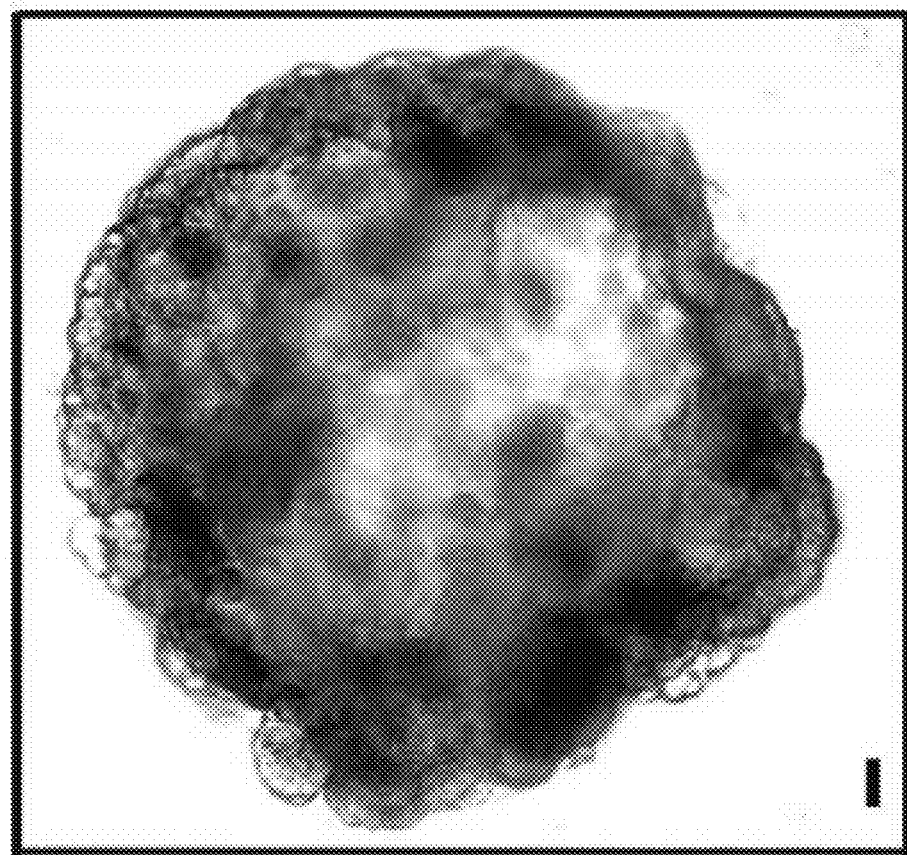
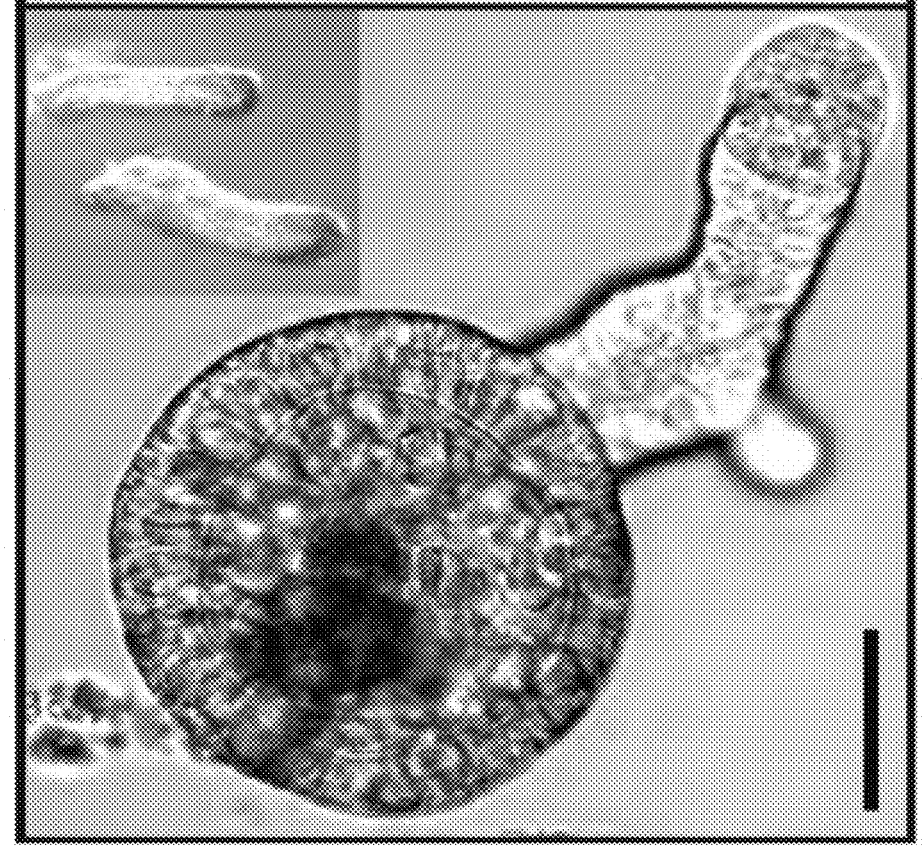
FIG. 35A

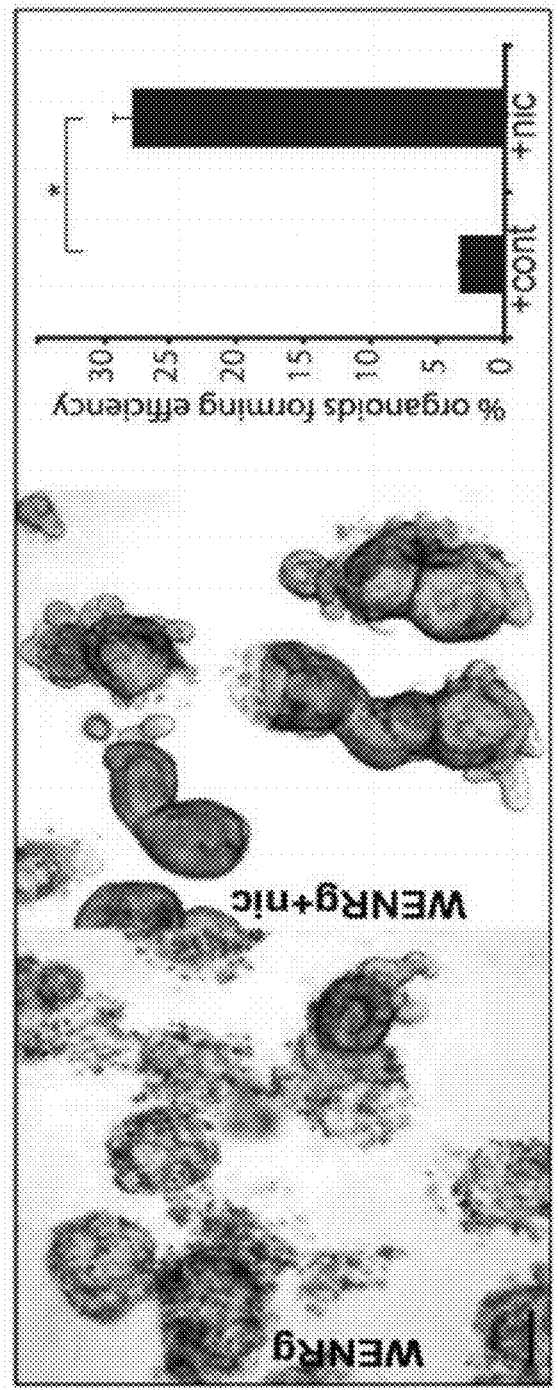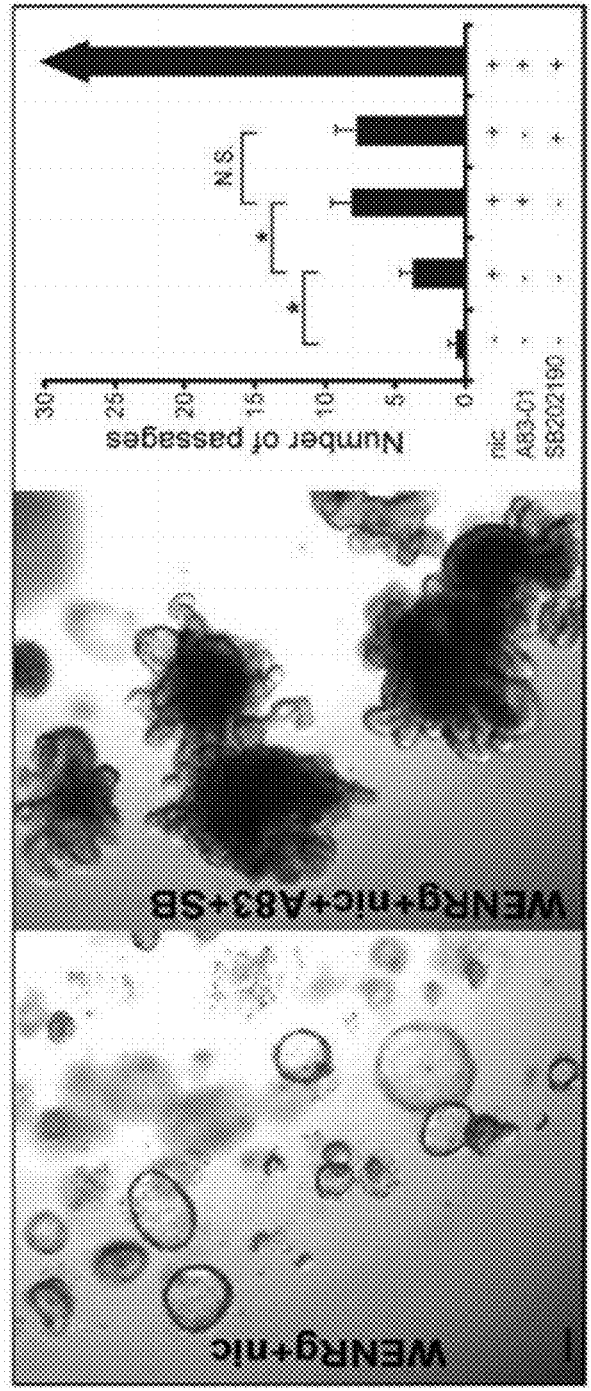
FIG. 36A
FIG. 36B

 
FIG. 37C

| Reagent name | Supplier | Cat No. | Solvent | Stock solution | final conc. |
|---|---|---|---|---|---|
| Matrigel GFR, phenol free | BD bioscience | 356231 | | | |
| GlutaMAX-I | Invitrogen | 35050-079 | | 200 mM | 2 mM |
| Penicillin Streptomycin | Invitrogen | 15140-122 | | 10000/10000 U/ml | 100/100 U/ml |
| N2 supplement | Invitrogen | 17502-048 | | 100x | 1x |
| B27 supplement | Invitrogen | 17504-044 | | 50x | 1x |
| N-Acetylcysteine | Sigma-Aldrich | A9165-5G | DW | 500 mM=81.5 mg/ml | 1 mM |
| EDTA | Sigma-Aldrich | 431788-25g | DW | 500 mM=14.6g/100ml | 2 mM |
| mouse recombinant noggin | Peprotech | 250-38 100 μg | PBS/BSA | 100 μg/ml | 100 ng/ml |
| mouse recombinant EGF | Invitrogen | PMG8043 | PBS/BSA | 500 μg/ml | 50 ng/ml |
| human recombinant R-spondin | Novus | 100-26 | PBS/BSA | 1 mg/ml | 1 μg/ml |
| human recombinant FGF10 | Peprotech | GF-160 | PBS/BSA | 100 μg/ml | 100 ng/ml |
| mouse recombinant Wnt-3A | Millipore | GF-160 | PBS | 10 μg/ml | 100 ng/ml |
| Y-27632 | Sigma-Aldrich | Y0503 | PBS | 10 mM=1g/338 μL | 10 μM |
| A-83-01 | Tocris | 2939 | DMSO | 500 μM | 500 nM |
| SB202190 | Sigma-Aldrich | S7067 | DMSO | 30 mM | 10 μM |
| Nicotinamide | Sigma-Aldrich | N0636 | DW | 1M | 10 mM |
| [Leu15]-Gastrin I | Sigma-Aldrich | G9145 | PBS/BSA | 100 μM | 10 nM |
| DNase | Sigma-Aldrich | DN25-1g | PBS | 200000 U/ml | 200 U/ml |

All stock solutions are stored in -20°C. Matrigel is aliquoted and stored in -20°C.

FIG. 45

| Reagent name | Supplier | Cat. No. |
|---|---|---|
| HEPES 1M | Invitrogen | 15630-056 |
| Advanced DMEM/F12 | Invitrogen | 12634-028 |
| TrypLE express | Invitrogen | 12605-036 |
| Collagenase type XI | Sigma-Aldrich | C9407 |
| Dispase | Invitrogen | 17105-041 |
| 70 μm Cell strainer | BD falcon | 352350 |

List of primers and probes for Real-time PCR

| | Gene name | Forward primer | SEQ ID NO: | Reverse primer | SEQ ID NO: | Taqman probe (UPL library number | SEQ ID NO: |
|---|---|---|---|---|---|---|---|
| Human | Villin1 | GCAGCATTACCTGCTCTACGTT | 72 | GCTTGATAAGCTGATGCTGTAATTT | 73 | #71 gcagccag | 74 |
| | Alkaline phosphatase, intestinal | CATGGACCGCTTCCCATA | 75 | GGCACCTGTCTGTCCACAT | 76 | #21 tggtctg | 77 |
| | Chromogranin B | CAGCCAACGCTGCTTCTC | 78 | TGGCATGGAATTGACAGC | 79 | #79 cctcctgg | 80 |
| | Lysozyme | CCGCTCTACTGGTGTAATGATGG | 81 | CATCAGCGATGTTATCTTGCAG | 82 | #68 aggagcag | 83 |
| | Mucin2 | GCCAGCTCATCAAGGACAG | 84 | GCAGGCATCGTAGTAGTGCTG | 85 | #61 ttgccag | 86 |
| | Hprt | TGACCTTGATTTATTTTGCATACC | 87 | CGAGCAAGACGTTCAGTCCT | 88 | #73 | |
| Mouse | Villin1 | gcttgccacaacttcctaagat | 89 | tcagttagtcatgtggacga | 90 | #77 ggtggtgg | 91 |
| | Muc2 | tgtggaaccgggaagatg | 92 | gaccacagagtatggttctgga | 93 | #22 tggtggag | 94 |
| | Chromogranin A | cgatccagaaagatgatggtc | 95 | cggaagcctctgtcttcc | 96 | #58 ggatggag | 97 |
| | Hprt | tcctcctcagaccgctttt | 98 | cctggttcatcatcgctaatc | 99 | #95 actcccag | 100 |

FIG. 45 (continued)

| | Reagent name | function | Company | Final concentration | Activity scale |
|---|---|---|---|---|---|
| Hormones, vitamines etc | Hydrocortisone | | Sigma | 500 nM | 0 |
| | [Leu15]-Gastrin I | | Sigma | 1 mM | 1+ |
| | Exendin4 | GLP1 analog | Sigma | 100 nM | 0 |
| | Nicotinamide | Vitamin B dehydrating | Sigma | 10 mM | 3+ |
| | L-Ascorbic acid | Vitamin C | Sigma | 10 mM | 0 |
| | Lipid mixture anti-oxidant mixture | | Sigma | 1x | 0 |
| | PGE2 | | Sigma | 10 nM | 1+ (Cystic) |
| | Cholera Toxin | | Sigma | 100 nM | 1+ (Cystic) |
| Growth factors | IGF | | Peprotech | 100 ng/ml | 0 |
| | HGF | | Peprotech | 100-500 ng/ml | 0 |
| | BDNF | | Peprotech | 100 ng/ml | 0 |
| | GDNF | | Peprotech | 100 ng/ml | 0 |
| | FGF2 | | Peprotech | 100 ng/ml | 0 |
| | FGF10 | | Peprotech | 100 ng/ml | 0 |
| | Follistatin | | Peprotech | 100 ng/ml | 0 |
| | Crtl1 | | Peprotech | 1 mg/ml | 0 |
| | LIF | | Millipore | 1000 U/ml | 0 |

FIG. 46

Reagents tested for optimization of human intestinal organoid culture. Each reagent was added to WENR culture condition. Activity scale plating efficiency was compared with control after 4 days culture. (no change, 1→<50% increase, 2→50-100% increase, 3→>100% increase, 1-→<50% decrease, 2-→50-100% decrease, 3-→>100% decrease

| Reagent name | function | Company | Final concentration | Activity scale |
|---|---|---|---|---|
| Small molecule inhibitors | | | | |
| PD98059 | ERK inhibitor | Sigma | 10 nM | 1- |
| SB203580 | p38 inhibitor | Sigma | 1-10 nM | 2+ |
| SB202190 | p38 inhibitor | Sigma | 1-10 nM | 2+ |
| SP600125 | JNK inhibitor | Sigma | 10 nM | 0 |
| PS48 | PDK1 activator | Sigma | 5 nM | 0 |
| Y27632 | ROCK inhibitor | Sigma | 10 nM | 1+ (cystic) |
| Cyclopamine | Hedgehog inhibitor | Sigma | 100 nM | 2+ |
| Trichostatin A | HDAC inhibitor | Stemolecule | 100 nM | 1- |
| 5-Azacitidin | DNA methylase inhibitor | Stemolecule | 20 nM | 1- |
| Dorsomorphin | BMP inhibitor | Stemolecule | 10 nM | 0 |
| A83-01 | ALK4,5,7 inhibitor | Tocris | 50 n-1 mM | 3+ |
| VO-OHpic trihydrate | PTEN inhibitor | Sigma | 500 nM | 3- |
| cyclic Pifithrin-α | p53 inhibitor | Sigma | 50 nM | 0 |
| BIX01294 | G9a HMTase inhibitor | Stemolecule | 10 nM | 1- |
| DBZ | Notch inhibitor | Ref.1 | 10 nM | 0 |

Small molecule inhibitors for optimization of human intestinal organoid culture.
Each inhibitor was added to WENR+ gastrin +Nicotinamide culture condition.
Activity scale:plating efficiency was compared with control after 4 days culture.
0=no change; 1+=<50% increase, 2+=50-100% increase, 3+=>100% increase, 1-=<50%, 2-=50-100% decrease, 3-=>100% decrease Reference 1: van Es JH et al. Nature 2005, 435, 959-63

FIG. 47

SI top 25 upregulated genes

| | Small intestinal organoids | | Colon organoids | |
|---|---|---|---|---|
| | Gene symbol | Fold difference vs small intestinal villi | Gene symbol | Fold difference vs small intestinal villi |
| 1 | CCL26 | 9.60 | ADORA2B | 10.19 |
| 2 | ADORA2B | 9.54 | NOX1 | 9.02 |
| 3 | LPL | 9.11 | LEFTY1 | 8.99 |
| 4 | LCN2 | 8.26 | CCL26 | 8.90 |
| 5 | DSG3 | 8.04 | CD24 | 8.72 |
| 6 | SMOC2 | 7.75 | EYA2 | 8.05 |
| 7 | CLDN1 | 7.64 | RHBDL2 | 7.93 |
| 8 | BX415272 | 7.50 | SMOC2 | 7.72 |
| 9 | CXCL3 | 7.48 | SPINK5 | 7.65 |
| 10 | AK022042 | 7.48 | TFCP2L1 | 7.58 |
| 11 | LGR6 | 7.17 | LCN2 | 7.49 |
| 12 | CTTNBP2 | 7.00 | C1orf125 | 7.48 |
| 13 | CD24 | 6.89 | BX415272 | 7.34 |
| 14 | MMP1 | 6.85 | CXCL3 | 7.29 |
| 15 | SERPINB5 | 6.76 | KIAA1199 | 7.00 |
| 16 | KIAA1199 | 6.61 | CTTNBP2 | 6.92 |
| 17 | CD44 | 6.37 | IL20RA | 6.91 |
| 18 | CEP55 | 6.36 | CEP55 | 6.83 |
| 19 | C18orf56 | 5.90 | E2F8 | 6.63 |
| 20 | LRRN1 | 5.89 | CD44 | 6.49 |
| 21 | AK095715 | 5.89 | MYB | 6.26 |
| 22 | JUB | 5.85 | AK021425 | 6.18 |
| 23 | GPX2 | 5.84 | IRX2 | 6.11 |
| 24 | HPDL | 5.82 | GPX2 | 6.06 |
| 25 | RHBDL2 | 5.82 | CCNA2 | 6.05 |

FIG. 48

SI bottom 25 downregulated genes

| | Small intestinal organoids | | Colon organoids | |
|---|---|---|---|---|
| | Gene symbol | Fold difference vs small intestinal villi | Gene symbol | Fold difference vs small intestinal villi |
| 1 | APOA1 | -9.41 | APOB | -10.68 |
| 2 | CD36 | -9.28 | CD36 | -9.69 |
| 3 | KLRB1 | -7.88 | SLC13A1 | -9.39 |
| 4 | HBB | -7.71 | APOA1 | -9.14 |
| 5 | CYP2C19 | -7.48 | APOC3 | -9.06 |
| 6 | APOC3 | -7.45 | NTS | -8.87 |
| 7 | SEPT3 | -7.17 | LRAT | -8.51 |
| 8 | FAM101B | -6.98 | KCNJ16 | -8.29 |
| 9 | SLC15A1 | -6.87 | SLC8A1 | -8.07 |
| 10 | GZMK | -6.81 | SLC15A1 | -7.63 |
| 11 | AV691872 | -6.70 | BE766438 | -7.51 |
| 12 | APOB | -6.62 | CYP2C19 | -7.48 |
| 13 | GNLY | -6.58 | SEMA3G | -7.44 |
| 14 | CLDN8 | -6.21 | SEPP1 | -7.38 |
| 15 | CD48 | -6.17 | HBB | -7.28 |
| 16 | CD69 | -6.05 | TRAF3IP3 | -7.28 |
| 17 | CD96 | -5.88 | SEPT3 | -7.17 |
| 18 | GPR171 | -5.85 | GIMAP6 | -7.10 |
| 19 | CD247 | -5.82 | FAM101B | -7.05 |
| 20 | RGS1 | -5.76 | FGF19 | -6.90 |
| 21 | BMP8B | -5.73 | GZMK | -6.81 |
| 22 | SLCO2A1 | -5.68 | AV691872 | -6.70 |
| 23 | IL18RAP | -5.65 | ADAMDEC1 | -6.50 |
| 24 | ARG2 | -5.64 | DFNA5 | -6.42 |
| 25 | C1QA | -5.57 | CD48 | -6.39 |

FIG. 48 (continued)

| Species | Organ | Organoids in stem cell culture condition | | | Organoids in differentiation condition | | |
|---|---|---|---|---|---|---|---|
| | | Proliferation | Differentiation | Apoptosis | Proliferation | Differentiation | Apoptosis |
| Mouse | Small intestine | 20-30% | AGEP | <1% | | | |
| | Colon | 20-30% | GE | <1% | 10-20% | AGE | <1% |
| | Adenoma | 40-60% | GEP | <1% | | | |
| Human | Small intestine | 20-30% | P | <1% | 10-20% | AGEP | <1% |
| | Colon | 20-30% | (-) | <1% | 10-20% | AGE | <1% |
| | Colon Cancer | 50-90% | GE | <1% | | | |
| | Barrett's epithelium | 20-30% | (-) | <1% | <1% | GP | <1% |

Proliferation was determined by Ki67 staining.
Apoptosis was determined by Caspase-3 staining
Differentiation markers; A: absorptive enterocyte, G: goblet cells, E: enteroendocrine cells, P: Paneth cells

FIG. 49

FIG. 50B background cutoff >7fold; dyeswap to Cy3/Cy5 (Cy3-samples; Cy5-reference RNA)

| FeatureNum | ProbeName | Description | GeneName | Adult pancreas gMedianSignal | Pancreas organoid gMedianSignal | Liver organoid E8 gMedianSignal |
|---|---|---|---|---|---|---|
| 58886 | A_52_P242199 | gb\|Mus musculus 12 days embryos spinal ganglion cDNA, RIKEN full-length enriched library, clone:D130036I05 product:unclassifiable, full insert sequence. [AK051635] | Asas | 84 | 98473 | 92 |
| 15415 | A_51_P406105 | ref\|Mus musculus ribosomal protein S4, Y-linked 2 (Rps4y2), non-coding RNA [NR_003634] | Rps4y2 | 408 | 1980 | 127 |
| 14485 | A_51_P189121 | ref\|Mus musculus ATPase, Ca++ transporting, type 2C, member 2 (Atp2c2), mRNA [NM_026922] | Atp2c2 | 1606 | 2198 | 144 |
| 35066 | A_52_P308205 | ref\|Mus musculus A kinase (PRKA) anchor protein 2 (Akap2) transcript variant 1, mRNA [NM_001035533] | Akap2 | 333 | 1738 | 115 |
| 3773 | A_51_P334499 | ref\|Mus musculus urotensin 2 (Uts2), mRNA [NM_011910] | Uts2 | 72 | 1563 | 112 |
| 38877 | A_52_P279868 | ref\|Mus musculus SRY-box containing gene 17 (Sox17), mRNA [NM_011441] | Sox17 | 75 | 658 | 88 |
| 38112 | A_51_P209122 | ref\|Mus musculus anterior gradient 2 (Xenopus laevis) (Agr2), mRNA [NM_011783] | Agr2 | 160 | 467 | 79 |

FIG. 53

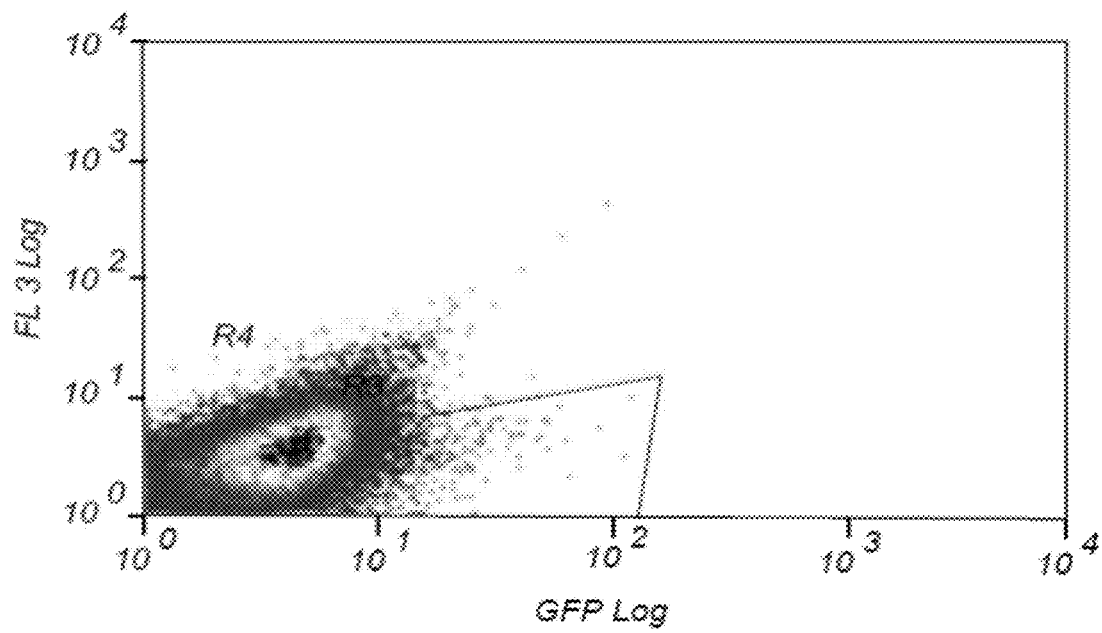
FIG. 58A
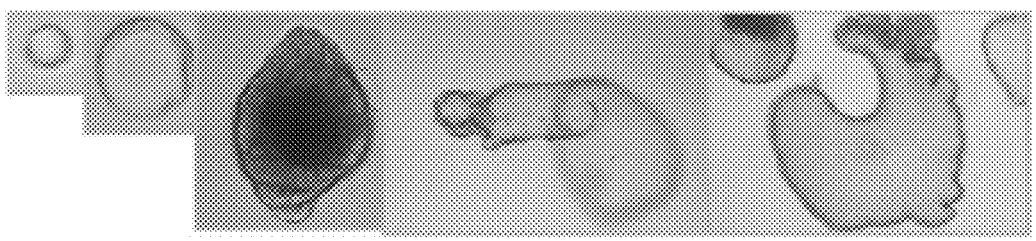
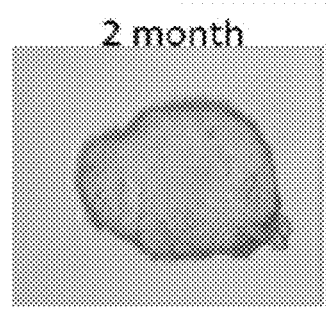
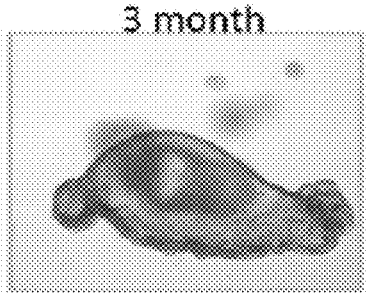
FIG. 58B

| | ER | ENR | ENRW | Liver (adult) |
|---|---|---|---|---|
| G6pc2 | 119.5 | 122 | 125 | 117.5 |
| G6pc3 | 4679.5 | 4340.5 | 4139.5 | 685.5 |
| Glul | 923.5 | 839.5 | 1387 | 18148 |
| Met | 5337 | 5743.5 | 4122 | 1828.5 |
| Hnf1a | 10980 | 9865 | 6176 | 8334 |
| Hnf1b | 2357 | 2632 | 2770.5 | 361 |
| Hnf4a | 1336 | 1283 | 1066 | 4033 |
| Cyp39a1 | 1190.5 | 1167 | 1391 | 1081 |
| Cyp2j6 | 938.5 | 918 | 998.5 | 1164 |
| Cyp3a13 | 344 | 426.5 | 344 | 10787 |
| Cyp4b1 | 1567 | 1567 | 370.5 | 2247 |
| Lap3 | 4704 | 4659.5 | 5069.5 | 30262 |
| Krt7 | 163790 | 161041 | 195354 | 386.5 |
| Krt19 | 88264 | 79407.5 | 54949.5 | 347 |

Mouse liver culture- 24months old
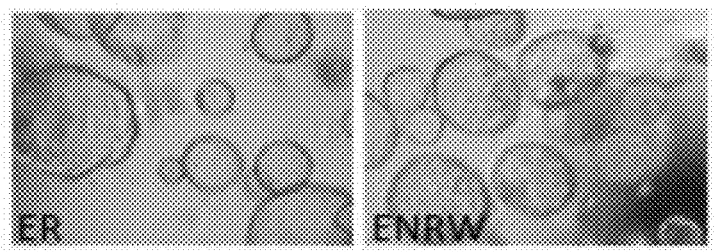
| n chromosomes | counts |
|---|---|
| 40 | 10/15 |
| 80 | 2/15 |
| 42 | 1/15 |
| 36 | 1/15 |
| 85 | 1/15 |
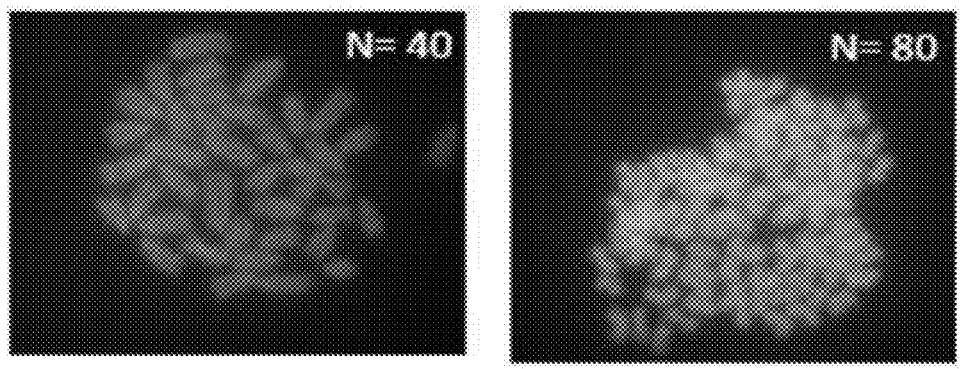
FIG. 60

After first split 5 days after differentiation

| Bile duct specific TF | E | ER | ER | ENRW | Mouse adult liver |
|---|---|---|---|---|---|
| Hnf1b | 3118.5 | 1997 | 2632 | 2705 | |
| Onecut2 | 14421.5 | 14177 | 71655 | 14926.5 | |
| Onecut1 | 6430 | 3473.5 | 5363 | 7721 | |
| Foxa2 | 16120 | 10462.5 | 10970 | 11677 | |
| Hes1 | 1050 | 965 | 1403.5 | 1018 | |
| Sox9 | 48615 | 7880 | 6738.5 | 7547 | 426 |

| HC specific TF | | | | | |
|---|---|---|---|---|---|
| Gata6 | 4081.5 | 5361 | 5124 | 5184 | 740 |
| Cebpa | 1431 | 1188 | 856 | 946 | |
| Hnf1a | 11640 | 10080 | 9865 | 6176 | |
| Hnf4a | 2573 | 1336 | 1283 | 1086 | |

| | | | | | |
|---|---|---|---|---|---|
| Prox1 | 495 | 219.5 | 379.5 | 319 | 2139 |
| Tbx3 | 196.5 | 214 | 208 | 180 | 1840.5 |
| NrSa2 | 132 | 139 | 131.5 | 141 | 1234 |

| Notch signaling | | | | | |
|---|---|---|---|---|---|
| Jag1 | 6832.5 | 3638.5 | 4111 | 3294 | 343 |
| Dll1 | 4035 | 3758 | 2791.5 | 2714.5 | 415.5 |
| Notch3 | 557 | 718 | 476 | 783 | 234 |

| TGFb signaling | | | | | |
|---|---|---|---|---|---|
| Tgfbr1 | 3439 | 2971 | 4281 | 3664 | |
| Tgfbr1 | 245 | 234 | 243 | 210 | |
| Tgfbr2 | 8442 | 9942 | 13874 | 11392 | |

FIG. 62

E=EGF 50ng/ml
A=A8301 50nM
D=DAPT 10nM
F=FGF10 100ng/ml
H=HGF 50ng/ml

Nic=Nicotinamide 10nM
R=Rspondin1 500ng/ml
Wnt= Wnt conditioned media 50%

E=EGF 50ng/ml
A=A8301 50nM
D=DAPT 10nM
F=FGF10 100ng/ml
H=HGF 50ng/ml

Nic=Nicotinamide 10nM
R=Rspondin1 500ng/ml
Wnt= Wnt conditioned media 50%
De= dexamethasone 10mM Staining for liver markers after 8 days of differentiation condition EADF Human-derived liver cultures ERFHNic culture conditions
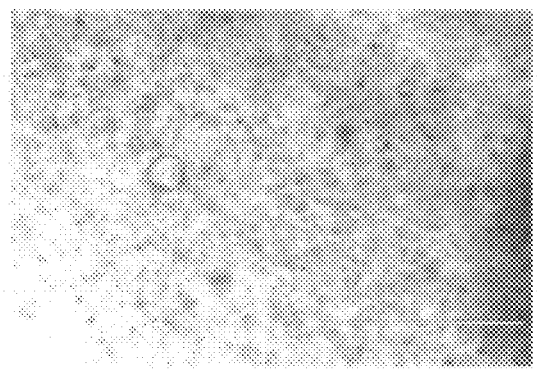
5 days after seeding 4x
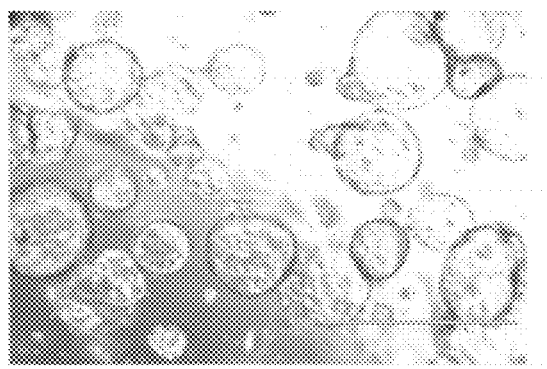
P1 (day 10) 4x
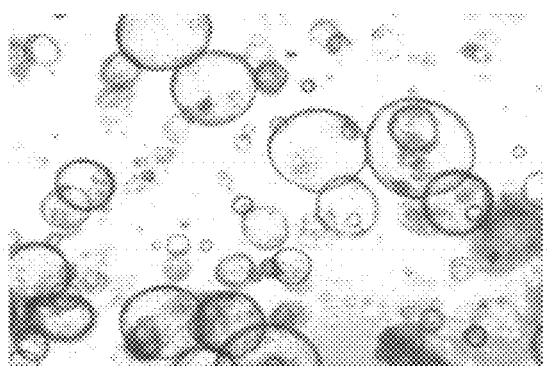
P2 (day 20) 4x
FIG. 64

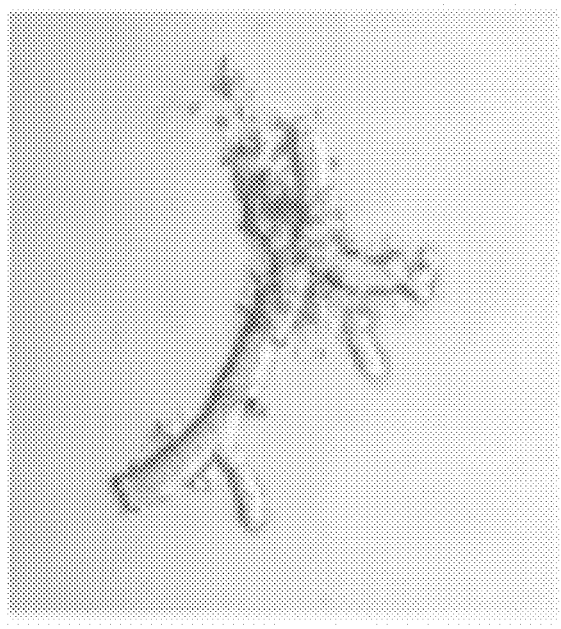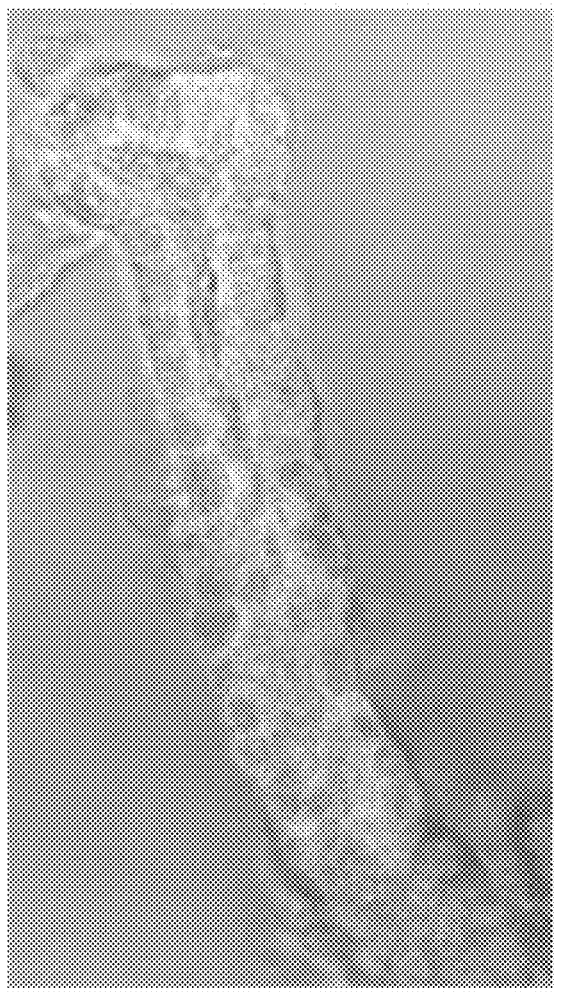
FIG. 67

FIG. 69C

| stem cell signature mouse liver | | liver/HC CG specific signature | | reprogramming genes | |
|---|---|---|---|---|---|
| positive for | negative for | positive for in expansion | negative for | positive | negative |
| lgr5 | lgr6 | Hnf1a | afp | Klf4 | Pou5f1 |
| lgr4 | | Hnf1b | Ins1 | Myc | Sox2 |
| epcam | | Hnf4a | Ins2 | | |
| Cd44 | | Hhex | Gcg | | |
| Tnfrsf19 | | Onecut1 | Ptf1a | | |
| Sox9 | | Onecut2 | Cela1 | | |
| Sp5 | | Prox1 | Cela2a | | |
| Cd24a | | Cdh1 | Cela3b | | |
| Prom1 | | Foxa2 | Neurod1 | | |
| Cdca7 | | Gata6 | Neurod2 | | |
| Elf3 | | Foxm1 | Neurog1 | | |
| | | Cebpa | Neurog2 | | |
| | | Cebpb | Neurog3 | | |
| | | Cebpd | Amy2a4 | | |
| | | Cebpg | Igf1r | | |
| | | Glul | Igf2 | | |
| | | Krt7 | Cd34 | | |
| | | Krt19 | | | |
| | | Met | | | |

SEQUENCE LISTING

```
<160> NUMBER OF SEQ ID NOS: 100

<210> SEQ ID NO 1
<211> LENGTH: 17
<212> TYPE: PRT
<213> ORGANISM: H. sapiens

<400> SEQUENCE: 1

Cys Asp Asp Tyr Tyr Tyr Gly Phe Gly Cys Asn Lys Phe Cys Arg Pro
1               5                   10                  15
```

Arg

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
tattgtatct accgtgaatc ttgg                                      24

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
cagttgtccg tggctctc                                             18

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
tccaacctca gcgtcttc                                             18

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
tgggaatgtg tgtcaaag                                             18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aagtttgttg ttggatatgc                                           20

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
catcttaggc tttgtatttg g                                         21

<210> SEQ ID NO 8
<211> LENGTH: 20
<212> TYPE: DNA

```
<213> ORGANISM: Artificial Sequence
<220> FEATURE:
<223> OTHER INFORMATION: Primer

<400> SEQUENCE: 8
tcctcggagc ttttctacga                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tgtgtctctg gggacacttg                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
aacaacctgc ctatgcaacc                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
acttggacgg gaactgacac                                              20

<210> SEQ ID NO 12
<211> LENGTH: 18
<212> TYPE: DNA
<213> ORGANISM: Artificial Sequence
<220> FEATURE:
<223> OTHER INFORMATION: Primer

<400> SEQUENCE: 12
aagatcattg gcggaaag                                                18

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gagtgctcag gatgttaag                                               19

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gctgacagca gagaagcggc t                                            21
```

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gacaggctct ctagctcctg g                                        21

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
aagttggaag aggaagtcag                                          20

<210> SEQ ID NO 17
<211> LENGTH: 18
<212> TYPE: DNA
<213> ORGANISM: Artificial Sequence
<220> FEATURE:
<223> OTHER INFORMATION: Primer

<400> SEQUENCE: 17
agaccttctg ctcagtcg                                            18

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tttgtcaagc agcacctttg                                          20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tctacaatgc cacgcttctg                                          20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gaggcaagga agatgctgtc                                          20

<210> SEQ ID NO 21
<211> LENGTH: 20
<212> TYPE: DNA
<213> ORGANISM: Artificial Sequence
<220> FEATURE:

<223> OTHER INFORMATION: Primer

<400> SEQUENCE: 21
gggcatcatt ctctgtctgg                                                    20

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ttactttgtg gctggattgc tt                                                 22

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
agtggcgttt gtcttcattc a                                                  21

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
ggaaatgctt tgacacacat tc                                                 22

<210> SEQ ID NO 25
<211> LENGTH: 23
<212> TYPE: DNA
<213> ORGANISM: Artificial Sequence
<220> FEATURE:
<223> OTHER INFORMATION: Primer

<400> SEQUENCE: 25
ggaagtcatc aaggttatta taa                                                23

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tgaatcctcg gccttctatg                                                    20

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
cagttaaagt tggtggcact tc                                                 22

```
<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ccaacctgtg ggtgtcttct                                           20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
ttagggacct ggatgctttg                                           20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgcatgctca atggtatggt                                           20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tgtgggctct ggagaagagt                                           20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ccatgaagtg ggagtgtgtg                                           20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ttgggatagc atccttccag                                           20

<210> SEQ ID NO 34
<211> LENGTH: 22
<212> TYPE: DNA
<213> ORGANISM: Artificial Sequence
<220> FEATURE:
<223> OTHER INFORMATION: Primer
```

<400> SEQUENCE: 34
gcccagcaga gaaaggaatc ca                                              22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
gcgcctcttt gacctcttcc                                                 20

<210> SEQ ID NO 36
<211> LENGTH: 20
<212> TYPE: DNA
<213> ORGANISM: Artificial Sequence
<220> FEATURE:
<223> OTHER INFORMATION: Primer

<400> SEQUENCE: 36
gccaactatt ccccagctct                                                 20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ggctctggaa gagtgttgct                                                 20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
gaggcaagga agatgctgtc                                                 20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
gggcatcatt ctctgtctgg                                                 20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
gaacggggcc atggtcagca                                                 20

<210> SEQ ID NO 41
<211> LENGTH: 20

```
<212> TYPE: DNA
<213> ORGANISM: Artificial Sequence
<220> FEATURE:
<223> OTHER INFORMATION: Primer

<400> SEQUENCE: 41
cataattggt cttgcatgcc                                           20

<210> SEQ ID NO 42
<211> LENGTH: 19
<212> TYPE: DNA
<213> ORGANISM: Artificial Sequence
<220> FEATURE:
<223> OTHER INFORMATION: Primer

<400> SEQUENCE: 42
cttgctgcag acgctcaac                                            19

<210> SEQ ID NO 43
<211> LENGTH: 20
<212> TYPE: DNA
<213> ORGANISM: Artificial Sequence
<220> FEATURE:
<223> OTHER INFORMATION: Primer

<400> SEQUENCE: 43
tctgtgtaca ccacccggta                                           20

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
aagcttgctg gtgaaaagga                                           20

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
ttgcgctcat cttaggcttt                                           20

<210> SEQ ID NO 46
<211> LENGTH: 23
<212> TYPE: DNA
<213> ORGANISM: Artificial Sequence
<220> FEATURE:
<223> OTHER INFORMATION: Primer

<400> SEQUENCE: 46
tggtcaaacg cctctccttg ctg                                       23

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
```
actgggccaa aatcccgccg        20

<210> SEQ ID NO 48
<211> LENGTH: 19
<212> TYPE: DNA
<213> ORGANISM: Artificial Sequence
<220> FEATURE:
<223> OTHER INFORMATION: primer

<400> SEQUENCE: 48
gaattaccaa gactccagg        19

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
tgagacaata cttccggagg        20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
gtcctacaga ttgacaatgc        20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
cacgctctgg atctgtgaca        20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
gcgcagatga cagggcggaa        20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
gtgccgtagc atgcgggagg        20

<210> SEQ ID NO 54
<211> LENGTH: 20
<212> TYPE: DNA
<213> ORGANISM: Artificial Sequence

```
<220> FEATURE:
<223> OTHER INFORMATION: primer

<400> SEQUENCE: 54
agcgatcacg caacgtggca                                               20

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
ggcttcgctg ggacacagat cttt                                          24

<210> SEQ ID NO 56
<211> LENGTH: 18
<212> TYPE: DNA
<213> ORGANISM: Artificial Sequence
<220> FEATURE:
<223> OTHER INFORMATION: primer

<400> SEQUENCE: 56
ttcaacagat gcattacc                                                 18

<210> SEQ ID NO 57
<211> LENGTH: 18
<212> TYPE: DNA
<213> ORGANISM: Artificial Sequence
<220> FEATURE:
<223> OTHER INFORMATION: primer

<400> SEQUENCE: 57
tctttgcccg cgatgatg                                                 18

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
acgactggag cgcacgagac                                               20

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
agggctggct gtggcagaga                                               20

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
tttggcagtg gctgaaaggc a                                             21
```

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
gggcccagga tccgctgact                                        20

<210> SEQ ID NO 62
<211> LENGTH: 21
<212> TYPE: DNA
<213> ORGANISM: Artificial Sequence
<220> FEATURE:
<223> OTHER INFORMATION: primer

<400> SEQUENCE: 62
actccccgta gaaggcagcg a                                      21

<210> SEQ ID NO 63
<211> LENGTH: 22
<212> TYPE: DNA
<213> ORGANISM: Artificial Sequence
<220> FEATURE:
<223> OTHER INFORMATION: primer

<400> SEQUENCE: 63
tctttccagc catgcctcca ct                                     22

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
ggaaatgctt tgacacacat tc                                     22

<210> SEQ ID NO 65
<211> LENGTH: 23
<212> TYPE: DNA
<213> ORGANISM: Artificial Sequence
<220> FEATURE:
<223> OTHER INFORMATION: primer

<400> SEQUENCE: 65
ggaagtcatc aaggttatta taa                                    23

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
atggtcaaag tcctggatgc                                        20

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
aattcatgga acggggaaat                                            20

<210> SEQ ID NO 68
<211> LENGTH: 18
<212> TYPE: DNA
<213> ORGANISM: Artificial Sequence
<220> FEATURE:
<223> OTHER INFORMATION: primer

<400> SEQUENCE: 68
aagatcattg gcggaaag                                              18

<210> SEQ ID NO 69
<211> LENGTH: 19
<212> TYPE: DNA
<213> ORGANISM: Artificial Sequence
<220> FEATURE:
<223> OTHER INFORMATION: primer

<400> SEQUENCE: 69
gagtgctcag gatgttaag                                             19

<210> SEQ ID NO 70
<211> LENGTH: 20
<212> TYPE: DNA
<213> ORGANISM: Artificial Sequence
<220> FEATURE:
<223> OTHER INFORMATION: primer

<400> SEQUENCE: 70
aagcttgctg gtgaaaagga                                            20

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
ttgcgctcat cttaggcttt                                            20

<210> SEQ ID NO 72
<211> LENGTH: 22
<212> TYPE: DNA
<213> ORGANISM: Artificial Sequence
<220> FEATURE:
<223> OTHER INFORMATION: primer

<400> SEQUENCE: 72
gcagcattac ctgctctacg tt                                         22

<210> SEQ ID NO 73
<211> LENGTH: 25
<212> TYPE: DNA
<213> ORGANISM: Artificial Sequence
<220> FEATURE:
<223> OTHER INFORMATION: primer

<400> SEQUENCE: 73
gcttgataag ctgatgctgt aattt                                      25

<210> SEQ ID NO 74

```
<211> LENGTH: 8
<212> TYPE: DNA
<213> ORGANISM: Artificial Sequence
<220> FEATURE:
<223> OTHER INFORMATION: probe

<400> SEQUENCE: 74 gcagccag                                                                  8

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
catggaccgc ttcccata                                                      18

<210> SEQ ID NO 76
<211> LENGTH: 19
<212> TYPE: DNA
<213> ORGANISM: Artificial Sequence
<220> FEATURE:
<223> OTHER INFORMATION: primer

<400> SEQUENCE: 76
ggcacctgtc tgtccacat                                                     19

<210> SEQ ID NO 77
<211> LENGTH: 8
<212> TYPE: DNA
<213> ORGANISM: Artificial Sequence
<220> FEATURE:
<223> OTHER INFORMATION: probe

<400> SEQUENCE: 77 tggctctg                                                                  8

<210> SEQ ID NO 78
<211> LENGTH: 18
<212> TYPE: DNA
<213> ORGANISM: Artificial Sequence
<220> FEATURE:
<223> OTHER INFORMATION: primer

<400> SEQUENCE: 78
cagccaacgc tgcttctc                                                      18

<210> SEQ ID NO 79
<211> LENGTH: 18
<212> TYPE: DNA
<213> ORGANISM: Artificial Sequence
<220> FEATURE:
<223> OTHER INFORMATION: primer

<400> SEQUENCE: 79
tggcatggaa ttgacagc                                                      18

<210> SEQ ID NO 80
<211> LENGTH: 8
<212> TYPE: DNA
<213> ORGANISM: Artificial Sequence
<220> FEATURE:
<223> OTHER INFORMATION: probe

<400> SEQUENCE: 80
``` cctcctgg                                                            8

<210> SEQ ID NO 81
<211> LENGTH: 21
<212> TYPE: DNA
<213> ORGANISM: Artificial Sequence
<220> FEATURE:
<223> OTHER INFORMATION: primer

<400> SEQUENCE: 81
ccgctactgg tgtaatgatg g                                             21

<210> SEQ ID NO 82
<211> LENGTH: 22
<212> TYPE: DNA
<213> ORGANISM: Artificial Sequence
<220> FEATURE:
<223> OTHER INFORMATION: primer

<400> SEQUENCE: 82
catcagcgat gttatcttgc ag                                            22

<210> SEQ ID NO 83
<211> LENGTH: 8
<212> TYPE: DNA
<213> ORGANISM: Artificial Sequence
<220> FEATURE:
<223> OTHER INFORMATION: probe

<400> SEQUENCE: 83 aggagcag                                                            8

<210> SEQ ID NO 84
<211> LENGTH: 19
<212> TYPE: DNA
<213> ORGANISM: Artificial Sequence
<220> FEATURE:
<223> OTHER INFORMATION: primer

<400> SEQUENCE: 84
gccagctcat caaggacag                                                19

<210> SEQ ID NO 85
<211> LENGTH: 21
<212> TYPE: DNA
<213> ORGANISM: Artificial Sequence
<220> FEATURE:
<223> OTHER INFORMATION: primer

<400> SEQUENCE: 85
gcaggcatcg tagtagtgct g                                             21

<210> SEQ ID NO 86
<211> LENGTH: 8
<212> TYPE: DNA
<213> ORGANISM: Artificial Sequence
<220> FEATURE:
<223> OTHER INFORMATION: probe

<400> SEQUENCE: 86 ttgcccag                                                            8

<210> SEQ ID NO 87
<211> LENGTH: 24
<212> TYPE: DNA

```
<213> ORGANISM: Artificial Sequence
<220> FEATURE:
<223> OTHER INFORMATION: primer

<400> SEQUENCE: 87
tgaccttgat ttattttgca tacc                                          24

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
cgagcaagac gttcagtcct                                               20

<210> SEQ ID NO 89
<211> LENGTH: 22
<212> TYPE: DNA
<213> ORGANISM: Artificial Sequence
<220> FEATURE:
<223> OTHER INFORMATION: primer

<400> SEQUENCE: 89
gcttgccaca acttcctaag at                                            22

<210> SEQ ID NO 90
<211> LENGTH: 22
<212> TYPE: DNA
<213> ORGANISM: Artificial Sequence
<220> FEATURE:
<223> OTHER INFORMATION: primer

<400> SEQUENCE: 90
tcagtttagt catggtggac ga                                            22

<210> SEQ ID NO 91
<211> LENGTH: 8
<212> TYPE: DNA
<213> ORGANISM: Artificial Sequence
<220> FEATURE:
<223> OTHER INFORMATION: probe

<400> SEQUENCE: 91 ggtggtgg                                                             8

<210> SEQ ID NO 92
<211> LENGTH: 18
<212> TYPE: DNA
<213> ORGANISM: Artificial Sequence
<220> FEATURE:
<223> OTHER INFORMATION: primer

<400> SEQUENCE: 92
tgtggaaccg ggaagatg                                                 18

<210> SEQ ID NO 93
<211> LENGTH: 21
<212> TYPE: DNA
<213> ORGANISM: Artificial Sequence
<220> FEATURE:
<223> OTHER INFORMATION: primer

<400> SEQUENCE: 93
gaccacaggt atggttctgg a                                             21
```

<210> SEQ ID NO 94
<211> LENGTH: 8
<212> TYPE: DNA
<213> ORGANISM: Artificial Sequence
<220> FEATURE:
<223> OTHER INFORMATION: probe

<400> SEQUENCE: 94 tggtggag                                                                 8

<210> SEQ ID NO 95
<211> LENGTH: 21
<212> TYPE: DNA
<213> ORGANISM: Artificial Sequence
<220> FEATURE:
<223> OTHER INFORMATION: primer

<400> SEQUENCE: 95
cgatccagaa agatgatggt c                                                 21

<210> SEQ ID NO 96
<211> LENGTH: 19
<212> TYPE: DNA
<213> ORGANISM: Artificial Sequence
<220> FEATURE:
<223> OTHER INFORMATION: primer

<400> SEQUENCE: 96
cggaagcctc tgtctttcc                                                    19

<210> SEQ ID NO 97
<211> LENGTH: 8
<212> TYPE: DNA
<213> ORGANISM: Artificial Sequence
<220> FEATURE:
<223> OTHER INFORMATION: probe

<400> SEQUENCE: 97 ggatggag                                                                 8

<210> SEQ ID NO 98
<211> LENGTH: 19
<212> TYPE: DNA
<213> ORGANISM: Artificial Sequence
<220> FEATURE:
<223> OTHER INFORMATION: primer

<400> SEQUENCE: 98
tcctcctcag accgctttt                                                    19

<210> SEQ ID NO 99
<211> LENGTH: 21
<212> TYPE: DNA
<213> ORGANISM: Artificial Sequence
<220> FEATURE:
<223> OTHER INFORMATION: primer

<400> SEQUENCE: 99
cctggttcat catcgctaat c                                                 21

<210> SEQ ID NO 100
<211> LENGTH: 8
<212> TYPE: DNA
<213> ORGANISM: Artificial Sequence
<220> FEATURE:

```
<223> OTHER INFORMATION: probe

<400> SEQUENCE: 100 actcccag                                                                          8
```

CULTURE MEDIUM FOR EPITHELIAL STEM CELLS AND ORGANOIDS COMPRISING THE STEM CELLS

CROSS-REFERENCE TO RELATED APPLICATIONS

This application is a continuation-in-part of co-pending application U.S. Ser. No. 13/147,163, filed Sep. 14, 2011, which is the national stage under 35 U.S.C. §371 of International Application Number PCT/NL2010/000017, filed Feb. 3, 2010, designating the United States of America, and published, in English, on Aug. 12, 2010 as WO 2010/090513, which claims priority under 35 U.S.C. §119(e) to U.S. provisional patent application Ser. No. 61/149,622, filed Feb. 3, 2009, and further claims priority under Article 8 of the PCT to European Patent Office applications EP 09151970.2, filed Feb. 3, 2009, and EP 09171831.2, filed Sep. 30, 2009. This application also claims the benefit under 35 U.S.C. §119(e) of U.S. Ser. No. 61/368,736, filed on Jul. 29, 2010, U.S. Ser. No. 61/520,569, filed on Jun. 10, 2011, and U.S. Ser. No. 61/571,663, filed Jun. 30, 2011. This application also claims priority under 35 U.S.C. §119 to European Patent Office application EP 10171265.1, filed Jul. 29, 2010, and British Patent Office application GB 1111244.8, filed on Jun. 30, 2011. The contents of each of these patent applications are incorporated herein by this reference.

STATEMENT ACCORDING TO 37 C.F.R. §1.821(c) or (e)—SEQUENCE LISTING SUBMITTED AS ASCII TEXT FILE

Pursuant to 37 C.F.R. §1.821(c) or (e), a file containing an ASCII text version of the Sequence Listing has been submitted herewith, the contents of which are hereby incorporated by reference.

TECHNICAL FIELD

The invention relates to a novel culture medium for culturing epithelial stem cells, especially intestinal and colonic epithelial stem cells, and for culturing organoids comprising the stem cells. The invention further relates to the progeny of cells and organoids that were cultured using a culture medium of the invention, and to the use of the progeny in toxicity assays or in regenerative medicine.

BACKGROUND

The self-renewing epithelium of the small intestine is ordered into crypts and villi (Gregorieff and Clevers, 2005, *Genes Dev.* 19, 877-90). Cells are newly generated in the crypts and are lost by apoptosis at the tips of the villi, with a resulting epithelial turn-over time of 5 days in the mouse. Self-renewing stem cells have long been known to reside near the crypt bottom and to produce the rapidly proliferating transit amplifying (TA) cells capable of differentiating towards all lineages. The estimated number of stem cells is between 4 and 6 per crypt (Bjerknes and Cheng, 1999, *Gastroenterology* 116, 7-14). Three differentiated cell types, enterocytes, goblet cells and enteroendocrine cells, form from TA cells and continue their migration in coherent bands along the crypt-villus axis. Each villus receives cells from multiple different crypts. The fourth major differentiated cell-type, the Paneth cell, resides at the crypt bottom.

A gene, Lgr5, was recently identified which is specifically expressed in a fifth cell type, cycling Crypt Base Columnar (CBC) cells, which are small cells that are interspersed between the Paneth cells (indicated by black arrows in FIG. 8b) (Barker et al., 2007, *Nature* 449: 1003-1007). Using a mouse in which a GFP/tamoxifen-inducible Cre recombinase cassette was integrated into the Lgr5 locus, it was shown by lineage tracing that the Lgr5$^+$ CBC cells constitute multipotent stem cells which generate all cell types of the epithelium even when assessed 14 months after Cre induction.

It was recently discovered that also Lgr6, besides Lgr5, but not Lgr4, is a unique marker for adult stem cells. While Lgr 5 is expressed in stem cells of brain, kidney, liver, retina, stomach, intestine, pancreas, breast, hair follicle, ovary, adrenal medulla, and skin, Lgr6 is expressed in stem cells of brain, lung, breast, hair follicle, and skin.

It is generally believed that an intimate contact between epithelial stem cells and subepithelial fibroblasts is required to anchor and support epithelial stem cells and to provide the correct orientation necessary to generate a properly polarized, three dimensional structure.

Although a variety of culture systems have been described for culturing primary epithelial stem cells, including intestinal epithelium stem cells (Bjerknes and Cheng, 2006 *Methods Enzymol.* 419: 337-83), to date no long-term culture system has been established which maintains the pluripotency of epithelial stem cells. Furthermore, no culture system is known that preserves the basic crypt-villus physiology of crypts that have been isolated from colon or intestine, or that preserves the basic physiology of isolated pancreatic fragments or gastric tissue fragments.

SUMMARY OF THE INVENTION

The invention, therefore, provides a method for culturing epithelial stem cells, isolated epithelial tissue fragments comprising the epithelial stem cells, or adenoma cells, the method comprising providing an extracellular matrix, incubating an epithelial stem cell, an isolated tissue fragment comprising the epithelial stem cells, or an adenoma cell with the extracellular matrix, culturing the stem cell, isolated tissue fragment, or adenoma cell in the presence of a cell culture medium, comprising a basal medium for animal or human cells to which is added a Bone Morphogenetic Protein (BMP) inhibitor, between 5 and 500 ngram/ml or at least 5 and not higher than 500 ngram/ml of a mitogenic growth factor, whereby a Wnt agonist is added if epithelial stem cells and isolated tissue fragments are cultured.

It was surprisingly found by the present inventors that a method of the invention allows culturing of epithelial stem cells, isolated fragments from the small intestine, colon, stomach and pancreas comprising the stem cells and adenoma cells, while preserving the presence of stem cells that retain an undifferentiated phenotype and self-maintenance capabilities. For example, isolated crypts that are cultured according to a method of the invention develop into crypt-villus organoids, comprising a central lumen lined by a villus-like epithelium. The growth of isolated crypts was fuelled by stem cells that are present in the crypts. The resulting organoids undergo multiple crypt fission events. Even more surprising was the observation that a method of the invention allows the outgrowth of single, isolated epithelial stem cells into crypt-villus organoids in the absence of a stem cell niche. Isolated gastric fragments from the pyloric region of the stomach behaved as intestinal crypt organoids. The opened upper part of the unit was sealed and the lumen was filled with apoptotic cells. The newly formed gastric organoids underwent continuous budding events (reminiscent of gland fission) while maintaining their polarity with a central lumen. Furthermore, culturing pancreatic fragments resulted in the appearance of pancreatic islet-like structures that express insulin and other pancreatic islet specific markers, resembling the pancreatic islets of Langerhans.

The epithelium lining the pyloric region of the small and large bowel encompasses luminal protrusions, villi, and invaginations, crypts. Each cell along the crypt-villus axis is polarized, whereby cells on the top of the intestinal villi, or in the upper positions of colonic crypts, are the most differentiated and are continuously lost into the lumen. Continuous proliferation of stem cells residing in the basis of the crypts, and massive proliferation of progenitor cells residing in the middle of the crypts, ensures proper replacement of the shed cells.

Stem cells are found in many organs of adult humans and mice. Although there may be great variation in the exact characteristics of adult stem cells in individual tissues, adult stem cells share the following characteristics: They retain an undifferentiated phenotype; their offspring can differentiate towards all lineages present in the pertinent tissue; they retain self-maintenance capabilities throughout life; and they are able to regenerate the pertinent tissue after injury. Stem cells reside in a specialized location, the stem cell niche, which supplies the appropriate cell-cell contacts and signals for maintenance of the stem cell population.

Epithelial stem cells are able to form the distinct cell types of which the epithelium is composed. Some epithelia, such as skin or intestine, show rapid cell turnover, indicating that the residing stem cells must be continuously proliferating. Other epithelia, such as the liver or pancreas, show a very slow turnover under normal conditions.

Crypts can be isolated from the duodenum, small and large intestine, including jejunum, ileum, and colon, and the pyloric region of the stomach by protocols that are known to the skilled person. For example, crypts can be isolated by incubation of isolated tissue with chelating agents that release cells from their calcium- and magnesium-dependent interactions with the basement membrane and stromal cell types. After washing the tissue, the epithelial cell layer is scraped from the submucosa with a glass slide and minced. This is followed by incubation in trypsin or, more preferred, EDTA and/or EGTA and separation of undigested tissue fragments and single cells from crypts using, for example, filtration and/or centrifugations steps. Other proteolytic enzymes, such as collagenase and/or dispase I, can be used instead of trypsin. Similar methods are used to isolate fragments of the pancreas and stomach.

Methods to isolate stem cells from epithelial tissue are known in the art. A preferred method is based on the fact that stem cells express Lgr 5 and/or Lgr 6 on their surface, which belong to the large G protein-coupled receptor (GPCR) superfamily. The Lgr subfamily is unique in carrying a large leucine-rich ectodomain important for ligand binding. Ligands for Lgr 5 and Lgr 6 are not yet described in the literature. A preferred method therefore comprises preparing a cell suspension from the epithelial tissue, contacting the cell suspension with an Lgr5 and/or 6 binding compound, isolating the Lgr5 and/or 6 binding compound, and isolating the stem cells from the binding compound. It is preferred that a single cell suspension comprising the epithelial stem cells is mechanically generated from the isolated crypts as it was found that at this stage epithelial stem cells treated with trypsin yielded rather low survival rates.

Preferred Lgr5 and/or 6 binding compounds comprises antibodies, such as monoclonal antibodies that specifically recognize and bind to the extracellular domain of either Lgr5 or Lgr6, such as monoclonal antibodies including mouse and rat monoclonal antibodies. Using such an antibody, Lgr5 and/or Lgr6-expressing stem cells can be isolated, for example with the aid of magnetic beads or through fluorescence-activated cell sorting, as is clear to a skilled person.

In a preferred method of the invention, the epithelial stem cells are isolated from the crypts, gastric fragments or pancreatic fragments. For example, the epithelial stem cells are isolated from crypts that are isolated from the bowel. Preferred epithelial stem cells are isolated from the small intestine, including duodenum, jejunum and ileum, pancreas or stomach.

Isolated stem cells are preferably cultured in a microenvironment that mimics at least, in part, a cellular niche in which the stem cells naturally reside. The cellular niche is mimicked by culturing the stem cells in the presence of biomaterials, such as matrices, scaffolds, and culture substrates that represent key regulatory signals controlling stem cell fate. The biomaterials comprise natural, semi-synthetic and synthetic biomaterials, and/or mixtures thereof. A scaffold provides a two-dimensional or three dimensional network. Suitable synthetic materials for the scaffold comprise polymers selected from porous solids, nanofibers, and hydrogels such as, for example, peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof (see, for example, Saha et al., 2007, *Curr. Opin. Chem. Biol.* 11(4): 381-387; Saha et al., 2008, *Biophysical Journal* 95: 4426-4438; Little et al., 2008, *Chem. Rev.* 108, 1787-1796). As is known to a skilled person, the mechanical properties such as, for example, the elasticity of the scaffold influences proliferation, differentiation and migration of stem cells. A preferred scaffold comprises biodegradable (co)polymers that are replaced by natural occurring components after transplantation in a subject, for example to promote tissue regeneration and/or wound healing. It is furthermore preferred that the scaffold does not substantially induce an immunogenic response after transplantation is a subject. the scaffold is supplemented with natural, semi-synthetic or synthetic ligands, which provide the signals that are required for proliferation and/or differentiation, and/or migration of stem cells. In a preferred embodiment, the ligands comprise defined amino acid fragments. Examples of the synthetic polymers comprise Pluronic® F127 block copolymer surfactant (BASF), and Ethisorb® (Johnson and Johnson).

A cellular niche is in part determined by the stem cells and surrounding cells, and the extracellular matrix (ECM) that is produced by the cells in the niche. In a preferred method of the invention, isolated crypts or epithelial stem cells are attached to an ECM. ECM is composed of a variety of polysaccharides, water, elastin, and glycoproteins, wherein the glycoproteins comprise collagen, entactin (nidogen), fibronectin, and laminin. ECM is secreted by connective tissue cells. Different types of ECM are known, comprising different compositions including different types of glycoproteins and/or different combination of glycoproteins. The ECM can be provided by culturing ECM-producing cells, such as for example fibroblast cells, in a receptacle, prior to the removal of these cells and the addition of isolated crypts or epithelial stem cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C. Alternatively, the ECM is commercially provided. Examples of commercially available extracellular matrices are extracellular matrix proteins (Invitrogen) and Matrigel™ (BD Biosciences). The use of an ECM for culturing stem cells enhanced long-term survival of the stem cells and the continued presence of undifferentiated stem cells. In the absence of an ECM, stem cell cultures could not be cultured for longer periods and no continued presence of undifferentiated stem cells was observed. In addition, the presence of an ECM allowed culturing of three-dimensional tissue organoids, which could not be cultured in the absence of an ECM.

A preferred ECM for use in a method of the invention comprises at least two distinct glycoproteins, such as two different types of collagen or a collagen and laminin. The ECM can be a synthetic hydrogel extracellular matrix or a naturally occurring ECM. A most preferred ECM is provided by Matrigel™ (BD Biosciences), which comprises laminin, entactin, and collagen IV.

A cell culture medium that is used in a method of the invention comprises any cell culture medium. A preferred cell culture medium is a defined synthetic medium that is buffered at a pH of 7.4 (preferably between 7.2 and 7.6 or at least 7.2 and not higher than 7.6) with a carbonate-based buffer, while the cells are cultured in an atmosphere comprising between 5% and 10% $CO_2$, or at least 5% and not more than 10% $CO_2$, preferably 5% $CO_2$. A preferred cell culture medium is selected from DMEM/F12 and RPMI 1640 supplemented with glutamine, insulin, Penicillin/streptomycin and transferrin. In a further preferred embodiment, Advanced DMEM/F12 or Advanced RPMI is used, which is optimized for serum free culture and already includes insulin. In this case, the Advanced DMEM/F12 or Advanced RPMI medium is preferably supplemented with glutamine and Penicillin/streptomycin. It is furthermore preferred that the cell culture medium is supplemented with a purified, natural, semi-synthetic and/or synthetic growth factor and does not comprise an undefined component such as fetal bovine serum or fetal calf serum. Supplements such as, for example, B27 (Invitrogen), N-Acetylcysteine (Sigma) and N2 (Invitrogen) stimulate proliferation of some cells and can further be added to the medium, if required.

A component that is added to the basal culture medium is a BMP inhibitor. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity.

The BMP inhibitor is defined as an agent that binds to a BMP molecule to form a complex wherein the BMP activity is neutralized, for example by preventing or inhibiting the binding of the BMP molecule to a BMP receptor. Alternatively, the inhibitor is an agent that acts as an antagonist or reverse agonist. This type of inhibitor binds with a BMP receptor and prevents binding of a BMP to the receptor. An example of a latter agent is an antibody that binds a BMP receptor and prevents binding of BMP to the antibody-bound receptor.

The BMP inhibitor inhibits a BMP-dependent activity in a cell to at most 90%, more preferred at most 80%, more preferred at most 70%, more preferred at most 50%, more preferred at most 30%, more preferred at most 10%, more preferred 0%, relative to a level of a BMP activity in the absence of the inhibitor. As is known to a skilled person, a BMP activity can be determined by measuring the transcriptional activity of BMP, for example as exemplified in Zilberberg et al., 2007, *BMC Cell Biol.* 8:41.

Several classes of natural BMP-binding proteins are known, including Noggin (Peprotech), Chordin and chordin-like proteins (R&D sytems) comprising chordin domains, Follistatin and follistatin-related proteins (R&D sytems) comprising a follistatin domain, DAN and DAN-like proteins (R&D sytems) comprising a DAN cysteine-knot domain, sclerostin/SOST (R&D sytems), decorin (R&D sytems), and alpha-2 macroglobulin (R&D systems).

A preferred BMP inhibitor for use in a method of the invention is selected from Noggin, DAN, and DAN-like proteins including Cerberus and Gremlin (R&D sytems). These diffusible proteins are able to bind a BMP ligand with varying degrees of affinity and inhibit their access to signaling receptors. The addition of any of these BMP inhibitors to the basal culture medium prevents the loss of stem cells, which otherwise occurs after about 2-3 weeks of culture.

A most preferred BMP inhibitor is Noggin. Noggin is preferably added to the basal culture medium at a concentration of at least 10 ng/ml, more preferred at least 20 ng/ml, more preferred at least 50 ng/ml, more preferred at least 100 ng/ml. A most preferred concentration is approximately 100 ng/ml or 100 ng/ml. During culturing of stem cells, the BMP inhibitor is preferably added to the culture medium every second day, while the culture medium is refreshed preferably every fourth day.

A further component that is added to the basal culture medium is a Wnt agonist. The Wnt signaling pathway is defined by a series of events that occur when a Wnt protein binds to a cell-surface receptor of a Frizzled receptor family member. This results in the activation of disheveled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist is defined as an agent that activates TCF/LEF-mediated transcription in a cell. Wnt agonists are therefore selected from true Wnt agonists that bind and activate a Frizzled receptor family member including any and all of the Wnt family proteins, an inhibitor of intracellular β-catenin degradation, and activators of TCF/LEF. The Wnt agonist stimulates a Wnt activity in a cell by at least 10%, more preferred at least 20%, more preferred at least 30%, more preferred at least 50%, more preferred at least 70%, more preferred at least 90%, more preferred at least 100%, relative to a level of the Wnt activity in the absence of the molecule. As is known to a skilled person, a Wnt activity can be determined by measuring the transcriptional activity of Wnt, for example by pTOPFLASH and pFOP-FLASH Tcf luciferase reporter constructs (Korinek et al., 1997, *Science* 275:1784-1787).

A Wnt agonist comprises a secreted glycoprotein including Wnt-1/Int-1; Wnt-2/Irp (Int-1-related Protein); Wnt-2b/13; Wnt-3/Int-4; Wnt-3a (R&D sytems); Wnt-4; Wnt-5a; Wnt-5b; Wnt-6 (Kirikoshi H. et al. 2001, *Biochem. Biophys. Res. Com.* 283: 798-805); Wnt-7a (R&D sytems); Wnt-7b; Wnt-8a/8d; Wnt-8b; Wnt-9a/14; Wnt-9b/14b/15; Wnt-10a; Wnt-10b/12; Wnt-11; and Wnt-16. An overview of human Wnt proteins is provided in "THE WNT FAMILY OF SECRETED PROTEINS," R&D Systems Catalog, 2004. Further Wnt agonists include the R-spondin family of secreted proteins, which is implicated in the activation and regulation of Wnt signaling pathway and which is comprised of 4 members (R-spondin 1 (NU206, Nuvelo, San Carlos, Calif.), R-spondin 2 ((R&D sytems), R-spondin 3, and R-spondin-4); and Norrin (also called Norrie Disease Protein or NDP) (R&D sytems), which is a secreted regulatory protein that functions like a Wnt protein in that it binds with high affinity to the Frizzled-4 receptor and induces activation of the Wnt signaling pathway (Kestutis Planutis et al. (2007) *BMC Cell Biol.* 8: 12). A small-molecule agonist of the Wnt signaling pathway, an aminopyrimidine derivative, was recently identified and is also expressly included as a Wnt agonist (Liu et al. (2005) *Agnew Chem. Int. Ed Engl.* 44, 1987-90).

Known GSK-inhibitors comprise small-interfering RNAs (siRNA; Cell Signaling), lithium (Sigma), kenpaullone (Biomol International; Leost, M. et al. (2000) *Eur. J. Biochem.* 267, 5983-5994), 6-Bromoindirubin-30-acetoxime (Meijer, L. et al. (2003) *Chem. Biol.* 10, 1255-1266), SB 216763 and SB 415286 (Sigma-Aldrich), and FRAT-family members and FRAT-derived peptides that prevent interaction of GSK-3 with axin. An overview is provided by Meijer et al., (2004) *Trends in Pharmacological Sciences* 25, 471-480, which is hereby incorporated by reference. Methods and assays for determining a level of GSK-3 inhibition are known to a skilled person and comprise, for example, the methods and assay as described in Liao et al. 2004 *Endocrinology* 145(6): 2941-9).

In a preferred embodiment, the Wnt agonist is selected from one or more of a Wnt family member, R-spondin 1-4, Norrin, and a GSK-inhibitor. It was found by the inventors that the addition of at least one Wnt agonists to the basal culture medium is essential for proliferation of the epithelial stem cells or isolated crypts.

In a further preferred embodiment, the Wnt agonist comprises or consists of R-spondin 1. R-spondin 1 is preferably added to the basal culture medium at a concentration of at least 50 ng/ml, more preferred at least 100 ng/ml, more preferred at least 200 ng/ml, more preferred at least 300 ng/ml, more preferred at least 500 ng/ml. A most preferred concentration of R-spondin 1 is approximately 500 ng/ml or 500 ng/ml. During culturing of stem cells, the Wnt family member is preferably added to the culture medium every second day, while the culture medium is refreshed preferably every fourth day.

In a preferred embodiment, a Wnt agonist is selected from the group consisting of: R-spondin, Wnt-3a and Wnt-6. More preferably, R-spondin and Wnt-3a are both used as Wnt agonist. This combination is particularly preferred since this combination surprisingly has a synergetic effect on organoid formation. Preferred concentrations are approximately 500 ng/ml or 500 ng/ml for R-spondin and approximately 100 ng/ml or 100 ng/ml for Wnt3a.

Yet a further component that is added to the basal culture medium is a mitogenic growth factor selected from a family of growth factors comprising epidermal growth factor (EGF; (Peprotech), Transforming Growth Factor-alpha (TGF-alpha; Peprotech), basic Fibroblast Growth Factor (bFGF; Peprotech), brain-derived neurotrophic factor (BDNF; R&D Systems), and Keratinocyte Growth Factor (KGF; Peprotech). EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells. A preferred mitogenic growth factor is EGF. EGF is preferably added to the basal culture medium at a concentration of between 5 and 500 ng/ml or of at least 5 and not higher than 500 ng/ml. A preferred concentration is at least 10, 20, 25, 30, 40, 45, or 50 ng/ml and not higher than 500, 450, 400, 350, 300, 250, 200, 150, or 100 ng/ml. A more preferred concentration is at least 50 and not higher than 100 ng/ml. An even more preferred concentration is about 50 ng/ml or 50 ng/ml. The same concentrations could be used for a FGF, preferably for FGF10 or FGF7. If more than one FGF is used, for example FGF7 and FGF10, the concentration of a FGF is as defined above and refers to the total concentration of FGF used. During culturing of stem cells, the mitogenic growth factor is preferably added to the culture medium every second day, while the culture medium is refreshed preferably every fourth day. Any member of the bFGF family may be used. Preferably, FGF7 and/or FGF10 is used. FGF7 is also known as KGF (Keratinocyte Growth Factor). In a further preferred embodiment, a combination of mitogenic growth factors such as, for example, EGF and KGF, or EGF and BDNF, is added to the basal culture medium. In a further preferred embodiment, a combination of mitogenic growth factors such as, for example, EGF and KGF, or EGF and FGF10, is added to the basal culture medium.

A further embodiment of a method according to the invention comprises a culture medium comprising a Rock (Rho-kinase) inhibitor. The addition of a Rock inhibitor was found to prevent anoikis, especially when cultering single stem cells. the Rock inhibitor is preferably selected from R)-(+)-trans-4-(1-aminoethyl)-N-(4-Pyridyl)cyclohexanecarboxamide dihydrochloride monohydrate (Y-27632; Sigma-Aldrich), 5-(1,4-diazepan-1-ylsulfonyl)isoquinoline (fasudil or HA1077; Cayman Chemical), and (S)-(+)-2-methyl-1-[(4-methyl-5-isoquinolinyl)sulfonyl]-hexahydro-1H-1,4-diazepine dihydrochloride (H-1152; Tocris Bioschience). The Rho-kinase inhibitor, for example Y-27632, is preferably added to the culture medium every second day during the first seven days of culturing the stem cells. A preferred concentration for Y27632 is $10'''$ µM.

In yet a further embodiment, a method according to the invention comprises a culture medium further comprising a Notch agonist. Notch signaling has been shown to play an important role in cell-fate determination, as well as in cell survival and proliferation. Notch receptor proteins can interact with a number of surface-bound or secreted ligands, including but not limited to Delta 1, Jagged 1 and 2, and Delta-like 1, Delta-like 3, Delta-like 4. Upon ligand binding, Notch receptors are activated by serial cleavage events involving members of the ADAM protease family, as well as an intramembranous cleavage regulated by the gamma secretase presinilin. The resultant is a translocation of the intracellular domain of Notch to the nucleus where it transcriptionally activates downstream genes. A preferred Notch agonist is selected from Jagged 1 and Delta 1, or an active fragment or derivative thereof. A most preferred Notch agonist is DSL peptide (Dontu et al., 2004, *Breast Cancer Res.* 6: R605-R615), with the sequence CDDYYYGFGC-NKFCRPR (SEQ ID NO:1). The DSL peptide (ANA spec) is preferably used at a concentration between 10 µM and 100 nM or at least 10 µM and not higher than 100 nM. The addition of a Notch agonist, especially during the first week of culturing, increases the culture efficiency by a factor of 2-3. The Notch agonist is preferably added to the culture medium every second day during the first seven days of culturing the stem cells.

A Notch agonist is defined as a molecule that stimulates a Notch activity in a cell by at least 10%, more preferred at least 20%, more preferred at least 30%, more preferred at least 50%, more preferred at least 70%, more preferred at least 90%, more preferred at least 100%, relative to a level of a Notch activity in the absence of the molecule. As is known to a skilled person, a Notch activity can be determined by measuring the transcriptional activity of Notch, for example, by a 4xwtCBF1-luciferase reporter construct as described (Hsieh et al., 1996, *Mol. Cell. Biol.* 16, 952-959).

The invention further provides a cell culture medium, comprising a basal medium for animal or human cells to which is added a Bone Morphogenetic Protein (BMP) inhibitor, a Wnt agonist; and between 5 and 500 nanogram/ml or at least 5 and not more than 500 nanogram/ml of a mitogenic growth factor selected from the group consisting of EGF, TGFα, KGF, FGF10 and a FGF. Preferably, a mitogenic factor is selected from the groups consisting of EGF, TGF-α and KGF or from EGF, TGF-α and FGF7 or from EGF, TGF-α and FGF or from EGF and KGF or from EGF and FGF7 or from EGF and a FGF or from TGFα and KGF or from TGFα and FGF7 or from TGFα and a FGF. EGF may be replaced by TGFα. Several preferred culture media are later on identified depending on the organoid to be obtained. A cell culture medium according to the invention allows the survival and/or proliferation and/or differentiation of epithelial stem cells or isolated crypts on an extracellular matrix. The term cell culture medium is synonymous with medium, culture medium or cell medium.

In a preferred method according to the invention, a first culture medium comprises Noggin as BMP inhibitor, both Epidermal Growth Factor and Keratinocyte Growth Factor as mitogenic growth factors, and R-spondin 1 as Wnt agonist, supplemented with B27, N2, and N-Acetylcysteine. KGF could be replaced by a FGF, or by FGF10. [Leu15]-Gastrin I, Exendin and/or Nicotinamide may also be added to this first medium.

In another preferred embodiment, the culture medium, called a second culture medium is identical as the first medium except that there is no Noggin and preferably no [Leu15]-Gastrin I, Exendin and/or Nicotinamide. The second culture medium therefore comprises both Epidermal Growth Factor and Keratinocyte Growth Factor as mitogenic growth factors, and R-spondin 1 as Wnt agonist, supplemented with B27, N2, and N-Acetylcysteine. KGF could also be replaced by a FGF, or by FGF10.

These two cell culture media support pancreatic fragments comprising pancreatic stem cells that are grown in these media in a Matrigel extracellular matrix to form pancreatic organoids comprising pancreatic islet-like structures on an extracellular matrix. The second medium without Noggin is a minimum medium whereas the first one with Noggin leads to an improved medium for expanding pancreatic fragments. An expanding medium is a medium which preferably promote survival and/or proliferation of cells during at least two days of culture.

A third medium has been designed which is able to promote, induce the differentiation of cells towards a pancreatic organoids within at least 5 days. One preferred differentiation marker towards the formation of a pancreatic organoid is Neurogenin-3 whose expression could be detected by RT-PCR or by immunohistochemistry. A differentiation medium as, for example, a third or fourth medium is to be functional when Neurogenin-3 could be detected by RT-PCR or by immunohistochemistry after at least five days of culture in the medium. This differentiation step is preferably carried out after a first expanding step in a medium as the first or second medium as defined above. This third medium is identical with the second medium identified above except that there is no FGF or KGF or FGF10. This third medium comprises Epidermal Growth Factor and R-spondin 1 as Wnt agonist, supplemented with B27, N2, and N-Acetylcysteine.

A fourth medium has been designed that is identical with the first medium wherein the fourth medium is also supplemented with [Leu15]-Gastrin I and/or Exendin. The third medium is a minimal differentiation medium, whereas the fourth medium is an improved differentiation medium. A differentiation medium is a medium which preferably induces or promotes a specific differentiation of cells during at least five days of culture. In the case of pancreatic organoid, differentiation may be measured by detecting the presence of a specific marker associated with the pancreatic lineage as defined earlier herein. Examples of other markers associated with the pancreatic lineage include: the secretion of insulin which is detectable by RTPCR or immunohistrochemistry after at least 7, 8, 9, 10 days of culture in a differentiation medium.

Therefore, in a preferred method for obtaining and/or culturing a pancreatic organoid, epithelial stem cells, isolated tissue fragments comprising the epithelial stem cells or adenoma cells are cultured in a first step either in the first or second medium, subsequently in a second step either in the third or fourth medium. The first step may have a duration of at least two weeks and may be longer. A first step may be carried out for more than 1, 2, 3, 4, 5, 6, 7, 8, 9, or more than 10 months. The second step may have a duration of 8, 9, 10, 11, 12, 13, 14, 15, 16 days or longer. Each step is preferably carried out using an extracellular matrix as defined herein. Preferred concentrations of each compound present in each medium have already been defined herein in the description or in the examples. In a preferred embodiment, if a pancreatic organoid is to be used for regenerative medicine, one starts from epithelial cells or from an isolated pancreatic fragment. In another preferred embodiment, if a pancreatic organoid is to be used as a drug discovery system, one starts from adenoma. Accordingly, a pancreatic organoid obtainable by a method of the invention is a further aspect of the invention. Accordingly, in a further aspect, the invention provides a first, second, third, fourth medium as defined herein.

To the best of our knowledge, this is the first time that a pancreatic organoid had been obtained that is functional and alive after at least ten month of culture (see experimental part). Functionality is preferably characterized by the secretion of insulin. Since the final amount of pancreas organoids obtained correlates with the duration of culture, the skilled person understands that the invention is a pioneer invention and potentially opens new possibilities in for example regenerative medicine.

Accordingly, in a preferred method for obtaining and/or culturing a pancreatic organoid, epithelial stem cells, isolated tissue fragments comprising the epithelial stem cells or adenoma cells are cultured in contact with an extracellular-matrix in a first step in a medium comprising EGF, KGF or FGF, and R-spondin 1 as Wnt agonist, supplemented with B27, N2, and N-Acetylcysteine, subsequently in a second step in a medium comprising EGF and R-spondin 1 as Wnt agonist, supplemented with B27, N2, and N-Acetylcysteine.

In a further preferred method according to the invention, a culture medium comprises Noggin as BMP inhibitor, Epidermal Growth Factor as mitogenic growth factor, R-spondin 1 and/or Wnt3a as Wnt agonist. This cell culture medium supports culturing of isolated small intestinal crypts in three-dimensional cultures comprising Matrigel as extracellular matrix.

In a further preferred method according to the invention, a culture medium comprises Noggin as BMP inhibitor, Epidermal Growth Factor as mitogenic growth factor, R-spondin 1 as Wnt agonist, Jagged-DSL peptide as Notch agonist and the Rho kinase inhibitor Y-27632. This cell culture medium supports culturing of isolated single epithelial stem cells in three-dimensional cultures comprising Matrigel as extracellular matrix.

In yet a further preferred method according to the invention, a culture medium comprises Noggin as BMP inhibitor, Epidermal Growth Factor and/or BDNF as mitogenic growth factors, R-spondin 1 and/or Wnt-3a as Wnt agonists, supplemented with at least one of B27, N2 and N-Acetylcysteine. Wnt-3a is a preferred Wnt agonist in this preferred method. This cell culture medium supports culturing of isolated colon crypts in three-dimensional cultures comprising Matrigel as extracellular matrix. This medium is able to promote survival and/or proliferation and/or differentiation of cells during at least two days of culture. A preferred differentiation marker towards the formation of a colon crypt may be selected from the following group: alkaline phosphatise indicating the presence of enterocyte, Muc2 indicating the presente of goblet cells and Neurogenic 3 or Chromogranin indicating the presence of endocrine cells. The expression of each of these markers could be detected by RTPCR or by immunohistochemistry. A medium functional for promoting survival and/or proliferation and/or differentiation of cells for obtaining a colon crypt is such that at least one of the identified markers could be detected after at least 2, 3, 4, 5, 6, 7, 8, 9, 10 days of culture of longer. A preferred medium comprises Noggin as BMP inhibitor, Epidermal Growth Factor as mitogenic growth factor, and R-spondin 1 and/or Wnt-3a as Wnt agonists, supplemented with at least one of B27, N2 and N-Acetylcysteine. This medium is called the firth medium of the invention which represents a further aspect of the invention.

Therefore, in a preferred method for obtaining and/or culturing a colon crypt, epithelial stem cells, isolated tissue fragments comprising the epithelial stem cells or adenoma cells are cultured in a medium as identified above, preferably the fifth medium. This method is preferably carried out using an extracellular matrix as defined herein. Preferred concentrations of each compound present in the medium have already been defined herein in the description or in the examples. Accordingly, a colon crypt obtainable by a method of the invention is a further aspect of the invention. To the best of our knowledge, this is the first time that a colon crypt had been obtained that is functional and alive after at least 1, 2, 3, 4, 5, 6, 7, 8, 9, 10, 11, 12 month of culture (see experimental part). Functionality is preferably characterized by the presence of at least one of the markers as identified above. The invention is a pioneer invention and potentially opens new possibilities in for example regenerative medicine.

Accordingly, in a preferred method for obtaining and/or culturing a colon crypt, epithelial stem cells, isolated tissue fragments comprising the epithelial stem cells or adenoma cells are cultured in contact with an extracellular matrix in a medium comprising Noggin, EGF, and R-spondin 1 and/or Wnt-3 as Wnt agonist, supplemented with B27, N2, and N-Acetylcysteine.

In yet a further preferred method according to the invention, a culture medium comprises Noggin as BMP inhibitor, Epidermal Growth Factor as mitogenic growth factor, R-spondin 1 as Wnt agonist, supplemented with either Wnt-3a or KGF, and further comprising B27, N2, N-Acetylcysteine. This medium is called the sixth medium and represents accordingly a further aspect of the invention. KGF may be replaced by a FGF or by FGF10. This medium preferably comprises Noggin as BMP inhibitor, Epidermal Growth Factor and FGF10 as mitogenic growth factor, R-spondin 1 and Wnt-3a as Wnt agonist, and further comprising B27, N2, N-Acetylcysteine. FGF10 is preferred as a FGF since it gives better results than for example FGF7 (FIG. 32). This cell culture medium supports culturing of isolated gastric fragments or gastric organoid in three-dimensional cultures comprising Matrigel as extracellular matrix.

This sixth medium is a medium for expanding a gastric fragment. An expanding medium is a medium which preferably promote survival and/or proliferation of cells during at least two days of culture. An additional medium, i.e., a seventh medium has been designed which is able to promote, induce the differentiation of cells towards a gastric organoid or gastric fragment within at least 2 days. This seventh medium is identical to the sixth medium identified above except that the concentration of Wnt-3a is reduced compared to the one present in the sixth medium. The concentration is reduced of at least 25%, 50%, 100%, 200%, 300%, 400%, 500%, 600% or more by comparison to the Wnt-3a concentration present in the sixth medium. This seventh medium comprises Epidermal Growth Factor and R-spondin 1 and Wnt-3a as Wnt agonist, Noggin and FGF10 supplemented with B27, N2, N-Acetylcysteine and Gastrin. Gastrin is preferably used at a concentration of 1 nM.

The seventh medium is a differentiation medium. A differentiation medium is a medium which preferably induces or promotes a specific differentiation of cells during at least two, 3, 4, 5, 6, 7, 8, 9, 10 days of culture or longer. In the case of a gastric organoid or gastric fragment, differentiation may be measured by detecting the presence of a specific marker associated with the gastric lineage. Examples of markers associated with the gastric lineage include: MUC5AC (a pit cell marker), GASTRIN and/or SOMATOSTATIN (both, endocrine cell markers). The presence of at least one of the markers is preferably carried out using RT-PCR and/or immunohistochemistry or immunofluorescence. The presence of at least one of these markers is preferably detectable after at least 6 days in the differentiation conditions, more preferably at least 10 days. A differentiation medium as for example a seventh medium is the to be functional when at least one of the above-identified markers could be detected by RT-PCR or by immunohistochemistry after at least six days of culture in the medium. This differentiation step is preferably carried out after a first expanding step in a medium as the sixth medium as defined above.

Therefore, in a preferred method for obtaining and/or culturing a gastric fragment, epithelial stem cells isolated tissue fragments comprising the epithelial stem cells or adenoma cells are cultured in a first step either in the sixth medium, subsequently in a second step either in the seventh medium. Each step is preferably carried out using an extracellular matrix as defined herein. The first step may have a duration of at least 3 days and may be longer. A first step may be carried out for more than 3, 4, 5, 6, 7, 8, 9, or more. The second step may have a duration of 6, 7, 8, 9, 10, 11, 12, 13, 14, 15, 16 days or longer. Preferred concentrations of each compound present in each medium have already been defined herein in the description or in the examples. Accordingly, a gastric fragment obtainable by a method of the invention is a further aspect of the invention.

Accordingly, in a preferred method for obtaining and/or culturing a gastric fragment, epithelial stem cells, isolated tissue fragments comprising the epithelial stem cells or adenoma cells are cultured in contact with an extracellular-matrix in a first step in a medium comprising Noggin as BMP inhibitor, Epidermal Growth Factor and FGF10 as mitogenic growth factor, R-spondin 1 and Wnt-3a as Wnt agonist, and further comprising B27, N2, N-Acetylcysteine, subsequently in a second step in a medium comprising Epidermal Growth Factor and R-spondin 1 and Wnt-3a as Wnt agonist, Noggin and FGF10 supplemented with B27, N2, and N-Acetylcysteine, wherein the concentration of Wnt-3 is reduced in the second step by comparison to the Wnt-3a concentration as present in the first step.

In yet a further preferred method according to the invention, a culture medium comprises Noggin as BMP inhibitor and Epidermal Growth Factor as mitogenic growth factor. This cell culture medium supports culturing of isolated adenoma fragments or isolated single adenoma cells in 3 dimensional cultures comprising Matrigel as extracellular matrix.

A ligand, such as for example Wnt3a, can be freshly added to a culture medium. Alternatively, a ligand is expressed in a cell line by transfecting or infected a cell line with a suitable expression construct expressing the ligand. The cell line is cultured and the culture medium comprising the secreted ligand is harvested at suitable time intervals. For example, cells will produce Wnt3a as soon as they reach confluency and stop growing. Culture medium from cells that were not transfected or infected with the expression construct is used as a control. The conditioned medium is harvested and tested, for example in an assay wherein luciferase expression in controlled by TCF responsive elements to test for the presence of a Wnt agonist such as Wnt3a (Korinek et al., 1997, *Science* 275:1784-1787). The medium is diluted when used in the cultures to regenerate tissue. As is known to the skilled person, the addition of an excess of ligand sometimes is as detrimental for the culture as is the addition of too little ligand. Therefore, the actual dilution of the conditioned medium will depend on the amount of ligand that is determined in the test.

The invention further provides the use of a culture medium according to the invention for culturing epithelial stem cells or isolated organoid structures that comprise these stem cells on an extracellular matrix, whereby the stem cells preferably do not comprise human embryonic stem cells. Preferred are human adult stem cells. Furthermore, single sorted epithelial stem cells from the small intestine, colon, and stomach are also able to initiate these three-dimensional organoids in a culture medium according to the invention. The invention further provides the use of a culture medium according to the invention for culturing pancreatic fragments comprising stem cells that form pancreatic organoids comprising pancreatic island-like structures.

It is preferred that the stem cells are pancreas, stomach, intestinal or colonic epithelial stem cells, whereby most preferred stem cells are small intestinal stem cells. A culture medium according to the invention allowed the establishment of long-term culture conditions under which single crypts undergo multiple crypt fission events, while simultaneously generating villus-like epithelial domains in which all differentiated cell types are present. Using a culture method according to the invention allowed culture periods of at least seven months, at least eight months, at least nine months, at least ten months.

Cultured crypts undergo dramatic morphological changes after taking them into culture. The upper opening of freshly isolated crypts becomes sealed and this region gradually balloons out and becomes filled with apoptotic cells, much like apoptotic cells are pinched off at the villus tip. The crypt region was found to undergo continuous budding events which create additional crypts, a process reminiscent of crypt fission. The crypt-like extensions comprise all differentiated epithelial cell types, including proliferative cells, Paneth cells, enterocytes and goblet cells. No myofibroblasts or other non-epithelial cells were identified in the organoids at any stage.

Expansion of the budding crypt structures created organoids, comprising >40 crypt-like structures surrounding a central lumen lined by a villus-like epithelium and filled with apoptotic cell bodies. The crypt-villus organoids comprise a central lumen lined by a villus-like epithelium. The lumen is opened at consecutive time intervals to release the content into the medium. The organoids can be passaged and maintained in culture for at least 6 months without losing the essential characteristics. Passaging preferably involves manual fragmentation of organoids.

A similar crypt-villus organoid structure is formed when single epithelial stem cells are cultured. After about one week, structures are formed that strongly resemble the crypt-villus organoid structures that are obtained with intact crypts. Histological analysis of these organoids also revealed the preservation of the basic crypt-villus architecture, the presence of all differentiated cell types, and the absence of non-epithelial elements.

In one aspect, the invention therefore provides crypt-villus organoids, comprising a central lumen lined by a villus-like epithelium that result from culturing of epithelial stem cells or isolated crypts in a culture medium of the invention. Preferably, the crypt-villus organoid is obtainable using a method of the invention.

In a further aspect, the invention provides pancreatic organoids generated or obtainable by culturing pancreatic fragments according to a method of the invention. Approximately 20% of the pancreatic organoids form a budding structure 7 days after the start of the culture. The pancreatic ducts rapidly proliferate, in contrast to the acinar tissue, which only grows very slowly. After passaging of the pancreatic organoids, pancreatic islet-like structures that secrete insulin are observed which resemble the pancreatic islets of Langerhans that are present in healthy pancreas tissue. The invention further provides a gastric organoid comprising a central lumen. Preferably the gastric organoid is obtainable by a method of the invention.

Further growth factors that may be added to a culture medium, for example to increase the presence of pancreatic islets in the organoids or to further support the culturing of isolated fragments such as gastric fragments, comprise cyclopamine (Sonic-hedgehog inhibitor; Tocris Bioscience), Activin, GLP (Glucagon like peptide) and its derivative (Exendin 4; California Peptide Research), gastrin (Genscript), a Notch agonist (Jagged peptide, Ana Spec), Nicotinamide and a Wnt agonist such as Wnt-3a. Wnt-3a is attractive to be used when one starts culture with a single cell.

The invention further provides a collection of crypt-villus, gastric or pancreatic organoids, each comprising more than 10, preferably more than 20, more preferably more than 40 organoids. The crypt-villus organoids surround a central lumen lined by a villus-like epithelium. The lumen is filled with apoptotic cell bodies. The cells in the crypt-villus organoids are polarized, with stem cells residing in the basis of the structures. The top of the crypt-like structures comprise apoptotic cells that are shed into the lumen. the collection of crypt-villus organoids preferably comprises at least 10% viable cells, more preferred at least 20% viable cells, more preferred at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS.

In a further aspect, the invention provides the use of the crypt-villus organoids, gastric organoids or pancreatic organoids according to the invention in a drug discovery screen, toxicity assay or in regenerative medicine.

For high-throughput purposes, the crypt-villus, gastric or pancreatic organoids are cultured in multiwell plates such as, for example, 96-well plates or 384-well plates. Libraries of molecules are used to identify a molecule that affects the organoids. Preferred libraries comprise antibody fragment libraries, peptide phage display libraries, peptide libraries (e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death. the crypt-villus, gastric or pancreatic organoids can also be used to identify drugs that specifically target epithelial carcinoma cells, but not the crypt-villus, gastric or pancreatic organoids.

The crypt-villus, gastric or pancreatic organoids can further replace the use of cell lines such as Caco-2 cells in toxicity assays of potential novel drugs or of known or novel food supplements.

Furthermore, the crypt-villus, gastric or pancreatic organoids can be used for culturing of a pathogen such as a norovirus which presently lacks a suitable tissue culture or animal model.

Cultures comprising crypt-villus organoids are useful in regenerative medicine, for example in post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome. Further use is present in the repair of the intestinal epithelium in patients with hereditary diseases of the small intestine/colon. Cultures comprising pancreatic organoids are also useful in regenerative medicine, for example as implants after resection of the pancreas or part thereof and for treatment of diabetes such as diabetes I and diabetes II.

In an alternative embodiment, the expanded epithelial stem cells are reprogrammed into related tissue fates such as, for example, pancreatic cells including pancreatic β-cells, and liver cells. Thus far, it has not been possible to regenerate pancreatic cells or liver stem, from adult stem cells. The culturing methods of the present invention will enable analysis for factors that trans-differentiate the closely related epithelial stem cell to a pancreatic cell, including a pancreatic β-cell, and a liver cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment.

In another aspect, the invention provides a method for culturing an epithelial adenoma cell, comprising providing an extracellular matrix, attaching an epithelial adenoma cell to the extracellular matrix, culturing the cell in the presence of a cell culture medium, comprising a basal medium for animal or human cells to which is added a Bone Morphogenetic Protein (BMP) inhibitor, and between 5 and 500 ngram/ml or at least 5 and not more than 500 ngram/ml of a mitogenic growth factor selected from EGF, TGF-alpha and KGF. KGF may be replaced by a FGF or FGF10.

An epithelial colon adenoma cell comprises an alteration in a gene coding for APC protein, which results in less efficient degradation of intracellular β-catenin by a complex of proteins comprising APC. Other mutations common in colon adenomas comprise mutations in β-catenin or Axing. The overall result is enhanced TCF/LEF signaling because of an increased amount of β-catenin in the nucleus. A culture medium without a Wnt agonist was found to be sufficient for proliferation of adenoma cells.

The adenoma cell can be isolated from epithelial adenoma by methods known in the art, comprising the use of dissociating agents such as EDTA. Alternatively, single Lgr5- or Lgr-6-positive adenoma cells can be isolated from the adenoma by using a Lgr5-binding compound, followed by magnetic beads or FACS analyses.

The invention further provides progeny of an epithelial adenoma cell that was cultured in the presence of a cell culture medium, comprising a basal medium for animal or human cells to which is added a Bone Morphogenetic Protein (BMP) inhibitor and between 5 and 500 ngram/ml or at least 5 and not more than 500 ngram/ml of Epidermal Growth Factor (EGF). The cultured adenoma cells are not able to develop a polarized three-dimensional structure such as a crypt-villus-like architecture. Rather, adenoma cells form balloon-like structures in which cells are randomly oriented towards either the periphery or the central lumen. There is no sign of differentiation into other epithelial cell types. This result indicates a role for APC in the three-dimension organization of the crypt-villus-like architecture.

In addition, the invention provides the use of the progeny of the adenoma cells for a targeted drug discovery screen to identify a drug that specifically affects adenoma cells compared to expanded normal epithelial cells that are cultured in the same culture medium. For high-throughput purposes, the progeny of adenoma cells is cultured in multiwell plates such as, for example, 96-well plates or 384-well plates. Libraries of molecules are used to identify a molecule that affects the progeny. Preferred libraries comprise antibody fragment libraries, peptide phage display libraries, peptide libraries (e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. A compound that affects adenoma cells is subsequently, or in parallel, tested for affecting expanded normal epithelial cells. The term "affecting" is used to cover any change in a cell, including a reduction in, or loss of, proliferation, a morphological change, and cell death. the progeny can also be used to identify drugs that specifically target epithelial carcinoma cells, compared to epithelial adenoma cells, including reversion of the carcinoma cells.

It will be clear that the progeny can also be used in a high throughput approach for the determination of in vitro metabolic stability and metabolic profiles of drug candidates.

The invention furthermore provides the use of the progeny of adenoma cells according to the invention, of pancreatic organoids, of gastric organoids and of crypt-villus organoids of the invention, in toxicity assays. the progeny and crypt-villus organoids are easy to culture and more closely resemble primary epithelial cells than, for example, epithelial cell lines such as Caco-2 (ATCC HTB-37), I-407 (ATCC CCL6), and XBF (ATCC CRL 8808) which are currently used in toxicity assays. It is anticipated that toxicity results obtained with primary adenoma cultures or with crypt-villus organoids more closely resemble results obtained in patients. A cell-based toxicity test is used for determining organ specific cytotoxicity. Compounds that are tested in the test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analyzed to determine the concentration that inhibited end point by 50 percent (TC50).

The inventors also demonstrated that the human intestinal organoids generated by media and methods of the present invention, mimicked in vivo cell fate decisions in response to external factors.

The invention also provides a population of stem cells, or organoids comprising the stem cells, that have been obtained using the culture medium of the invention. The stem cells or organoids comprising the stem cells may be used, for example, for transplantation purposes or other therapeutic applications.

Stem Cells Cultured According to the Invention

Stem cells are found in many organs of adult humans and mice. Although there may be great variation in the exact characteristics of adult stem cells in individual tissues, adult stem cells share at least the following characteristics: they retain an undifferentiated phenotype; their offspring can differentiate towards all lineages present in the pertinent tissue; they retain self-maintenance capabilities throughout life; and they are able to regenerate the pertinent tissue after injury. Stem cells reside in a specialized location, the stem cell niche, which supplies the appropriate cell-cell contacts and signals for maintenance of the stem cell population.

In one embodiment, the invention provides a population of cells or one or more organoids comprising the stem cells that have been generated or obtained by culturing stem cells or tissue fragments according to the invention, which have been cultured for at least 3 months, preferably at least 4 months, at least 5 months, at least 6 months, at least 7 months, at least 9 months, or at least 12 months or more.

A "population" of cells is any number of cells greater than 1, but is preferably at least $1\times10^3$ cells, at least $1\times10^4$ cells, at least $1\times10^5$ cells, at least $1\times10^6$ cells, at least $1\times10^7$ cells, at least $1\times10^8$ cells, or at least $1\times10^9$ cells.

The stem cells of the invention cultured according to the invention may be human stem cells. The stem cells of the invention cultured according to the invention may be epithelial stem cells.

In a preferred embodiment, the stem cells may be human epithelial stem cells. Human epithelial stem cells include stem cells of human epithelial tissue origin. These include, but are not limited to pancreatic, small intestinal, large intestinal, corneal, olfactory, respiratory tissues, gastric tissues, liver and skin, for example, a tissue selected from the group consisting of pancreatic, small intestinal, large intestinal, corneal, olfactory, and respiratory tissues. Epithelial stem cells are able to form the distinct cell types of which the epithelium is composed. Some epithelia, such as skin or intestine, show rapid cell turnover, indicating that the residing stem cells must be continuously proliferating. Other epithelia, such as the liver or pancreas, show a very slow turnover under normal conditions.

The self-renewing epithelium of the small intestine is ordered into crypts and villi (Gregoreff and Clevers, 2005 *Genes Dev.* 19, 877-90). Each cell along the crypt-villus axis is polarized, whereby cells on the top of the intestinal villi, or in the upper positions of colonic crypts, are the most differentiated and are continuously lost into the lumen by apoptosis. Continuous proliferation of stem cells residing in the base of the crypts, and massive proliferation of progenitor cells residing in the middle of the crypts, ensures proper replacement of the shed cells. There is a resulting epithelial turnover time of 5 days in the mouse. Self-renewing stem cells have long been known to reside near the crypt bottom and to produce the rapidly proliferating transit amplifying (TA) cells capable of differentiating towards all lineages. The estimated number of stem cells is between 4 and 6 per crypt (Bjerknes and Cheng, 1999 *Gastroenterology* 1 16, 7-14). Three differentiated cell types, enterocytes, goblet cells and enteroendocrine cells, form from TA cells and continue their migration in coherent bands along the crypt-villus axis. Each villus receives cells from multiple different crypts. The fourth major differentiated cell-type, the Paneth cell, resides at the crypt bottom.

Crypts can be isolated from the duodenum, small and large intestine, including jejunum, ileum, and colon, and the pyloric region of the stomach by protocols that are known to the skilled person. For example, crypts can be isolated by incubation of isolated tissue with chelating agents that release cells from their calcium- and magnesium-dependent interactions with the basement membrane and stromal cell types. After washing the tissue, the epithelial cell layer is scraped from the submucosa with a glass slide and minced. This is followed by incubation in trypsin or, more preferred, EDTA and/or EGTA and separation of undigested tissue fragments and single cells from crypts using, for example, filtration and/or centrifugations steps. Other proteolytic enzymes, such as collagenase and/or dispase I, can be used instead of trypsin. Similar methods are used to isolate fragments of the pancreas and stomach.

Methods to isolate stem cells are known and suitable methods for use with this invention can be selected by the skilled person depending on the stem cell type that is used. For example, isolation of epithelial stem cells may be performed using compounds that bind to Lgr5 and/or Lgr6, which are unique cell surface markers on epithelial stem cells. Examples of such compounds are anti-Lgr5 and anti-Lgr6 antibodies.

In some embodiments of the invention, single Lgr5+ epithelial stem cells, for example from the colon, small intestine, or pancreas, may be used to form organoids, such as colonic, crypt-villus or pancreatic organoids respectively.

Cultured crypts undergo dramatic morphological changes after taking them into culture. The upper opening of freshly isolated crypts becomes sealed and this region gradually balloons out and becomes filled with apoptotic cells, much like apoptotic cells are pinched off at the villus tip. The crypt region undergoes continuous budding events which create additional crypts, a process reminiscent of crypt fission. In a preferred embodiment of the invention, the organoids comprise crypt-like extensions which comprise all differentiated epithelial cell types, including proliferative cells, Paneth cells, enterocytes and goblet cells. No myofibroblasts or other non-epithelial cells were identified in the organoids at any stage.

Expansion of the budding crypt structures creates organoids, comprising crypt-like structures surrounding a central lumen lined by a villus-like epithelium and filled with apoptotic cell bodies. The crypt-villus organoids comprise a central lumen lined by a villus-like epithelium. The lumen is opened at consecutive time intervals to release the content into the medium.

A similar crypt-villus organoid structure is formed when single epithelial stem cells are cultured. After about one week, structures are formed that strongly resemble the crypt-villus organoid structures that are obtained with intact crypts.

In one embodiment, the invention provides crypt-villus organoids or gastric organoids or pancreatic organoids or colon organoids or Barrett's Esophagus organoids or adenocarcinoma organoids or colon carcinoma organoids generated or obtained by culturing human stem cells or tissue fragments according to a method of the invention. Such a population of organoids, for example, crypt-villus, gastric or pancreatic organoids, generated or obtained by culturing human stem cells or tissue fragments according to a method of the invention, may each comprise more than 10, preferably more than 20, more preferably more than 40 organoids. the collection of organoids preferably comprises at least 10% viable cells, more preferred at least 20% viable cells, more preferred at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS.

The culture media and methods of the invention may be used for culture of cancer cell lines, including colorectal cancer and adenocarcinoma. Accordingly, the stem cells according to the invention may be cancer stem cells. In some embodiments of the invention, cancer stem cells can form adenoma or colon cancer organoids. In some embodiments, these organoids comprise cells which are Ki67+ (Thermo Scientific*Cellomics, Millipore).

There is some confusion in the literature as to the definition of a cancer stem cell. Here, we follow the consensus reached at a recent AACR workshop (Clarke et al., 2006, Cancer Res. 66:9339-44), which states that the cancer stem cell "is a cell within a tumor that possesses the capacity to self-renew and to cause the heterogeneous lineages of cancer cells that comprise the tumor. Cancer stem cells can thus only be defined experimentally by their ability to recapitulate the generation of a continuously growing tumor." Alternative terms in the literature include tumor-initiating cell and tumorigenic cell. Assays for cancer stem cell activity need to address the potential of self-renewal and of tumor propagation. The gold-standard assay currently is serial xeno-transplantation into immunodeficient mice.

Genomic and Phenotypic Integrity of Stem Cells and Organoids Comprising the Stem Cells Clinical and research applications for stem cells and their differentiated progeny require reproducible stem cell culture methods that provide populations of cells of suitable quality. Generally, in vitro expansion of stem cells aims to provide a population of cells which resemble their in vivo counterparts as closely as possible. This property is herein referred to as the "genomic and phenotypic integrity" of the cells.

For the first time, the inventors have discovered that it is possible to expand human epithelial stem cells in culture, with minimal loss of genomic and phenotypic integrity, for at least 3 months, preferably at least 4 months, at least 5 months, at least 6 months, at least 7 months, at least 9 months, or at least 12 months or more (see Example 11). The inventors also demonstrated that the human intestinal organoids generated by media and methods of the present invention, mimicked in vivo cell fate decisions in response to external factors. For example, it has previously been shown that Notch inhibition in intestinal stem cells, terminates intestinal epithelial proliferation and induces goblet cell hyperplasia in vivo. The inventors were able to show that the intestinal organoids of the invention, when treated with a Notch inhibitor, ceased proliferation and most cells converted into goblet cells within 3 days.

These results show the dramatic improvement in the genomic and phenotypic integrity of the stem cells and organoids produced by the methods and media of the present invention compared to previous methods and media.

The genomic integrity of stem cells of the invention can be confirmed by karyotype analysis. Stem cells and their progeny can be karyotyped using known methods as described in Sato, T. et al., Single Lgr5 stem cells build crypt-villus structures in vitro without a mesenchymal niche, Nature 459, 262-265, 2009.

A "normal karyotype" is one where all chromosomes are present (i.e., euploidy) with no noticeable alterations. Accordingly, in preferred embodiments of the invention more than 50%; more than 70%; more than 80%; more than 90%; more than 95%; or more than 99% of the stem cells and differentiated cells in an expanded population exhibit normal karyotypes after 1, 2, 3, 4, 5, 6, 9, 12 or more months.

A "normal phenotype" refers to cells which display, to a first approximation, the same visual characteristics, gene expression and behaviour as the average in vivo counterpart cell. In preferred embodiments of the invention more than 50%; more than 70%; more than 80%; more than 90%; more than 95%; or more than 99% of the stem cells in an expanded population cultured according to the invention exhibit normal phenotypes after 1, 2, 3, 4, 5, 6, 9, 12 or more months.

For example, visually a normal phenotype may be judged by the number of dead cells outside the organoid, the amount of 'budding' of the organoid compared to cystic growth (budding structures are preferred), and the overall integrity of the single layer of epithelial cells (e.g., columnar squamous phenotype).

Preferred properties of the stem cells and organoids of the invention are outlined below.

When mouse genes are referred to herein, a human organoid of the invention may have a similar gene profile but wherein the human gene counterparts are substituted for the mouse genes. Thus, also provided by the invention is a human organoid having a gene expression profile as described herein, but in respect of the corresponding human genes. The human counterparts of the mouse genes listed herein will be readily available to the skilled person.

Stem Cell Markers

In one embodiment, the invention provides a population of adult stem cells characterized by natural expression of Lgr5. In a preferred embodiment, the invention provides a population of adult stem cells characterized by natural expression of at least Lgr5 and one or more of stem cell markers from the group consisting of: LGR4, epcam, Cd24a, Cdca7, Axin, CK19, Nestin, Somatostatin, CXCR4+, CD133+, DCAMKL-1, CD44, Sord, Sox9, CD44, Prss23, Sp5, Hnf1α, Hnf4a, Sox9, KRT7 and KRT19, Tnfrsf19. The stem cell markers may be tissue specific. For example, pancreatic stem cells or organoids may be characterized by natural expression of one or more (for example 1, 2, 3 or 4) of: CK19, Nestin, Somatostatin, insulin, glucagon, CXCR4+, Ngn3, Pdx1, NeuroD, NRx2.2, NRx6.1, Pax6, Mafa, Hnf1b at a significant level; gastric organoids may be characterized by natural expression of one or more (for example 1, 2 or 3) of: CD133+, DCAMKL-1, CD44, at a significant level; and crypt-villus organoids may be characterized by expression of one or more or all (for example 1 or 2) of: Sord and/or Prss23, at a significant level all genes of table/FIG. 48.

The term "significant level" as used herein in the context of marker expression is used synonymously with the term "detectable level," as described below.

Small intestinal and gastric organoid cell populations also express markers of progenitor populations common to the small intestine and stomach, such as one or both of Cd44 and Sox9 (Barker & Huch et al. *Cell Stem Cell* 2010). These are highly expressed in the stem cells according to the invention. Cells according to this aspect of the invention may also up-regulate Wnt target genes, including for example, one, two or all of MMP7, Sp5 and Tnfrs19, axin2. This provides strong evidence of the requirement for an active and robust canonical Wnt signaling activity to maintain the self renewing capacity of these cultures.

The inventors have observed that expression of the 'stem cell' genes is present in the early organoids at a level significantly higher then the differentiated cells that become the offspring of these stem cells. For example, the genes LGR5, LGR4, Epcam, CD44, Tnfrsf19, Sox9, Cd24a, Sp5, Prom1/CD133, Cdca7 are preferably expressed in the organoids of the invention but are preferably significantly downregulated upon differentiation of the pancreas, liver, small intestine and colon organoids.

By "natural expression" is meant that the cells have not been manipulated recombinantly in any way, i.e., the cells have not been artificially induced to express these markers or to modulate these markers' expression by introduction of exogenous genetic material, such as introduction of heterologous (non-natural) or stronger promoters or other regulatory sequences operably linked to either the endogenous genes or exogenously-introduced forms of the genes. Natural expression is from genomic DNA within the cells, including introns between the exon coding sequences where these exist. Natural expression is not from cDNA. Natural expression can if necessary be proven by any one of various methods, such as sequencing out from within the reading frame of the gene to check that no extraneous heterogenous sequence is present. "Adult" means post-embryonic. With respect to the stem cells of the present invention, the term "adult stem cell" means that the stem cell is isolated from a tissue or organ of an animal at a stage of growth later than the embryonic stage.

This stem cell population can also be characterized by a lack of natural expression of certain markers at any significant level, many of which are associated with cellular differentiation. Specifically, the cells of the isolated adult stem cell population do not naturally express one or more of Cd11b, CD13, CD14, AFP, Pdx1, any CYP member (e.g., CYP3A11, CYP 11A1) at a significant level. As defined herein, these markers are to be negative markers.

Detecting Markers and Isolating Cells

The term "expressed" is used to describe the presence of a marker within a cell. In order to be considered as being expressed, a marker must be present at a detectable level. By "detectable level" is meant that the marker can be detected using one of the standard laboratory methodologies such as PCR, blotting or FACS analysis. A gene is considered to be expressed by a cell of the population of the invention if expression can be reasonably detected after 30 PCR cycles, which corresponds to an expression level in the cell of at least about 100 copies per cell. The terms "express" and "expression" have corresponding meanings. At an expression level below this threshold, a marker is considered not to be expressed. The comparison between the expression level of a marker in a cell of the invention, and the expression level of the same marker in another cell, such as for example an embryonic stem cell, may preferably be conducted by comparing the two cell types that have been isolated from the same species. Preferably this species is a mammal, and more preferably this species is human. Such comparison may conveniently be conducted using a reverse transcriptase polymerase chain reaction (RT-PCR) experiment.

In some embodiments, a population of cells or an organoid of the invention is considered to express a marker if at least about 5%, (for example, at least 10%, at least 20%, at least 30%, at least 40%, at least 60%, at least 70%, at least 80%, at least 90%, at least 95%, at least 97%, at least 98%, at least 99% or 100%) of the cells in the cell population or organoid according to the invention show expression of the marker.

In some embodiments, the cells express a cell marker at a significant level if they comprise between $1 \times 10^2$ to $1 \times 10^5$, for example $5 \times 10^2$ to $1 \times 10^4$ or $1 \times 10^3$ to $1 \times 10^4$ fold more copies of the mRNA encoding the cell marker relative to the number of mRNA copies of the housekeeping gene GADPH.

In some embodiments, the expression of a gene in an organoid or cell of the invention when cultured in expansion medium is several fold (e.g., at least 1.5 fold, 2 fold, 3 fold, 4 fold, 5 fold) higher than when the organoid or cell is cultured in differentiation medium or in the fully differentiated adult tissue. In some embodiments, a cell or organoid of the invention when cultured under differentiation conditions, exhibits an increase in expression of genes that are known as differentiation genes compared to a cell or organoid of the invention when cultured under expansion conditions and also may show a decrease in the level of expression of at least one or more stem cell/progenitor genes compared to a cell or organoid of the invention when cultured in expansion medium.

Any one of a number of physical methods of separation known in the art may be used to select the cells of this aspect of the invention and distinguish these from other cell types. Such physical methods may involve FACS and various immuno-affinity methods based upon makers specifically expressed by the cells of the invention. As described above, Lgr5, CD44 and Sox9 are three of the cell markers expressed at high levels in the stem cells of the invention. Therefore, by way of illustration only, the stem cells of the invention may be isolated by a number of physical methods of separation, which rely on the presence of these.

In one embodiment, the cells of the invention may be isolated by FACS utilizing an antibody, for example, against one of these markers. Fluorescent activated cell sorting (FACS) can be used to detect markers characteristic of a particular cell type or lineage. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOR®), PE-Cy5.5, PI, PE-Alexa Fluor® 750, and PE-Cy7. This list is provided by way of example only, and is not intended to be limiting.

It will be apparent to a person skilled in the art that FACS analysis using an anti-Lgr5 antibody will provide a purified stem cell population. However, in some embodiments, it may be preferable to purify the cell population further by performing a further round of FACS analysis using one or more of the other identifiable markers.

Immunohistochemistry may also be used to understand the distribution and localization of biomarkers and differentially expressed proteins in different parts of a cell population or organoid. Visualising an antibody-antigen interaction can be accomplished in a number of ways that are well known in the art, such as those that are described in described in Barker et al., Identification of stem cells in small intestine and colon by marker gene Lgr5, *Nature* 2007 Oct. 25; 449(7165):1003-7.

In another embodiment, the cells of the invention may be isolated by immuno-affinity purification, which is a separation method well known in the art. By way of illustration only, the cells of the invention may be isolated by immuno-affinity purification directed towards c-kit. As will be apparent to one skilled in the art, this method relies upon the immobilization of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilized anti-c-kit antibody, and permits the cells to be released from the column.

It will be apparent to a person skilled in the art that immuno-affinity purification using an immobilized antibody will provide a purified cell population. However, in some embodiments, it may be preferable to purify the cell population further by performing a further round of immuno-affinity purification using one or more of the other identifiable markers, and use an aliquot of the isolated clones to ascertain the expression of other relevant intracellular markers.

It will be apparent to a person skilled in the art that the sequential purification steps are not necessarily required to involve the same physical method of separation. Therefore, it will be clear that, for example, the cells may be purified through a FACS step using an anti-Lgr5 antibody, followed by an immuno-affinity purification step using a SSEA-1 affinity column. In certain embodiments, the cells may be cultured after isolation for at least about 15, at least about 20 days, at least about 25 days, or at least about 30 days. In certain aspects, the cells are expanded in culture longer to improve the homogeneity of the cell phenotype in the cell population.

Microarray analysis, cluster analysis and comparative gene expression profiling can be used to compare population phenotype with phenotype of the original parent cells or of the appropriate in vivo counterparts (Sato T. et al., Paneth cells constitute the niche for Lgr5 stem cells in intestinal crypts, *Nature* 469 415-418).

Lineage tracing of Lgr5+ stem cells shows preservation of crypt-villus characteristics in organoids.

In another embodiment, high content analysis may be used to assess phenotypic integrity of stem cells of the invention. For example, a number of high content screening kits and platforms exist, such as point scanning 4 color ImageXpress ULTRA (Molecular Devices, Union City, USA), the spinning disk (nipkow disk) Pathway 855 and 435 from BD Biosciences (formerly Atto Biosciences, Rockville, Md.), Opera (PerkinElmer Inc., Waltham, Mass.) and the slit scanning IN Cell 3000 (GE/Amersham Biosciences, Cardiff, UK), Arrayscan VTI (Cellomics (Cellomics)), IN Cell Analyzer 2000 (GE Healthcare Piscataway, N.J., USA), Acumen eX3 (TTP LabTech Ltd (Acumen eX3)), Scanalyzer (Scanalyzer LemnaTec, Aachen Germany) and ImagXpress MICRO (Molecular Devices, Union City, USA), IN Cell 1000 (GE/Amersham Biosciences Piscataway, N.J., USA), the Pathway HT (Becton Dickinson Biosciences) and the ImageXpress MICRO (Molecular Devices, Union City, USA), Scan^R (Olympus Soft Imaging Solutions, Germany).

Organoids

The cells described above grow into organoids. Accordingly, an organoid obtainable by a method of the invention is a further aspect of the invention. Also provided is an organoid as described herein. The organoid is preferably a human organoid. To the best of our knowledge, this is the first time that human organoids have been obtained that are functional and alive after such an extended period of time (i.e at least 3 months, preferably at least 4 months, at least 5 months, at least 6 months, at least 7 months, at least 9 months, or at least 12 months or more of culture; see examples included herein). Functionality is preferably characterized by the presence of tissue-specific markers and/or by the structure of the organoid as defined herein. Since the final amount of organoids obtained correlates with the duration of culture, the skilled person will understand that the invention is a pioneer invention and potentially opens new possibilities in for example regenerative medicine. Thus, there is provided an organoid as described herein that is functional and alive after at least 3 months (e.g., at least 4, 5, 6, 7, 8 or more months) of culture. For example, there is provided an organoid as described herein that retains at least one or more (e.g., 1, 2 or 3) of its structure, marker expression and function after at least 3 months (e.g., at least 4, 5, 6, 7, 8 or more months) of culture.

For example, an organoid according to the present invention may comprise a population of cells of at least $1 \times 10^3$ cells, at least $1 \times 10^4$ cells, at least $1 \times 10^5$ cells, at least $1 \times 10^6$ cells, at least $1 \times 10^7$ cells or more. Each organoid comprises between approximately $1 \times 10^3$ cells and $5 \times 10^3$ cells. The inventors have shown that it is possible to grow organoids from single Lgr5+ stem cells into organoids comprising a population of cells as described above or comprising a population of cells of approximately $10^4$ cells. For example, it has now been shown for mouse that it is possible to start growth of an organoid from single stem cells. Thus, the invention provides a method for generating an organoid from a single stem cell. In some embodiments, the organoid comprises approximately 104 cells. In some embodiments, 10-20, or 20-30 or 30-40 or 40-50 organoids may be grown together in one well of a 24-well plate.

Organoids of the invention may be obtained using cells isolated from any suitable source. Generally, the cells used to generate an organoid will be isolated from the same tissue type as the organoid which is generated. The organoids are preferably mammalian, for example, murine, bovine, porcine or human. Most preferably, the organoids are human.

Organoid Structure and Morphology

Image analysis may be used to assess characteristics of cells in culture such as cell morphology; cell structures; evidence for apoptosis or cell lysis; and organoid composition and structure. Many types of imaging analysis are well known in the art, such as electron microscopy, confocal microscopy, stereomicroscopy, fluorescence microscopy. Histological analysis can reveal basic architecture and cell types.

Illustrative examples of organoids generated according to the invention are given in the accompanying figures. It can be seen that organoids according to the invention may possess a layer of cells with at least one bud and a central lumen. The organoids in the outside of the matrigel tend to be larger than the organoids in the center of the matrigel, perhaps because they have better access to the necessary growth factors. Structurally, organoids according to the invention are often elongated in shape. They may include one or more budding structure—a single cell epithelial layer with similarities to ducts or islets. Under confocal microscopy, the structures may stain positive for keratin. They may include cells with polarized nuclei and small cytoplasm. The organoids may have a section which is formed of multiple layers; such cells often tend to have their nuclei more central to the cells, i.e., not polarized. The cells in the multilayer section may organise themselves to include a gap, or lumen between the cells.

Morphologically, the cells appear like their corresponding in vivo tissue counterpart.

Crypt-Villus Organoids

In small intestinal crypt-villus organoids the structural arrangement of the organoids is very similar to the structure of in vivo crypt-villi: the Lgr5+ stem cell and their niche cells (Paneth cells) are next to each other at the base of the crypt, followed by the transit amplifying cells, just above the base of the crypt and leading into the sides of the villi and finally the differentiated cells, such as enterocytes that make up the rest of the villi and become more and more differentiated towards the top of the villi. It can be seen that organoids according to the invention may possess a layer of cells with at least one bud and a central lumen. The organoids in the outside of the matrigel tend to be larger than the organoids in the center of the matrigel, perhaps because they have better access to the necessary growth factors. Structurally, organoids according to the invention are often elongated in shape. Under confocal microscopy, the structures may stain positive for keratin. They may include cells with polarized nuclei and small cytoplasm. The crypt-villus organoids are generally single-layered.

Human intestinal organoids display budding organoid structures, rather than the cystic structures seen under previous culture conditions. The upper opening of freshly isolated crypts becomes sealed and this region gradually balloons out and becomes filled with apoptotic cells, much like apoptotic cells are pinched off at the villus tip. Thus, in some embodiments, the crypt-villus organoids have a crypt-like structure surrounding a central lumen lined by a villus-like epithelium and filled with apoptotic cell bodies. In some embodiments, the lumen is opened at consecutive time intervals to release the content into the medium.

In some embodiments, the crypt region undergoes continuous budding events which create additional crypts, a process reminiscent of crypt fission.

The inventors also demonstrated that the human intestinal organoids of the invention mimicked in vivo cell fate decisions in response to external factors. For example, it has previously been shown that Notch inhibition in intestinal stem cells, terminates intestinal epithelial proliferation and induces goblet cell hyperplasia in vivo. Thus in some embodiments, when a crypt-villus organoid of the invention is treated with a Notch inhibitor, proliferation ceases and most cells (for example more than 50%, more than 60%, more than 70%, more than 80%, more than 90%, more than 95%, more than 98%) convert into goblet cells within 3 days.

Metaphase spreads of organoids more than 3 months old consistently revealed 46 chromosomes in each of the 20 cells taken from three different donors. Furthermore, microarray analysis revealed that the stem cells in culture possessed similar molecular signatures to intestinal crypt cells including intestinal stem cell genes.

Colon organoids exhibit a similar cell composition to crypt-villus organoids. Thus, the comments for crypt-villus organoids above apply to colon organoids mutatis mutandis.

Colon Organoids

In some aspects, colon organoids are provided by the invention.

In some embodiments, a mouse colon organoid has a maximal diameter of approximately 200-700 uM, for example 250-600 uM, 300-500 uM, 320-450 uM, 340-400 uM, 300-380 uM, for example approximately 360 uM. In some embodiments, a colon organoid has a minimal diameter of approximately 100-400 uM, for example, 150-350 uM, 170-300 uM, 190-280 uM, 195-250 uM, for example, approximately 235 uM. In a further embodiment, the organoids can have a diameter of up to 1 mm.

In some embodiments, a human colon organoid has a maximal diameter of approximately 300-800 uM, for example, 350-700 uM, 400-600 uM, 450-550 uM, 475-540 uM, 500-530 uM, for example approximately 500 uM. In some embodiments, a colon organoid has a minimal diameter of approximately 200-500 uM, for example, 250-450 uM, 300-415 uM, 350-400 uM, 325-380 uM, for example, approximately 375 uM. In a further embodiment, the organoids can have a diameter of up to 1 mm.

In some embodiments, a colon organoid of the invention comprises budding structures. These may be visible by using EdU stain to visualize proliferating cells.

Pancreatic Organoids

Pancreatic organoids of the invention preferably exhibit budding. In some embodiments, the pancreatic organoids are from 100-1000 micrometers in diameter, for example, 200-900 micrometers, 300-1000 micrometers, 400-700 micrometers. The pancreatic organoids are preferably single layered. There are only the very beginnings of islet or ductal structures. Budding structure are indicative of a healthy proliferation status and stem cell maintenance.

Adenocarcinoma and Colon Cancer Organoids

Adenocarcinoma and colon cancer organoids generally form cystic structures instead of budding structures. This is reminiscent of the absence of good cell niche support. Adeno(carcino)ma and colon cancer organoids may provide useful research tools and drug screening models.

Barrett's Esophagus (BE) Organoids

A BE organoid of the invention comprises budding structures.

Morphologically, the cells in the organoids of the invention appear like their corresponding in vivo tissue counterpart.

Organoid Composition and Gene Expression

The crypt-villus, colon crypt and pancreatic organoids typically comprise stem cells and/or progenitor cells and, therefore, these organoids share certain patterns of gene expression. In some embodiments, one or more (for example, 1, 2, 3, 4, 5 or 6) or all of the following markers can be detected: LGR5, LGR4, epcam, Cd44, Sox9, Cd24a, and CD133/Prom1. In another embodiment, the expression of one or two or all of the following progenitor genes can be detected: Pdx1, NRx2.2, and NRx6.1. After differentiation, gene expression patterns of the crypt-villus, colon crypt and pancreatic organoids are expected to diverge as the differentiated organoids express tissue-specific adult markers, such as insulin in the pancreas for example.

Crypt Villus Organoids

In some embodiments of the invention, the organoids comprise crypt-villus like extensions which comprise all differentiated epithelial cell types, including proliferative cells, Paneth cells, enterocytes and goblet cells. In some embodiments, the crypt-villus organoids of the invention do not contain myofibroblasts or other non-epithelial cells. A crypt-villus organoid of the invention preferably comprises enterocytes, including absorptive enterocytes, goblet cells, enteroendocrine cells, and Paneth cells in a crypt-villus-like structure. Preferably at least one (for example, 2, 3, 4, 5 or 6) of the following markers could be detected: SMOC2, CDCA7, OLFM4, ASCL2, AXIN2 and/or Lgr5 Tnfrsf19, CD24a, Sox9, CD44, Prom1 (see FIG. 36e and FIG. 48). In some embodiments, one or more (for example 1, 2, 3, 4 or 5 or all of SMOC2, CDCA7, OLFM4, ASCL2, AXIN2 and/or Lgr5 are at least 2-fold, 3-fold, or 4-fold upregulated in crypts, whereas markers that are at least 2-fold, 3-fold, or 4-fold downregulated in crypts include at least one or more (for example 1, 2, 3 or 4) or all of ABCG1, ENPP3, CSTE, MUC17 and/or APOA1. In this context "upregulation" is relative to the villus of the intestine or to the top section of the colon crypt. Microarray analysis, comparing the gene expression of differentiated organoid cells to stem cells, revealed that the small intestinal crypt-villus and colonic organoids possess comparable molecular signatures of intestinal crypts including the expression of intestinal stem cell genes. Thus, the invention also provides a colonic organoid having the molecular signature described above for crypt-villus organoids. Organoids cultured in-vitro clearly exhibit a similar expression profile to freshly isolated small intestinal crypts and express known stem cell markers.

In some embodiments, the mRNA encoding one or more genes (e.g., 1, 2, 3, 4, 5, 6, 7, 8, 9, 10, 11, 12, 13, 14, 15, 16, 17, 18, 19, 20, 21, 22, 23, 24 or 25) listed in FIG. 48 (for example, all of the genes shaded in FIG. 48) as being upregulated in crypt-villus organoids or colon organoids respectively is upregulated in a crypt-villus organoid or colon organoid of the invention compared to a freshly isolated small intestinal villi, as determined by microarray. In some embodiments, the mRNA encoding one or more (e.g., 1, 2, 3, 4, 5, 6, 7, 8, 9, 10, 11, 12, 13, 14, 15, 16, 17, 18, 19, 20, 21, 22, 23, 24 or 25) genes listed in FIG. 48 (for example all of the genes shaded in FIG. 48) as being downregulated in crypt-villus organoids or colon organoids respectively is downregulated in a crypt-villus organoid or colon organoid of the invention compared to a freshly isolated small intestinal villi, as determined by microarray. In some embodiments, the fold upregulation or downregulation is as indicated in FIG. 48 +/−25%, for example, +/−20%, +/−15%, +/−10%, +/−5%, +/−3% or approximately as quoted in FIG. 48. For example, a crypt-villus organoid of the invention may have ADORA2B upregulated 9.54 fold +/−25% compared to freshly isolated small investinal villi. The same applies, mutatis mutandis, to the other genes listed in FIG. 48.

In some embodiments, the crypt villus organoids show natural expression of Lgr5. In some embodiments, the crypt villus organoids show natural expression of at least Lgr5 and one or more (for example 1, 2, 3, 4, 5, 6, 7, 8, 9, 10, 11, 12, 13, 14, 15, 16) or all of stem cell markers from the group consisting of: CK19, Nestin, Somatostatin, CXCR4$^+$, CD133$^+$, DCAMKL-1, CD44, Sord, Sox9, CD44, Prss23, Sp5, Hnf1α, Hnf4a, Sox9, KRT7 and KRT19. In addition or alternatively, crypt-villus organoids may be characterized by expression of one or more or all (for example 1 or 2) of: Sord and/or Prss23. In addition or alternatively, crypt-villus organoids may be characterized by expression of CD44 and/or Sox9. In another embodiment, the crypt-villus organoids show expression of one or more (for example 1, 2, 3, 4, 5, 6, 7, 8, 9) or all of the markers from the group consisting of: lgr5, lgr4, epcam (tacstd1), Cd44, Tnfrsf19, Sox9, Sp5, Cd24a, Prom1, and Cdca7.

In some embodiments, a crypt villus organoid comprises Paneth cells expressing lysozyme.

Colon Organoids

In some embodiments, a colon organoid contains enteroendocrine cells (e.g., as detectable using chromagranin A stain), goblet cells (as detectable using mucin 2 stain). In some embodiments, less than 10% of the cells in the colon organoid are enteroendocrine cells (e.g., 0.01-5%, 0.1-3%). In some embodiments, less than 30% of the cells in the colon organoid are goblet cells (e.g., 1-25%, 1-15%, 5-10%). In some embodiments, the distribution of the enteroendocrine cells and/or the goblet cells is as shown in the FIG. 1d.

In some embodiments, a colon organoid contains mature enterocytes (e.g., as visualized by alkaline phosphatise staining). In some embodiments, less than 10% of the cells in the colon organoid are mature enterocytes (e.g., less than 5%, less than 3%, 0.01-5%, 0.1-3%, 0.1-5%).

In preferred embodiments, a colon organoid does not comprise Paneth cells because there are no Paneth cells in an naturally occurring in vivo colon.

In some embodiments, the colon organoids show natural expression of Lgr5.

In some embodiments, a colon organoid expresses one or more (e.g., 1, 2, 3 or 4) of Villin1, Alpi, ChgA and Muc2. In some embodiments, the relative amount of Villin1 mRNA expressed by a colon organoid of the invention compared to a freshly isolated colon crypt is at least 3% (e.g., at least 5%, at least 8%, at least 10%), for example between 5-15%. In some embodiments, the relative amount of Alpi mRNA expressed by a colon organoid of the invention compared to a freshly isolated colon crypt is at least 0.5% (e.g., at least 1%, at least 2%), for example, between 0.5-5%. In some embodiments, the relative amount of ChgA mRNA expressed by a colon organoid of the invention compared to a freshly isolated colon crypt is at least 15% (e.g., at least 20%, at least 22%), for example, between 15-30%. In some embodiments, the relative amount of Muc2 mRNA expressed by a colon organoid of the invention compared to a freshly isolated colon crypt is at least 20% (e.g., at least 25%, at least 30%, at least 35%), for example, between 25-37%.

In some embodiments, a human colon organoid of the invention expresses known stem cell markers.

Pancreatic Organoids

The pancreas contains three classes of cell types: the ductal cells, the acinar cells, and the endocrine cells. The endocrine cells produce the hormones glucagon, insulin somatostatin and pancreatic polypeptide (PP), which are secreted into the blood stream and help the body regulate sugar metabolism. The acinar cells are part of the exocrine system, which manufactures digestive enzymes, and ductal cells from the pancreatic ducts, which connect the acinar cells to digestive organs. During development, Islets of Langerhans are thought to descend from progenitor endocrine cells which emerge from the pancreatic duct and after differentiation aggregate to form Islets of Langerhans. Islets of Langerhans comprise α cells, β cells, δ cells, and PP cells.

Pancreatic organoid cells may have an expression pattern that resembles ductal cell markers, such as one or more of K7, K19 and Hnf1b and/or one or more general stem cell markers such as Sox9 and/or Onecut1. This is likely to be part of their stem cell signature. Generally, fewer differentiation markers are seen. In some embodiments in which a cell is isolated from a pancreatic duct in order to generate a pancreatic organoid of the invention the cell type that gives rise to a pancreatic organoid of the invention is not a ductal cell (meaning the epithelial cells positive for keratin 7 and keratin 19 that form the ductal tube), but it is a cell attached to the pancreatic duct, meaning a cell that is located in the next layer of cells after the duct in contact with the pancreatic tissue (i.e., not facing the lumen of the duct.) Thus, in embodiments in which the cell type that gives rise to a pancreatic organoid is not a ductal cell, the pancreatic organoid will not express K7 or K19. However, such a pancreatic organoid will still preferably express one or more general stem cell progenitor markers such as Sox9.

A pancreatic organoid of the invention preferably comprises α cells, β cells, δ cells, and PP cells. In a further preferred embodiment, a pancreatic organoid comprises beta-cells. For example, a pancreatic organoid may comprise more than 1%, more than 5%, more than 10%, more than 15%, or more than 20% beta-cells. Expression of insulin may be used as a marker for beta cells. In an alternative embodiment, the pancreatic organoid comprises progenitor cell types, optionally with a ductal origin, that can give rise to differentiated cell-types upon transplantation into a human or animal. In a preferred embodiment, the progenitor cell types can give rise to insulin-secreting beta-cells upon transplantation into a human or animal. The inventors have shown that human pancreatic organoids of the invention, can be transplanted into mice and stimulate insulin-secreting cells within one month (see example 14). It can be easily understood that this could lead to revolutionary treatments for patients with diabetes and insulin-deficiencies.

In some embodiments, a pancreatic organoid of the invention may comprise ductal cells, acinar cells and endocrine cells. In some embodiments, K19 is used as a marker for ductal cells.

In some embodiments, a beta-cell exists within pancreatic islands or Islets of Langerhans. An islet generally comprises around 1500 cells in vivo, for example, 1300-1700 cells. In one embodiment, a pancreatic organoid comprises at least 0.5%, at least 1%, at least 1.5%, at least 2%, at least 3%, at least 5%, at least 10%, at least 15%, at least 20%, at least 25%, at least 30% or more Islets of Langerhans by mass. In some embodiments, the Islets of Langerhans of the pancreatic organoid are composed of approximately 65 to 90% beta cells, approximately 15 to 20% alpha-cells, approximately 3 to 10% delta cells, and approximately 1% PP cells. However, this is by no means exclusive. For example, in some embodiments, it is desirable to have many beta cells in an organoid of the invention. Alternatively, an organoid may comprise progenitor cells that may be transplanted so that they differentiate in vivo.

In some embodiments, a pancreatic organoid expresses one, two or all three of Pdx1, NRx2.2 and NRx6.1. A pancreatic organoid may express one, two, three or all four NeuroD, Pax6, Pax4 and Mafa. Pax4 serves as a marker for the presence of insulin producing cells because it is an essential transcription factor for the differentiation of insulin producing cells from endocrine progenitor cells during embryonic development. A pancreatic organoid may express Ngn3.

In some embodiments, at least one (for example 1, 2, 3, 4, 5) of the following markers can be detected in a pancreatic organoid of the invention: insulin (ins1 and/or ins2), glucagon (Gcg), somatostatin, Pdx1 and NeuroD. In some embodiments, at least one (for example 1, 2, 3, 4, 5) of the following markers can be detected in a pancreatic organoid of the invention: insulin (ins1 and/or ins2), glucagon (Gcg), somatostatin, Pdx1 and NeuroD and the following markers are not detected: ptf1a, amy2a4, Pnlip and cela1. In some embodiments, at least one (for example 1, 2, 3, 4, 5, 6, 7, 8 or 9) of the following markers can be detected in a pancreatic organoid of the invention: Ptf1a, pancreatic amylase (Amy2a4), pancreatic lipase (Pnlip), insulin (ins1 and/or ins2), glucagon (Gcg), somatostatin, chymotrypsin (cela1), Pdx1 and NeuroD.

In some embodiments, the pancreatic organoids show natural expression of Lgr5. In some embodiments, the pancreatic organoids show natural expression of at least Lgr5 and one or more (e.g., 1, 2, 3, 4, 5, 6, 7, 8, 9, 10, 11, 12, 13, 14, 15) stem cell markers selected from the group consisting of: CK19, Nestin, CXCR4+, CD133+, DCAMKL-1, CD44, Sord, Sox9, CD44, Prss23, Sp5, Hnf1α, Hnf4α, Sox9, KRT7 and KRT19, prom1, Cd24a, Lgr4, epcam. Alternatively or additionally, in some embodiments, pancreatic organoids may be characterized by natural expression of one or more (for example 1, 2, 3 or 4) of: CK19, Nestin, (insulin, glucagon) and CXCR4+.

In some embodiments, the pancreatic organoids or cells of the invention express Somatostatin, Somatostatin is a hormone expressed in differentiated delta cells and so may serve as a marker for delta cells.

Alternatively or additionally, in some embodiments, pancreatic organoids show natural expression of one or more early endocrine markers, for example at least one or more (e.g., 1, 2, 3, 4, 5 or 6) of the following early endocrine markers: Sox9, Hnf1b, Hnf6, Hnf1α, NRx2.2, NRx6.1 and Pdx1.

Alternatively or additionally, in some embodiments, pancreatic organoids show natural expression of one or more early endocrine markers, for example at least one or more (e.g., 1, 2, 3 or 4) of the following endocrine markers: Foxa2, Hnf6, Hnf1b and Sox9. In some embodiments, although the pancreatic organoids show natural expression of one or more (e.g., 1, 2, 3 or 4) of the following endocrine markers: Foxa2, Hnf6, Hnf1b and Sox9, they do not show expression of Ngn3.

Alternatively or additionally, in some embodiments, pancreatic organoids show natural expression of one or more ductal markers, for example, one or both of keratin 7 and keratin 19. In some embodiments, the pancreatic organoids show natural expression of one or more ductal markers at a significant or detectable level. Thus, in some embodiments, the pancreatic organoids have a ductal phenotype. In some embodiments, pancreatic organoids show expression of one or more (for example, 1, 2, 3, 4, 5, 6, 7, 8, 9, 10, 11, 12, 13, 14, 15) or all of the following markers, selected from the group: Hnf1A, Hnf1B, Hnf4A, HHEX, ONECUT1, ONECUT2, CDH1, FOXA2, GATA6, CEBPB, CEBPD, CEBPG, Glu1, Krt7, Krt19 and MET.

However, the pancreatic organoids may have some ductal features in combination with features of insulin-producing precursor cells. For example, they may express one or more ductal markers as shown in FIG. 50B. In some embodiments, a pancreatic organoid exhibits a gene expression profile relative to adult pancreas or liver organoids approximately as shown in FIG. 50B. For example, in some embodiments, these genes are upregulated or down regulated in pancreatic organoids compared to adult pancreas liver organoids to approximately the same fold ratio as in FIG. 50B, for example, less than +/−3%, less than +/−5%, less than +/−10%, less than +/−20%.

In some embodiments, insulin-positive cells appear from the ductal lining in the pancreatic organoids.

In some embodiments, one or more, preferably all of the following genes are upregulated in pancreas organoids compared to liver organoids: Aaas, Rps4y2, Atp2c2, Akap2, Uts2, Sox17, Agr2. For example, in some embodiments, these genes are upregulated in pancreatic organoids compared to liver organoids to approximately the same fold ratio as in FIG. 53, for example, less than +/−3%, less than +/−5%, less than +/−10%, less than +/−20%.

In one embodiment, a pancreatic organoid comprises at least $10^3$, at least $10^4$, at least $10^5$ or more cells in total. In one embodiment, a pancreatic organoid comprises more than 50%, more than 60%, more than 70% or more than 80% ductal-like endocrine progenitor cells. However, lower percentages of ductal-like endocrine progenitor cells are also envisaged.

Barrett's Esophagus (BE) Organoids

A BE organoid of the invention is Ki67+.

Preferably a BE organoid has a minimal number (e.g., less than 25%, less than 20%, less than 10%, less than 5%, less than 2%, less than 1% cells) of PAS+ and Mucin+ cells 4 days after withdrawal of Nicotinamide and SB202190 from the expansion medium to covert it to the differentiation medium.

In some embodiments, a BE organoid comprises goblet cells. In some embodiments, a Barrett's Esophagus organoid of the invention comprises Paneth cells.

In some embodiments, a Barrett's Esophagus organoid of the invention expresses lysozyme.

Gastric Organoids

In some embodiments, the gastric organoids of the invention show natural expression of Lgr5. In some embodiments, gastric organoids of the invention show natural expression of at least Lgr5 and one or more of stem cell markers from the group consisting of: CK19, Nestin, Somatostatin, $CXCR4^+$, $CD133^+$, DCAMKL-1, CD44, Sord, Sox9, CD44, Prss23, Spy, Hnf1α, Hnf4a, Sox9, KRT7 and KRT19. Alternatively or additionally, in some embodiments gastric organoids may be characterized by natural expression of one or more (for example 1, 2 or 3) of: $CD133^+$, DCAMKL-1 and CD44. Alternatively or additionally, gastric organoids may be characterized by CD44 and Sox9.

Organoid Functions

Preferably, cells and organoids generated according to the invention also possess tissue-specific functions.

Pancreatic Organoids

A pancreatic organoid preferably possesses endocrine and exocrine pancreatic functions, such as expressing one or more (for example, 1, 2 or all 3) of insulin, glucagon and somatostatin. The expression of these hormones is tightly regulated by a set of endocrine pancreas-specific transcription factors, the most important being Pdx1 and NeuroD. The exocrine pancreas is formed by acinar and ductal compartments responsible of producing the digestive enzymes amylase, pancreatic lipase and chymotrypsin, among others. The expression of these genes is also regulated by specific exocrine pancreatic genes as Ptf1a.

Pancreatic cells and organoids according to the present invention may preferably be capable of secreting insulin, for example, at a rate of between approximately 1 μg per hour per $10^6$ cells and 10 μg per hour per $10^6$ cells, for example, between 2 μg and 6 μg per hour per $10^6$ cells. The level of insulin secretion can be detected by methods well known in the art, for example, by Western Blot compared to a reference or by C-peptide Elisa. The preferred method to demonstrate that pancreatic organoids can secrete insulin is by testing production of C-peptide. Proinsulin C-peptide serves as an important linker between the A- and the B-chains of insulin and facilitates the efficient assembly, folding, and processing of insulin in the endoplasmic reticulum. Equimolar amounts of C-peptide and insulin are then stored in secretory granules of the pancreatic beta cells and both are eventually released to the portal circulation. Thus, C-peptide is a preferred marker of insulin secretion.

Thus, in one embodiment there is provided a pancreatic organoid that secretes insulin following transplantation in vivo. In some embodiments, following transplantation in vivo, the pancreatic organoid secretes insulin at a rate of at least 1 μg per hour per $10^6$ cells, for example, at least 2 μg per hour per $10^6$ cells, at least 4 μg per hour per $10^6$ cells, at least 6 μg per hour per $10^6$ cells, at least 8 μg per hour per $10^6$ cells or at least 10 μg per hour per $10^6$ cells. In some embodiments, the cells in the pancreatic organoid are not capable of secreting insulin and/or do not express insulin as a marker when cultured in vitro. However, cells from a pancreatic organoid of the present invention are preferably capable of secreting insulin in vivo when transplanted into a patient, for example, into the patient's pancreas. In some embodiments, the ability to secrete insulin may not be present immediately upon transplantation, but is present by about one month after transplantation, for example, by 6 weeks, 2 months or 3 months after transplantation.

If an enriched endocrine cell sample is obtained from a pancreatic organoid of the invention, in some embodiments, 75-85% of the cells in the enriched endocrine cell sample would be insulin-secreting cells.

Crypt-Villus Organoids

A crypt-villus organoid preferably possesses secretory and self-renewal functions. For example, a crypt-villus organoid preferably secretes mucin, enzymatic and hormonal secretions, such as lysozyme, cholecystokinin, secretin and gastric inhibitory peptide, and other glycoproteins.

Tissue Fragments

Within the context of the invention, a tissue fragment is a part of an adult tissue, preferably a human adult tissue, such as part of a human adult small intestine, colon or pancreas. Preferably an organoid as identified herein is therefore not a tissue fragment. An organoid is preferably obtained using a cell from an adult tissue, preferably an epithelial stem cell from an adult tissue, more preferably an epithelial stem cell from an adult tissue expressing Lgr5.

In an embodiment, an organoid is an organoid which is still being cultured using a method of the invention and is therefore in contact with an extracellular matrix. Preferably, an organoid is embedded in a non-mesenchymal extracellular matrix. Within the context of the invention, "in contact" means a physical or mechanical or chemical contact, which means that for separating the organoid from the extracellular matrix a force needs to be used. In some embodiments, the extracellular matrix is a gelatinous protein mixture secreted by Engelbreth-Holm-Swarm (EHS) mouse sarcoma cells, such as Matrigel (BD Biosciences). In other embodiments of the invention, organoids may be removed from culture and used for transplantation or regenerative purposes. Thus the invention provides an organoid of the invention for use in transplantation into a mammal, preferably into a human.

Survival Rate

The inventors show here, for the first time, that addition of an inhibitor of ALK4, ALK5, ALK7 or p38 kinase, to the previously described stem cell culture medium, improved culture plating efficiency by at least 50% and by more than 100% in some cases (see table 1). The inventors have also shown that including both inhibitors (an ALK inhibitor and a p38 inhibitor, e.g., A83-01 and SB-202190) in the culture medium synergistically prolongs the culture period.

Accordingly, in one embodiment of the invention, the stem cells survive for at least 3 months, preferably at least 4 months, at least 5 months, at least 6 months, at least 7 months, at least 9 months, or at least 12 months or more.

Speed of Proliferation

The speed of proliferation may be assessed in terms of the cell population doubling level. The population doubling level refers to the total number of times the cells in the population have doubled since their primary isolation in vitro. The population doubling level can be determined by cell counting. Alternatively, the speed of proliferation can be assessed by a cellular proliferation assay, for example in which specific fluorescent probes measure DNA synthesis activity by BrdU incorporation and cell proliferation state by Ki67 expression (Thermo Scientific*Cellomics, Millipore).

Further examples of cellular proliferation assays for stem cells are readily available can be found online or in journals such as Current Protocols. One example of many is: http://products.invitrogen.com/ivgn/en/US/adirect/invitrogen?cmd=catDisplayStyle&catKey=101&filterD ispName=Cellular Proliferation Assays for Stem Cells&filterType=1&OP=filter&filter=ft_1101%2Ff_494303*&_bcs_=H4-sIAAAAAAAAAH2NsQrDMAxEv0ZTsEkdKFmz-ZC70C4IjakFsGVuOfz%2FK0I6F4x284c48YJxfhffm%0ApQ7gnsMby0ke6x8fRDJMC7hV03u31E6Swh9M1-nNUWU1Qq1UFJkXgeIvvotnSbn6Lbl1yPshvQpyq%0A-DRIPfQE33RlnKQ21L vuql7CrAAAA.

The inventors have observed that using the culture media of the invention cells can expand by up to an average of 5 times a week. For example, growing a single cell for two weeks would give approximately 25 cells on average. The skilled person will understand that the average population doubling time of the stem cells of the invention may vary according to several factors, such as passage number, culture conditions etc.

In one embodiment, the average population doubling time may be 6 to 48 hours, 12 to 36 hours, 18 to 30 hours, or approximately 24 hours. For example, a stem cell population cultured using a culture medium of the invention may be expected to double approximately 4-7 times, or approximately 5 times per week.

In another embodiment, the average population doubling time is 12 to 96 hours, 24 to 72 hours, or approximately 72 hours. In another embodiment, the cell population doubles on average more than once, more than twice, more than three times, more than four times or more than five times a week.

Other Properties of Organoids of the Invention

In a preferred embodiment, an organoid could be cultured during at least 2, 3, 4, 5, 6, 7, 8, 9, 10 weeks or 1, 2, 3, 4, 5, 6 months or longer.

In another preferred embodiment, an organoid originates from a single cell, preferably expressing Lgr5, more preferably wherein the single cell comprises a nucleic acid construct comprising a nucleic acid molecule of interest.

The invention further provides an organoid, preferably comprising at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS.

The viable cells preferably possess tissue-specific functions, or characteristics of tissue-specify functions, as described above.

The inventors have also shown that organoids generated by media and methods of the present invention can be frozen and stored at −80° C. Frozen organoids can be thawed and put into culture without losing their 3D structure and integrity and without significant cell death. Therefore, in one embodiment, the invention provides frozen organoids stored at below −5° C., below −10° C., below −20° C., below −40° C., below −60° C., or below −80° C.

The cells and organoids of the present invention differ from any cells and organoids that have been made previously (WO2009/022907 and WO2010/016766) in that they have better phenotypic (better differentiation profile including goblet cell conversion upon addition of gamma secretase inhibitors for the crypt-villus organoids) and karyotypic integrity, as determined by the methods outlined above, better survival rates and faster speeds of cellular proliferation. Accordingly, an organoid of the present invention clearly represents the human intestinal, colon or pancreas epithelium, with full preservation of phenotypic and karyotypic integrity and maintenance of proliferation and differentiation Uses of Stem Cells or Organoids of the Invention In a further aspect, the invention provides the use of the expanded stem cell population or intestinal crypt-villus, organoids or pancreatic organoids according to the invention in a drug discovery screen, toxicity assay or in medicine, such as regenerative medicine.

For high-throughput purposes, the expanded stem cell population or crypt-villus, organoids or pancreatic organoids are cultured in multiwell plates such as, for example, 96-well plates or 384-well plates. Libraries of molecules are used to identify a molecule that affects the organoids. Preferred libraries comprise antibody fragment libraries, peptide phage display libraries, peptide libraries (e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one of more genes in the progeny of the stem cells. These genetic libraries comprise cDNA libraries, antisense libraries, and siRNA or other non-coding RNA libraries. The cells are preferably exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death. the expanded stem cell population or crypt-villus, organoids or pancreatic organoids can also be used to identify drugs that specifically target epithelial carcinoma cells, but not the expanded stem cell population or crypt-villus, organoids or pancreatic organoids.

The expanded stem cell population or crypt-villus, organoids or pancreatic organoids can further replace the use of cell lines such as Caco-2 cells in toxicity assays of potential novel drugs or of known or novel food supplements.

Furthermore, the expanded stem cell population or crypt-villus, organoids or pancreatic organoids can be used for culturing of a pathogen such as a norovirus which presently lacks a suitable tissue culture or animal model.

Cultures comprising expanded stem cell population or crypt-villus, organoids or pancreatic organoids are useful in regenerative medicine, for example in post-radiation and/or post-surgery repair of the intestinal epithelium, in the repair of the intestinal epithelium in patients suffering from inflammatory bowel disease such as Crohn's disease and ulcerative colitis, and in the repair of the intestinal epithelium in patients suffering from short bowel syndrome. Further use is present in the repair of the intestinal epithelium in patients with hereditary diseases of the small intestine/colon. Cultures comprising pancreatic organoids are also useful in regenerative medicine, for example as implants after resection of the pancreas or part thereof and for treatment of diabetes such as diabetes I and diabetes II.

In an alternative embodiment, the expanded epithelial stem cells are reprogrammed into related tissue fates such as, for example, pancreatic cells including pancreatic beta-cells. Thus far, it has not been possible to regenerate pancreatic cells from adult stem cells. The culturing methods of the present invention will enable analysis for factors that trans-differentiate the closely related epithelial stem cell to a pancreatic cell, including a pancreatic beta-cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a nonfunctional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment.

Since small biopsies taken from adult donors can be expanded without any apparent limit or genetic harm, the technology may serve to generate transplantable epithelium for regenerative purposes. The fact that organoids can be frozen and thawed and put into culture without losing their 3D structure and integrity and without significant cell death further adds to the applicability of organoids for transplantation purposes.

As mentioned above, the invention provides an organoid or population of cells of the invention for use in transplantation into a mammal, preferably into a human. Also provided is a method of treating a patient in need of a transplant comprising transplanting an organoid or population of cells of the invention into the patient, wherein the patient is a mammal, preferably a human.

Advantageously, the invention enables a small biopsy to be taken from an adult donor and expanded without any apparent limit or genetic harm and so the technology provided herein may serve to generate transplantable epithelium for regenerative purposes.

Significantly, the inventors have found that when human pancreatic organoids of the invention are transplanted under the peri-renal capsule in mice, these cells differentiate to form mature beta cells that secrete insulin. This is significant as it means that even if the population of cells or organoid of the invention does not secrete insulin at a detectable level whilst the cells or organoids are being cultured in vitro, these cells may be useful for transplantation into a patient for the treatment of an insulin-deficiency disorder such as diabetes.

Thus the invention comprises a method of treating an insulin-deficiency disorder such as diabetes, or a patient having a dysfunctional pancreas, comprising transplanting a pancreatic organoid of the invention or cells from a pancreatic organoid of the invention into the patient.

In some embodiments, the cells or organoid do not express or secrete insulin upon transplantation into the patient but differentiate within the patient such that they secrete insulin. For example, the ability to secrete insulin may not be detectable immediately upon transplantation, but may be present by about one month after transplantation, for example, by 6 weeks, 2 months or 3 months after transplantation.

The patient is preferably a human, but may alternatively be a non-human mammal, such as a cat, dog, horse, cow, pig, sheep, rabbit or mouse.

Thus, included within the scope of the invention are methods of treatment of a human or non-human animal patient through cellular therapy. Such cellular therapy encompasses the application of the stem cells or organoids of the invention to the patient through any appropriate means. Specifically, such methods of treatment involve the regeneration of damaged tissue. In accordance with the invention, a patient can be treated with allogeneic or autologous stem cells or organoids. "Autologous" cells are cells which originated from the same organism into which they are being re-introduced for cellular therapy, for example in order to permit tissue regeneration. However, the cells have not necessarily been isolated from the same tissue as the tissue they are being introduced into. An autologous cell does not require matching to the patient in order to overcome the problems of rejection. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection.

Generally the cells or organoids of the invention are introduced into the body of the patient by injection or implantation. Generally the cells will be directly injected into the tissue in which they are intended to act. Alternatively, the cells will be injected through the portal vein A syringe containing cells of the invention and a pharmaceutically acceptable carrier is included within the scope of the invention. A catheter attached to a syringe containing cells of the invention and a pharmaceutically acceptable carrier is included within the scope of the invention.

As discussed above, cells of the invention can be used in the regeneration of tissue. In order to achieve this function, cells may be injected or implanted directly into the damaged tissue, where they may multiply and eventually differentiate into the required cell type, in accordance with their location in the body. Alternatively, the organoid can be injected or implanted directly into the damaged tissue. Tissues that are susceptible to treatment include all damaged tissues, particularly including those which may have been damaged by disease, injury, trauma, an autoimmune reaction, or by a viral or bacterial infection. In some embodiments of the invention, the cells or organoids of the invention are used to regenerate the colon, small intestine, pancreas, esophagus or gastric system.

For example, in one embodiment, the cells or organoids of the invention are injected into a patient using a Hamilton syringe.

The skilled person will be aware what the appropriate dosage of cells or organoids of the invention will be for a particular condition to be treated.

In one embodiment the cells or organoids of the invention, either in solution, in microspheres or in microparticles of a variety of compositions, will be administered into the artery irrigating the tissue or the part of the damaged organ in need of regeneration. Generally such administration will be performed using a catheter. The catheter may be one of the large variety of balloon catheters used for angioplasty and/or cell delivery or a catheter designed for the specific purpose of delivering the cells to a particular local of the body. For certain uses, the cells or organoids may be encapsulated into microspheres made of a number of different biodegradable compounds, and with a diameter of about 15 µm. This method may allow intravascularly administered cells or organoids to remain at the site of damage, and not to go through the capillary network and into the systemic circulation in the first passage. The retention at the arterial side of the capillary network may also facilitate their translocation into the extravascular space.

In another embodiment, the cells or organoids may be retrograde injected into the vascular tree, either through a vein to deliver them to the whole body or locally into the particular vein that drains into the tissue or body part to which the cells or organoids are directed. For this embodiment many of the preparations described above may be used.

In another embodiment, the cells or organoids of the invention may be implanted into the damaged tissue adhered to a biocompatible implant. Within this embodiment, the cells may be adhered to the biocompatible implant in vitro, prior to implantation into the patient. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the cells or organoids of the invention may be embedded in a matrix, prior to implantation of the matrix into the patient. Generally, the matrix will be implanted into the damaged tissue of the patient. Examples of matrices include collagen based matrices, fibrin based matrices, laminin based matrices, fibronectin based matrices and artificial matrices. This list is provided by way of illustration only, and is not intended to be limiting.

In a further embodiment, the cells or organoids of the invention may be implanted or injected into the patient together with a matrix forming component. This may allow the cells to form a matrix following injection or implantation, ensuring that the cells or organoids remain at the appropriate location within the patient. Examples of matrix forming components include fibrin glue liquid alkyl, cyanoacrylate monomers, plasticizers, polysaccharides such as dextran, ethylene oxide-containing oligomers, block copolymers such as poloxamer and Pluronics, non-ionic surfactants such as Tween and Triton'8', and artificial matrix forming components. This list is provided by way of illustration only, and is not intended to be limiting. It will be clear to a person skilled in the art, that any combination of one or more matrix forming components may be used.

In a further embodiment, the cells or organoids of the invention may be contained within a microsphere. Within this embodiment, the cells may be encapsulated within the centre of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

In a further embodiment, the cells or organoids of the invention may be adhered to a medical device intended for implantation. Examples of such medical devices include stents, pins, stitches, splits, pacemakers, prosthetic joints, artificial skin, and rods. This list is provided by way of illustration only, and is not intended to be limiting. It will be clear to a person skilled in the art, that the cells may be adhered to the medical device by a variety of methods. For example, the cells or organoids may be adhered to the medical device using fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

Barrett's Esophagus

Barrett's Esophagus is a disease marked by the presence of columnar epithelium in the lower esophagus, replacing the normal squamous cell epithelium as a result of metaplasia. The histological hallmark of Barrett's esophagus is the presence of intestinal goblet cells in the esophagus. Exploiting the similarity between Barrett's Esophagus and the intestinal epithelium, the inventors showed that Barrett's Esophagus epithelium may be maintained for up to 1 month. Thus, a Barrett's Esophagus organoid is an example of an organoid of the invention. In some embodiments, a Barrett's Esophagus organoid has a budding structure. In some embodiments, a Barrett's Esophagus organoid has a cystic structure. In some embodiments, a Barrett's Esophagus organoid of the invention comprises Paneth cells. In some embodiments, a Barrett's Esophagus organoid of the invention expresses lysozyme.

In some embodiments, Barrett's Esophagus organoids express Ki67 and have a minimal number, preferably less than 10%, less than 5% or less than 1% PAS-positive cells and Mucin-positive cells. In some embodiments, the Barrett's Esophagus organoids comprise lysozyme-positive Paneth cells.

The invention also provides a liver organoid. The present application describes the first time that liver organoids have been grown ex vivo.

The liver organoid may be obtained by culturing a single Lgr5+ stem cell, a population of cells comprising at least one Lgr5+ stem cell, and/or a liver fragment. Herein, where "cells in/of the culture medium" are referred to, the meaning includes a single Lgr5+ stem cell, a population of cells comprising at least one Lgr5+ stem cell, and/or a liver fragment.

In contrast to mature hepatocytes, which grow to confluence for a short period of time, before dying, liver epithelial stem cells isolated according to the invention are self-renewing and grow indefinitely. It has been found that the self-renewing population of cells are those which are capable of expressing Lgr5 on their surface. Lgr5 negative cells do not self-renew. The term "self-renewing" should be understood to represent the capacity of a cell to reproduce itself whilst maintaining the original proliferation and differentiation properties of cells of the invention. Such cells proliferate by dividing to form clones, which further divide into clones and therefore expand the size of the cell population without the need for external intervention, without evolving into cells with a more restricted differentiation potential.

In another preferred method, a liver organoid originates from one single cell, preferably a cell expressing Lgr5, more preferably wherein the single cell comprises a nucleic acid construct comprising a nucleic acid molecule of interest. The cell may also express liver-specific markers such as Hnf1α, and Hnf4.

The isolation of certain cell types expressing Lgr5 has already been described previously (see, for example, WO2009/022907 and WO2010/016766). However, liver specific stem cells expressing Lgr5 of the type disclosed herein have not previously been described. Accordingly, the invention provides a population of adult stem cells characterized by natural expression of at least Lgr5 and one or more of the following markers Hnf1α, Hnf4a, Sox9, KRT7 and KRT19 at a significant level. This cell population also expresses markers of progenitor populations common to the small intestine and stomach, such as Cd44 and Sox9 (Barker & Huch et al. *Cell stem cell* 2010). These are highly expressed in the stem cells according to the invention, but are not expressed in adult liver, reinforcing the self-renewal capacity of the liver cultures described herein. Cells according to this aspect of the invention may also up-regulate Wnt target genes, including for example, MMP7, Sp5 and Tnfrs19. This provides strong evidence of the requirement for an active and robust canonical Wnt signaling activity to maintain the self renewing capacity of these cultures.

This stem cell population can also be characterized by a lack of natural expression of certain markers at any significant level, many of which are associated with cellular differentiation. Specifically, the cells of the isolated adult stem cell population do not naturally express one or more of Cd11b, CD13, CD14, AFP, Pdx1, any CYP member (e.g., CYP3A11, CYP 11A1) at a significant level. As defined herein, these markers are to be negative markers.

The term "expressed" is used to describe the presence of a marker within a cell. In order to be considered as being expressed, a marker must be present at a detectable level. By "detectable level" is meant that the marker can be detected using one of the standard laboratory methodologies such as PCR, blotting or FACS analysis. A gene is considered to be expressed by a cell of the population of the invention if expression can be reasonably detected after 30 PCR cycles, which corresponds to an expression level in the cell of at least about 100 copies per cell. The terms "express" and "expression" have corresponding meanings. At an expression level below this threshold, a marker is considered not to be expressed. The comparison between the expression level of a marker in a cell of the invention, and the expression level of the same marker in another cell, such as for example an embryonic stem cell, may preferably be conducted by comparing the two cell types that have been isolated from the same species. Preferably this species is a mammal, and more preferably this species is human. Such comparison may conveniently be conducted using a reverse transcriptase polymerase chain reaction (RT-PCR) experiment.

Any one of a number of physical methods of separation known in the art may be used to select the cells of this aspect of the invention and distinguish these from other cell types. Such physical methods may involve FACS and various immuno-affinity methods based upon makers specifically expressed by the cells of the invention. As described above, Lgr5, Hnf1α and Hnf4 are 3 of the cell markers expressed at high levels in the cells of the invention. Therefore, by way of illustration only, the cells of the invention may be isolated by a number of physical methods of separation, which rely on the presence of these markers.

In one embodiment, the cells of the invention may be isolated by FACS utilizing an antibody, for example, against one of these markers. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOR®), PE-Cy5.5, PI, PE-Alexa Fluor® 750, and PE-Cy7. This list is provided by way of example only, and is not intended to be limiting.

It will be apparent to a person skilled in the art that FACS analysis using an anti-Lgr5 antibody will provide a purified cell population. However, in some embodiments, it may be preferable to purify the cell population further by performing a further round of FACS analysis using one or more of the other identifiable markers, preferably Hnf1α and Hnf4, but others may also be used.

In another embodiment, the cells of the invention may be isolated by immuno-affinity purification, which is a separation method well known in the art. By way of illustration only, the cells of the invention may be isolated by immuno-affinity purification directed towards c-kit. As will be apparent to one skilled in the art, this method relies upon the immobilization of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilized anti-c-kit antibody, and permits the cells to be released from the column.

It will be apparent to a person skilled in the art that immuno-affinity purification using an immobilized antibody will provide a purified cell population. However, in some embodiments, it may be preferable to purify the cell population further by performing a further round of immuno-affinity purification using one or more of the other identifiable markers, for example Hnf4, and use an aliquot of the isolated clones to ascertain the expression of other relevant intracellular markers.

It will be apparent to a person skilled in the art that the sequential purification steps are not necessarily required to involve the same physical method of separation. Therefore, it will be clear that, for example, the cells may be purified through a FACS step using an anti-Lgr5 antibody, followed by an immuno-affinity purification step using a SSEA-1 affinity column. In certain embodiments, the cells may be cultured after isolation for at least about 15, at least about 20 days, at least about 25 days, or at least about 30 days. In certain aspects, the cells are expanded in culture longer to improve the homogeneity of the cell phenotype in the cell population.

Organoids of the Invention

The cells described above grow into bodies which are herein termed "organoids." Accordingly, a liver organoid obtainable by a method of the invention is a further aspect of the invention. To the best of our knowledge, this is the first time that a liver organoid has been obtained that is functional and alive after such an extended period of time (i.e., at least 7 months of culture; see examples included herein). Functionality is preferably characterized by the presence of a liver marker as defined herein and/or by the structure of the organoid as defined herein. Since the final amount of liver organoids obtained correlates with the duration of culture, the skilled person will understand that the invention is a pioneer invention and potentially opens new possibilities in for example regenerative medicine.

For example, an organoid according to the present invention may comprise a population of cells of at least $1\times10^3$ cells, at least $1\times10^4$ cells, at least $1\times10^5$ cells, at least $1\times10^6$ cells, at least $1\times10^7$ cells or more. In some embodiments, each organoid comprises between approximately $1\times10^3$ cells and $5\times10^3$ cells; generally, 10-20 organoids may be grown together in one well of a 24-well plate.

Cells and organoids according to the present invention may be non-human animal or human. The inventors have shown, for the first time, that it is possible to grow and maintain both animal and human liver organoids in vitro, using the culture media and methods of the invention.

Illustrative examples of organoids generated according to the invention are given in the accompanying figures. It can be seen that organoids according to the invention may possess a cystic structure, with on the outside, a layer of cells with at least one bud and a central lumen. The organoids in the outside of the matrigel tend to be larger than the organoids in the center of the matrigel, perhaps because they have better access to the necessary growth factors. Structurally, organoids according to the invention are often elongated in shape. They may include one or more budding structure—a single cell epithelial layer which has a structure not unlike a bile duct. Under confocal microscopy, the structures may stain positive for keratin. They may include cells with polarized nuclei and small cytoplasm. The organoids may have a section which is formed of multiple layers; such cells often tend to have their nuclei more central to the cells, i.e., not polarized. The cells in the multilayer section may organise themselves to include a gap, or lumen between the cells.

A liver organoid preferably comprises a hepatocyte and a cholangiocyte cell, more preferably wherein at least one of the following markers could be detected: at least one hepatocyte marker such as albumin, transthyretrin, B-1 integrin and Glutamine synthetase and/or at least one of CYP3A11, FAH, tbx3, TAT and Gck and/or at least one cholangiocyte maker such as Keratin 7 and 19. The skilled person knows how to detect each of these markers (i.e., RT-PCR and/or immunohistochemistry). Preferably the expression of each of these markers is assessed as carried out in the experimental part. Each of these markers is usually expressed after at least two weeks, three weeks or one month of culture using a method of the invention. Microarray analysis of the organoids in both culture conditions showed that liver organoids resemble adult liver tissue.

In some embodiments, approximately 35% of the cells in a liver organoid express a hepatocyte surface marker, for example, 25-45%, 30-40%, 33-37%, 35% or less, or 15-35% of cells.

Preferably, cells and organoids generated according to the invention also possess hepatocyte functions, such as expressing or staining positive for the mature hepatic markers albumin, B-1 integrin, CK-8, CK-18, transthyretin (TTR), glucose 6P, Met, Glutamine synthase (Glu1), transferrin, Fand1, Fand2a, K7, K19 and cytochrome P450 isoforms 3A13 (CYP3A13), 51 (CYP51) 2D10 (CYP2D10), 2j6 (CYP2j6), 39A1 (CYP39A1), 4A10 (CYP4A10), 4F13 (CYP4F13) 4F16 (CYP4F16), CYP4B1 and 20A1 (CYP20A1). Also, embryonic liver gene AFP is in some embodiments not detected in neither of both culture conditions, as in adult liver. In some embodiments, the expression of alpha fetal protein is just above the background gene expression.

Also, the well known liver transcription factors as HNF1a, HNF1b and HNF4a are highly expressed in both conditions.

Since liver and pancreas are closely related organs, we investigated whether our liver cultures also expressed pancreas-specific genes. The pancreas is functionally divided into endocrine and exocrine pancreas. The endocrine pancreas is mainly characterized for expressing insulin, glucagon and somatostatin. The expression of these hormones is tightly regulated by a set of endocrine pancreas-specific transcription factors, the most important being Pdx1 and NeuroD. The exocrine pancreas is formed by acinar and ductal compartments responsible of producing the digestive enzymes amylase, pancreatic lipase and chymotrypsin, among others. The expression of these genes is also regulated by specific exocrine pancreatic genes as Ptf1.

The pancreas specific genes Ptf1a, pancreatic amylase (Amy2a4), pancreatic lipase (Pnlip), insulin (ins1 and ins2), glucagon (Gcg), chymotrypsin (cela1), Pdx1 and NeuroD were absent in the liver cultures here described.

In some embodiments, one or more or all of the following genes are expressed in the liver organoids at a similar level to the corresponding gene in adult liver hepatocytes: Agp1, Bmp2, Apo3, Apo17a, Sord, C3, Ppara, Pparg, tbx3, lgf1, ll17rb, ll1b, Tgfbi, Apoa1, Apoa4, Apob, Cyp26b1, Cyp27a1, Cyp2b13, Cyp2b9, Cyp2c37, Cyp2f2, Cyp2g1, Cyp2j13, Cyp3a11, Cyp4a10 and Cypf14. For example, see FIG. 69A.

In some embodiments, one or more of the following genes is expressed in the liver organoids at a similarly shut down level compared to the corresponding gene in adult liver hepatocytes: Ccl2, Osmr, Icam1 and Cxcl2.

In some embodiments, one or both of the following genes is differentially expressed in both a liver organoid and newborn liver: mKi67 and cdkn3.

In some embodiments, one, two or all of the following genes are expressed at a similar level in a liver organoid and a newborn liver: cyp2j6, olfm4 and Lefty 1. For example, see FIG. 69B.

In some embodiments, a liver organoid of the invention has a ductal phenotype when cultured in expansion medium of the invention (e.g., EM1 or EM2).

In some embodiments, a liver organoid of the invention expresses adult liver markers when cultured in a differentiation medium of the invention.

In one embodiment, a liver organoid of the invention has a gene expression profile as shown in FIG. 69C.

In a particularly preferred embodiment, a mouse liver cell population or organoid of the invention has the gene expression profile as shown in FIG. 71. For example, in one preferred embodiment, a mouse liver cell population or organoid of the invention:

a) expresses at least one (e.g., 1, 2, 3, 4, 5, 6, 7, 8, 9, 10, 11), preferably all of the following stem cell markers: lgr5, lgr4, epcam, Cd44, Tnfrsf19, Sox9, Spy, Cd24a, Prom1, Cdca7 and Elf3; and/or b) does not express the following stem cell marker: lgr6; and/or c) expresses at least one (e.g., 1, 2, 3, 4, 5, 6, 7, 8, 9, 10, 11, 12, 13, 14, 15, 16, 17, 18, 19), preferably all of the following hepatocyte or cholangiocyte markers when grown in expansion medium of the invention: Hnf1a, Hnf1, Hnf4a, Hhex, Onecut1, Onecut2, Prox1, Cdh1Foxa2, Gata6, Foxm1, Cebpa, Cebpb, Cebpd, Cebpg, Glu1, Krt7, Krt19 and Met; and/or d) does not express at least one (e.g., 1, 2, 3, 4, 5, 6, 7, 8, 9, 10, 11, 12, 13, 14, 15, 16, 17) of the following genes when grown in expansion medium of the invention: afp, Ins1, Ins2, Gcg, Ptf1a, Cela1, Cela2a, Cela3b, Neurod1, Neurod2, Neurog1, Neurog2, Neurog3, Amy2a4, Igf1r, Igf2 and Cd34; and/or e) expresses at least one (e.g., 1, 2 or 3) of the following reprogramming genes: Klf4, Myc and Pou5f1 and/or f) does not express the following reprogramming gene: Sox2.

wherein the expression of the genes is preferably detected by measuring expression at the mRNA level, for example, using a microarray.

More preferably a mouse liver cell population or organoid of the invention has all of features a) to above.

In some embodiments, the gene expression profile described above for a mouse cell population or organoid of the invention is for a mouse cell population or organoid cultured in expansion medium of the invention.

In some embodiments, there is provided a human liver cell population or organoid of the invention that has the gene expression signature shown in FIG. 72. For example, a human liver cell population or organoid cultured in EM1 of the invention preferably expresses the genes indicated in FIG. 72 as being expressed in EM1 cell culture medium. For example, a human liver cell population or organoid cultured in EM2 of the invention preferably expresses the genes indicated in FIG. 72 as being expressed in EM2 cell culture medium. For example, a human liver cell population or organoid cultured in DM of the invention preferably expresses the genes indicated in FIG. 72 as being expressed in DM cell culture medium.

For example, in one preferred embodiment, a human liver cell population or organoid of the invention:

a) expresses at least one (e.g., 1, 2, 3, 4, 5, 6, 7, 8, 9), preferably all of the following stem cell signature genes: LGR4, TACSTD1/Epcam, CD44, SOX9, SP5, CD24, PROM1, CDCA7 and ELF3; and/or b) expresses at least one (e.g., 1, 2, 3, 4), preferably all of the following reprogramming genes: KLF4, MYC, POU5F1 and SOX2; and/or c) expresses at least one (e.g., 1, 2, 3, 4, 5, 6, 7, 8, 9, 10, 11, 12, 13, 14, 15, 16, 17, 18, 19), preferably all of the following hepatocyte/cholangiocyte specific genes: HNF1A, HNF1B, HNF4A, HHEX, ONECUT1, ONECUT2, PROX1, CDH1, FOXA2, GATA6, FOXM1, CEBPA, CEBPB, CEBPD, CEBPG, GLUL, KRT7, KRT19 and MET; and/or d) does not express at least one (e.g., 1, 2, 3, 4, 5, 6), preferably all of the following hepatocyte/cholangiocyte specific genes: NEUROG2, IGF1R and CD34, AFP, GCG and PTF1A, for example, it does not express NEUROG2, IGF1R and CD34; and/or e) expresses at least one (e.g., 1, 2, 3, 4, 5, 6, 7, 8, 9, 10, 11, 12, 13, 14, 15, 16, 17, 18), preferably all of the following hepatocyte specific genes: TTR, ALB, FAH, TAT, CYP3A7, APOA1, HMGCS1, PPARG, CYP2B6, CYP2C18, CYP2C9, CYP2J2, CYP3A4, CYP3A5, CYP3A7, CYP4F8, CYP4V2 and SCARB1;

wherein the expression of the genes is preferably detected by measuring expression at the mRNA level, for example, using a microarray.

More preferably a human liver cell population or organoid of the invention has all of features a) to e) above.

In some embodiments, the genes in a human liver cell population or organoid of the invention are upregulated or downregulated relative to expression of a reference RNA as shown in FIG. 72. Preferably, the reference RNA is Universal Human Reference RNA (Stratagene, Catalog #740000). In some embodiments, a gene is upregulated or downregulated relative to the reference RNA if it is also shown in FIG. 72 as being upregulated or downregulated relative to the reference RNA but the extent of upregulation or downregulation need not be the same. In other embodiments, the extent of upregulation or downregulation is +/−35%, +/−30%, +/−25%, +/−20%, +/−20%, +/−15%, +/−10%, +/−5%, +/−3 or approximately the same as shown in FIG. 72. In other embodiments, the absolute level of expression of the genes in a human organoid of the invention is +/−35%, +/−30%, +/−25%, +/−20%, +/−15%, +/−10%, +/−5%, +/−3% or approximately the same as shown in FIG. 72.

The human liver cell population or organoids of the invention also preferably express Lgr5 and/or Tnfrsf19, preferably both. In some embodiments, the human liver cell population or organoids, when cultured in expansion medium of the invention express Lgr5 and/or Tnfrsf19, preferably both. Preferably, expression of Lgr5 and/or Tnfrsfr19 is detected by RT PCR. In some embodiments, Lgr5 and/or Tnfrsf19 are present at much lower levels of expression in organoids or cells when cultured in the differentiation medium compared to their level of expression organoids or cells when cultured in the expansion medium (for example at least 2-fold, at least 3-fold, at least 4-fold, at least 5-fold, at least 10-fold, at least 15-fold lower).

Cells and organoids according to the present invention may preferably be capable of secreting albumin, for example, at a rate of between approximately 1 µg per hour per $10^6$ cells and 10 µg per hour per $10^6$ cells, preferably between 2 µg and 6 µg per hour per $10^6$ cells.

Furthermore, such cells and organoids may secrete urea. For example, in a 35 mm dish of cells, the activity of urea synthesis may be between 1 µg and 50 µg in 48 hours, preferably between 5 µg and 30 µg.

Cells and organoids according to the invention may show visible glycogen stores, for example, when stained. The capacity for cells and organoids according to the invention to synthesize glycogen actively can be tested by switching the culture media from low-glucose differentiation media to high-glucose DMEM supplemented with 10% FBS and 0.2 µM dexamethasone for two days.

Cells and organoids according to the invention may possess inducible cytochrome P450 activity (e.g., CYP1A). Such activity may be tested, for example, using an ethoxy-resorufin-O-deethylase (EROD) assay (Cancer Res, 2001, 61: 8164-8170). For example, cells or organoids may be exposed to a P450 substrate such as 3-methylcholanthrene and the levels of EROD activity compared to control cells.

Morphologically, the cells appear hepatocyte-like.

A preferred liver organoid comprises or consists of a cystic structure with on the outside a layer of cells with buds and a central lumen as depicted in FIG. 55. This liver organoid may have one or more (e.g., 2, 3, or all 4) of the following characteristics: (a) having a cell density of >5×10$^5$ cells/cm$^3$, preferably >10×10$^5$ cells/cm$^3$; (b) having a thickness equivalent to 2-30 layers of cells, preferably a thickness equivalent to 2-15 layers of cells; (c) the cells mutually contact in three dimensions, (d) demonstrate a function inherent to healthy liver tissue, (e) have an elongated shape, with 2 defined domains, i.e., a single layered epithelial domain where highly polarized cells are detected and keratin markers are expressed (this domain resembles the bile duct domain) and the other domain constitutes the main body of the organoid and is formed by a multilayered epithelia with non-polarized cells wherein albumin expression may be detected. It is clear to the skilled person that such a liver organoid is preferably not a liver fragment and/or does not comprise a blood vessel, and/or does not comprise a liver lobule or a bile duct.

Within the context of the invention, a liver fragment is a part of an adult liver, preferably a human adult liver. Preferably a liver organoid as identified herein is therefore not a liver fragment. A liver organoid is preferably obtained using a cell from an adult liver, preferably an epithelial stem cell from an adult liver, more preferably an epithelial stem cell from an adult liver expressing Lgr5.

In some embodiments, a liver organoid comprises cells that express Lgr5. For example, in some embodiments, at least 2%, more preferably at least 5%, at least 10%, at least 20%, at least 30%, at least 40%, at least 50%, at least 60%, at least 70%, at least 80%, at least 90%, at least 95% of the cells in the liver organoid express Lgr5. Similarly, the invention provides a cell or a population of cells which express Lgr5, wherein the cells are obtained from a liver organoid of the invention. The progeny of such cells is also encompassed by the invention.

In an embodiment, a liver organoid is a liver organoid which is still being cultured using a method of the invention and is therefore in contact with an extracellular matrix. Preferably, a liver organoid is embedded in a non-mesenchymal extracellular matrix. Within the context of the invention, "in contact" means a physical or mechanical or chemical contact, which means that for separating the liver organoid from the extracellular matrix a force needs to be used.

In a preferred embodiment, a liver organoid could be cultured during at least 2, 3, 4, 5, 6, 7, 8, 9, 10 weeks or 1, 2, 3, 4, 5, 6, 7, 8, 9, 10 months or longer.

In another preferred embodiment, a liver organoid originates from a single cell, preferably expressing Lgr5, more preferably wherein the single cell comprises a nucleic acid construct comprising a nucleic acid molecule of interest.

The invention further provides a liver organoid, preferably comprising at least 50% viable cells, more preferred at least 60% viable cells, more preferred at least 70% viable cells, more preferred at least 80% viable cells, more preferred at least 90% viable cells. Viability of cells may be assessed using Hoechst staining or Propidium Iodide staining in FACS.

The viable cells preferably possess hepatic functions, or characteristics of hepatocytes, as described above.

Uses of Cells and Organoids of the Invention

In a further aspect, the invention provides the use of a liver cell or organoid according to the invention as described above in a drug discovery screen, toxicity assay or in regenerative medicine.

The invention furthermore provides the use of the progeny of liver organoids of the invention, in toxicity assays. Such toxicity assays may be in vitro assays using a cell derived from a liver organoid or a liver organoid or part thereof. Such progeny and liver organoids are easy to culture and more closely resemble primary epithelial cells than, for example, epithelial cell lines such as Caco-2 (ATCC HTB-37), I-407 (ATCC CCL6), and XBF (ATCC CRL 8808) which are currently used in toxicity assays. It is anticipated that toxicity results obtained with liver organoids more closely resemble results obtained in patients. A cell-based toxicity test is used for determining organ specific cytotoxicity. Compounds that are tested in the test comprise cancer chemopreventive agents, environmental chemicals, food supplements, and potential toxicants. The cells are exposed to multiple concentrations of a test agent for certain period of time. The concentration ranges for test agents in the assay are determined in a preliminary assay using an exposure of five days and log dilutions from the highest soluble concentration. At the end of the exposure period, the cultures are evaluated for inhibition of growth. Data are analyzed to determine the concentration that inhibited end point by 50 percent (TC50).

For example, induction of cytochrome P450 enzymes in liver hepatocytes is a key factor that determines the efficacy and toxicity of drugs. In particular, induction of P450s is an important mechanism of troublesome drug-drug interactions, and it is also an important factor that limits drug efficacy and governs drug toxicity. Cytochrome P450 induction assays have been difficult to develop, because they require intact normal human hepatocytes. These cells have proven intractable to production in numbers sufficient to sustain mass production of high throughput assays.

For example, according to this aspect of the invention, a candidate compound may be contacted with cell or organoid as described herein, and any change to the cells or in to activity of the cells may be monitored. Examples of other non-therapeutic uses of the cells or organoids of the present invention include research of liver embryology, liver cell lineages, and differentiation pathways; gene expression studies including recombinant gene expression; mechanisms involved in liver injury and repair; research of inflammatory and infectious diseases of the liver; studies of pathogenetic mechanisms; and studies of mechanisms of liver cell transformation and aetiology of liver cancer.

For high-throughput purposes, the liver organoids are cultured in multiwell plates such as, for example, 96-well plates or 384-well plates. Libraries of molecules are used to identify a molecule that affects the organoids. Preferred libraries comprise antibody fragment libraries, peptide phage display libraries, peptide libraries (e.g., LOPAP™, Sigma Aldrich), lipid libraries (BioMol), synthetic compound libraries (e.g., LOP AC™, Sigma Aldrich) or natural compound libraries (Specs, TimTec). Furthermore, genetic libraries can be used that induce or repress the expression of one of more genes in the progeny of the adenoma cells. These genetic libraries comprise cDNA libraries, antisense libraries, and siRNA or other non-coding RNA libraries. The cells are preferably exposed to multiple concentrations of a test agent for certain period of time. At the end of the exposure period, the cultures are evaluated. The term "affecting" is used to cover any change in a cell, including, but not limited to, a reduction in, or loss of, proliferation, a morphological change, and cell death. the liver organoids can also be used to identify drugs that specifically target epithelial carcinoma cells, but not the liver organoids.

Liver organoids according to the invention can further replace the use of cell lines such as Caco-2 cells in toxicity assays of potential novel drugs or of known or novel food supplements.

Furthermore, such liver organoids can be used for culturing of a pathogen.

Cultures comprising liver organoids are useful in regenerative medicine, for example in post-radiation and/or post-surgery repair of the liver epithelium, in the repair of the epithelium in patients suffering from chronic or acute liver failure or disease. Liver diseases include, but are not limited to Hepatocellular Carcinoma, Alagille Syndrome, Alpha-1-Antitrypsin Deficiency, Autoimmune Hepatitis, Biliary Atresia, Chronic Hepatitis, Cancer of the Liver, Cirrhosis Liver Cysts Fatty Liver, Galactosemia Gilbert's Syndrome, Primary Biliary Cirrhosis, Hepatitis A, Hepatitis B, Hepatitis C, Primary Sclerosing Cholangitis, Reye's Syndrome, Sarcoidosis, Tyrosinemia, Type I Glycogen Storage Disease, Wilson's Disease, Neonatal Hepatitis, Non-alchoholic Steato-Hepatitis, Porphyria, and Hemochromatosis.

Genetic conditions that lead to liver failure could benefit from cell-based therapy in the form of partial or full cell replacement using cells cultured according to the media and/or methods of the invention. A non-limiting list of genetic conditions that lead to liver failure includes: Progressive familial intrahepatic cholestasis, Glycogen storage disease type III, Tyrosinemia, Deoxyguanosine kinase deficiency, Pyruvate carboxylase deficiency, Congenital dyserythropoietic anemia, Polycystic Liver Disease Polycystic Kidney Disease, Alpha-1 antitrypsine deficiency, Ureum cycle defects, Organic acidemiea, lysosomal storage diseases, and Fatty Acid Oxydation Disorders. Other conditions that may also benefit from cell-based therapy include Wilson's Disease and Hereditary Amyloidosis (FAP).

Other non-hepatocyte related causes of liver failure that would require a full liver transplant to reach full therapeutic effect, may still benefit from some temporary restoration of function using cell-based therapy using cells cultured according to the media and/or methods of the invention. A non-limiting list of examples of such conditions includes: Primary Biliary Cirrhosis, Primary Sclerosing Cholangitis, Aglagille syndrome, Homozygous Familial hypercholesterolemia, Hepatitis B with cirrhosis, Hepatitis C with cirrhosis, Budd-Chiari syndrome, Primary hyperoxaluria, Autoimmune Hepatitis, and Alcoholic liver disease.

The liver organoids of the invention may be used in a method of treating a hereditary disease that involves malfunctioning hepatocytes. Such diseases may be early onset or late onset. Early onset disease include metabolite related organ failure (e.g., alpha-1-antitrypsin deficiency), glycogen storage diseases (e.g., GSD II, Pompe's disease), tyrosinemia, mild DGUOK, CDA type I, Ureum cycle defects (e.g., OTC deficiency), organic academia and fatty acid oxidation disorders. Late onset diseases include primary hyperoxaluria, familial hypercholesterolemia, Wilson's disease, Hereditary Amyloidosis and Polycystic liver disease. Partial or full replacement with healthy hepatocytes arising from liver organoids of the invention may be used to restore liver function or to postpone liver failure.

The liver organoids of the invention may be used in a method of treating chronic liver failure arising due to hereditary metabolic disease or as a result of hepatocyte infection. Treatment of a hereditary metabolic disease may involve administration of genetically modified autologous liver organoids of the invention. Treatment of hepatocyte infections may involve administration of allogeneic liver organoids of the invention. In some embodiments, the liver organoids are administered over a period of 2-3 months.

The liver organoids of the invention may be used to treat acute liver failure, for example, as a result of liver intoxication which may result from use of paracetamol, medication or alcohol. In some embodiments, the therapy to restore liver function will comprise injecting hepatocyte suspension from frozen, ready to use allogenic hepatocytes obtained from organoids of the invention. The ability to freeze suitable organoids means that the organoids can be available for immediate delivery and so it is not necessary to wait for a blood transfusion.

In the case of replacement or correction of deficient liver function, it may be possible to construct a cell-matrix structure from one or more liver organoids generated according to the present invention. It is thought that only about 10% of hepatic cell mass is necessary for adequate function. This makes implantation of organoid unit compositions into children especially preferable to whole organ transplantation, due to the relatively limited availability of donors and smaller size of juvenile organs. For example, an 8-month-old child has a normal liver that weighs approximately 250 g. That child would therefore need about 25 g of tissue. An adult liver weighs-approximately 1500 g; therefore, the required implant would only be about 1.5% of the adult liver. When organoid units according to the invention are implanted, optionally attached to a polymer scaffold, proliferation in the new host will occur, and the resulting hepatic cell mass replaces the deficient host function. The inventors have shown, for the first time, that it is possible to generate mature hepatocytes from adult liver stem cells or liver tissue fragments comprising stem cells that are suitable for transplantation into non-human animals or humans. Using the first culture medium according to the invention, the inventors have demonstrated that it is possible to maintain and expand a population of liver stem cells. Using the second culture medium according to the invention, the inventors have shown that hepatoblasts can be differentiated in vivo to mature hepatocytes suitable for transplantation purposes. Hence, the inventors provide a new source of hepatocytes for liver regeneration, replacement or correction of deficient liver function.

The inventors have also demonstrated successful transplantation of the organoids, grown by methods of the present invention, into immunodeficient mice (see example 60), with transplanted organoid-derived cells generating both cholangyocytes and hepatocytes in vivo. Therefore, in one embodiment the invention provides organoids or organoid-derived cells of the invention for transplanting into human or animals.

The use of human liver organoids for transplantation purposes is advantageous over the use of fetal or adult hepatocytes for a number of reasons. Firstly, the culture methods of the invention provide unlimited expansion of cells and hence, an unlimited supply. In particular, the inventors have shown that under the correct culture conditions, that Lgr5+ cells can undergo more than 1000 divisions in vitro. Therefore, Lgr5+ cells can be extracted from the liver organoids and repassaged providing a continual self-renewing source of transplantable hepatocyte and cholangyocyte-generating cells. By contrast, fetal or adult hepatocytes are derived from donor livers which only provide a single round of transplantation. Furthermore, donor cells can only be kept alive for a few days but lose their hepatocyte properties. This means the transplants must be made as soon as the donor becomes available. Organoid-derived cells, on the other hand, retain their phenotype over multiple divisions and over prolonged periods of time meaning that they are ready and available for transplantation at any stage. This could also allow the organoid-derived cells to be used as a temporary liver treatment to extend the lifespan of patients for patients on the waiting list for liver transplants. A further advantage of the liver organoids of the invention is that they can be frozen and later be defrosted without loss of function. This enables cell banking, easy storage and rapid availability for acute use. This could be useful for example, in the preparation of an "off-the-shelf" product that might be used for the treatment of acute liver toxicity. Organoids can also be grown from cells or tissue fragments taken as small biopsies from live donors minimising any ethical objections to the treatment. The donor may even be from the patient that is to be treated, which could reduce any negative side-effects associated with transplantation of foreign cells and organs and reduce the need for immunosuppressive drugs.

Accordingly, included within the scope of the invention are methods of treatment of a human or animal patient through cellular therapy. The term "animal" here denotes all mammalian animals, preferably human patients. It also includes an individual animal in all stages of development, including embryonic and foetal stages. For example, the patient may be an adult, or the therapy may be for pediatric use (e.g., newborn, child or adolescent). Such cellular therapy encompasses the administration of cells or organoids generated according to the invention to a patient through any appropriate means. Specifically, such methods of treatment involve the regeneration of damaged tissue. The term "administration" as used herein refers to well recognized forms of administration, such as intravenous or injection, as well as to administration by transplantation, for example transplantation by surgery, grafting or transplantation of tissue engineered liver derived from cells or organoids according to the present invention. In the case of cells, systemic administration to an individual may be possible, for example, by infusion into the superior mesenteric artery, the celiac artery, the subclavian vein via the thoracic duct, infusion into the heart via the superior vena cava, or infusion into the peritoneal cavity with subsequent migration of cells via subdiaphragmatic lymphatics, or directly into liver sites via infusion into the hepatic arterial blood supply or into the portal vein.

Between $10^4$ and $10^{13}$ cells per 100 kg person may be administered per infusion. Preferably, between about 1-5×$10^4$ and 1-5×$10^7$ cells may be infused intravenously per 100 kg person. More preferably, between about 1×$10^4$ and 10×$10^6$ cells may be infused intravenously per 100 kg person. In some embodiments, a single administration of cells or organoids is provided. In other embodiments, multiple administrations are used. Multiple administrations can be provided over an initial treatment regime, for example, of 3-7 consecutive days, and then repeated at other times.

In some embodiments it is desirable to repopulate/replace 10-20% of a patient's liver with healthy hepatocytes arising from a liver organoid of the invention.

It is also possible to reconstitute a liver organoid from one single cell expressing Lgr5 as defined herein. This single cell may have been modified by introduction of a nucleic acid construct as defined herein, for example, to correct a genetic deficiency or mutation. It would also be possible to specifically ablate expression, as desired, for example, using siRNA. Potential polypeptides to be expressed could be any of those that are deficient in metabolic liver diseases, including, for example, AAT (alpha antitrypsin). For elucidating liver physiology, we might also express or inactivate genes implicated in the Wnt, EGF, FGF, BMP or notch pathway. Also, for screening of drug toxicity, the expression or inactivation of genes responsible for liver drug metabolism (for example, genes in the CYP family) would be of high interest In one embodiment, the expanded epithelial stem cells may be reprogrammed into related tissue fates such as, for example, liver cells including a hepatocyte and a cholangiocyte cell. Thus far, it has not been possible to regenerate liver cells from adult stem cells. The culturing methods of the present invention will enable analysis for factors that trans-differentiate the closely related epithelial stem cell to a liver cell, including a hepatocyte and a cholangiocyte cell.

It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a non functional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment. For example, organoid-derived cells may be genetically modified in culture before transplantation into patients.

The inventors have found that Lgr5 is not detectable in healthy liver, although residual Lgr5 may be detected. Thus, the invention further provides a method of diagnosing liver injury comprising detecting whether Lgr5 is expressed, wherein the expression of Lgr5 protein indicates liver injury. The invention also provides a method of monitoring the repair or regeneration of the liver by monitoring the expression of Lgr5 in the liver. Lgr5 expression may be detected by any suitable method, for example, flow cytometry, immunohistochemistry or by use of PCR methods.

The invention also provides a composition or cell culture vessel comprising cells and/or organoids according to any one of the aspects of the invention described above, and a culture medium according to any one of the aspects of the invention described above. For example, such a composition or cell culture vessel may comprise any number of cells or organoids cultured according to a method of the invention, in a culture medium as described above.

"Adult" means post-embryonic. With respect to the stem cells of the present invention, the term "adult stem cell" means that the stem cell is isolated from a tissue or organ of an animal at a stage of growth later than the embryonic stage.

This stem cell population can also be characterized by a lack of natural expression of certain markers at any significant level, many of which are associated with cellular differentiation. Specifically, the cells of the isolated adult stem cell population do not naturally express one or more of Cd11b, CD13, CD14, AFP, Pdx1, any CYP member (e.g., CYP3A11, CYP 11A1) at a significant level. As defined herein, these markers are to be negative markers.

Any one of a number of physical methods of separation known in the art may be used to select the cells of this aspect of the invention and distinguish these from other cell types. Such physical methods may involve FACS and various immuno-affinity methods based upon makers specifically expressed by the cells of the invention. As described above, Lgr5, Hnf1α and Hnf4 are 3 of the cell markers expressed at high levels in the cells of the invention. Therefore, by way of illustration only, the cells of the invention may be isolated by a number of physical methods of separation, which rely on the presence of these markers.

In one embodiment, the cells of the invention may be isolated by FACS utilizing an antibody, for example, against one of these markers. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOR®), PE-Cy5.5, PI, PE-Alexa Fluor® 750, and PE-Cy7. This list is provided by way of example only, and is not intended to be limiting.

It will be apparent to a person skilled in the art that FACS analysis using an anti-Lgr5 antibody will provide a purified cell population. However, in some embodiments, it may be preferable to purify the cell population further by performing a further round of FACS analysis using one or more of the other identifiable markers, preferably Hnf1α and Hnf4, but others may also be used.

In another embodiment, the cells of the invention may be isolated by immuno-affinity purification, which is a separation method well known in the art. By way of illustration only, the cells of the invention may be isolated by immuno-affinity purification directed towards c-kit. As will be apparent to one skilled in the art, this method relies upon the immobilization of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilized anti-c-kit antibody, and permits the cells to be released from the column.

It will be apparent to a person skilled in the art that immuno-affinity purification using an immobilized antibody will provide a purified cell population. However, in some embodiments, it may be preferable to purify the cell population further by performing a further round of immuno-affinity purification using one or more of the other identifiable markers, for example Hnf4, and use an aliquot of the isolated clones to ascertain the expression of other relevant intracellular markers.

It will be apparent to a person skilled in the art that the sequential purification steps are not necessarily required to involve the same physical method of separation. Therefore, it will be clear that, for example, the cells may be purified through a FACS step using an anti-Lgr5 antibody, followed by an immuno-affinity purification step using a SSEA-1 affinity column. In certain embodiments, the cells may be cultured after isolation for at least about 15, at least about 20 days, at least about 25 days, or at least about 30 days. In certain aspects, the cells are expanded in culture longer to improve the homogeneity of the cell phenotype in the cell population.

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a product as defined herein may comprise additional component(s) than the ones specifically identified, the additional component(s) not altering the unique characteristic of the invention. In addition a method as defined herein may comprise additional step(s) than the ones specifically identified, the additional step(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one." The word "about" or "approximately" when used in association with a numerical value (about 10) preferably means that the value may be the given value of 10 more or less 1% of the value.

All patent and literature references cited in the present specification are hereby incorporated by reference in their entirety.

The following examples are offered for illustrative purposes only, and are not intended to limit the scope of the present invention in any way.

DESCRIPTION OF FIGURES

FIG. 19. Paneth cells are located adjacent to Lgr5+ stem cells in the small intestines. Crypts were isolated from the small intestine of Lgr5-EGFP-ires-CreERT2 knock-in mice. Examples of representative crypts are presented here. The GFP+ cells are Lgr5+ (light grey, indicated by black arrows) and these are generally located adjacent to Paneth cells (indicated by *).

FIG. 20. In the absence of viable Paneth cells, efficiency of organoid formation is reduced. Isolated crypts were incubated with 1 uM Newport Green-DCF (Molecular probe) in PBS+ 0.1% Pluronic 127 (Sigma) for 3 min at room temperature, following by PBS wash. After this, crypts were embedded in Matrigel and cultured using the standard conditions as described above.

FIG. 30. Human pancreas fragments were freshly isolated and cultured in EM. Pictures were taken of the cultures at the indicated time points after the start of the culture.

FIG. 45. List of reagents used for organoid culture.

FIG. 46. List of reagents used for optimization of human intestinal organoid culture.

FIG. 47. List of small molecule inhibitors used for optimization of human intestinal organoids culture.

FIG. 48. List of the 25 most up- and down-regulated genes mRNA from human small intestinal organoids or colon organoids are compared with that from freshly isolated small intestinal villi by microarray. The 25 most upregulated and downregulated genes are shown. Hatched lines highlight genes which were in the top 70 most upregulated and downregulated genes in freshly isolated human small intestinal crypts vs. villi.

FIG. 49. Summary of proliferation, differentiation and apoptosis status of each organoid culture condition.

FIG. 53. Pancreatic organoid gene expression This table shows the pancreatic gene expression of the most upregulated genes when compared to liver organoids.

FIG. 60. Mouse liver organoid culture shows stable karyotyping after long-term culture. A—DIC images of liver organoids maintained in EGF (E) and R-spondin 1 (R), supplemented with FGF10, HGF and Nicotinamide (left figure, ER) or maintained in the same combination supplemented with Noggin (N) and Wnt3A conditioned media (W) (right figure, ENRW) for a period of 24 months. B—Karyotype analysis of mouse liver organoids after 8 months in culture. Normal chromosomal counts (n=40, left panel figure) and polyploidy, a typical hepatocyte feature, were found (n=80, right panel figure)

FIG. 62. Table showing the quantification of different hepatocyte and cholangiocyte specific transcription factors in cells from three different liver culture conditions and in adult liver tissue. Also shown is the expression of the key components of the Notch and TGF-beta signaling pathways. E=EFHNic, ER=ERFHNic, ENRW=ENRWFHNic.

FIG. 64. Human-derived liver cultures under ERFHNic culture conditions.

FIG. 67. Isolated duct staining for K19. Lgr5LacZ duct isolation. K19 staining confirms that the isolated and seeded structures are indeed intrahepatic ducts.

FIG. 71. Mouse liver signature genes. Table showing a) markers expressed in mouse liver stem cells; b) markers not expressed in mouse liver stem cells; c) hepatocyte and cholangiocyte markers expressed in mouse liver stem cell signature for mouse liver organoids in expansion media; d) hepatocyte and cholangiocyte markers not expressed in mouse liver stem cell signature for mouse liver organoids in expansion media; e) reprogramming genes expressed in mouse liver organoids; f) reprogramming genes not expressed in mouse liver organoids. The results were obtained using a liver microarray using the Universal Mouse Reference RNA (Strategene, Catalog #740100) as a reference RNA. If the absolute figures detected were less than 100, the gene was consider as undetected.

Figure 72:
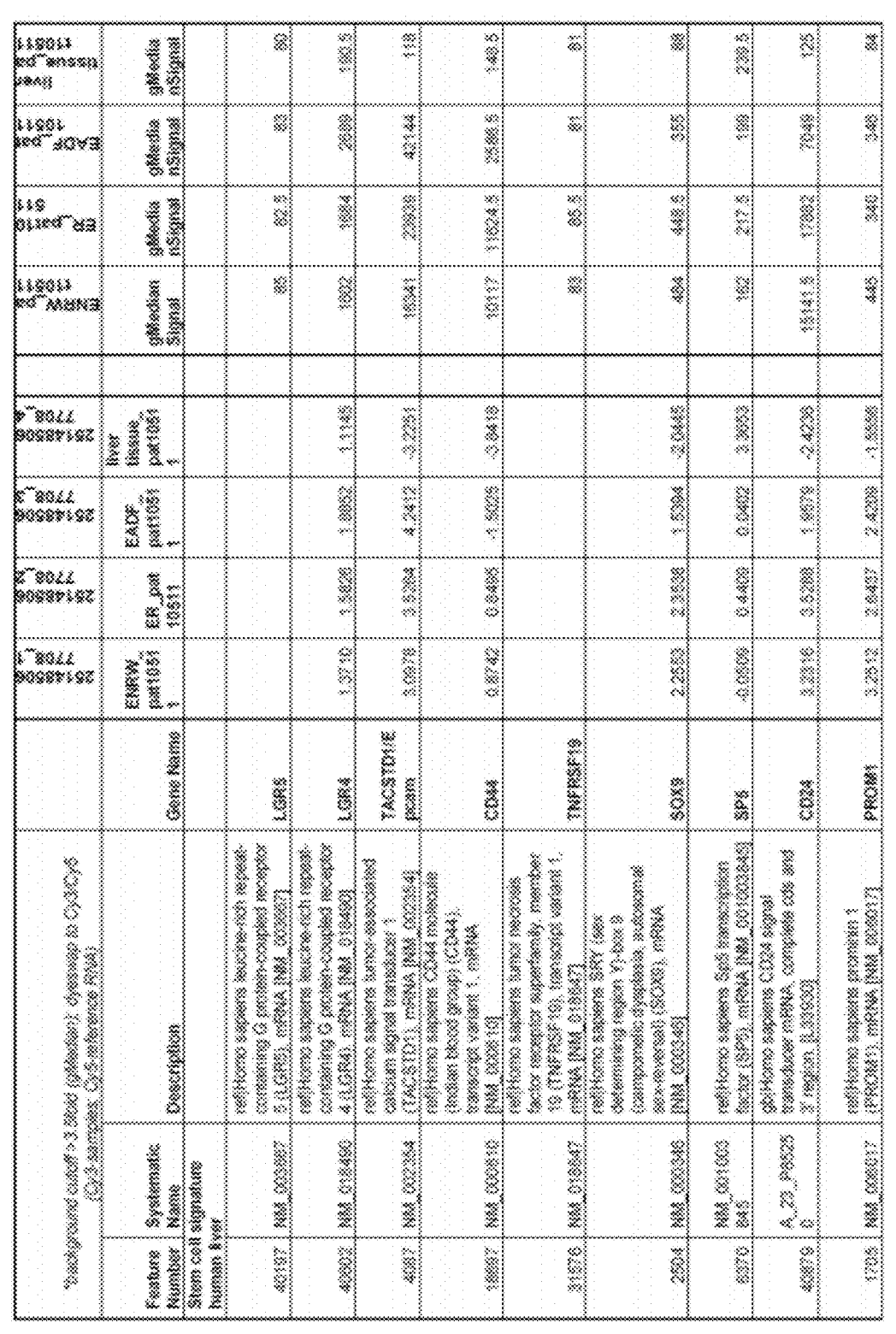
Figure 72:
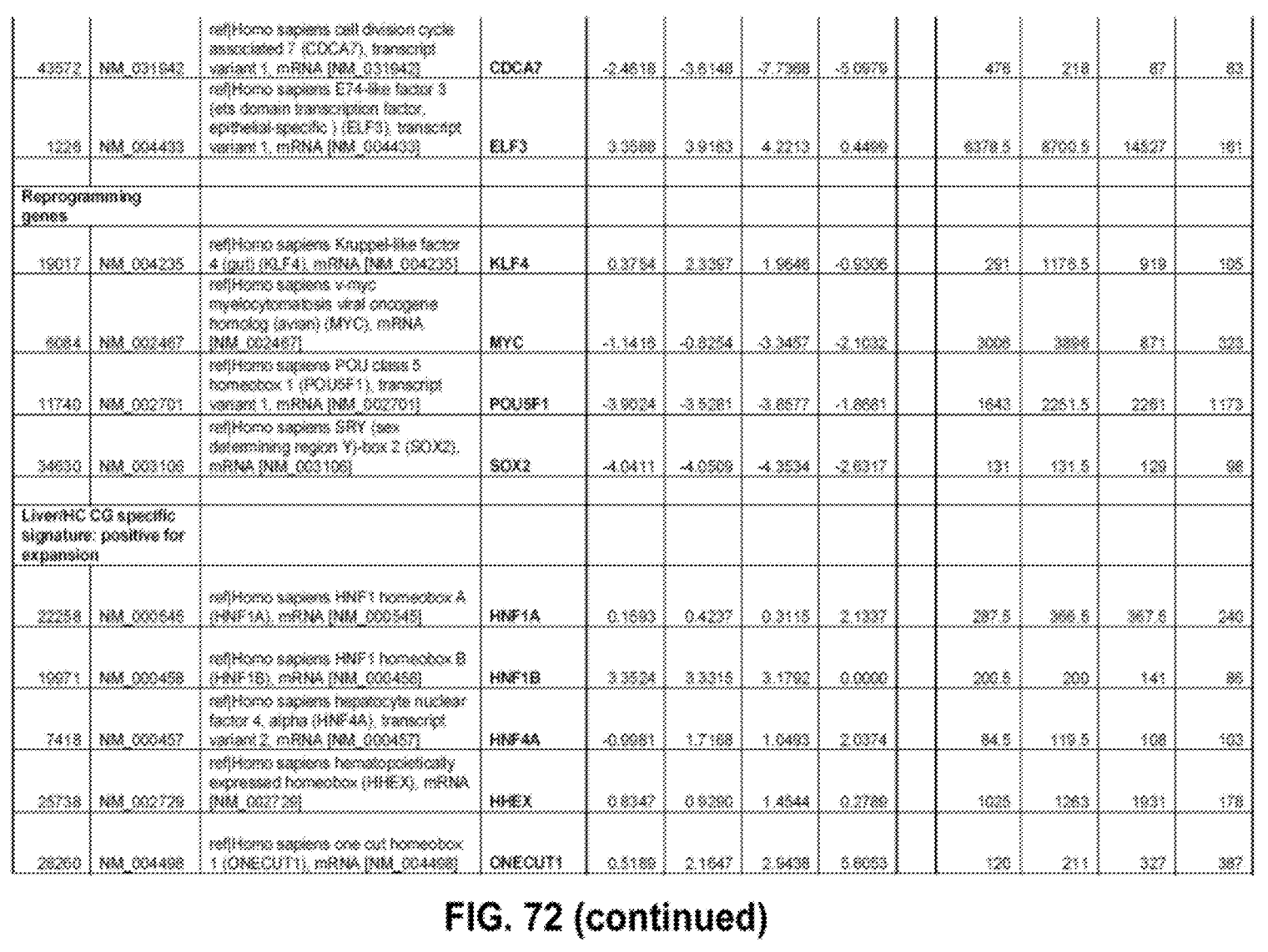
Figure 72:
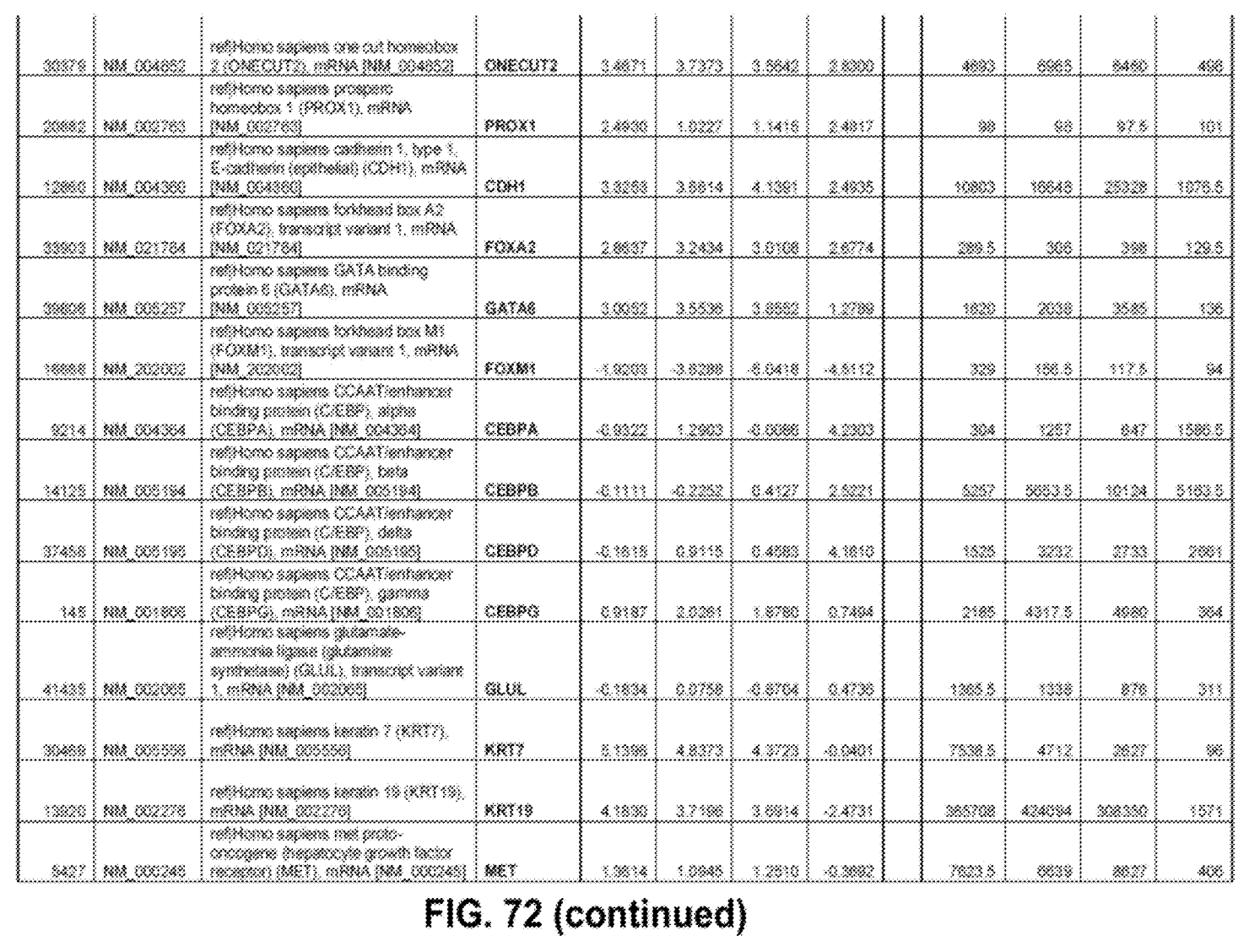
Figure 72:
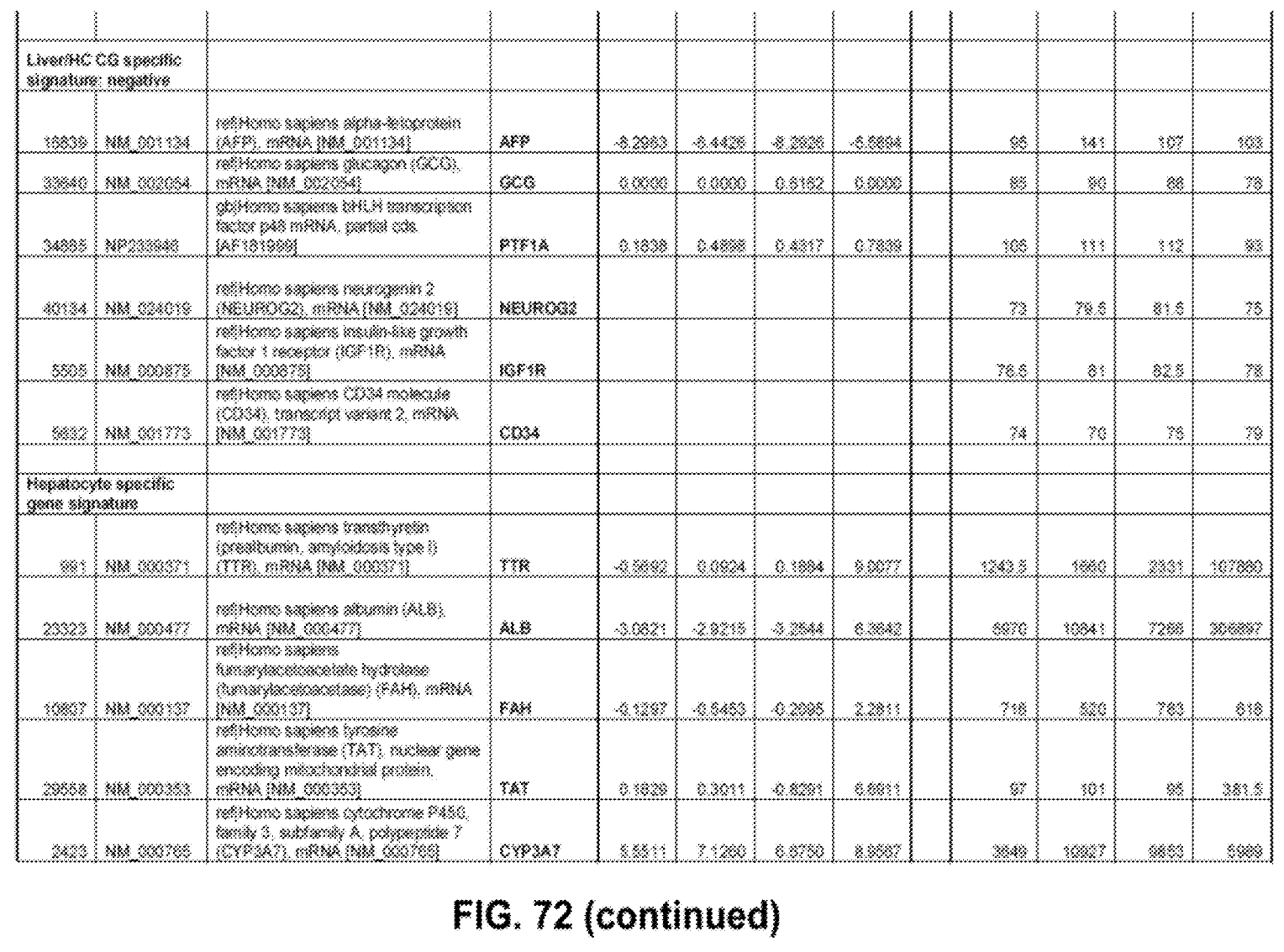
Figure 72:
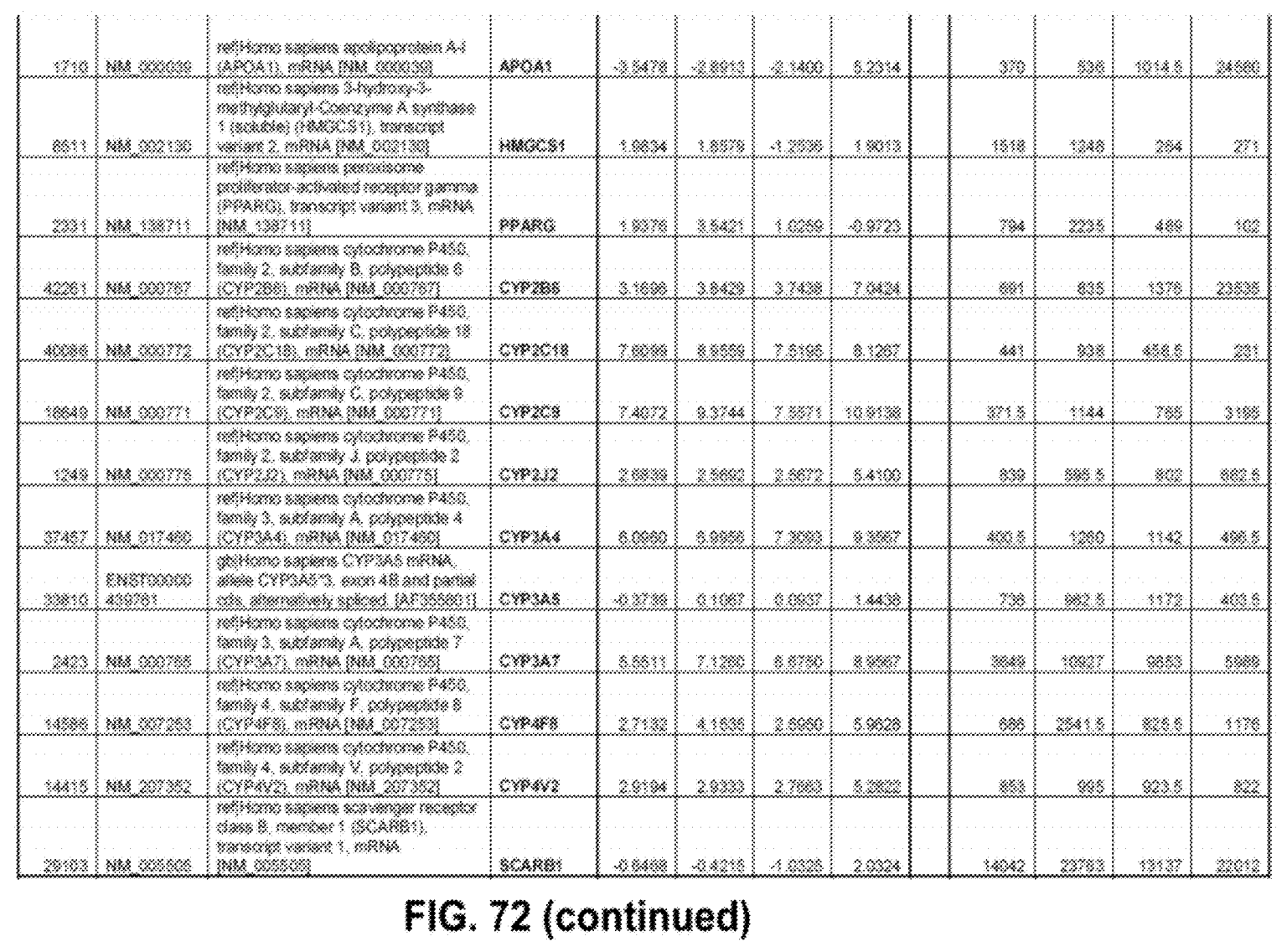

FIG. 72. Human liver signature genes. Table showing results of liver mircroarray of human organoids. From left to right, the results are shown for a) expansion medium EM1, b) expansion medium EM2, c) differentiation medium, d) adult liver. The numbers (log 2) in the left four columns are the result of a comparison between the sample and a reference (commercial) RNA sample which is used for all arrays. The relative expression of mRNA in each sample compared to the RNA present in the reference sample is shown. The reference RNA used was Universal Human Reference RNA (Stratagene, Catalog #740000). Thus, negative numbers in these columns do not relate to real expression levels it just means there is less of that RNA then in the Reference sample. The 4 columns on the right are absolute figures. If they are below 100, they are considered as undetected.

EXAMPLES

Figure 1:
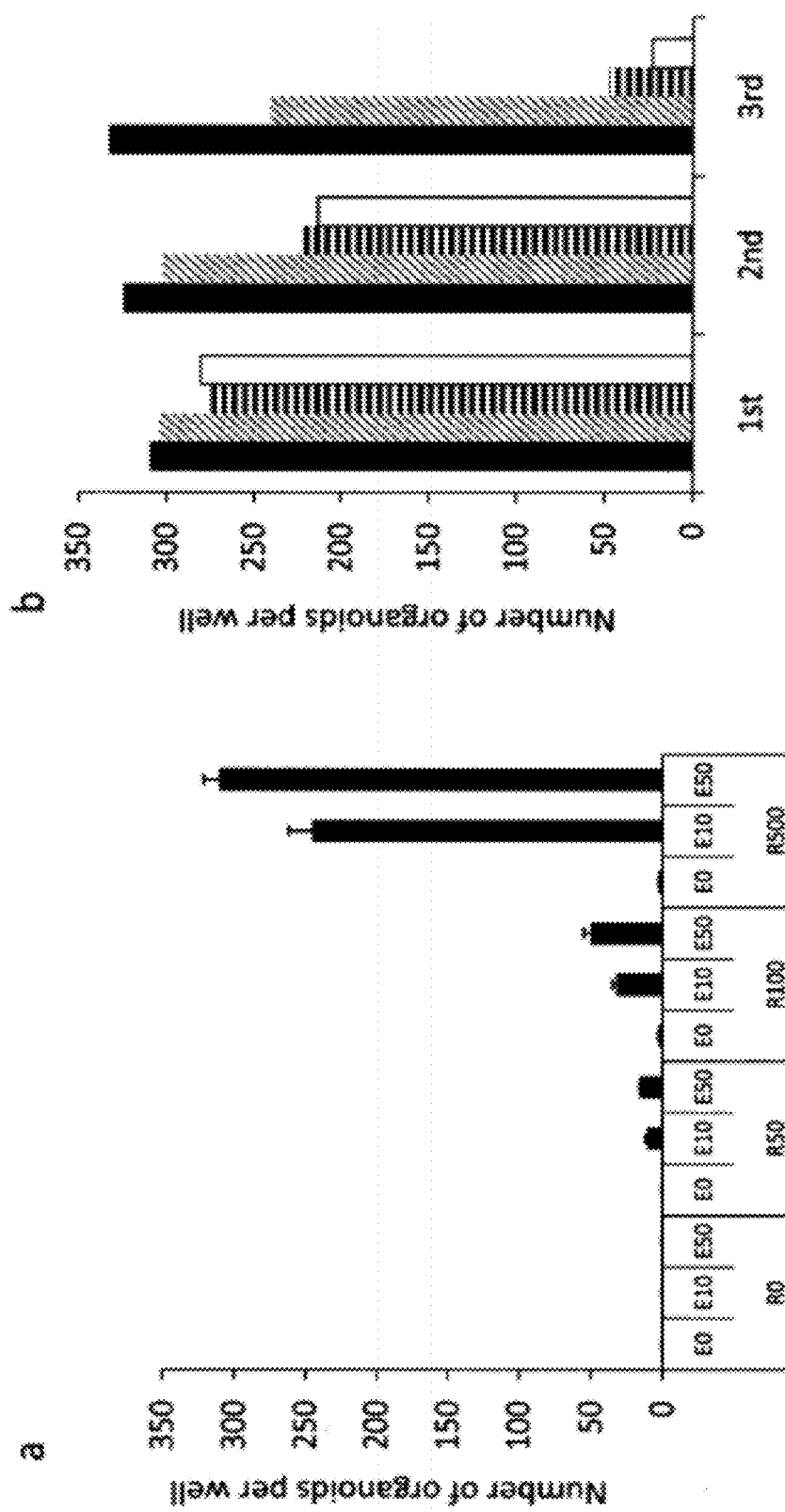
FIG. 1. Growth factor requirement of crypt culture. a: 500 crypts were seeded with EGF (E; 0-50 ng/ml) and R-spondin 1 (R: 0-500 ng/ml) in triplicate; crypt organoids were counted 7 days after seeding. b: 500 Crypts/crypt organoids were cultured with EGF (50 ng/ml) and R-spondin 1 (500 ng/ml) with the indicated amounts of Noggin and followed for 3 passages. Crypt organoids were counted at each passage. The experiment was repeated three times with comparable results.

Example 1: Culturing of Small Intestine Crypts and Villi in Vitro

Materials and Methods

Mice: Outbred mice of 6-12 weeks of age were used. Generation and genotyping of the Lgr5-EGFP-Ires-Cre-ERT2 allele[1] has been previously described[1]. Rosa26-lacZ or YFP Cre reporter mice were obtained from Jackson Labs.

Crypt isolation, cell dissociation and culture: Crypts were released from murine small intestine by incubation in 2 mM EDTA/PBS for 30 min at 4° C. Isolated crypts were counted and pelleted. 500 crypts were mixed with 50 µl Matrigel (BD Bioscience) and plated in 24-well plates. After polymerization of Matrigel, 500 µl of crypt culture medium (Advanced DMEM/F12 with growth factors (10-50 ng/ml EGF (Peprotech), 500 ng/ml R-spondin 1[11] and 100 ng/ml Noggin (Peprotech)) was added. For sorting experiments, isolated crypts were incubated in culture medium for 45 min at 37° C., following by resuspension with a glass pipette. Dissociated cells were passed through 20-µm cell strainer. GFP$^{hi}$, GFP$^{low}$ or GFP$^-$ cells were sorted by flow cytometry (MoFlo, Dako). Single viable epithelial cells were gated by forward scatter, side scatter and pulse-width parameter, and negative staining for propidium iodide. Sorted cells were collected in crypt culture medium and embedded in Matrigel including Jagged-1 peptide (Ana Spec, 1 µM) at 1 cell/well (in 96-well plate, 5 µl Matrigel). Crypt culture medium (250 µl for 48-well plate, 100 µl for 96-well plate) including Y-27632 (10 µM) was overlaid. Growth factors were added every other day and the entire medium was changed every 4 days. For passage, organoids were removed from Matrigel and mechanically dissociated into single-crypt domains, and transferred to new Matrigel. Passage was performed every 1-2 weeks with 1:5 split ratio.

Reagents; Murine recombinant EGF and Noggin were purchased from Peprotech. Human recombinant R-spondin 1[11], Y-27632 (Sigma), 4-hydroxytamoxifen (Sigma) and Edu (Invitrogen) were used for culture experiments. The following antibodies were used for immunostaining: anti-lysozyme (Dako), anti-Synaptophysin (Dako), anti-BrdU (Roche), anti-β-catenin (BD Bioscience), anti-E-cadherin (BD Bioscience), anti-Smooth muscle actin (Sigma), anti-EphB2 and B3 (R&D), anti-villin, anti-Muc2, anti-chromogranin A (Santa Cruz), anti-caspase-3 (Cell Signaling).

Crypt Isolation: Isolated small intestines were opened longitudinally, and washed with cold PBS. The tissue was chopped into around 5 mm pieces, and further washed with cold PBS. The tissue fragments were incubated in 2 mM EDTA with PBS for 30 min on ice. After removal of EDTA medium, the tissue fragments were vigorously suspended by 10 ml pipette with cold PBS. The supernatant was the villous fraction and was discarded; the sediment was resuspended with PBS. After further vigorous suspension and centrifugation, the supernatant was enriched for crypts. This fraction was passed through a 70-um cell strainer (BD bioscience) to remove residual villous material. Isolated crypts were centrifuged at 300 rpm for 3 min to separate crypts from single cells. The final fraction consisted of essentially pure crypts and was used for culture or single cell dissociation.

Tamoxifen induction and X-gal staining: To activate Cre-ERT2, crypts were incubated with low dose 4-hydroxytamoxifen (100 nM) for 12 hr and cultured in crypt culture medium. X-gal staining was performed as previously described[1]. No staining was seen without 4-hydroxytamoxifen treatment.

Electron microscopy analysis: As described previously[1] Matrigel including crypt organoids were fixed in Karnovsky's fixative (2% paraformaldehyde, 2.5% glutaraldehyde, 0.1 M Na-cacodylate, 2.5 mM $CaCl_2$ and 5 mM $MgCl_2$, pH 7.4) for 5 hr at room temperature. The samples were embedded in Epon resin and were examined with a Phillips CM10 microscope (Eindhoven, The Netherlands).

Microarray analysis: Gene expression analysis of colonic crypts, small intestinal crypts and organoids. Freshly isolated small intestinal crypts from two mice were divided into two parts. RNA was directly isolated from one part (RNeasy Mini Kit, Qiagen), the other part was cultured for one week, followed by RNA isolation. We prepared labeled cRNA following the manufacturer's instruction (Agilent Technologies). Differentially labelled cRNA from small intestinal crypts and organoids were hybridized separately for the two mice on a 4×44k Agilent Whole Mouse Genome dual colour Microarrays (G4122F) in two dye swap experiments, resulting in four individual arrays. Additionally, isolated colonic crypts were hybridized against differentially labelled small intestinal crypts in two dye swap experiments, resulting in four individual arrays. Microarray signal and background information were retrieved using Feature Extraction (V.9.5.3, Agilent Technologies). All data analyses were performed using ArrayAssist (5.5.1, Stratagene Inc.) and Microsoft Excel (Microsoft Corporation). Raw signal intensities were corrected by subtracting local background. Negative values were changed into a positive value close to zero (standard deviation of the local background) in order to allow calculation of ratios between intensities for features only present in one channel (small intestinal crypts or organoids) or (small intestinal crypts or colonic crypts). Normalization was performed by applying a Lowess algorithm and individual features were filtered if both (small intestinal crypts or organoids) or (small intestinal crypts or colonic crypts) intensities were changed or if both intensities were less than two times the background signal. Furthermore, non-uniform features were filtered. Data are available at GEO (Gene Expression Omnibus, number GSE14594) upon publication. Unsupervised hierarchical clustering was performed on normalized intensities (processed signal in Feature Extraction) of small intestinal/colonic crypts and organoids using Cluster 3 (distance: city block, correlation: average linkage) and visualized with TreeView. Genes were considered significantly changed if they were consistently in all arrays more than 3-fold enriched in organoids or crypts.

Imaging analysis: The images of crypt organoids were taken with either confocal microscopy (Leica, SP5), inverted microscope (Nikon DM-IL) or stereomicroscope (Leica, MZ16-FA). For immunohistochemistry, samples were fixed with 4% paraformaldehyde (PFA) for 1 hr at room temperature, and Paraffin sections were processed with standard technique[1]. Immunohistochemistry was performed as previously described[1]. For whole-mount immunostaining, crypts organoids were isolated from matrigel using with Dispase (Invitrogen), and fixed with 4% PFA, following by permiabilization with 0.1% Triton-X. EdU staining was performed following the manufacturer's protocol (Click-IT, Invitrogen). DNA was stained by DAPI or ToPro-3 (Molecular Probe). 3D images were acquired with confocal microscopy (Leica, SP5) and reconstructed with Volocity Software (Improvision).

Results

The intestinal epithelium is the most rapidly self-renewing tissue in adult mammals. We have recently demonstrated the presence of approximately six cycling $Lgr5^+$ stem cells at the bottoms of small intestinal crypts[1]. We have now established long-term culture conditions under which single crypts undergo multiple crypt fission events, whilst simultaneously generating villus-like epithelial domains in which all differentiated cell types are present. Single sorted $Lgr5^+$ stem cells can also initiate these crypt-villus organoids. Tracing experiments indicate that the $Lgr5^+$ stem cell hierarchy is maintained in organoids. We conclude that intestinal crypt-villus units are self-organizing structures, which can be built from a single stem cell in the absence of a non-epithelial cellular niche.

The self-renewing epithelium of the small intestine is ordered into crypts and villi. Cells are newly generated in the crypts and are lost by apoptosis at the tips of the villi, with a turn-over time of 5 days in the mouse. Self-renewing stem cells have long been known to reside near the crypt bottom and to produce the rapidly proliferating transit amplifying (TA) cells. The estimated number of stem cells is between 4 and 6 per crypt. Enterocytes, goblet cells and enteroendocrine cells develop from TA cells and continue their migration in coherent bands along the crypt-villus axis. The fourth major differentiated cell-type, the Paneth cell, resides at the crypt bottom. We have recently identified a gene, Lgr5, which is specifically expressed in cycling Crypt Base Columnar cells that are interspersed between the Paneth cells[1]. Using a mouse in which a GFP/tamoxifen-inducible Cre recombinase cassette was integrated into the Lgr5 locus, we showed by lineage tracing that the $Lgr5^+$ cells constitute multipotent stem cells which generate all cell types of the epithelium[1], even when assessed 14 months after Cre induction[3].

Although a variety of culture systems has been described[4-7], no long-term culture system has been established which maintains basic crypt-villus physiology.

Figure 2:
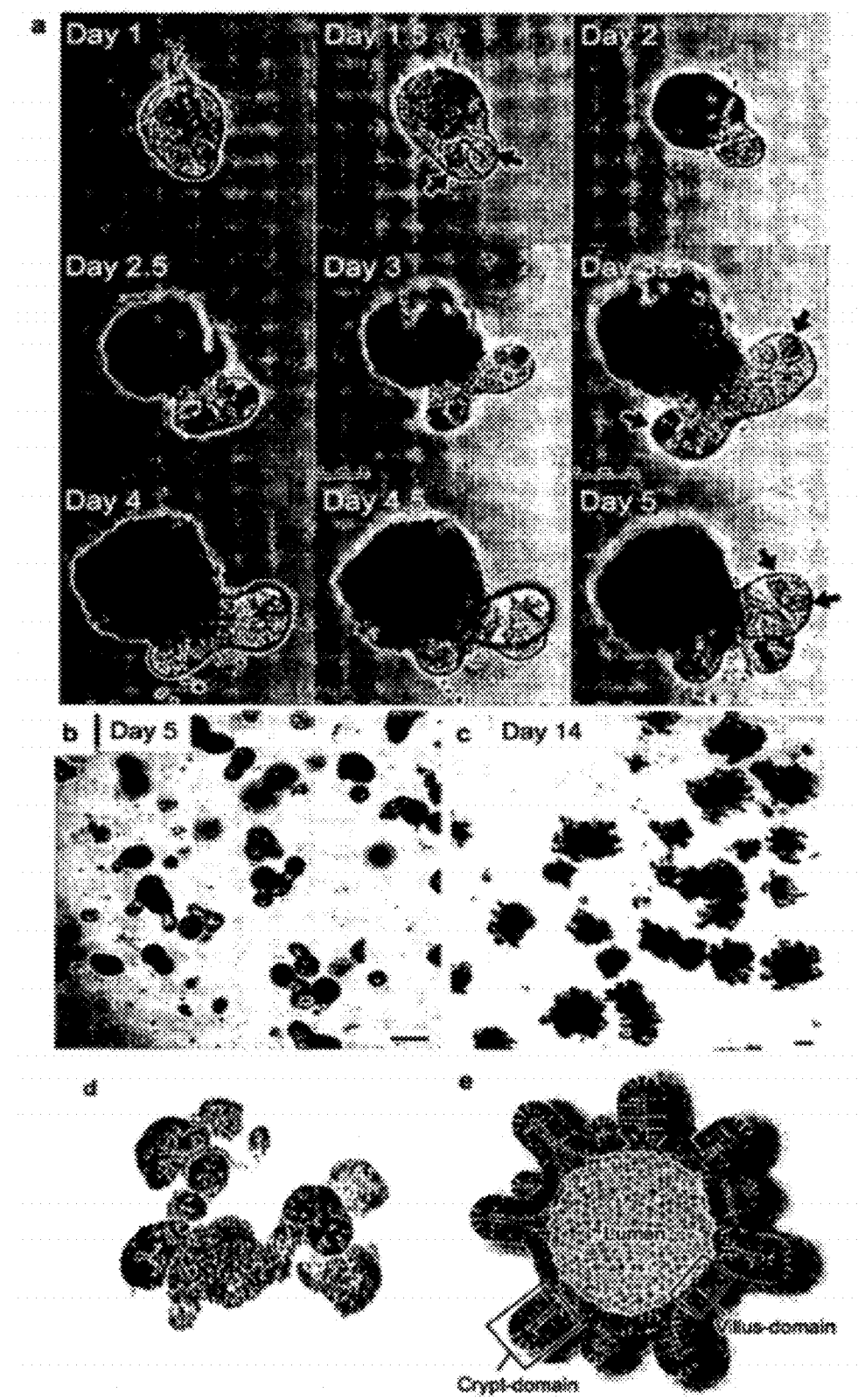
FIG. 2. Establishment of intestinal crypt culture system. a: Time course of an isolated single crypt growing into an organoid. Differential interference contrast image reveals granule-containing Paneth cells at crypt bottoms (arrows). b, c: Single isolated crypts efficiently form crypt organoids. Through repeated crypt fission, the structures generate numerous octopus-like crypt organoids at day 14. d: 3D reconstructed confocal image of a single organoid after a 3 week culture. Lgr5-GFP$^+$ stem cells (light grey) are localized at the tip of crypt-like domains. Counterstaining for DNA: ToPro-3 (dark grey). e: Schematic representation of a crypt organoid. The organoid consists of a central lumen lined by villus-like epithelium and a number of surrounding crypt-like domains. Dark grey cells at the tip of the crypt domain indicates the position of Lgr5$^+$ stem cells, which are present in each crypt domain. Scale bar indicates 50 µm.
Figure 3:
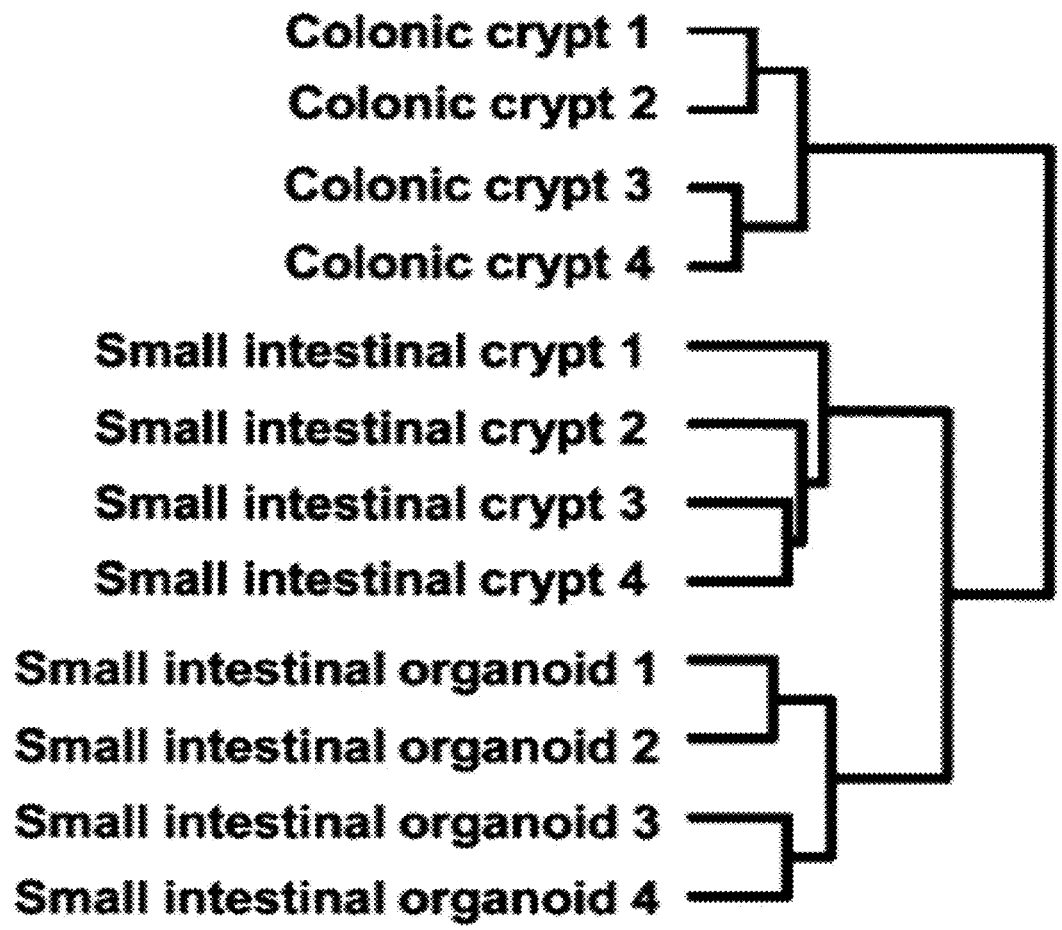
FIG. 3. Cluster analysis of gene expression profiling. Cluster analysis of expression levels using freshly isolated colonic and small intestinal crypts as well as small intestinal organoids showed high degree of similarity between small intestinal organoids and the tissue they were derived from, small intestinal crypts. Colonic crypts clustered on a separate branch, indicating a different gene expression pattern of this closely related tissue. Of note, only 1.2% of all genes expressed were significantly enriched in organoids relative to small intestinal crypts, while—vice versa—2% were enriched in small intestinal crypts. Ingenuity Pathway analysis on these differential genes revealed the specific presence of a lymphocyte signature in freshly isolated crypts, while no significant pathway could be identified in the small number of genes enriched in the organoids (not shown). We conclude that the latter group represents biological noise, while the lymphocyte signature derives from contaminating intraepithelial immune cells, lost upon culture.

Mouse crypt preparations were suspended in Matrigel. Crypt growth required EGF and R-spondin 1 (FIG. 1a). Passaging revealed a requirement for Noggin (FIG. 1b). The cultured crypts behaved in a stereotypical manner (FIG. 2a). The upper opening rapidly became sealed, and the lumen filled with apoptotic cells. The crypt region underwent continuous budding events, reminiscent of crypt fission[17]. Paneth cells were always present at the bud site. The majority of crypts could be cultured (FIG. 2b). Further expansion created organoids, comprising >40 crypt-domains surrounding a central lumen lined by a villus-like epithelium ("villus domain") (FIGS. 2c-e). E-cadherin staining revealed a single cell layer (Data not shown). Weekly, organoids were mechanically dissociated and replated at ⅕ of the pre-plating density. Organoids were cultured for >6 months without losing the characteristics described below. Expression analysis by microarray revealed that organoids remained highly similar to freshly isolated small intestinal crypts, when compared for instance to fresh colon crypts (FIG. 3).

Figure 4:
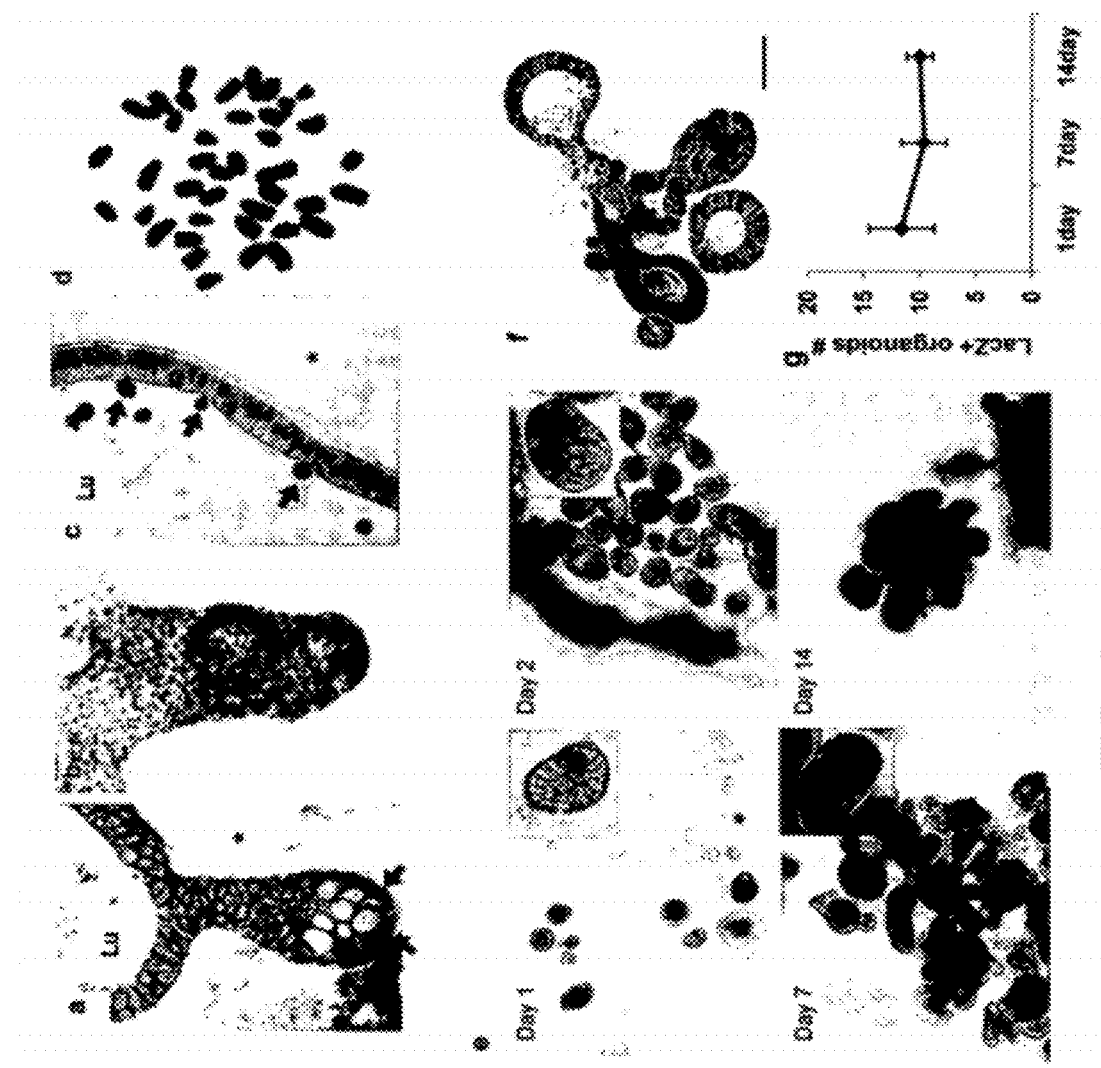
FIG. 4. Crypt organoids preserve basic crypt-villus characteristics. a-e The Wnt activation code is preserved in crypt domains. a: Nuclear β-catenin (dark grey, arrows) was only seen in crypt domains. Higher resolution image in FIG. 5. Asterisk, matrigel; Lu, lumen b: EphB2 (light grey) is expressed in a gradient on CBC cells and TA cells. Note Lgr5-GFP$^+$ stem cells as indicated by white arrow c: Caspase-3$^+$ apoptotic cells (dark grey, arrows) shedding into the central lumen lined by enterocytes. d: 40 chromosomes in a spread of cells from a >3 months old crypt culture e-g: Lineage tracing of Lgr5$^+$ stem cells in vitro. e: Crypts from Lgr5-EGFP-ires-CreERT2/Rosa26-lacZ reporter mice were stimulated by tamoxifen in vitro for 12 hr, and cultured for the indicated days. LacZ staining (dark grey) shows that scattered single LacZ$^+$ cells (day 1) generated entire LacZ$^+$ crypts in vitro (Day2-14). Insets show higher magnification of stained crypt organoids. f: Histological analysis shows an entire LacZ$^+$ crypt-domain (dark grey/black) feeds into the villus domain. g: The percentage of crypt organoids with LacZ$^+$ cells remained steady over time, indicating that Lgr5$^+$ cells possess long-term stem cell activity. 500 crypts were seeded in triplicate, and LacZ$^+$ crypt organoids were counted. Error bars are standard deviation of triplicates. The experiment was repeated three times with similar results.
Figure 5A:
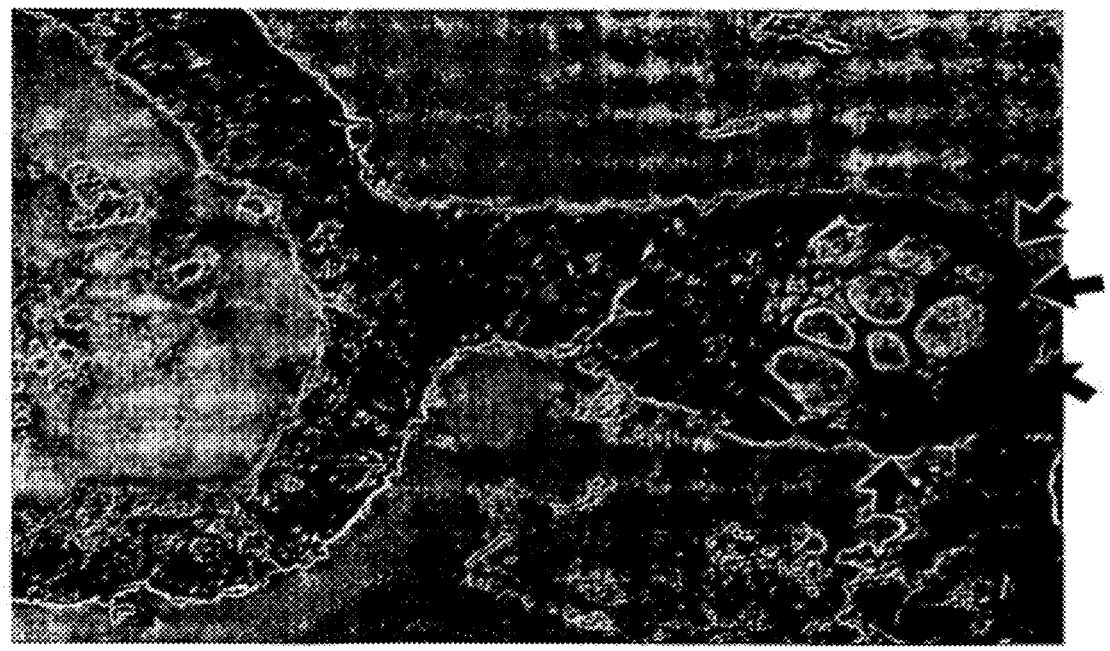
FIG. 5. Higher resolution image of FIG. 4$a$, FIGS. 11$m$ and 11$p$.
Figure 5B:
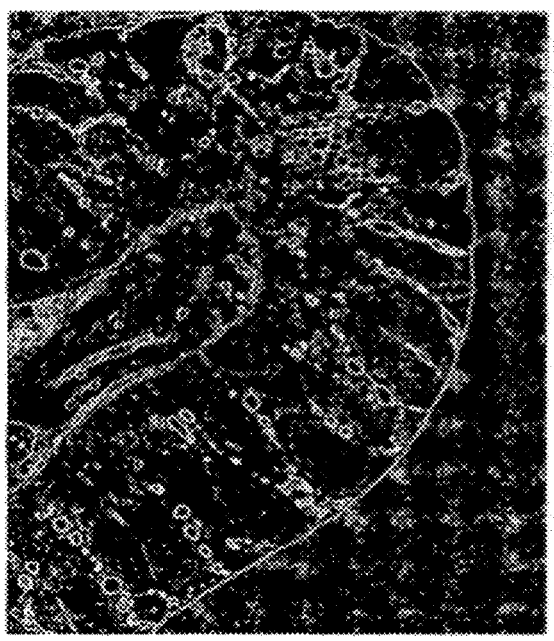
Figure 5C:
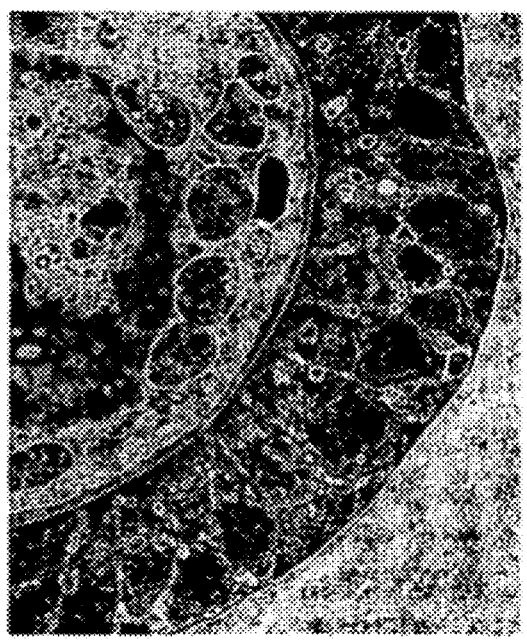
Figure 6:
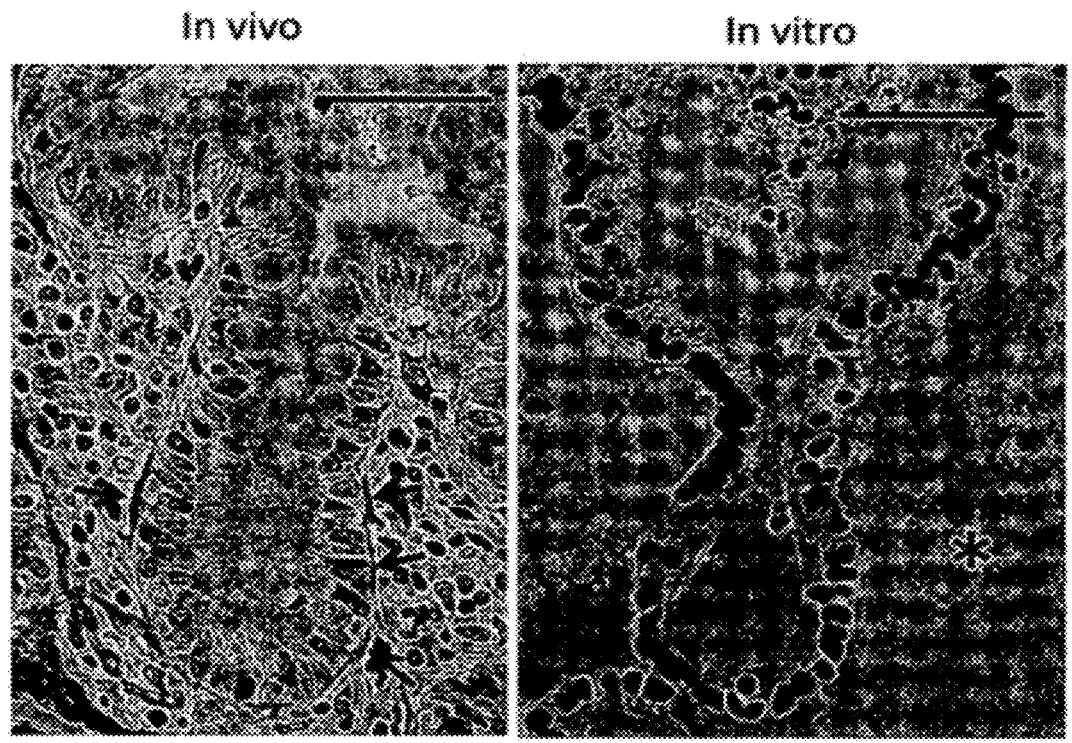
FIG. 6. No evidence of subepithelial fibroblasts in crypt organoids. a: Immunostaining for smooth muscle actin (SMA; dark grey, examples indicated by black arrows) demonstrates the presence of subepithelial fibroblasts beneath the epithelial layer. b: Absence of SMA+ cells in matrigel (asterisk) indicates the absence of subepithelial fibroblasts in the culture system. Scale bar; 50 µm.

Culture of Lgr5-EGFP-ires-CreERT2 crypts revealed Lgr5-GFP$^+$ stem cells intermingled with Paneth cells at the crypt base. Wnt activation, as evidenced by nuclear β-catenin (FIG. 4a, FIG. 5) and expression of the Wnt target genes Lgr5 (FIG. 2d) and EphB2[18] (FIG. 4b) was confined to the crypts. Apoptotic cells were shed into the central lumen, a process reminiscent of the shedding of apoptotic cells at villus tips in vivo (FIG. 4c). Metaphase spreads of >3 months-old organoids consistently revealed 40 chromosomes/cell (n=20) (FIG. 4d). Surprisingly, we found no evidence for the presence of myofibroblasts or other non-epithelial cells (FIG. 6).

Figure 7:
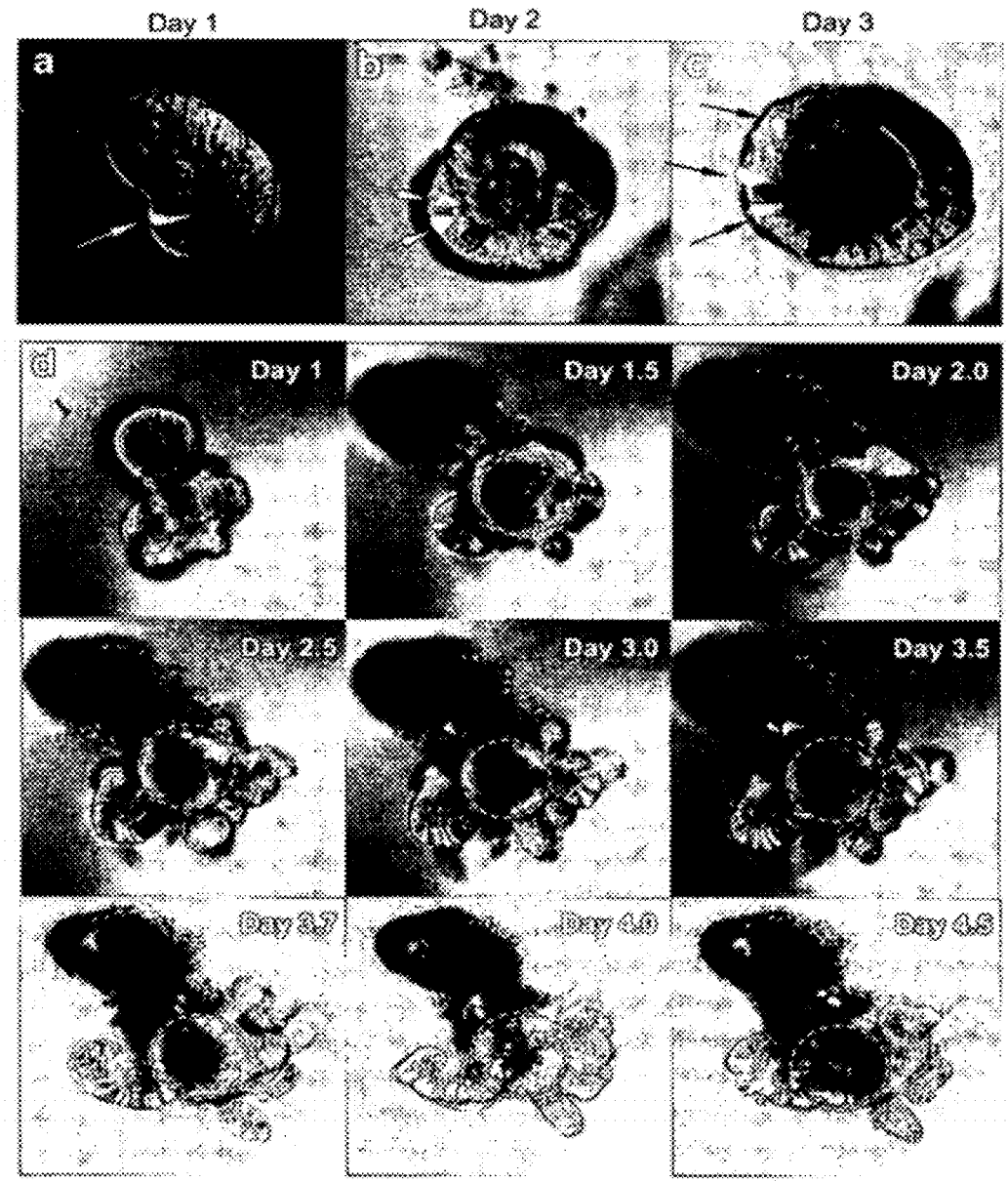
FIG. 7. a-c: A crypt from an Lgr5-EGFP-ires-CreERT2/Rosa26-YFP reporter mouse was stimulated by tamoxifen in vitro for 12 hr, and imaged for the indicated days. Lgr5$^+$ cells are light grey and indicated by the white arrows. d: Seven-day-old organoids derived from an Lgr5-EGFP-ires-CreERT2/Rosa26-YFP crypts were stimulated by tamoxifen in vitro for 12 hr, and cultured and imaged for the indicated days. YFP fluorescence (light grey) shows that scattered single YFP$^+$ cells (day 1) generated multiple offspring in vitro over the next five days. The villus domain burst during Day 1-1.5, following by new villus domain formation (white circle). Note that YFP+ cells are migrating toward villus domain.

We cultured crypts from Lgr5-EGFP-ires-CreERT2 mice crossed with the Cre-activatable Rosa26-LacZ reporter to allow lineage tracing. Directly after induction by low-dose tamoxifen, we noted single labeled cells (FIGS. 4e, 4g). More than 90% of these generated entirely blue crypts (FIGS. 4e-4g), implying that the Lgr5-GFP$^+$ cells indeed retained stem cell properties. Crypts from the Cre-activatable Rosa26-YFP reporter[19] mouse allowed lineage tracing by confocal analysis. Directly after tamoxifen treatment, we noted single labeled cells that induced lineage tracing over the following days, both in freshly isolated crypts (FIGS. 7a-7c) and in established organoids (FIG. 7d).

Figure 8:
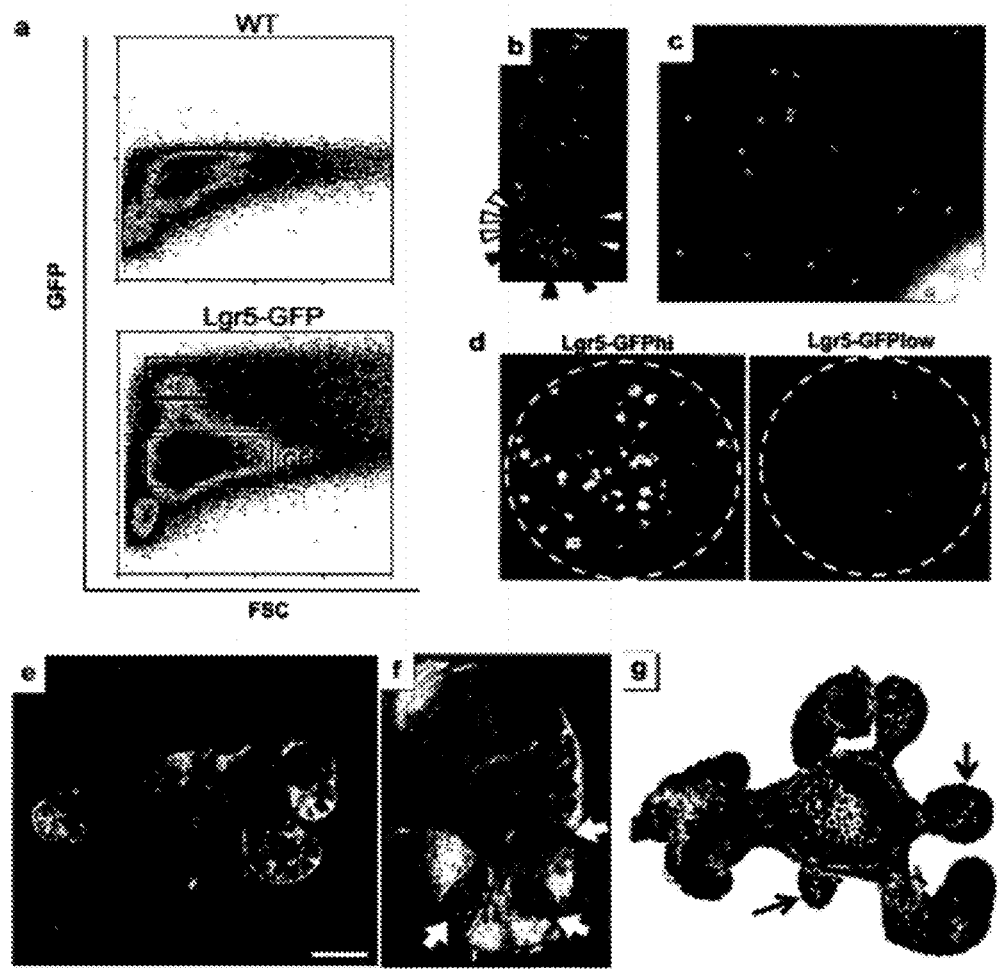
FIG. 8. Single sorted Lgr5$^+$ stem cells generate entire crypt-villus structures. a: Lgr5-GFP$^+$ cells prepared from an Lgr5-EGFP-ires-CreERT2 intestine (bottom) compared to wild-type littermate (top). GFP$^+$ cells were divided into two populations; GFP$^{hi}$ and GFP$^{low}$ b: Confocal microscopic analysis of a freshly isolated crypt shows GFP$^{hi}$ in CBC cells (black arrowheads) and GFP$^{low}$ above CBC (white arrowheads). c: Sorted GFP$^{hi}$ cells. d: 1000 sorted GFP$^{hi}$ cells (left) and GFP$^{low}$ cells (right) after 14 day culture e-f: Fourteen days after sorting, single GFP$^{hi}$ cells form crypt organoids, with Lgr5-GFP$^+$ cells (light grey cells) and Paneth cells (white arrows) located at crypt bottoms. Scale bar; 50 µm. f: Higher magnification of crypt bottom in e.g: To visualize proliferating cells, the organoids were cultured with the thymidine analog EdU (light grey, examples indicated by white arrows) for 1 hr, after which they were fixed. Note that only crypt domains incorporated EdU. Counterstain: DAPI (dark grey).

Recently, mammary gland epithelial structures were established from single stem cells in vitro[21]. When single Lgr5-GFP$^{hi}$ cells were sorted, these died immediately. The Rho kinase inhibitor Y-27632, significantly decreased this cell death. A Notch agonistic peptide[24] was found to support maintenance of proliferative crypts[23]. Under these conditions, significant numbers of Lgr5-GFP$^{hi}$ cells survived and formed large crypt organoids. Organoids formed rarely when GFP$^{low}$ daughter cells were seeded (FIG. 8d). Multiple Lgr5-GFP$^{hi}$ cells were intermingled with Paneth cells at crypt bottoms (FIGS. 8e and 8f). EdU (thymidine analog) incorporation revealed S-phase cells in the crypts (FIG. 8g).

Figure 9A:
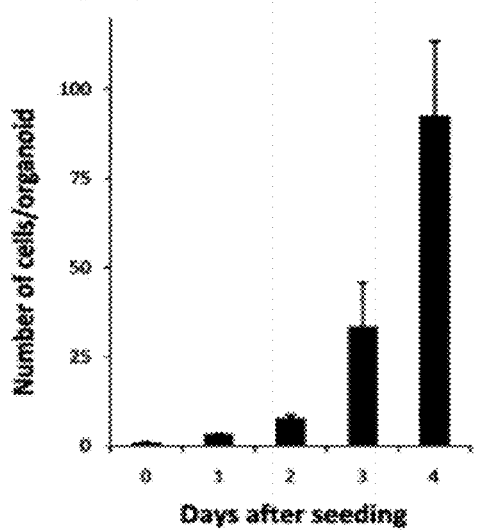
FIG. 9. a: Colony-forming efficiency of single cells sorted in individual wells. The average is given for 4 individual experiments, of which in each experiment 100 cells were visually verified and then followed for growth. b: An example of a successfully growing single GFP$^{hi}$ cell. c: Numbers of cells per single organoid averaged for 5 growing organoids. d: Single cell suspension derived from a single-cell-derived-organoid was replated and grown for 2 weeks.
Figure 9C:
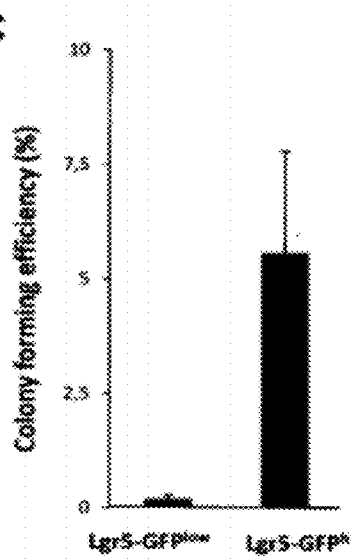
Figure 9D:
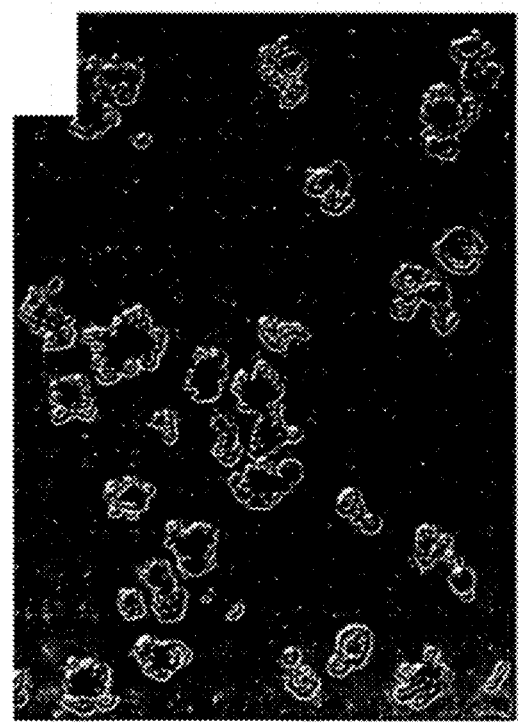
Figure 9B:
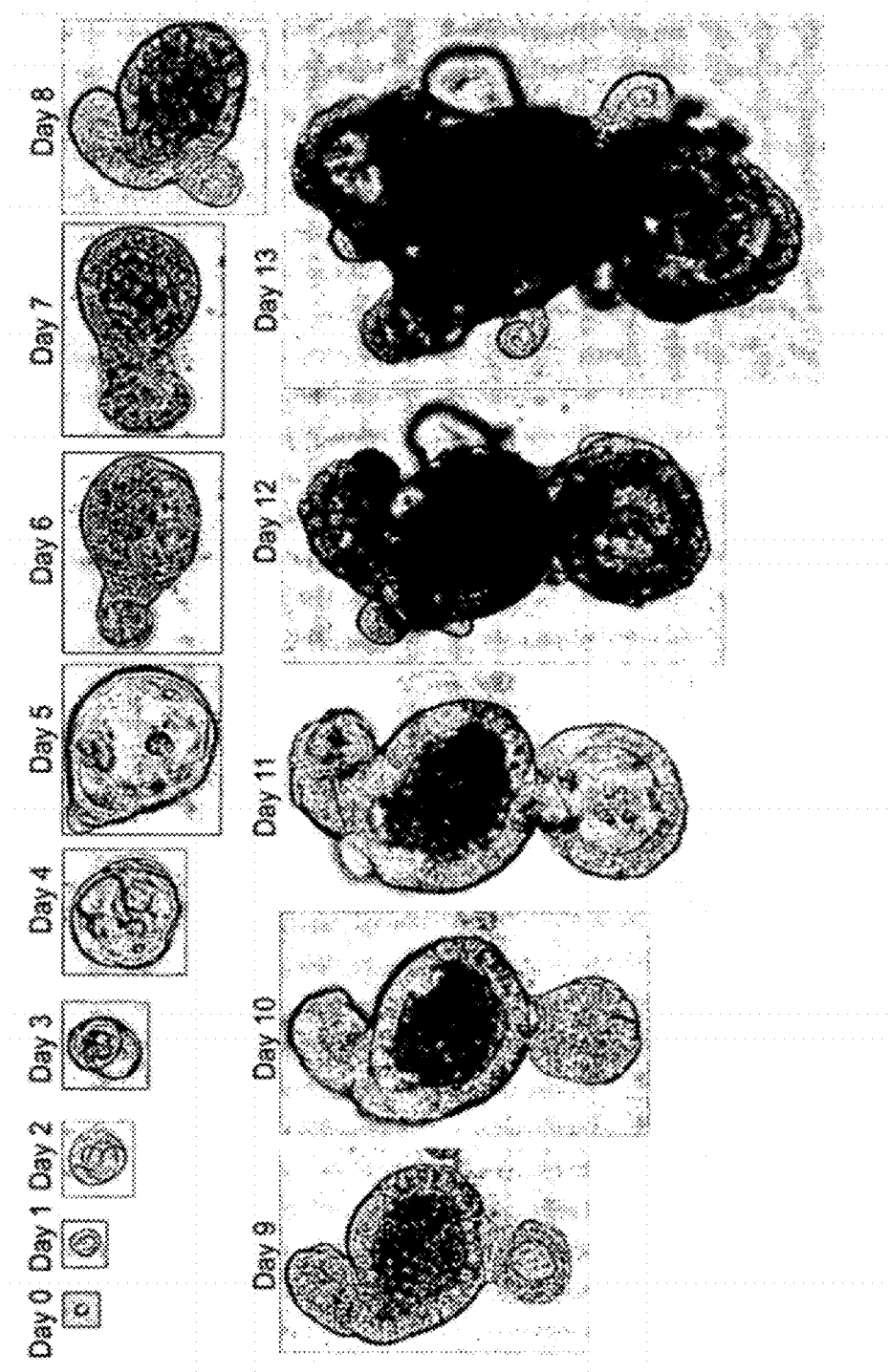
Figure 10:
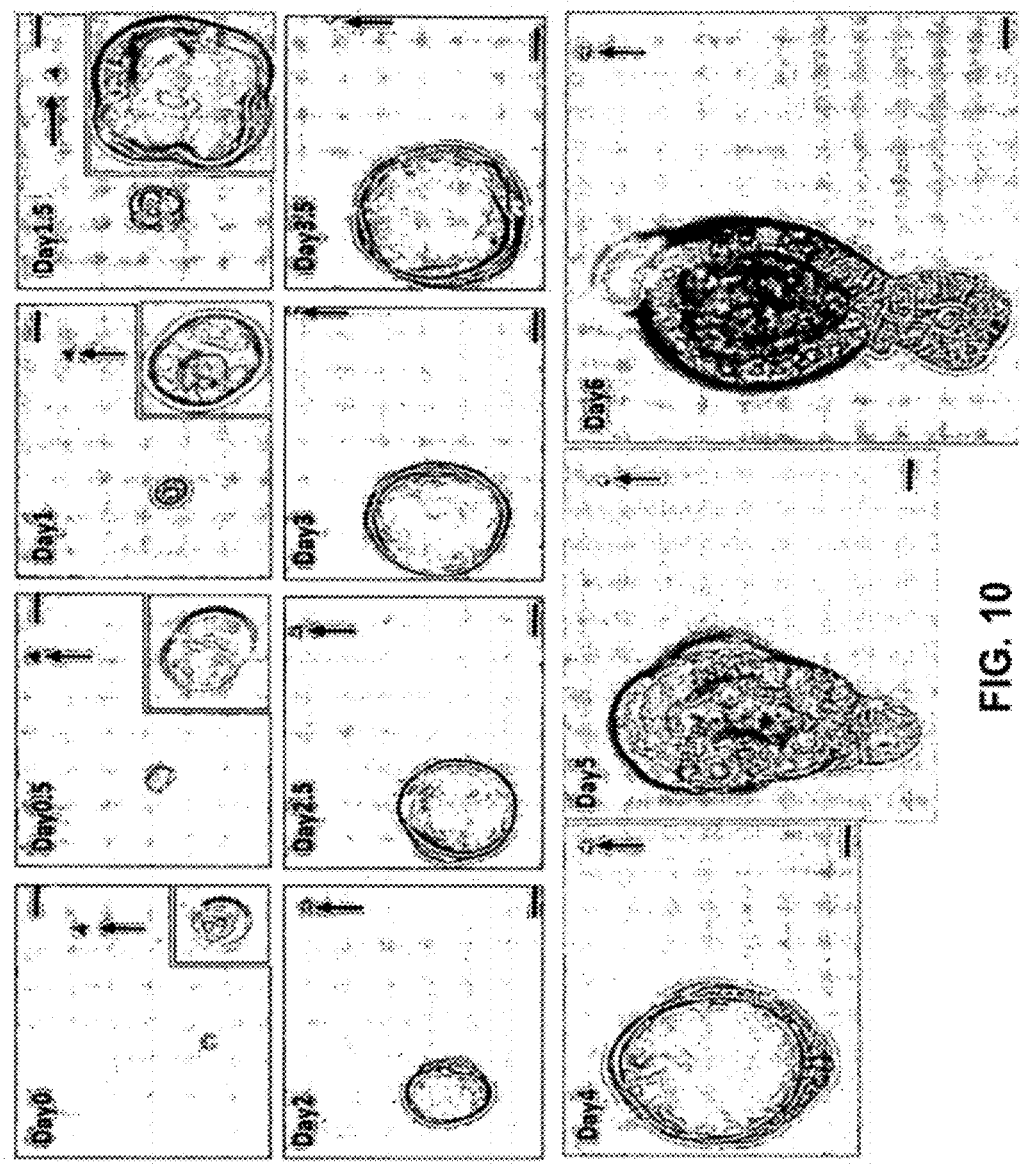
FIG. 10. Colony-forming potency of a single cell sorted in an individual well. An example of a successfully growing single GFP$^{hi}$ cell. The arrows point to a dust particle as a landmark. Scale bar: 50 µm.

We sorted cells at 1 cell/well, visually verified the presence of single cells and followed the resulting growth. In each of four individual experiments, we identified and followed 100 single cells. On average, approximately 6% of the Lgr5-GFP$^{hi}$ cells grew out into organoids, while the remaining cells typically died within the first 12 hours, presumably due to physical and/or biological stress inherent to the isolation procedure. GFP$^{low}$ cells rarely grew out (FIG. 9a). FIG. 9b and FIG. 10 illustrate the growth of an organoid from a single Lgr5-GFP$^{hi}$ cell. By four days of culture, the structures consisted of around 100 cells, consistent with the 12 hour-cell cycle of proliferative crypt cells[25] (FIG. 9c). After two weeks, the organoids were dissociated into single cells and replated to form new organoids (FIG. 9d). This procedure could be repeated at least four times on a 2-weekly basis, without apparent loss of replating efficiency.

Figure 11:
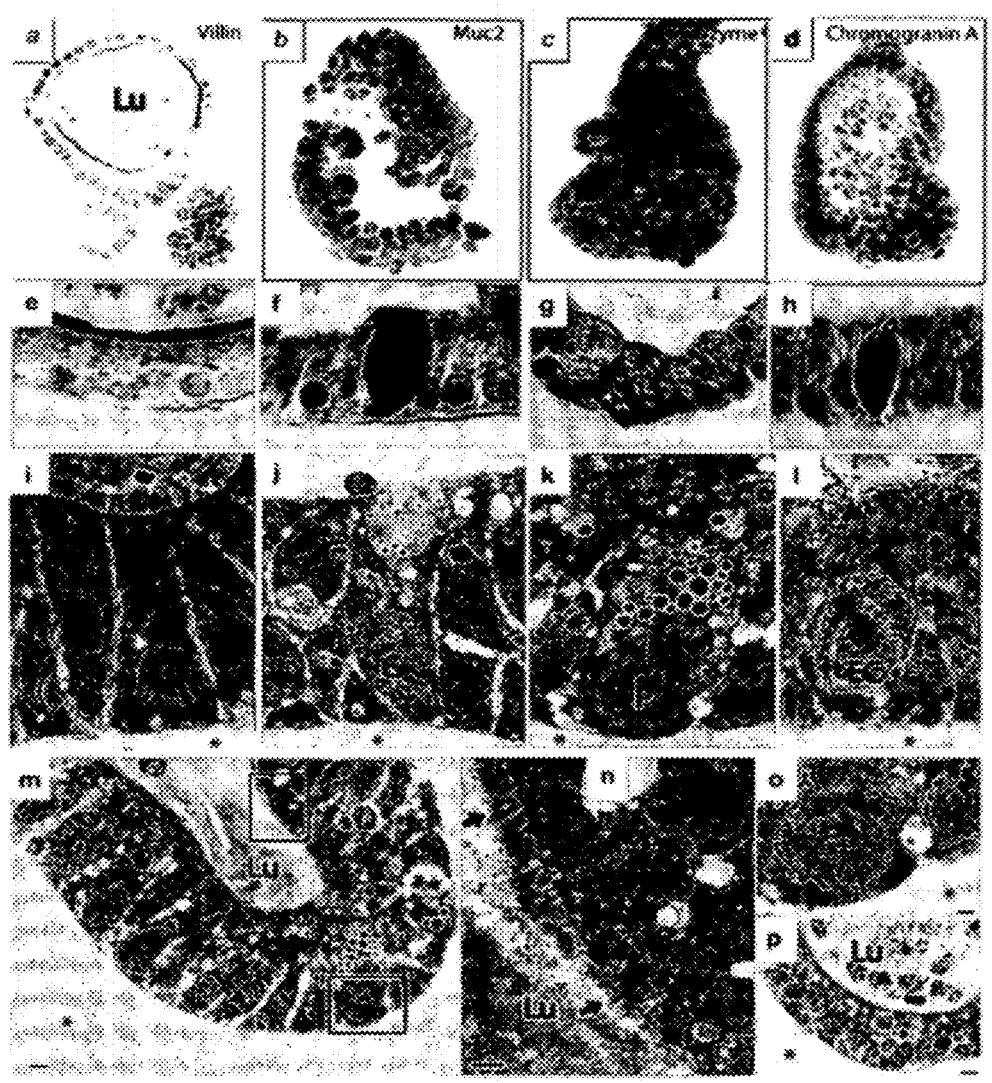
FIG. 11. Composition of single stem cell-derived organoids. a-d: Three dimensional reconstructed confocal image for a: Villin in light grey (apex of enterocytes lining central lumen) b: Muc2 staining indicated by white arrows (goblet cells), c: lysozyme in light grey (Paneth cells), d: Chromogranin A in light grey (enteroendocrine cells). Nucleus was counterstained with DAPI. e-g: Paraffin section staining e: Alkaline phosphatase in black (apex of enterocytes lining central lumen) f: PAS in dark grey (goblet cells), g: lysozyme in dark grey (Paneth cells), h: Synaptophysin in dark grey (enteroendocrine cells). i-p: Electron microscopy sections of crypt organoids demonstrates the presence of enterocytes (i), goblet cells (j), Paneth cells (k) and enteroendocrine cells (l). m/o: Low power crypt image illustrates absence of stromal cells. n-o: Higher magnification of m. n: Maturation of brush border towards the luminal compartment of the organoid, as indicated by the difference of length of microvilli (black arrows). p: Low power image of villus domain. Lu, lumen of crypt organoid filled with apoptotic bodies and lined by polarized enterocytes. G, goblet cells; EC, enteroendocrine cells; P, Paneth cells; asterisk, matrigel. Scale bar: 5 µm (m, p), 1 µm (n, o).
Figure 12:
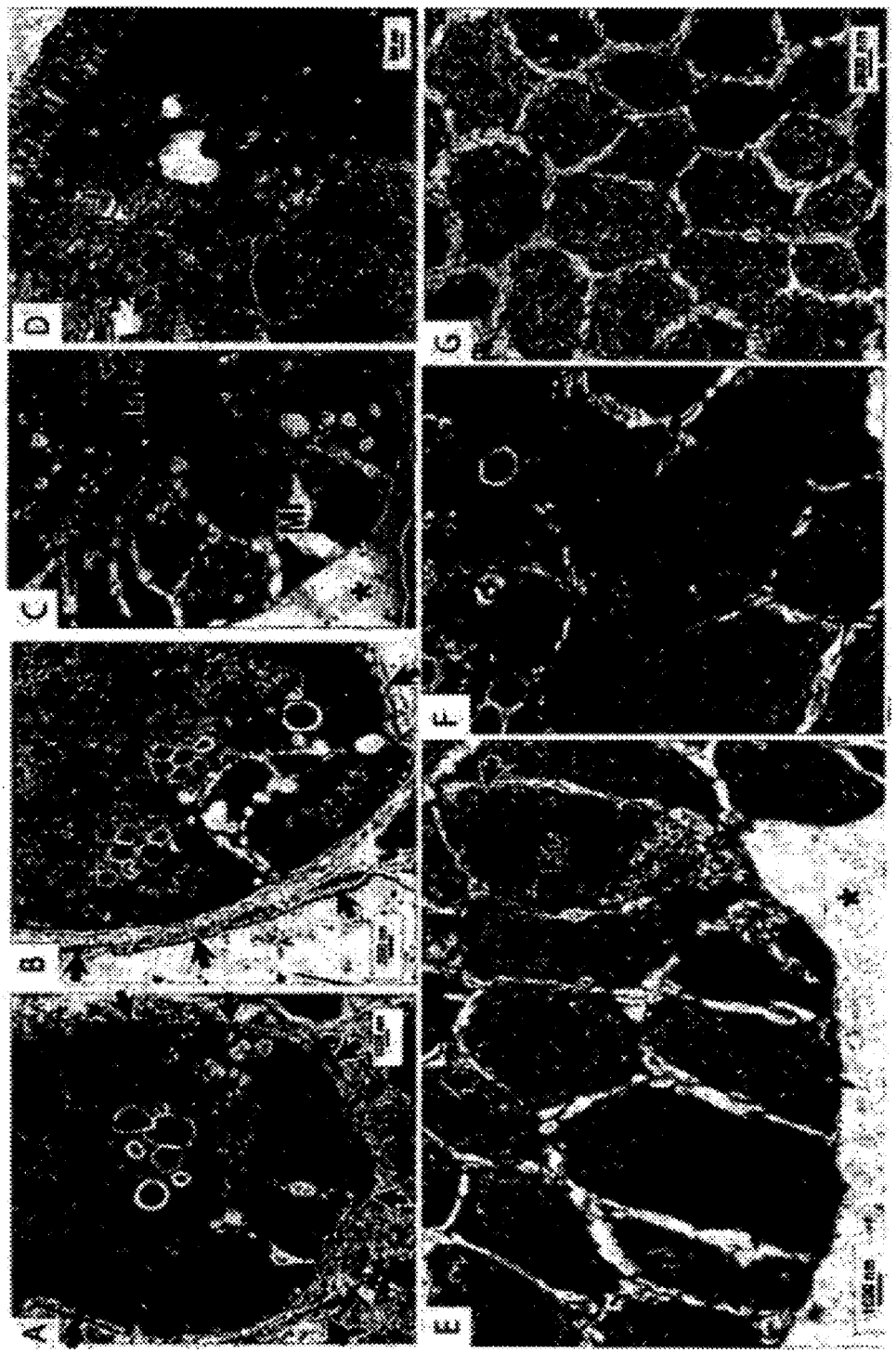
FIG. 12. Comparison of electron microscopic images between in vivo crypt and in vitro cultured crypt. a, b: Normal intestine at the base of the crypt with the connective tissue underneath (arrows). For comparison see c-g of the organoids also taken at the base of a crypt. d: High magnification image from the apical membrane; There are intercellular clefts (arrows) between the membranes of two adjacent cells. Note the desmosome (arrow head) followed by an intercellular cleft. e: High magnification from the basal site where the membrane of two adjacent cells can be followed by intracellular clefts. These images are comparable to a and b from the intestine of a normal mouse. The cause of these intercellular clefts may be osmotic shock during aldehyde fixation. f,g: All cells that make up the organoid are in a healthy state and lack large vacuoles or other signs of stress. One can observe mitosis figures (c) and in each cell many nuclear pores (f, arrows) and intact mitochondria. ER and Golgi (g) can be seen without any evidence of swelling. There is no sign of karyorexis, karyolysis or karyopyknosis. Therefore, no sign of cell lysis or apoptosis is observed. Cells in the lumen of the organoid show the expected apoptotic features as one can observe in the gut of a normal mouse. f shows another example of an enteroendocrine cell. Mi: mitotic cells, Lu: lumen, EC: enteroendocrine cells, G: Golgi.

The single stem cell-derived organoids appeared indistinguishable from those derived from whole crypts. Paneth cells and stem cells were located at crypt bottoms (FIGS. 8e, 8f, FIGS. 11c, 11g). Fully polarized enterocytes as evidenced by Villin$^+$ mature brush borders and apical alkaline phosphase lined the central lumen (FIGS. 11a, 11e, 11i). Goblet cells (Muc2$^+$, FIG. 11b; PAS$^+$, FIG. 11f) and enteroendocrine cells (chromogranin A$^+$, FIG. 11d; synaptophysin$^+$, FIG. 11h) were scattered throughout the organoid structure. Four types of mature cells were recognized by electron microscopy (FIGS. 11i-11l). Non-epithelial (stromal/mesenchymal) cells were absent, an observation confirmed by EM imaging (FIGS. 11i-11p, FIGS. 12c-12g). Both the crypts (FIGS. 11m, 11o) and the central luminal epithelium (FIG. 11p) consisted of a single layer of polarized epithelial cells resting directly on the matrigel support. High resolution images of these EM pictures are given in FIG. 5. Organoid stained for E-cadherin in red and counter stained with nuclei in blue, reveals the single-layered nature of the organoid epithelium (data not shown).

It is well known that epithelial crypts are in intimate contact with subepithelial myofibroblasts[26-28] and it is generally believed that the latter cells create a specialized cellular niche at crypt bottoms[27, 29, 30]. Such a niche would create a unique environment to anchor and support the intestinal stem cells. We now show that a self-renewing epithelium can be established by a limited set of growth signals that are uniformly presented. Despite this, the isolated stem cells autonomously generate asymmetry in a highly stereotypic fashion. This rapidly leads to the formation of crypt-like structures with de novo generated stem cells and Paneth cells located at their bottoms and filled with TA cells. These crypt-like structures feed into villus-like luminal domains consisting of postmitotic enterocytes, where apoptotic cells pinch off into the lumen, reminiscent of cell loss at villus tips. The paradoxical observation that single cells exposed to a uniform growth-promoting environment can generate asymmetric structures is particularly evident upon scrutiny of the Wnt pathway. While all cells are exposed to R-spondin 1, only cells in crypts display hallmarks of active Wnt signaling, i.e., nuclear β-catenin and the expression of Wnt target genes. Apparently, differential responsiveness to Wnt signaling rather than differential exposure to extracellular Wnt signals lies at the heart of the formation of a crypt-villus axis.

In summary, we conclude that a single Lgr5$^{+ve}$ intestinal stem cell can operate independently of positional cues from its environment and that it can generate a continuously expanding, self-organizing epithelial structure reminiscent of normal gut. The described culture system will simplify the study of stem cell-driven crypt-villus biology. Moreover, it may open up new avenues for regenerative medicine and gene therapy.

Example 2: Culturing of Colon Crypts and Villi in Vitro

Material and Methods
Wnt3a Conditioned Medium

A Wnt3a ligand expressing cell line and the same cell line, without the Wnt3a ligand (control medium) are cultured for a period of 3-4 weeks. The cells will produce Wnt3a as soon as they stop grown at confluency. The medium will be harvested and tested in the TOPflash assay, a luciferase assay using a TCF responsive elements-luc construct (TOP) and the same construct, but with mutations in the TCF responsive elements (FOP). The ratio between TOP/FOP should be more than 20 for the medium to be used in cultures. The medium is diluted 25-50% when used in the cultures to regenerate tissue.

Freshly isolated colon was opened and washed with PBS or DMEM, and cut into small pieces. The fragments were incubated with 2 mM EDTA/PBS for 1 hour at 4° C. under gentle rocking. Following removal of EDTA solution, the tissue fragments were vigorously suspended in 10 ml of cold PBS with a 10 ml pipette. The first supernatant containing debris was discarded and the sediment was suspended with 10-15 ml PBS. After further vigorous suspension of the tissue fragments the supernatant is enriched in colonic crypts. The fragments were pelleted and mixed with matrigel and cultured as small intestinal organoid culture system. The matrigel was incubated for 5-10 min at 37° C. After matrigel polymerization, 500 µl of tissue culture media (50% Advanced-DMEM/F12/50% Wnt-3a conditioned medium-supplemented with 200 ng/ml N-Acetylcysteine, 50 ng/ml EGF, 1 µg/ml R-spondin1, 100 ng/ml Noggin, 100 ng/ml BDNF (Peprotech) was added. The entire medium was changed every 2-3 days. For passage, the organoids were removed from the Matrigel using a 1000 µl pipette and were dissociated mechanically into small fragments and transferred to fresh Matrigel. Passage was performed in 1:4 split ratio at least once every two weeks. Under these conditions cultures have been maintained for at least for 3 months.

Results

Figure 13:
FIG. 13. Colon derived crypts can be maintained in culture as well. Single isolated crypts derived from colon efficiently form crypt organoids using the same culturing conditions as used for small intestinal crypts. Through repeated crypt fission, the structures generate numerous octopus-like crypt organoids at day 14.
Figure 14A:
FIG. 14. Addition of BDNF increases culture efficiency. Single isolated colon crypts were cultured in the presence of EGF, Noggin, R-Spondin and BDNF. Images of colon crypt organoids taken at day 0, 4 and 14 after the start of the culture.
Figure 14B:
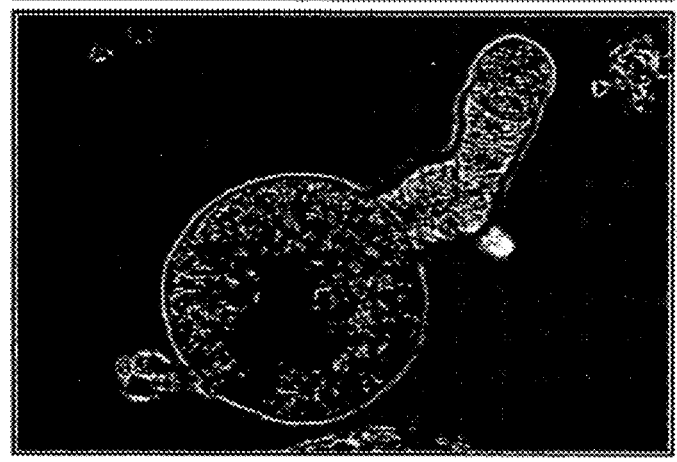
Figure 14C:
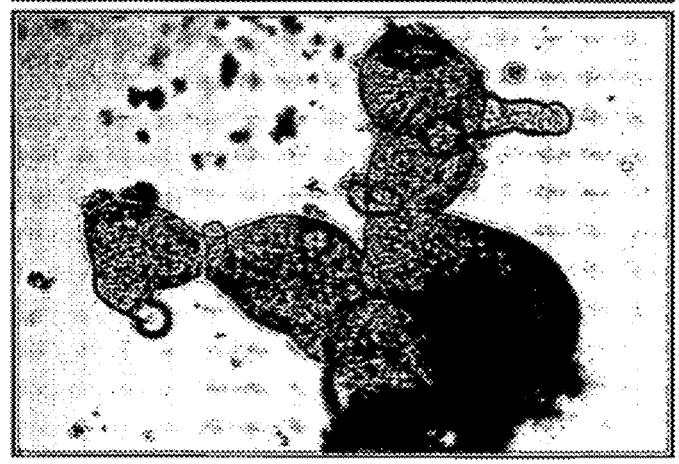
Figure 15:
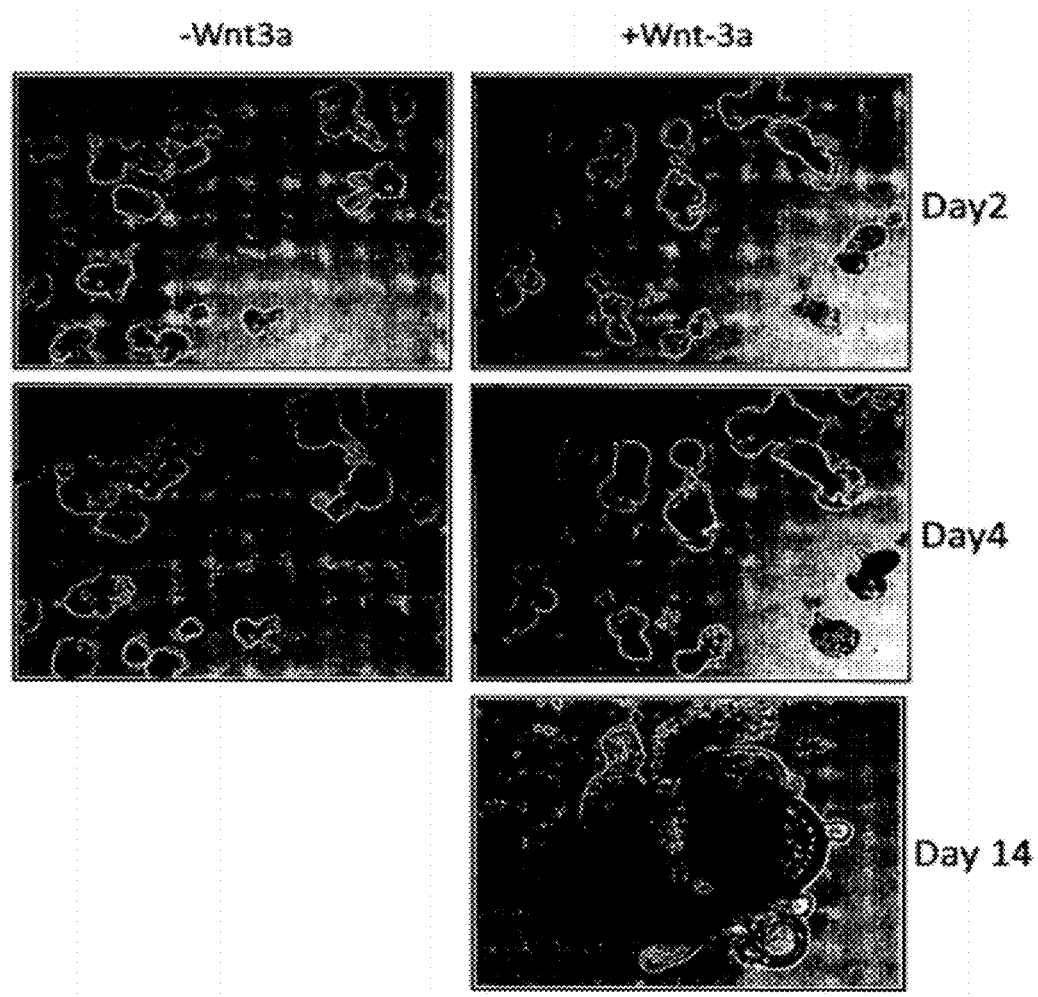
FIG. 15. Addition of Wnt3a further increases culture efficiency of colon crypt organoids. Single isolated colon crypts were cultured in the presence of EGF, Noggin, R-Spondin. The use of Wnt3a conditioned medium (+Wnt3a) increased culture efficiency up to 30% compared to culturing colon organoids in control medium (−Wnt3a).

Colonic organoids grow slower and less efficient as compared with small intestinal organoids. With the same growth factors condition as small intestine, less than 5% of colonic crypts isolated from distal colon grew and formed organoid structure (FIG. 13). It was difficult to grow colonic crypts from proximal part of colon. Since we found upregulation of trkB, the receptor of BDNF (Brain derived neurotrophic factor), in the microarray analysis (colon Lgr5-GFP hi cells vs colon Lgr5-GFP low cells), we determined the effect of BDNF for colonic organoids. We constantly observed around 2-fold higher culture efficiency in BDNF+ culture than BDNF− culture. Typically, one colon organoid would contain approximately 10 crypt domains (FIG. 14). Consistent with their origin, no Paneth cells could be detected. Compared with small intestinal organoids, colonic crypt possesses no Wnt-3a producing Paneth cells in the crypt base, therefore supplementation of Wnt-3 increases culture efficiency of colonic crypts but not that of small intestinal crypts. Typically, we obtained up to 30% culture efficiency when we added Wnt-3a conditioned medium (FIG. 15).

In conclusion, both small intestine derived and colon derived crypts can be maintained and propagated in vitro using the above described conditions, making this the first culture method ever described to result in the generation of intestinal epithelium in an artificial system.

Example 3: Culturing of Adenomas in Vitro

Materials and Methods
(See example 1)
Results

Figure 16:
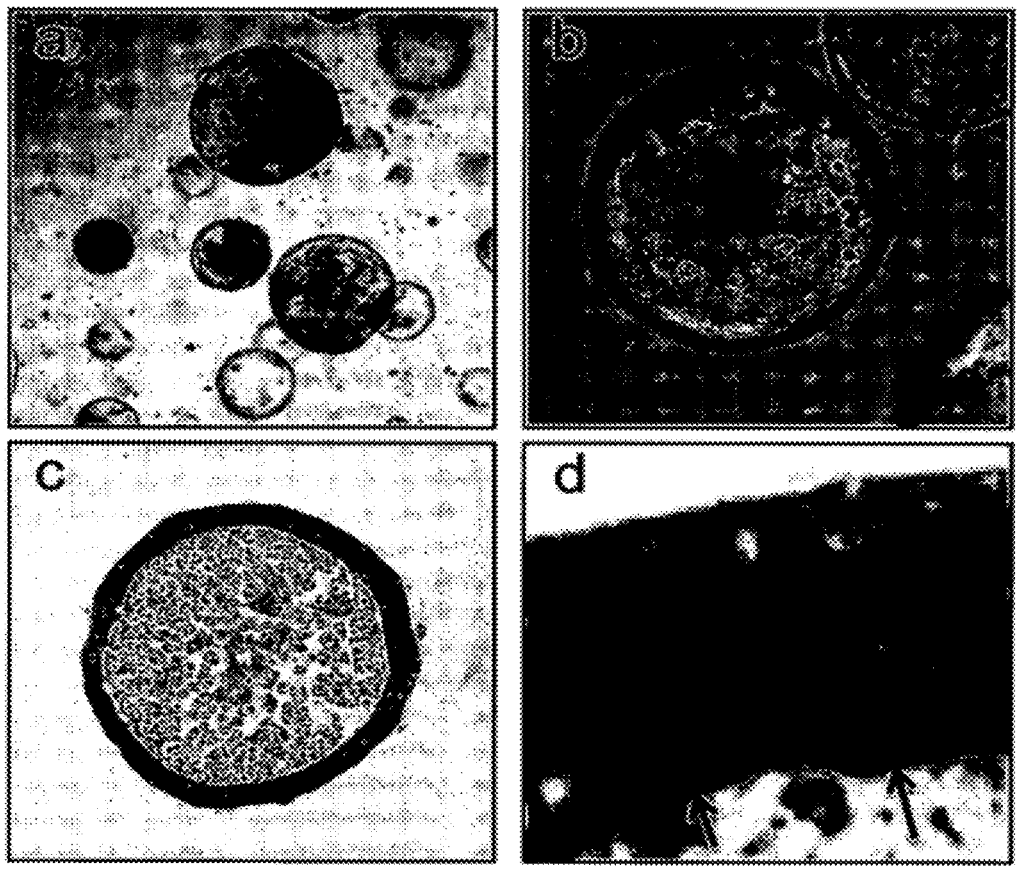
FIG. 16. Adenoma isolated from APC−/− mice can grow in vitro. Single isolated adenoma from APC−/− mice were dissociated and cultured using conditions as described above with the exception that R-spondin was not included in the culture media. a: Adenoma organoids as shown here on day 4 generally grow as a simple cyst, containing one central lumen containing apoptotic cells. b: A larger magnification of one adenoma organoid. c: One adenoma organoid was stained with β-Catenin (dark grey) and hematoxylin (light grey in lumen). The outer layer of the organoid consists of epithelial cells with a nuclear β-Catenin staining. The inner lumen contains dead cells that have taken up hematoxylin, staining dark grey. d: A larger magnification of the outer layer of epithelial cells showing clear nuclear β-Catenin.

Adenomas have been historically difficult to culture in vitro. Since the above described conditions were used to successfully culture healthy crypts derived from small intestine as well as colon, it was determined whether similar conditions could sustain adenomas in vitro. After isolation of adenoma from APC−/− mice using 2.5 mM EDTA, single adenomas were cultured under similar conditions as described above. Importantly, these conditions were adequate to maintain growth of the adenomas in vitro, however, R-spondin had become redundant. This can be easily explained by the fact that it no longer is necessary to induce the Wnt signaling pathway, since the absence of APC in these cells will automatically result in nuclear β-Catenin. This makes R-spondin, a Wnt agonist, redundant in culturing adenomas in vitro. FIG. 16a, and in larger magnification in FIG. 16b, show that, in contrast to normal crypt organoids, in which you can see crypt budding with central lumen, adenoma organoids simply grow as cysts. Dead cells are shed off into the lumen, as can be concluded from the presence of a large quantity of dead cells inside the lumen. In normal crypt organoids, nuclear β-catenin is only seen in base of crypt-domain (see FIG. 4a). In adenoma organoids (FIG. 16c and a larger magnification in 16d), nuclear β-catenin was seen in every epithelial cell, consistent with the genetic APC mutation. These organoids can be passaged indefinitely.

It was further tested whether single Lgr5+ sorted cells derived from the adenomas in Lgr5-EGFP-Ires-CreERT2/APCflox/flox mice were able to form similar adenoma organoids in vitro using the aforementioned culture conditions (without R-spondin). Indeed, this was the case and the organoids obtained were highly comparable in structure to those that were obtained using complete adenomas as starting material for the in vitro culture (data not shown).

Example 4: Testing the Effect of Other Wnt Agonists

To determine whether other Wnt agonists have the same effect as R-spondin does, namely facilitate formation of crypt-villus organoids in vitro, soluble Wnt3a was added to Lgr5+ sorted single cells and the effect on crypt-villus formation in vitro was assessed.

Materials and Methods

Lgr5-GFP$^{hi}$ cells were sorted and cultured with or without Wnt3a (100 ng/ml) in addition to conventional single cell culture condition (EGF, noggin, R-spondin, Notch ligand and Y-27632, as described above for single cells). We seeded 100 cells/well and counted the number of organoids 14 days after seeding.

Isolated crypts were incubated with 1 uM Newport Green-DCF (MolecularProbes) in PBS+0.1% Pluronic 127 (Sigma) for 3 min at room temperature, following by PBS wash. After this, crypts were embedded in Matrigel and cultured using the standard conditions as described above.

Results

Figure 17A:
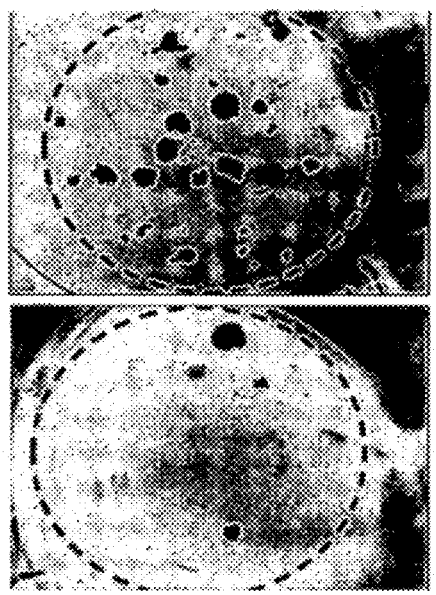
FIG. 17. Addition of Wnt3a increases the efficiency of organoid formation. a: Lgr5-GFP$^{hi}$ cells were sorted and cultured with or without Wnt3a (100 ng/ml) in addition to conventional single cell culture condition (EGF, noggin, R-spondin, Notch ligand and Y-27632, as described above for single cells). These images of dishes with cultured organoids in the presence and absence of Wnt3a are representative. b: 100 cells/well were seeded and the number of organoids were 14 days after seeding. The number of organoids/dish is represented in this graph.
Figure 17B:
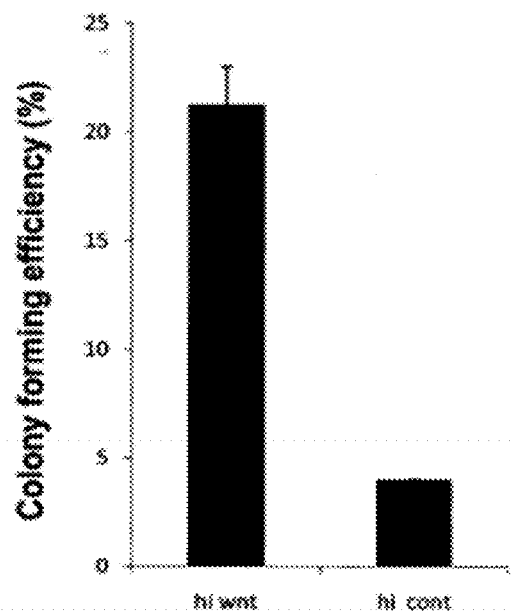
Figure 18:
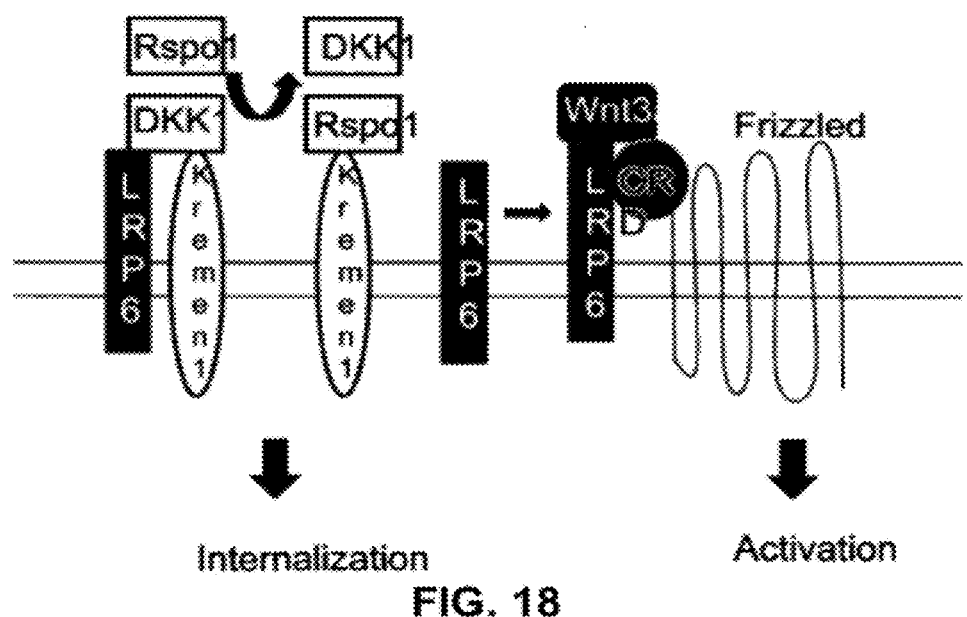
FIG. 18. Model for R-spondin1 function. Wnt/β-catenin signaling is initiated upon binding of a canonical Wnt ligand to Frizzled and association with LRP5/6 receptors. In the absence of R-spondin 1, Wnt signaling is limited by the amount of LRP6 on the cell surface, which is kept low by DKK1/Kremen1-mediated internalization. R-spondin1 enhances Wnt signaling by antagonizing DKK1/Kremen1-mediated LRP6 turnover, resulting in increased cell surface levels of LRP6. This figure was taken from PNAS 104: 14700, 2007.

The addition of Wnt3a in the absence of R-spondin did not have any effect on colony formation: little to no colonies were formed in the absence of R-spondin. However, in the presence of R-spondin, an increased efficiency in organoid formation was observed only in the presence of Wnt3a (FIG. 17). This indicates that both factors support each other in their ability to stimulate and support differentiation of stem cells into all cells necessary for the formation of a complete epithelial cell layer. The current hypothesis is that R-spondin is responsible for inhibition of internalization of a co-receptor of Frizzled, LRP6, prior to signaling through Frizzled. Upon binding of the Wnt factor to Frizzled and the co receptor LRP6, the Wnt signaling pathway is activated[31]. When LRP6 is present on the cell surface, will Wnt activation take place (FIG. 18). Therefore, if R-spondin is not present in the culture medium, Wnt3a will not be able to activate the Wnt pathway, since LRP6 is internalized and not available for signaling in combination with the Wnt factor, thereby preventing activation of the Wnt pathway.

Wnt3a is a soluble factor that, under physiological circumstances, is produced by Paneth cells. These cells are generally located adjacent to the stem cells (FIG. 19) and it is hypothesized that these cells support the maintenance of the ongoing differentiation of the intestinal epithelial cell layer. Other Wnt factors that are also secreted by Paneth cells are Wnt6, 9b and 11. It is anticipated that Wnt6 will have the same effect on stem cell differentiation as Wnt3a does. These findings support the notion that Paneth cells are important for the formation of a stem cell niche. These data are surprising, since a stem cell niche has been extensively speculated on, but so far no experimental data have supported the existence of such a niche. Additional support for the presence of a stem cell niche comes from an experiment in which Paneth cells were selectively killed. Crypts were isolated from the mouse small intestine and cultured in vitro in the presence of a zinc chelator[32] that specifically eradicates Paneth cells. This was used at such low concentrations and for such a short time that it only affects the Paneth cells and not other cells within the crypt. After treatment with the zinc chelator, organoid formation was assessed. A significant reduction of organoid formation was observed when Paneth cells were no longer present in the original crypts (FIG. 20). In the presence of Wnt3a, this reduction was partially restored (data not shown). This supports a role for the Paneth cell in the maintenance of a stem cell niche, which supports the differentiation of the Lgr5$^+$ stem cells in the crypt.

Example 5: Culture Conditions Support the Growth of Stomach Organoids as Well

The stomach consists of 3 topographic regions (fundus, corpus, and antrum) and 2 functional glandular areas (oxyntic and pyloric). The oxyntic gland area comprises 80% of the organ whereas the pyloric area comprises the 20% of the organ. The mammalian gastric epithelium is organized into gastric units consisting of a planar surface epithelium, a short pit and a long gland. The pit is lined by mucus secreting cells whereas the gland is composed of secreting cells separated in three regions: the isthmus, the neck and the base. The gastric epithelium is constantly renewed. Tracing studies performed in our laboratory have shown that LGR5 positive cells located at the gland base fulfil the definition of stemness (Barker et al. under preparation).

So far, gastric monolayer cultures have not been able to recapitulate the features of the gastric unit, which is formed by several differentiated gastric cells. Furthermore, the 3-D culture method systems reported only reconstruct highly differentiated gastric surface mucous cells, without showing any endocrine cells. Moreover, these cultures had only been carried out over a period of 7 days, thus indicating a lack of self-renewing capacity (Ootani A, Toda S, Fujimoto K, Sugihara H., *Am. J. Pathol.* 2003 June; 162(6):1905-12). Here we have developed a method to isolate gastric units from the pyloric region of the murine stomach and have been able to develop a 3D-culture system that shows longer-lived maintenance.

Materials and Methods
Gastric Unit Isolation

Isolated stomachs were opened longitudinally and washed in cold Advanced-DMEM/F12 (Invitrogen). Under the stereoscope, the pyloric region was excised and isolated from the body and forestomach and the pyloric mucosa was carefully separated from the muscle layer with tweezers. Then, the tissue was chopped into pieces of around 5 mm and further washed with cold isolation buffer ($Na_2HPO_4$ 28 mM+$KH_2PO_4$ 40 mM+NaCl 480 mM+KCl 8 mM+Sucrose 220 mM+D-Sorbitol 274 mM+DL-Dithiotreitol 2.6 mM). The tissue fragments were incubated in 5 mM EDTA with isolation buffer for 2 h at 4° C. under gentle rocking. Following removal of EDTA solution, the tissue fragments were vigorously suspended in 10 ml of cold isolation buffer with a 10 ml pipette. The first supernatant containing dead cells was discarded and the sediment was suspended with 10-15 ml cold isolation buffer. After further vigorous suspension of the tissue fragments the supernatant is enriched in gastric units. Every 10-20 suspensions the supernatant is replaced for fresh cold isolation buffer and is kept on ice and checked for the presence of gastric units. This procedure is repeated until the complete release of the gastric units, usually 4-5 times. Enriched gastric unit suspensions are centrifuged at 600 rpm for 2-3 min to separate the isolated gastric units from single cells and the sediment is used for culture.

Gastric Culture

Entire gastric units containing the gland, isthmus and pit regions were isolated from the pyloric region of murine stomach by incubating with 5 mM EDTA at 4° C. for 2 h as indicated in the previous section. Isolated gastric units were counted and pelleted. 100 gastric units were mixed with 25 µl of Matrigel (BD Bioscience), seeded on 48-well tissue culture plates and incubated for 5-10 min at 37° C. until complete polymerization of the Matrigel. After polymerization, 250 µl of tissue culture media (Advanced-DMEM/F12 supplemented with B27, N2, 200 ng/ml N-Acetylcysteine, 50 ng/ml EGF, 1 µg/ml R-spondin1, 100 ng/ml Noggin, 100 ng/ml Wnt3A, 50 or 100 ng/ml KGF) was added. The entire medium was changed every 2 days. For passage, the organoids were removed from the Matrigel using a 1000 µl pipette and were dissociated mechanically into small fragments and transferred to fresh Matrigel. Passage was performed in 1:4 split ratio once or twice per week. Under these conditions cultures have been maintained for at least 1 month.

Reagents

Advanced DMEM/F12 and supplements N2 and B-27 Serum-Free Supplement were purchased from Invitrogen and N-Acetylcysteine from Sigma. Murine recombinant EGF, Noggin and human KGF were purchased from Peprotech, and Wnt3A recombinant protein from Stem Cell Research. From the mentioned growth factors, different concentrations have only been tested for R-Spondin1 and KGF. At 50 ng/ml R-Spondin 1 inhibits culture growth. KGF can be used either at 50 or 100 ng/ml but the budding efficiency is higher in the 100 ng/ml condition.

Wnt3A conditioned media was prepared as previously described (Willert K., Brown J. D., Danenberg E., Duncan A. W., Weissman I. L., Reya T., Yates J. R. 3rd, Nusse R. *Nature* 2003 May 22; 423(6938):448-52).

Immunohistochemistry and Imaging Analysis

For X-gal staining, organoids were directly fixed in the matrigel with 0.25% glutaraldehyde (Sigma) in 100 mM $MgCl_2$ in PBS, for 1-2 h at room temperature. After, cultures were washed 3-times with washing solution (0.01% Sodium Deoxycholate+0.02% NP40+5 mM $MgCl_2$ in PBS) and incubated for 16 h at 37° C. with 1 mg/ml X-Gal (Invitrogen) in the presence of 0.21% $K_4Fe(CN)_6$ and 0.16% $K_3Fe(CN)_6$. After washing in PBS, cultures were post fixed with 2% PFA in PBS for 15 min at room temperature. All reagents were acquired from Sigma.

For immunohistochemistry, organoids were isolated from the matrigel using trypsine (Tryple Select, Invitrogen), fixed with 4% PFA for 1 h at room temperature and embedded in paraffin. Paraffin sections were processed with standard techniques and immunohistochemistry was performed as previously described. The following antibodies were used anti-mouse Ki67 (clone MM1, Monosan) (1:200), anti-rabbit cleaved caspase-3 (Cell Signaling Technology)

(1:400) and anti-human gastric mucin 5AC (Novocastra clone 45M1) (1:200). Citrate buffer antigen retrieval was performed in all cases. Sections were counterstained with Mayer's haematoxylin.

The images of gastric organoids and isolated gastric glands were taken with either inverted microscope (Nikon DM-IL) or confocal microscopy (Leica SP5).

Results

So far, gastric cultures have been grown in monolayers. Monolayer cultures, however, lack the ability to recapitulate the features of the entire gastric unit, which is formed by several differentiated gastric cells (pit mucous cells, enteroendocrine cells and proliferating mucous-free cells). Recently our laboratory has demonstrated by in vivo lineage tracing, that the Lgr5 positive cells present at the bottom of the intestinal crypts are true intestinal stem cells (Barker N., van Es J. H., Kuipers J., Kujala P., van den Born M., Cozijnsen M., Haegebarth A., Korving J., Begthel H., Peters P. J., Clevers H. *Nature* 2007; 449:1003-7). As the intestinal epithelium, the gastric epithelium is constantly renewed. Lgr5 positive cells have been found at the bottom of the pyloric gastric gland units and, tracing studies have shown that these LGR5 positive cells fulfil the definition of stemness by showing self-renewal and multipotency capability (Barker et al. under preparation). Since we have been able to culture intestinal crypts from single Lgr5+ cells in 3-D structures, it was determined whether similar conditions could sustain the growth of pyloric gastric units in vitro.

Figure 21A:
FIG. 21. Efficiency of gastric organoid culture. (a) GFP (arrows, indicating GFP positive cells) and DIC image of isolated gastric glands from the pyloric region of the stomach of a Lgr5-GFP mice. Nuclei are stained with DAPI. Magnification 63× (b) 100 gastric glands/well were seeded in duplicates with EGF (E), R-spondin 1 (R), Noggin (N), EGF+R-spondin 1 (ER), EGF+Noggin (EN), EGF+R-spondin 1+Noggin (ERN), EGF+R-spondin 1+Noggin+Wnt3A (ERNW) or EGF+R-spondin 1+Noggin+Wnt3A+KGF (ERNWK). The number of gastric organoids was counted 2, 5 and 7 days later. Results are shown as mean±SEM of 2 independent experiments. (b) 100 gastric glands/well were seeded in duplicates with Wnt3A recombinant protein (ENRWK) or Wnt3A conditioned media (ENRWCMK) supplemented with the other growth factors described in a. The number of budding organoids was counted at day 7 after seeding and at day 2 after the first passage.
Figure 21B:
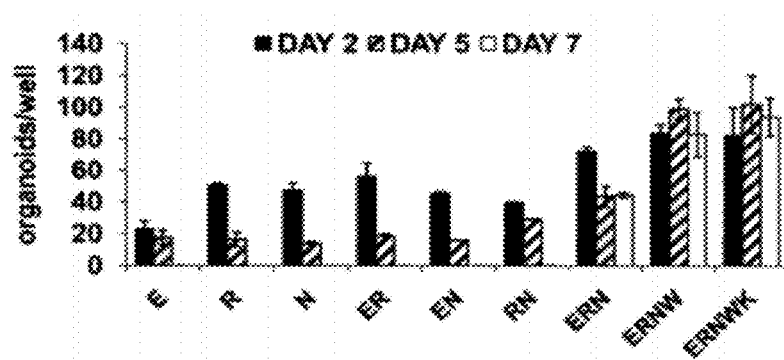
Figure 21C:
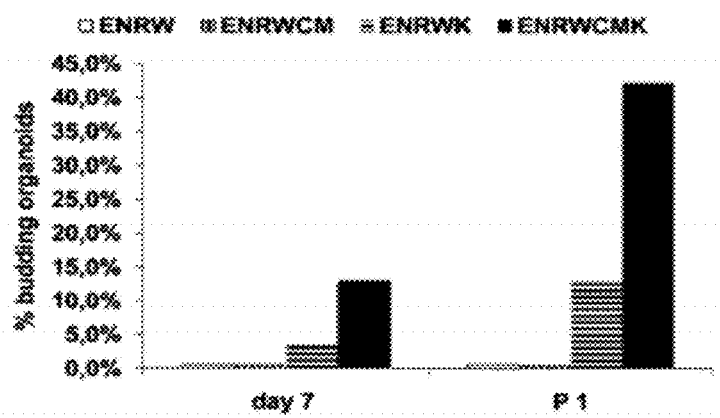

After isolation of gastric gland units using 5 mM EDTA, gastric glands (FIG. 21*a*) were suspended in Matrigel. Gastric culture growth required EGF (50 ng/ml), Noggin (100 ng/ml), R-spondin 1 (1 ug/ml) and Wnt3A (100 ng/ml) (FIG. 21*b*). KGF (50 or 100 ng/ml) was essential for the formation of budding events and, therefore, the expansion of the cultures. Thus, the cultured pyloric units behaved as the intestinal crypt organoids. The opened upper part of the unit is sealed and the lumen is filled in with apoptotic cells. The newly formed gastric organoids underwent continuous budding events (reminiscent of gland fission) while maintaining their polarity with the gastric glands budding with a central lumen. When Wnt3A conditioned media, which shows 10-100 times higher Wnt activity when compared to the recombinant Wnt3A recombinant protein, was used a significant increase in the efficiency of budding formation was detected (FIG. 21*c*), revealing a Wnt dose-dependence for the budding formation and morphogenesis.

Figure 22A:
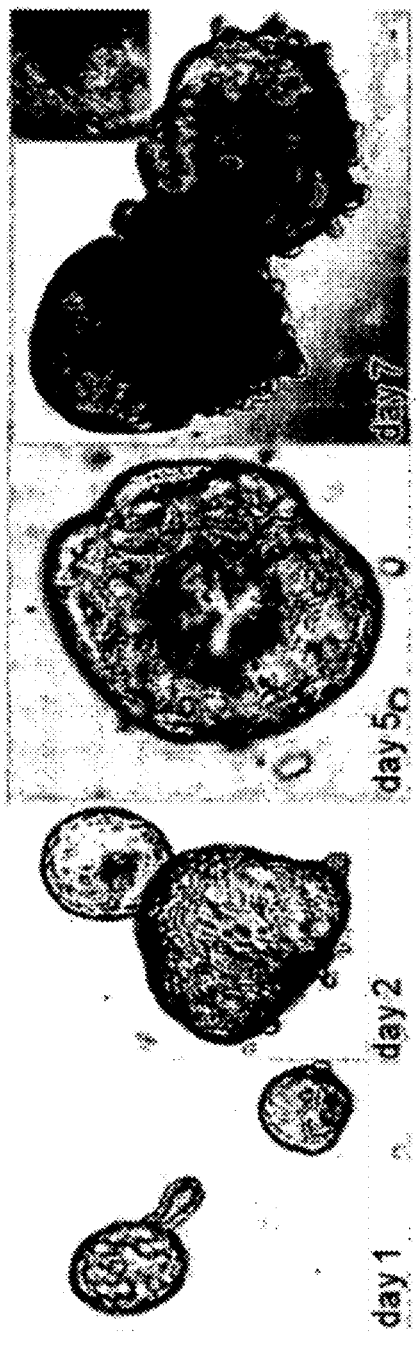
FIG. 22. Formation of gastric organoids in vitro. (a) Isolated gastric glands growing into organoids. Differential interference contrast images from days 1, 2, 5 and 7 after seeding. Magnification 10× (days 1, 2, 5). Day 7 magnification 4×, inset 10×. (b) Cultures were passage every 4-7 days by mechanical dissociation. Cultures have been grown at least for one month. Representative images showing budding structures coming out from the organoids at different passages. Passage 1 (P1), passage 2 (P2) and passage 4 (P4) representing days 8, 11, 20 respectively.
Figure 22B:
Figure 23:
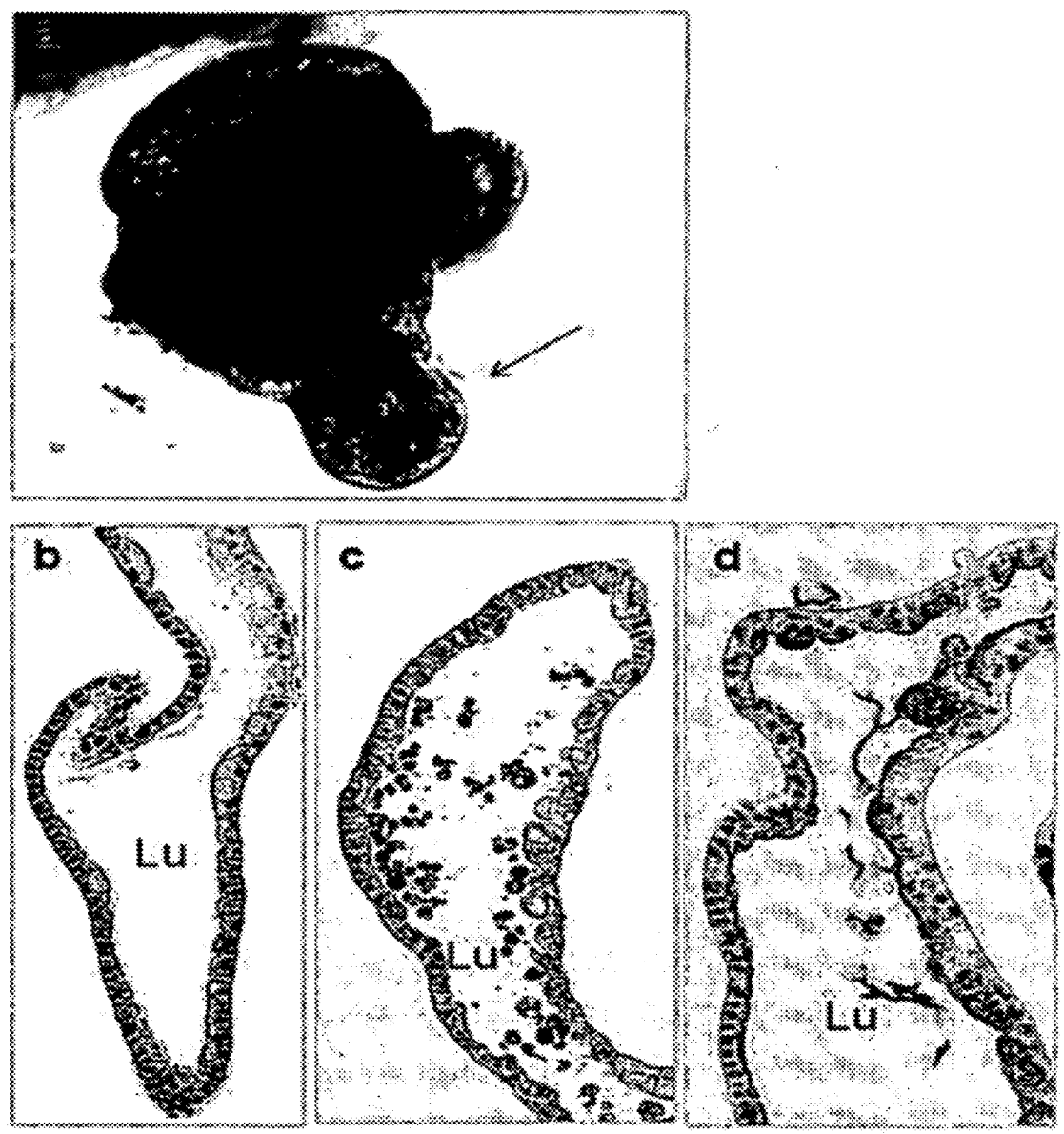
FIG. 23. Markers of gastric glands (a) gastric cultures from Lgr5-LacZ mice. Lac Z expression was detected in the gastric budding at day 5 after seeding (see arrow, indicating LacZ positive (dark grey) cells), indicating the presence of Lgr5 positive cells. Magnification 20×. (b) Ki67 staining (black) shows positive proliferating cells at the base of the gland-like structure. (c) caspase-3 (dark grey) apoptotic cells present inside the lumen of the organoid (d) Gastric mucin 5AC (dark grey) positive cells present in the gastric organoids. Lu, organoid lumen. Magnification 20×.

Organoids have been cultured for at least 1 month without losing the properties described. Weekly, organoids are passaged 1:4 by mechanical dissociation (FIG. 22). Culture of Lgr5-LacZ pyloric gastric units revealed the presence of Lgr5 positive stem cells in the gastric organoids (FIG. 23*a*). As evidenced by Ki67 staining, proliferating cells are located at the base of the gland-like structures (FIG. 23*b*) while apoptotic caspase 3 positive cells are found extruded into the lumen (FIG. 23*c*). The gastric mucin 5AC (MUC5AC) is a specific marker of the gastric pit cells, also named as foveolar cells. MUC5AC positive cells are found in the organoids, indicating the presence of at least one differentiated gastric cell lineage (FIG. 23*d*). However, no endocrine derived cells have been detected. Therefore, additional factors are required. These would include gastrin releasing peptide, activators or inhibitors of the Hedgehog and Notch families, other activators of the Wnt pathway and other inhibitors of the BMP family, activators of the TGF family.

Example 6a

Pancreas Organoids can be Grown In Vitro

Material and Methods

Freshly isolated pancreas was cut into small pieces, and incubated in DMEM (Invitrogen) with digestive enzyme mixture (300 U/ml Collagenase typeXI (Sigma), 0.01 mg Dispase I (Roche) and 0.1 mg DNase) for 10 minutes in orbital shaker (80 rpm, 37° C.). After incubation, the tissue fragments were mildly dissociated by mechanical pipetting. Undigested fragments were settled down for 1 minute with normal gravity, and the supernatant was transferred to a new tube. The supernatant was passed through 70 um-cell strainer, and the residue was washed with DMEM. The fragments remaining on the cell strainer were harvested by rinsing the inverted cell strainer with DMEM, and pelletted. The fragments mostly consist of pancreatic acinar tissue and included pancreatic ducts. The pellet was mixed with matrigel and cultured as small intestinal organoid culture system (see materials and methods of example 1). The matrigel was incubated for 5-10 min at 37° C. After polymerization of matrigel, 500 μl of tissue culture media (Advanced-DMEM/F12 supplemented with B27, N2, 200 ng/ml N-Acetylcysteine, 50 ng/ml EGF, 1 μg/ml R-spondin 1, 100 ng/ml Noggin, 50 or 100 ng/ml KGF (Peprotech) was added. The growth factors were added every 2 days. The entire medium was changed every 4-6 days. For passage, the organoids were removed from the Matrigel using a 1000 μl pipette and were dissociated mechanically into small fragments and transferred to fresh Matrigel. Passage was performed in 1:4 split ratio once or twice per week. Under these conditions cultures have been maintained for at least for 2 months.

Results

Figure 24A:
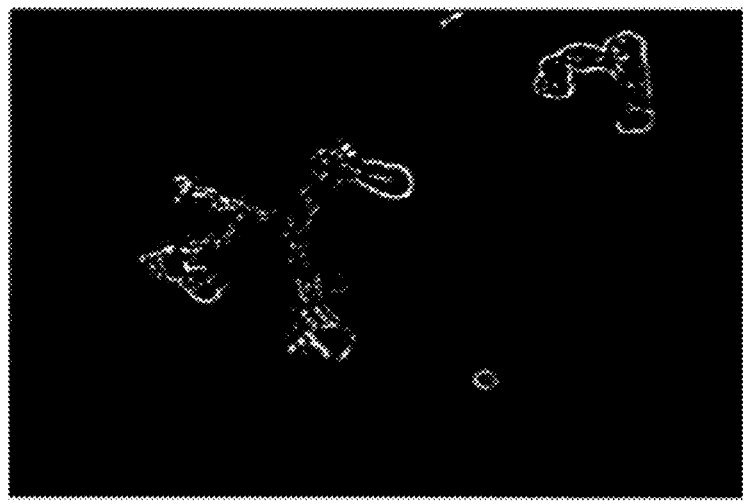
FIG. 24. Pancreatic ducts can form pancreatic like organoids in vitro. Freshly isolated pancreatic ducts were cultured in the presence of EGF, Noggin, R-spondin-1 and KGF. Differential interference contrast images from days 0, 4 and 14 after seeding.
Figure 24B:
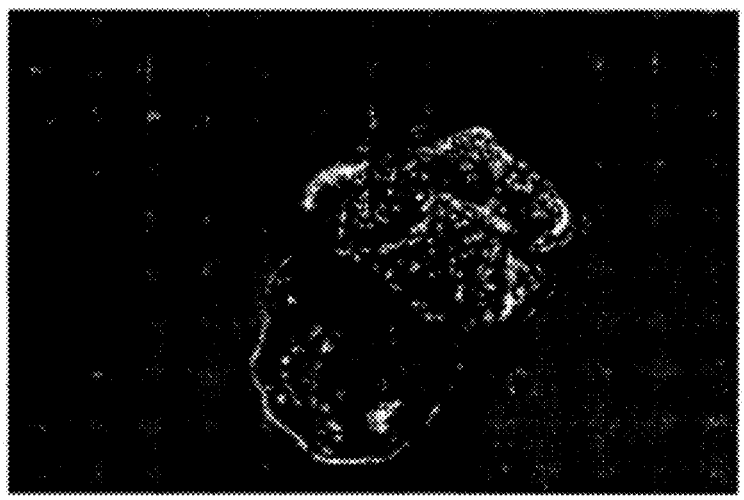
Figure 24C:
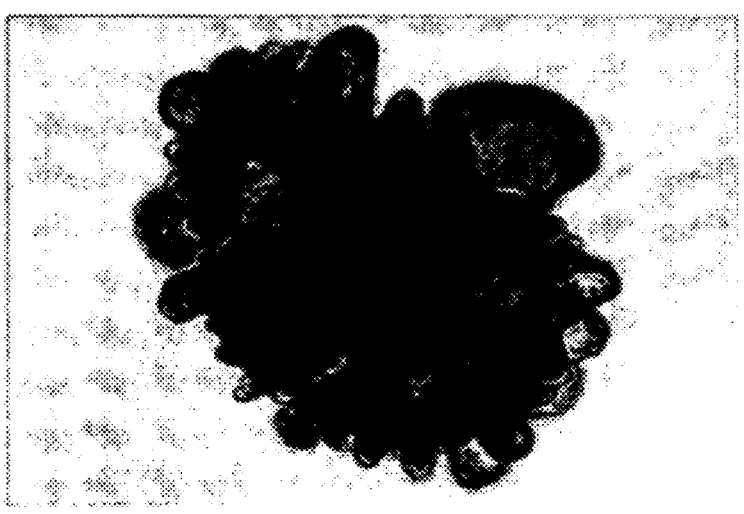

Pancreatic tissue formed simple cyst structure 3-4 days after culture in the presence of EGF. Noggin and R-spondin synergistically increased the size of cyst structure, but did not affect morphogenesis of organoids. KGF significantly induced budding formation as well as culture efficiency. Using the optimal combination of growth factors (EGF, Noggin, R-spondin-1 and KGF), more than 80% of pancreatic duct grew in the best combination of growth factors Once the pancreatic ducts had been taken in culture, the ducts quickly sealed both ends of the structure and form a simple structure. Approximately 20% of organoids started to form a budding structure 7 days after the start of the culture (FIG. 24). The pancreatic ducts rapidly proliferate, in contrast to the acinar tissue, which only grows very slowly.

Figure 25A:
FIG. 25. Pancreatic islet like structures form after appr. 3 weeks of in vitro culture. Differential interference contrast images from day 21 after seeding.
Figure 25B:
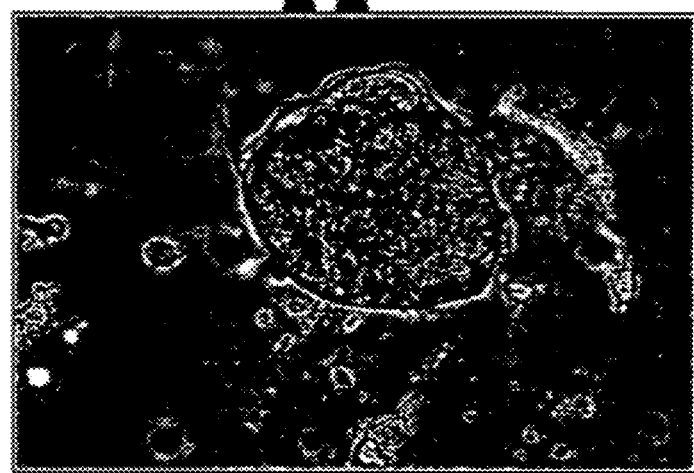
Figure 25C:
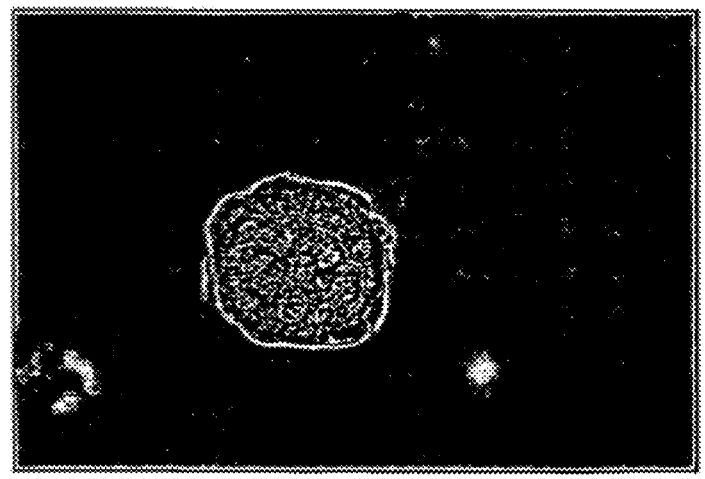

Interestingly, after passage of the organoids, appr. 2-3 weeks after the start of the culture, pancreatic islet-like structure were observed (FIG. 25). These islet-like structures are generally not observed before passage. The islets survive for at least 7 days, but proliferate very slowly or not at all. These islet-like structure resemble the pancreatic islets of Langerhans that are present in healthy pancreas tissue. Such islets contain, among others, alpha cells and beta cells that produce glucagon and insulin respectively. The observed islet-like structures contain cells that express insulin, neurogenin 3, and Pdx-1. Several growth factors will be tested to determine whether they increase the presence of pancreatic β cells in the organoids that are derived from pancreas tissue. Candidate growth factors comprise cyclopamine (Sonic-hedgehog inhibitor), Activin, GLP (Glucagon like peptide) and its derivative (Exendin 4), gastrin and Nicotinamide.

Example 6b

Pancreas Organoids can be Grown In Vitro

Material and Methods

Freshly isolated pancreas was cut into small pieces, and incubated in DMEM (Invitrogen) with digestive enzyme mixture (300 U/ml Collagenase typeXI (Sigma), 0.01 mg/ml Dispase I (Roche) and 0.1 mg/ml DNase) for 10 minutes in orbital shaker (80 rpm, 37° C.). After incubation, the tissue fragments were mildly dissociated by mechanical pipetting. Undigested fragments were settled down for 1 minute with normal gravity. The undigested fragments were further digestive with the digestive enzyme mixture for 10 minutes. This digestion procedure was repeated until the undigested fragments were mostly consist of pancreas ducts. Pancreas duct structures were manually picked up from undigested fragments under the microscopy. The pancreas ducts were mixed with matrigel and cultured as small intestinal organoid culture system (see materials and methods of example 1). The matrigel was incubated for 5-10 min at 37° C. After polymerization of matrigel, 500 µl of tissue culture media (Advanced-DMEM/F12 supplemented with 1× Glutamax, Penicilin/Streptomycin, 10 mM Hepes, B27, N2, 10 mM N-Acetylcysteine, 10 nM [Leu$^{15}$]-Gastrin I, 100 nM Exendin4, 10 mM Nicotinamide, 50 ng/ml EGF, 1 µg/ml R-spondin 1, 100 ng/ml Noggin, 50 or 100 ng/ml FGF7 (KGF) or FGF10 (Peprotech) was added. The culture medium was changed every 2 days. For passage, the organoids were removed from the Matrigel using a 1000 µl pipette and were dissociated mechanically into small fragments and transferred to fresh Matrigel. Passage was performed in 1:4 split ratio once or twice per week. Under these conditions cultures have been maintained for at least for 10 months.

Results

Pancreatic tissue formed simple cyst structure 3-4 days after culture in the presence of EGF. Noggin and R-spondin synergistically increased the size of cyst structure, but did not affect morphogenesis of organoids. FGF7 (KGF)/FGF10 significantly induced budding formation as well as culture efficiency. Using the optimal combination of growth factors (EGF, Noggin, R-spondin-1 and FGF7 (KGF)/FGF10), more than 80% of pancreatic duct grew in the best combination of growth factors Once the pancreatic ducts had been taken in culture, the ducts quickly sealed both ends of the structure and form a simple structure. Approximately 80% of organoids started to form a budding structure 7 days after the start of the culture (FIG. 24). The pancreatic ducts rapidly proliferate, in contrast to the acinar tissue, which only grows very slowly.

Interestingly, after passage of the organoids, appr. 2-3 weeks after the start of the culture, pancreatic islet-like structure were observed (FIG. 25). These islet-like structures are generally not observed before passage. The islets survive for at least 14 days, but proliferate very slowly or not at all. These islet-like structure resemble the pancreatic islets. of Langerhans that are present in healthy pancreas tissue. Such islets contain, among others, alpha cells and beta cells that produce glucagon and insulin respectively. The observed islet-like structures contain cells that express insulin, neurogenin 3, and Pdx-1. Several growth factors will be tested to determine whether they increase the presence of pancreatic β cells in the organoids that are derived from pancreas tissue. Candidate growth factors comprise cyclopamine (Sonic-hedgehog inhibitor), Activin, GLP (Glucagon like peptide) and its derivative (Exendin 4), Gastrin and Nicotinamide.

Example 7: Unimpeded Expansion of Adult Pancreatic Progenitors In Vitro by Driving a Wnt/Lgr5 Regenerative Response Materials and Methods Mice, Reagents and Tissues Pancreatic tissue was obtained from the following mice: Axin-LacZ knock in (Lustig et al., *Mol. Cell. Biol.* 2002), Lgr5-LacZ Knockin (Barker et al., 2007), Lgr5-GFP (Barker et al., 2007). Axin-LacZ mice were injected IP with 100 µg of purified human R-spondin 1 (kindly provided by A. Abo, Nuvelo Inc, CA, USA) and sacrificed 48 hours later for LacZ expression analysis in the pancreas.

Pancreatic duct ligation was performed as described in rats (Wang et al., 1995) with some minor modifications: The experimental procedure for PDL was the following: animals are anesthetized with a mixture of fluanisone:fentanyl:midazolam injected intraperitoneally at a dosage of 3.3 mg/Kg, 0.105 mg/Kg and 1.25 mg/Kg respectively. Animals are placed in supine position and the abdominal surface is shaved and cleaned with antiseptic solution (iodine solution). Following, a median incision at the upper anterior abdominal wall from the xiphisternum is performed and the pancreas is exposed. Under a dissecting microscope, the pancreatic splenic lobe is localized and the pancreatic duct is ligated with a 7-0 polypropylene suture monofilament at approximately 1 mm distal to the junction with the gastric lobe duct. Following surgery the analgesic buprenorphine is administered s.c. at a dose 0.01-0.05 mg/Kg. Following, the abdominal wall and skin was closed with 5-0 silk sutures.

Freshly isolated pancreas was treated as described under example 6, resulting in pancreatic fragments that were cultured under conditions as described below. The main pancreatic duct and first branch of ducts are mechanically isolated. The fragments were cut into small pieces and incubated in DMEM (Invitrogen) with digestive enzyme mixture (300 U/ml Collagenase type XI (Sigma), 0.01 mg/ml Dispase I (Roche) and 0.1 mg/ml DNase) for 30 minutes in orbital shaker (80 rpm, 37° C.). After the digestion, most of acinar cells were released from the fragments. Undigested fragments mostly consist of pancreatic duct cells were settled down for 1 minute with normal gravity, and the supernatant was discarded. After three times washing with PBS, the undigested fragments were incubated with 2 mM EDTA/PBS for 30 min at room temperature. The fragments were vigorously pipetted and settled down for 1 minute with normal gravity. The supernatant enriched with duct cells were transferred to new tubes and washed with PBS for three times. The duct cells were pelleted and mixed with the Matrigel. The matrigel was incubated for 5-10 min at 37° C. After polymerization of matrigel, 500 µl of Expansion medium (Advanced-DMEM/F12 supplemented with 1× Glutamax, Penicilin/Streptomycin, 10 mM Hepes, B27, N2, 1 mM N-Acetylcysteine, 10 nM [Leu$^{15}$]-Gastrin I, 100 nM Exendin4, 10 mM Nicotinamide, 50 ng/ml EGF, 1 µg/ml R-spondin1, 100 ng/ml Noggin, 50 or 100 ng/ml FGF7 (KGF) or FGF10 (Peprotech) was added. The entire medium was changed every 2 days. For passage, the organoids were removed from the Matrigel using a 1000 µA pipette and were dissociated mechanically into small fragments and transferred to fresh Matrigel. Passage was performed in 1:4 split ratio once per week. Under these conditions cultures have been maintained for at least for 2 months. For differentiation, expansion medium were changed into differentiation medium (Advanced-DMEM/F12 supplemented with Glutamax, Penicilin/Streptomycin, 10 mM Hepes, B27, N2, 200 ng/ml N-Acetylcysteine, 10 nM [Leu15]-Gastrin I, 100 nM Exendin4, 50 ng/ml EGF, 1 μg/ml R-spondin 1, 100 ng/ml Noggin).

FGF10 was obtained from Peprotech. BrdU was obtained from Sigma.

Q-PCR

RNA was isolated by RNA easy mini kit (Quiagen), and reverse transcribed using Moloney Murine Leukemia Virus reverse transcriptase (Promega). cDNA was amplified in a thermal cycler.

Primers used are shown below.

```
mmTBP (forward):
TATTGTATCTACCGTGAATCTTGG       (SEQ ID NO: 2)

mmTBP (reverse):
CAGTTGTCCGTGGCTCTC             (SEQ ID NO: 3)

Lgr5 (forward)
TCCAACCTCAGCGTCTTC             (SEQ ID NO: 4)

Lgr5 (reverse)
TGGGAATGTGTGTCAAAG (Tm = 57° C.)  (SEQ ID NO: 5)
```

PCR

All primers were designed to flank or span intron sequences in order to distinguish genomic DNA.

```
Hprt
(F) AAGTTTGTTGTTGGATATGC       (SEQ ID NO: 6)

(R) CATCTTAGGCTTTGTATTTGG      (SEQ ID NO: 7)
(Tm) 57° C., 106 bp

Ngn3
(F) TCCTCGGAGCTTTTCTACGA       (SEQ ID NO: 8)

(R) TGTGTCTCTGGGGACACTTG       (SEQ ID NO: 9)
(Tm) 60° C., 239 bp/373 bp (genomic band)

Pax6
(F) AACAACCTGCCTATGCAACC       (SEQ ID NO: 10)

(R) ACTTGGACGGGAACTGACAC       (SEQ ID NO: 11)
TM 60° C., 206 bp

Glucokinase
(F) AAGATCATTGGCGGAAAG         (SEQ ID NO: 12)

(R) GAGTGCTCAGGATGTTAAG        (SEQ ID NO: 13)
(Tm) 57° C. 193 bp

Chromogranin A
(F) GCTGACAGCAGAGAAGCGGCT      (SEQ ID NO: 14)

(R) GACAGGCTCTCTAGCTCCTGG      (SEQ ID NO: 15)
(Tm) 60° C. 231 bp

Glut2 (slc2a2)
(F) AAGTTGGAAGAGGAAGTCAG       (SEQ ID NO: 16)

(R) AGACCTTCTGCTCAGTCG         (SEQ ID NO: 17)
(Tm) 57° C. 124 bp

Insulin
(F) TTTGTCAAGCAGCACCTTTG       (SEQ ID NO: 18)

(R) TCTACAATGCCACGCTTCTG       (SEQ ID NO: 19)
(Tm) 57° C., 214 bp

Somatostatin
(F) GAGGCAAGGAAGATGCTGTC       (SEQ ID NO: 20)

(R) GGGCATCATTCTCTGTCTGG       (SEQ ID NO: 21)
(Tm) 57° C., 214 bp

Glucagon
(F) TTACTTTGTGGCTGGATTGCTT     (SEQ ID NO: 22)

(R) AGTGGCGTTTGTCTTCATTCA      (SEQ ID NO: 23)
(Tm) 57° C., 149 bp
```

Image Analysis

The images of crypt organoids were taken by either confocal microscopy with a Leica SP5, an inverted microscope (Nikon DM-IL) or a stereomicroscope (Leica, MZ16-FA). For immunohistochemistry, samples were fixed with 4% paraformaldehyde (PFA) for 1 h at room temperature, and paraffin sections were processed with standard techniques (Barker et al., Nature 2007). Immunohistochemistry was performed as described previously (Barker et al., Nature 2007). For whole-mount immunostaining, pancreas organoids were isolated from Matrigel using Dispase (Invitrogen), and fixed with 4% PFA, followed by permeabilization with 0.1% Triton X-100. Following antibodies were used for immunohistochemistry; anti-BrdU (Amersham), anti-Ki67 (Dako), anti-Insulin (Sigma), anti-C-peptide (Cell signaling), anti-Ngn3 (Developmental hybridoma studies bank)

DNA was stained with DAPI or ToPro-3 (Molecular Probes). Three-dimensional images were acquired with confocal microscopy. The staining with X-gal was performed as described under example 5 under immunohistochemistry and imaging analysis.

FACS

Pancreatic organoids were cultured in the presence or absence of R-Spondin (1 μg/ml) were removed from matrigel mechanically or enzymatically (TrypLE). Isolated organoids were further digested by TrypLE for 10 min at 37 C. Dissociated cells were passed through 40 um cell strainer (BD bioscience) and stained with APC conjugated anti-EpCAM (eBioscience). LacZ was stained by FluoReporter kit(Invitrogen) following manufacturer's protocol. Single viable cells were gated with Pulse-width, Side scatter parameter and propidium iodide staining.

In Vitro Expansion of Single Axin2-LacZ Positive Pancreatic Cells

Pancreas was isolated from mice 7 days after PDL treatment, and pancreas ducts were isolated as described above. Isolated pancreas ducts were incubated with TrypLE Express (Invitrogen) for 20 min at 37 C, following by passing through 40 um cell strainer (BD bioscience). Cells were stained with EpCAM-APC and fluorescent substrate for LacZ (FluoroReporter kit) as described in Example 7. Cells were analyzed and single viable epithelial cells were sorted by flow cytometer (MoFlo; Dako Cytomation), and collected in the EM medium. Sorted cells were pelleted, mixed with Matrigel and cultured with EM medium including 50% Wnt conditioned medium and 10 mM Y-27632 for 4 days. Culture medium was changed into EM medium without Wnt and Y-27632 after 4 days.

Results

Single Wnt-dependent Lgr5+ stem cells derived from the small intestine can be cultured to form continuously expanding gut-like organoids (Sato et al., 2009) In healthy adult pancreas, the Wnt pathway is inactive and -consequently- Lgr5 is not expressed. Upon injury by partial duct ligation (PDL), we find that the Wnt pathway becomes robustly activated, while Lgr5 expression appears at the buds of regenerating ducts. Under conditions modified from the intestinal culture system, freshly isolated adult duct fragments initiate expression of Lgr5 and form budding cysts which expand 10-fold weekly for >30 weeks. Removal of growth stimuli converts these cysts into structures with immature islet morphology, expressing endocrine and β-cell markers. Single Wnt-stimulated cells from injured pancreas can also initiated these long-term cultures. We conclude that the Hayflick limit does not apply to adult progenitor cells when cultured under optimized conditions. Thus, culture methods favoring expansion of organ-specific adult stem cells may represent an alternative to ES- or iPS-based tissue generation.

While development of the exocrine and endocrine compartments of the embryonic pancreas are understood in great detail (Jensen, 2004), much less is known about the generation of islet cells in the postnatal pancreas (Bonner-Weir and Weir, 2005; Bouwens and Rooman, 2005). Genetic lineage tracing has provided proof that pre-existing β cells, rather than stem/progenitor cells, generate new β cells in adult mice both under normal physiological conditions and after partial pancreatectomy (Dor et al., 2004; Teta et al., 2007). The existence of multipotent progenitor cells in the ductal lining of the pancreas of adult mice has recently described, which can be activated in injured pancreas to increase the functional β cell mass (Xu et al. 2008). Controlled injury was obtained by performing PDL on the pancreas of adult mice carrying a promoter reporter of Ngn3, which encodes a master switch for embryonic islet cell progenitors (Apelqvist et al., 1999; Gradwohl et al., 2000; Gu et al., 2002; Schwitzgebel et al., 2000) and which is silent in normal postnatal pancreas (Gu et al., 2002). Differentiation of these β cell progenitors is Ngn3-dependent and gives rise to all islet cell types, including glucose-responsive β cells (Xu et al., 2008). It is currently not known which signals drive the appearance of these progenitors upon injury. Such insights appear important as they may guide the design of in vitro approaches to progenitor expansion.

Figure 26A:
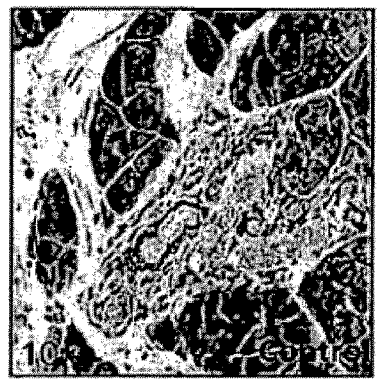
FIG. 26. Axin-LacZ mice were injected with vehicle alone (A) or R-Spondin (B). After 2 days, the pancreas was isolated and the presence of LacZ expression was determined by staining with X-gal. The middle panel of B shows a larger magnification of a duct that shows positive staining for LacZ, indicating the expression of Axin-LacZ along the lining of the pancreatic duct. The right panel shows that small duct cells in centroacinar or intercalated duct cells expressed Axing-LacZ (examples of which are indicated by black arrows). Magnifications are shown in the corner of each image. Pancreatic duct ligation was performed in wild type mice. At different times after PDL, the pancreas was isolated and tissue sections obtained from the PDL and non-PDL area were stained with H&E. Magnifications are shown for each time point (C). Pancreatic duct ligation was performed in wt and Axin2-LacZ mice. 7 days after PDL, the pancreas was isolated and Axin2-LacZ expression was determined by staining with X-gal of fixed tissue sections (D) or whole mounted organ fragments (E). The white circles indicate ligated portion of the pancreas. Expression of Ki67 (examples indicated by arrows) in pancreas tissue sections 5 days after PDL. Magnifications are shown (F). Incorporation of BrdU (examples indicated by arrows) in pancreas tissue 2 days after in vivo treatment with R-spondin. Magnifications are shown (G). Lgr5 mRNA expression was determined by Q-PCR in pancreas tissue obtained from mice undergoing PDL or a sham operation. In the PDL pancreas, the PDL area and non-PDL area was subjected to Q-PCR. The fold increase of Lgr5 expression compared to TATA box binding protein (tbp), a housekeeping gene, is shown (H). 13 days after PDL, the pancreas was isolated and Lgr5-LacZ expression was determined by staining with X-gal of fixed tissue sections. Examples of stained cells are indicated by black arrows (I).
Figure 26B:
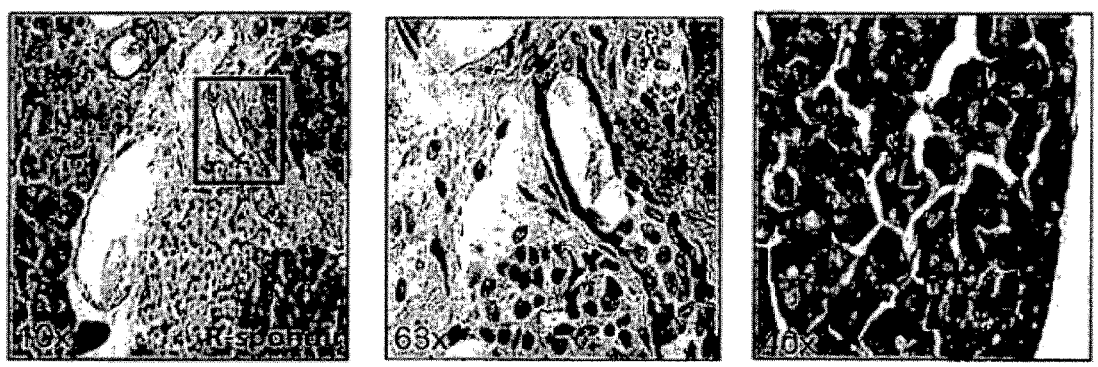
Figure 26C:
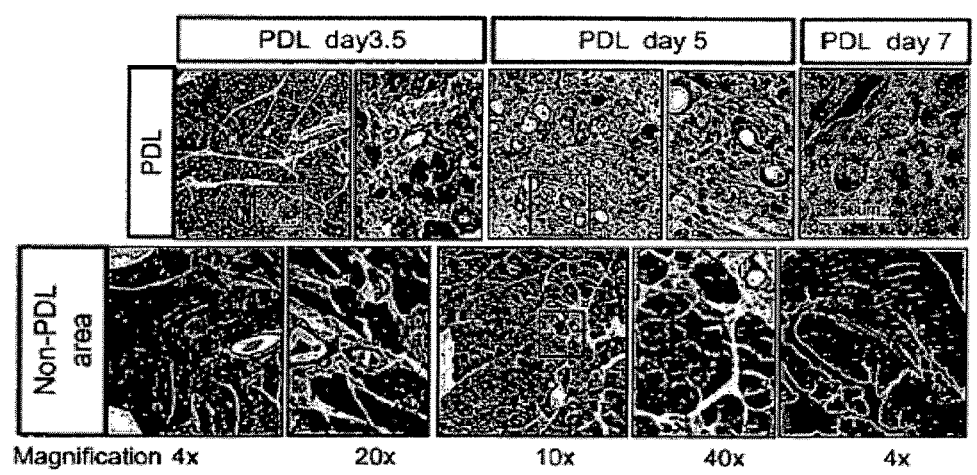
Figure 26D:
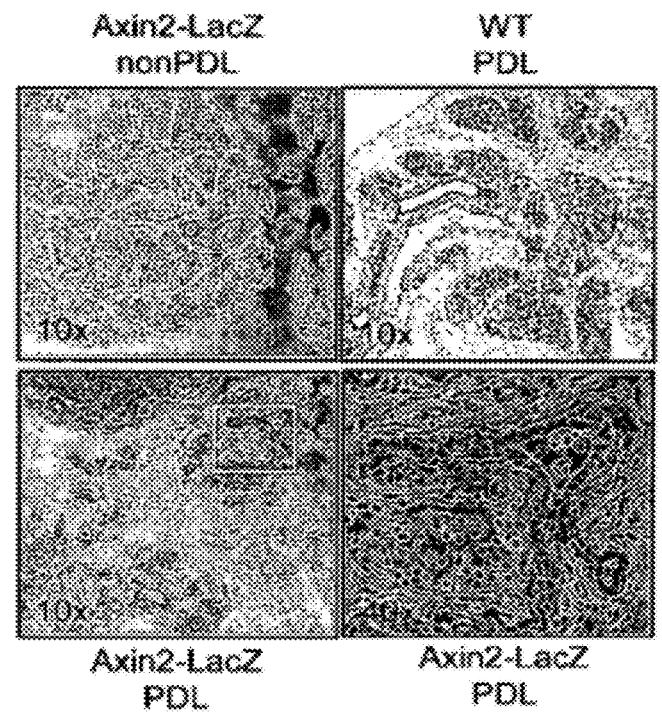
Figure 26E:
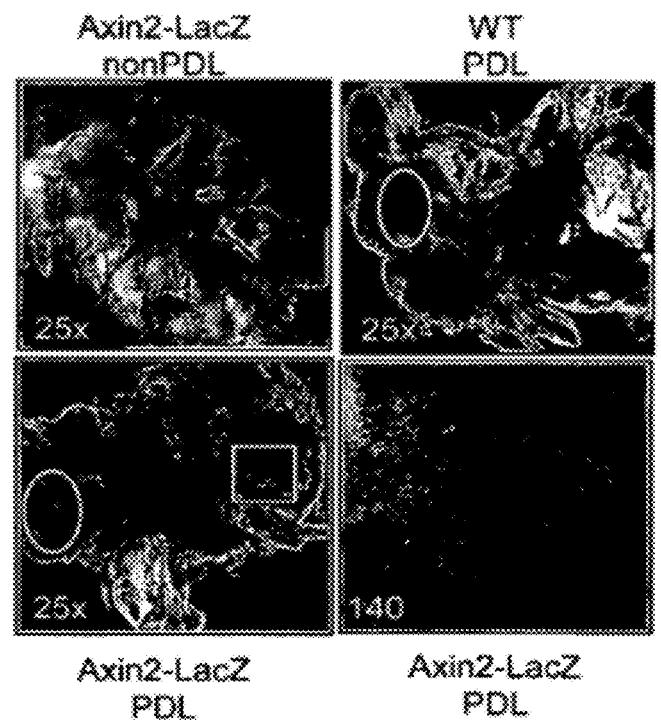
Figure 26F:
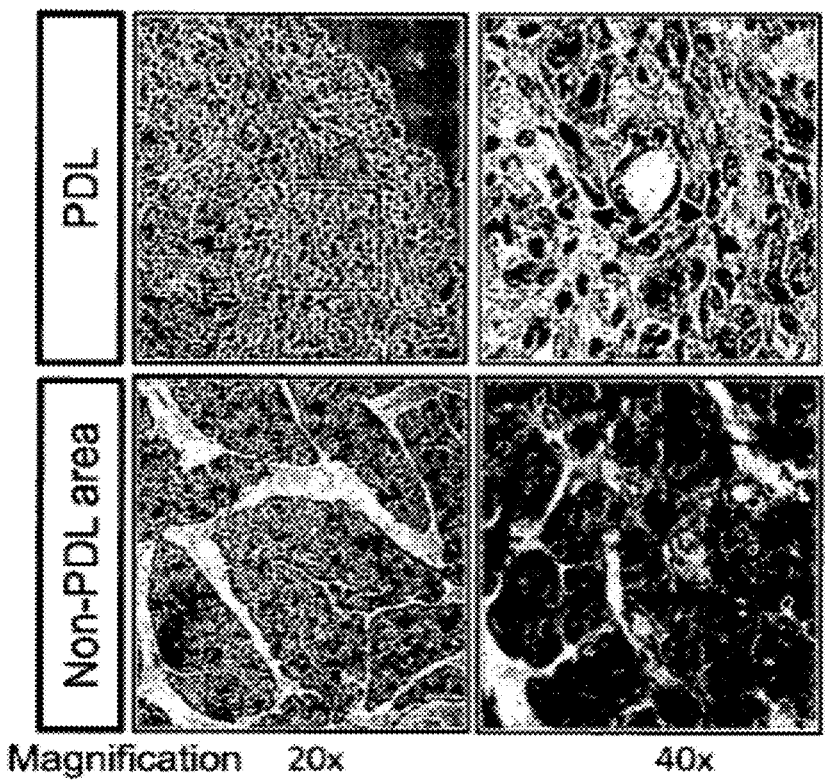
Figure 26G:
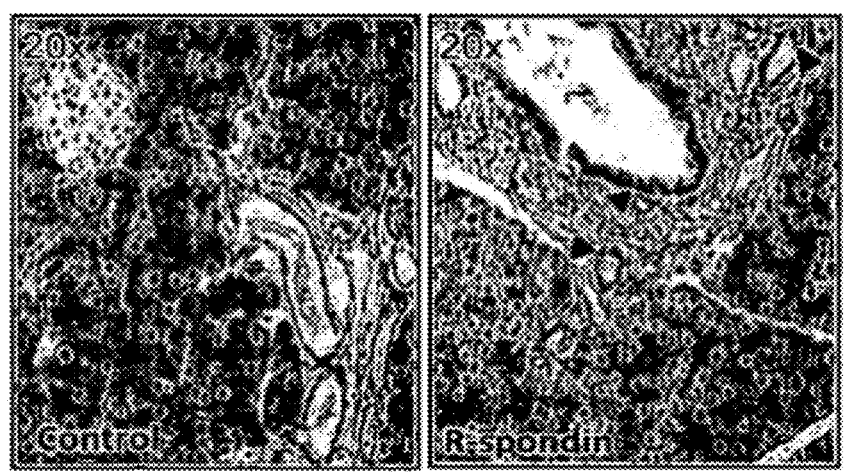

To determine whether Wnt signaling plays a role in the induction of β cell progenitors, the expression of the Axin2-LacZ allele was followed in the adult pancreas. The Axin2-LacZ allele has proven to represent a faithful, general reporter for Wnt signaling (Lustig et al., *Mol. Cell. Biol.* 2002). As expected, the reporter was inactive in adult pancreas (FIG. 26A). However, when we injected the Wnt agonist Rspo1 (Kim et al., 2005) into Axin2-LacZ mice to activate the Wnt signaling pathway, we noticed the presence of Wnt-responsive cells along the ducts, but not in acini or islets of the pancreas (FIG. 26B). Since β cell progenitors have previously been detected only upon injury of the pancreas, we then tested if a Wnt-response was physiologically activated in these cells upon injury by performing PDL. FIG. 26C shows H&E staining of pancreas tissue sections isolated from the PDL and non-PDL area. As has been reported previously (Abe et al. 1995), the acinar cells become apoptotic after 5 days and are replaced by newly formed duct structures by a mechanism not completely understood. After 7 days, an increase in islet number (islet neogenesis) as well and in islet size is also observed (as indicated by an asterisk). This indicates that the PDL was successful. Indeed, the Axin2-LacZ reporter was specifically activated along the ducts of the ligated part of the pancreas, while the unligated part did not show this response (FIGS. 26D and 26E). Moreover, the proliferative response, as determined by Ki67 staining, was mostly restricted to the ducts of the ligated part, whereas in ducts of the unligated part no nuclear Ki67 could be detected (FIG. 26F). This resembled the detection of proliferative, BrdU positive cells in the pancreas after treatment with R-Spondin (FIG. 26G).

Figure 26H:
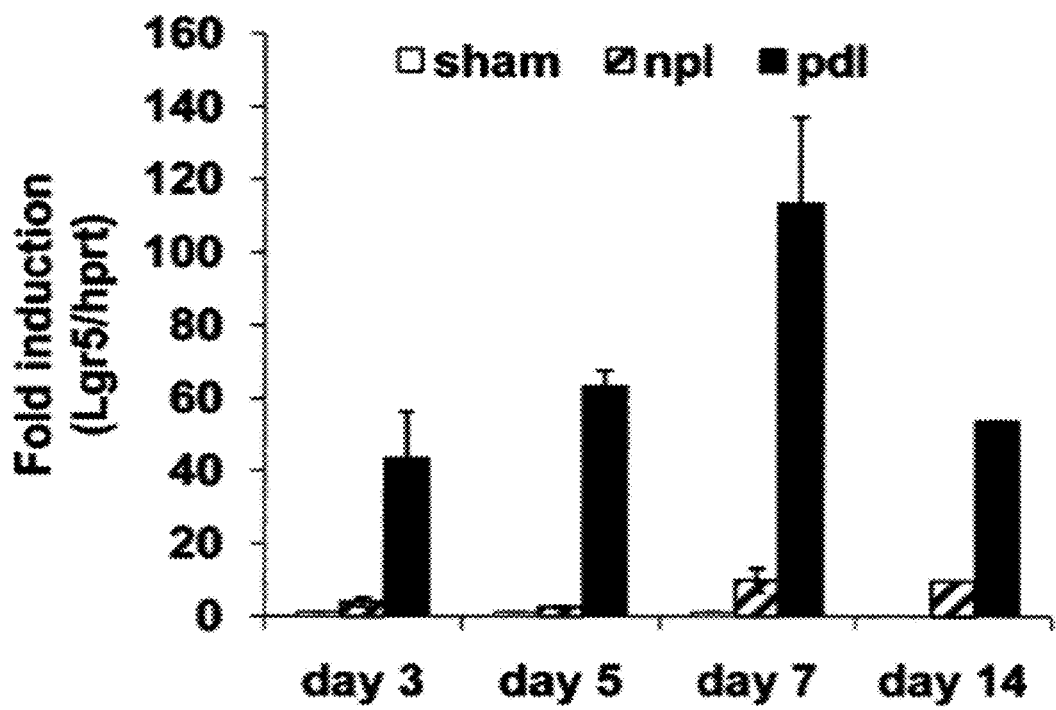
Figure 26I:
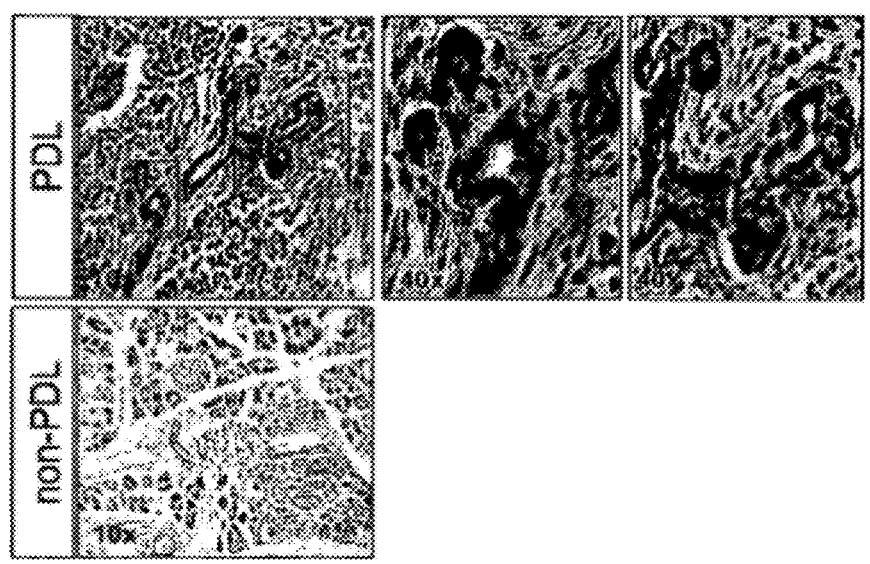

We have previously shown in the intestines that a certain population of Wnt responsive cells are stem cells (Barker et al., 2007). A marker for that population of cells was Lgr5. The Lgr5 gene is, like Axin2, a Wnt-responsive gene. Yet in the intestine and the skin it is only expressed in Wnt-stimulated stem cells but not in transit amplifying cells (Barker et al., 2007; Jaks et al., 2008)). It is therefore considered to be a genuine stem cell marker. We hypothesized that, similar to the Lgr5+ cells in the intestines, Lgr5+ cells in the pancreas may also be the origin of the β cell progenitors as detected after injury. To test this hypothesis, we performed PDL in in the pancreas of Axin-LacZ and Lgr5-LacZ mice and determined Lgr5 mRNA expression and LacZ staining. Interestingly, Lgr5 became readily detectable by qPCR in a post-PDL time course (FIG. 26H). Moreover, PDL in Lgr5-LacZ knockin mice resulted in specific activity of the reporter in the buds of regenerating ducts (indicated by the asteriks), as demonstrated by X-gal staining (FIG. 26I). The appearance of Lgr5 expression at sites of active regeneration suggested that Lgr5 might not only mark stem cells in physiological self-renewal (e.g., in the intestine, stomach or hair follicle), but that its expression may also herald the activation by Wnt of regenerative stem cells/progenitors upon injury.

Given the appearance of the Wnt-dependent Lgr5 stem cell marker, we reasoned that adult pancreas progenitors may by expanded in the previously defined gut organoid culture conditions (Sato et al., 2009). Cultures of heterogeneous populations of pancreas cells have been previously established and typically include growth factors such as EGF (Githens et al. *In Vitro Cell Dev. Biol.* 1989), FGF10 (Miralles et al. *Proc. Natl. Acad. Sci. U.S.A.* 1999) and HGF (Lefebvre et al. *Diabetes* 1998, Suzuki et al., *Diabetes* 53, 2004) and serum supplements such as Gastrin (Rooman et al. *Gastroenterology* 2001), Nicotinamide (Rooman et al. *Diabetologia* 2000) and others. A number of such cultures resulted in the in vitro generation of cells with a β cell-like phenotypes (Bonner-Weir et al., 2000; Seaberg et al., 2004; Suzuki et al., 2004) that under certain conditions were able to reverse hyperglycemia when transplanted in diabetic mice (Hao et al., 2006; Ramiya et al., 2000). Most of these approaches start with mixed cell populations that undergo senescence over time. It appears fair to say that no robust, long-term culture system exists today which maintains robust expansion of defined, non-transformed adult pancreas progenitors over long periods of time that maintain the capacity to differentiate along the endocrine lineage.

Figure 27A:
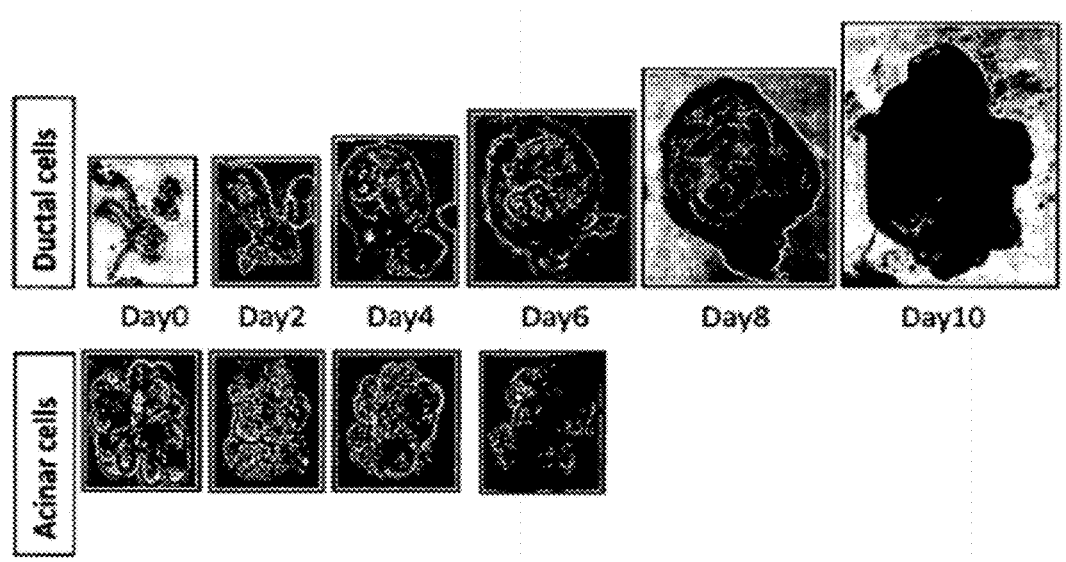
FIG. 27. Images of pancreatic ductal fragments grown in vitro in EM taken at different time points after isolated from a wild type mouse (A, top panel). Centroacinar cells did not grow for periods longer than 7 days, after which they disintegrated (A, bottom panel). Pancreatic fragments were grown in the presence or absence of EGF (50 ng/ml), R-spondin (1 µg/ml), FGF10 (100 ng/ml) or Noggin (100 ng/ml). Images of the cultures were taken 7 and 14 days after the start of the culture with freshly isolated pancreatic fragments. Cultures without EGF did not survive for longer that 10 days (B). Pancreatic fragments isolated from Axin2-LacZ mice were cultured in the absence or presence of R-spondin (1 µg/ml) for 3 days. X-gal staining showed expression of Wnt-responsive Axin-LacZ in the ductal cells after 3 and 14 days only in the presence of R-spondin (examples indicated by white arrows). No X-gal staining was detected in the acinar or islet cells (C). Ductal fragments were isolated from Lgr5-LacZ mice and cultured for 3 days in the absence or presence of R-spondin. Expression of Lgr5-LacZ, as indicated by X-gal staining, shows Lgr5+ cells on the tips of the buds, similar to its expression after PDL (D). FACS staining of cells obtained from pancreatic fragments cultured in the presence of a Wnt agonist, R-spondin. Cells were stained for EpCAM, a pan-epithelial cell marker, and LacZ (Fluorescein-di-galactopyranoside, FDG). The percentage of Lgr5+ cells is significantly increased when pancreatic fragments are cultured in the presence of a Wnt signal (E).
Figure 27B:
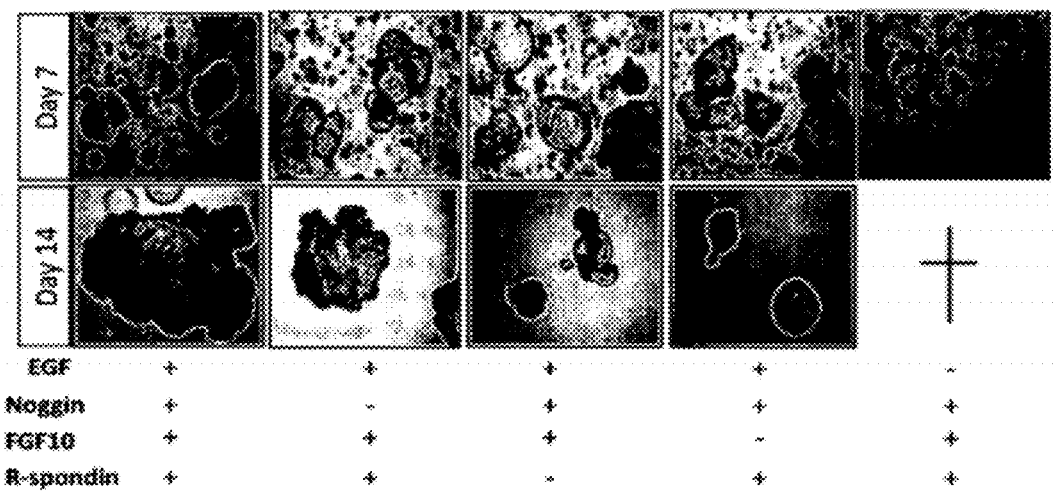

We first attempted to grow purified duct fragments in Expansion Medium (EM). As shown in FIG. 27A, small duct fragments immediately underwent expansion into cyst-like structures undergoing continuous budding, while islets (data not shown) and acini (bottom panel) gradually disintegrated. The cultures expand 10-fold/week (and are passaged weekly) for over 30 weeks. Multiple growth factors have been tested to determine the required signals for optimal expansion of pancreatic cells in vitro (FIG. 27B). Clearly, in the absence of EGF, cultures disintegrated after 7 days. Also the absence of R-spondin or FGF10 reduced the viability of the cultures after 14 days. In contrast, Noggin, a BMP inhibitor, did not have any effect on the sustained growth of pancreatic fragments. The addition of Nicotinamide, Exendin4, Gastrin to the expansion medium was not essential but resulted in an increase in culture efficiency (data not shown).

Figure 27C:
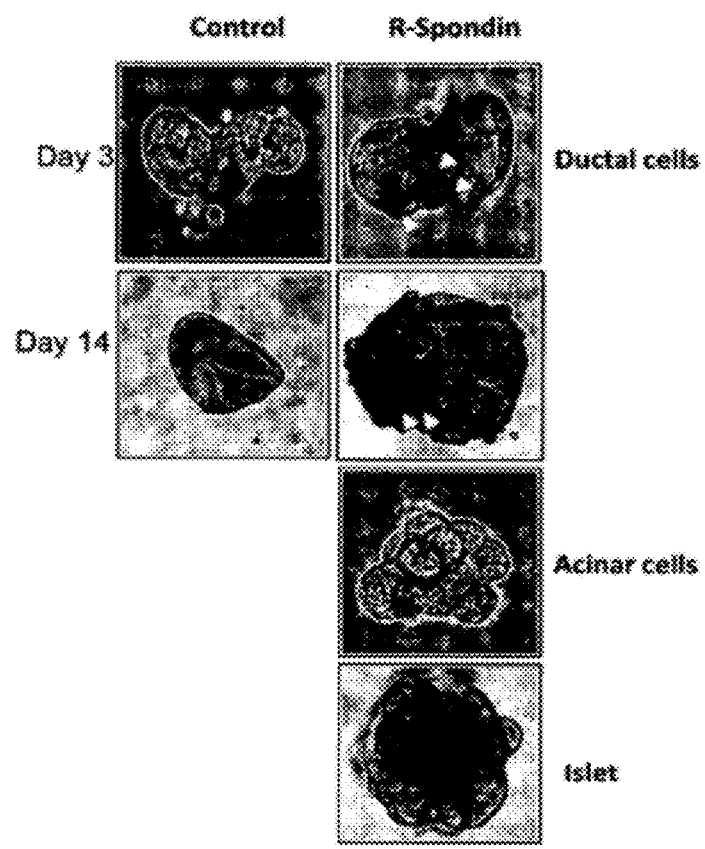
Figure 27D:
Figure 27E:
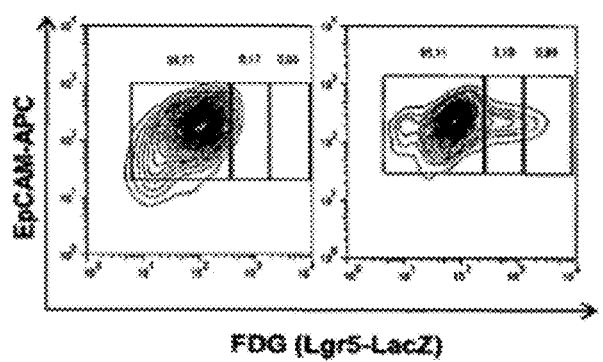

Since we demonstrated that Wnt signaling was activated upon PDL, the effect of addition of a Wnt agonist to freshly isolated pancreatic fragments in vitro on sustained growth was determined. When ducts were isolated from Axin2-LacZ mice, the entire budding cysts stained blue only in the presence of the Wnt agonist Rspondin1 (FIG. 27C), resembling the situation in vivo after PDL (FIGS. 26D and 26E). No blue staining was observed in freshly isolated islets or acini from Axin2-LacZ pancreas. In line with the in vivo observations upon PDL, only the buds of Lgr5-LacZ cysts stained blue (FIG. 27D). Moreover, culturing of pancreatic Lgr5-LacZ organoids for 14 days in the presence of R-spondin increased the percentage of Lgr5+ cells significantly (FIG. 27E). Importantly, when pancreatic fragments were cultured in the absence of R-Spondin in EM, organoids cease to proliferate within 1 month, whereas in the presence of R-spondin, they can be expanded for an unlimited time period. These observations imply that Wnt-responsive progenitors located near ducts fueled the growth of the budding cysts, which were subsequently maintained by Lgr5-expressing cells with stem cell-like properties.

Figure 28:
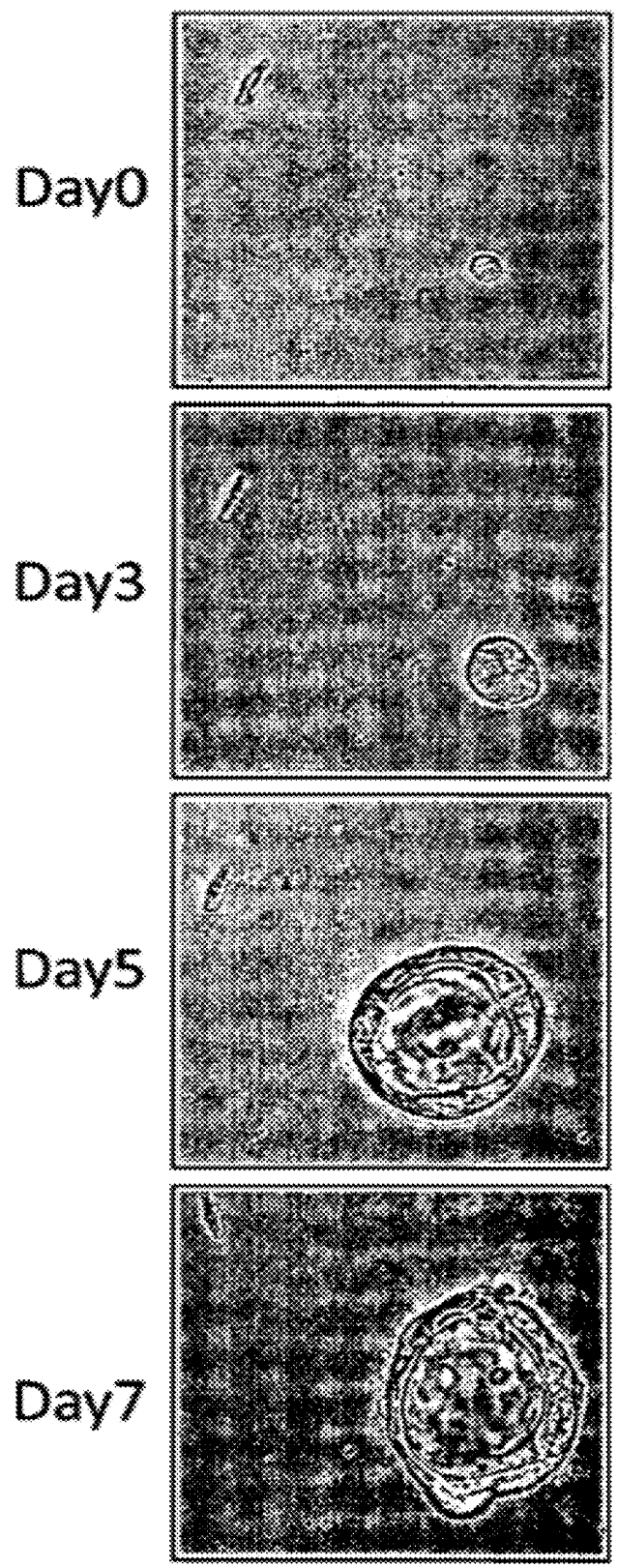
FIG. 28. Pancreas was isolated from mice 7 days after PDL treatment and pancreatic cells were stained with EpCAM-APC and fluorescent substrate for LacZ (FluoroReporter kit), sorted and cultured in EM including 50% Wnt3A conditioned medium and 10 mM Y-27632 for 4 days. Culture medium was changed into EM medium without Wnt and Y-27632 after 4 days. Pictures were taken on the indicated days and a 40× magnification is shown.

To test this notion directly we sorted Axin2-LacZ positive cells from mice 7 days post PDL and found that these cells efficiently initiated budding cysts that were indistinguishable from duct-initiated cysts (FIG. 28). The single cells require the presence of Wnt3a in the medium. Comparison of culture efficiency in the presence of absence of Wnt3A after single cell dissociation showed that the single cells cultured in the absence of Wnt3A initially grow as small cyst structures, but stop proliferation after 2-4 days. This is not the case for pancreas cultures started from isolated pancreas fragments. Interestingly, the Wnt3A could be removed after 4 days, indicating that either this signal was no longer necessary to stimulate growth or that the production of Wnt3A was initiated by cells derived from the single sorted cells the culture had started with.

Figure 29A:
FIG. 29. Pancreatic organoids were transferred from EM to DM. The effect of removal of FGF10 from the expansion medium, resulting in DM, induced differentiation into islets. Pancreatic organoids were cultured for 10 days in DM after which islet like structures could be detected in vitro. Pictures of the cultures in the presence and absence of FGF10 are shown (A) and shows increased expression of certain differentiation markers, Ngn3 and somatostatin as measured by PCR. Hprt is a housekeeping gene (B). At several time points after the transferal to DM, expression of a number of markers was assessed by PCR(C). Change in morphology from pancreatic cysts to β cell-like structures (D) accompanied the appearance of certain β cell markers, such as Insulin and C-peptide as detected by immunofluorescence (E). The presence of R-spondin in DM is essential for the regeneration of β cell progenitors, as indicated by positive immunofluorescent staining for Ngn3 (examples are indicated by white arrows) (F).
Figure 29B:
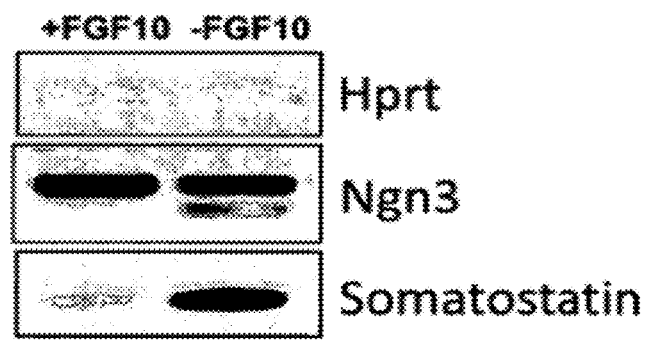
Figure 29E:
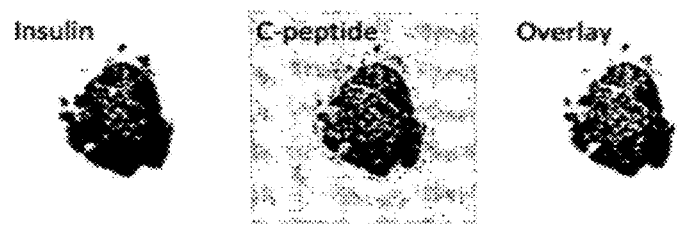
Figure 29F:
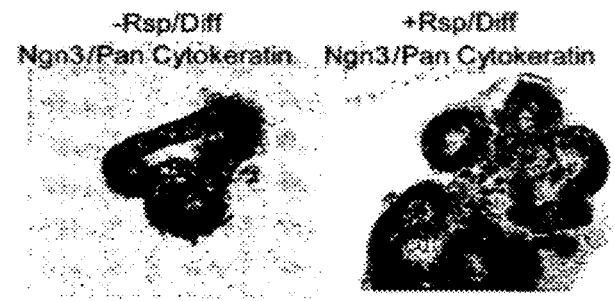
Figure 29C:
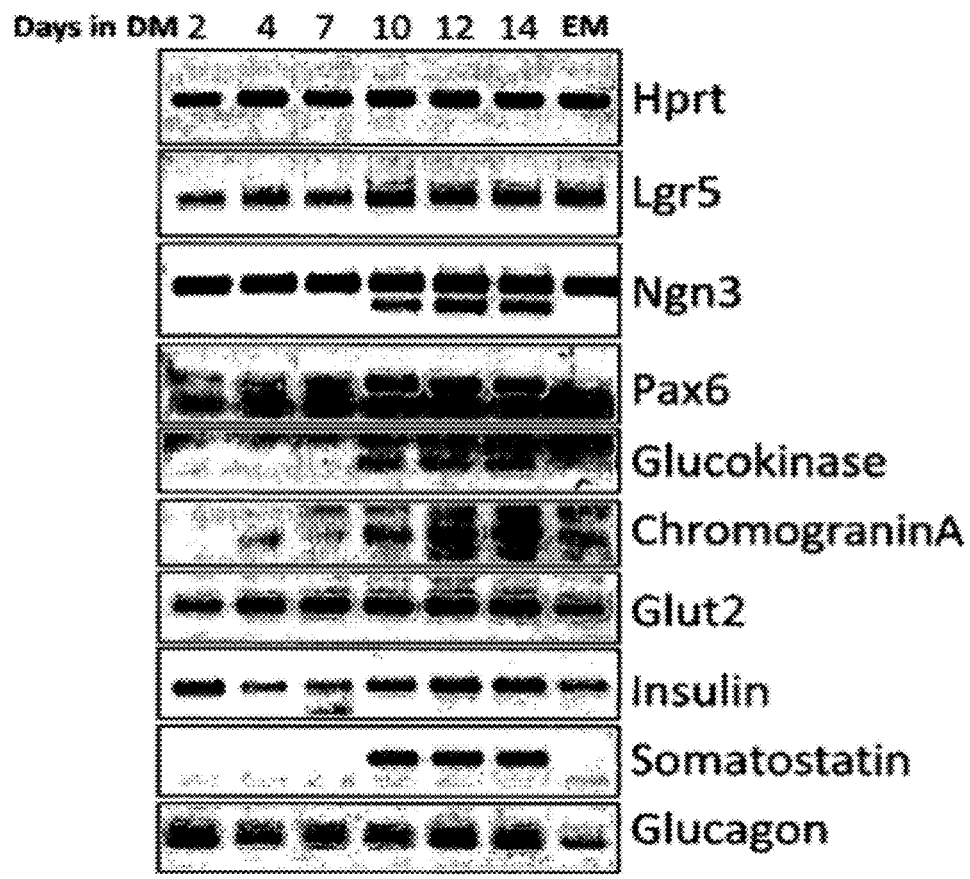

We then attempted to assess the potential of the budding cysts to generate endocrine lineage cells. To this end, we tested a number of changes to the EM to define a Differentiation Medium (DM). A series of factors was tested for their effect on the differentiation into the endocrine lineages. The removal of FGF10 seemed to be crucial to the induction of differentiation. Only in the absence of FGF10 did the islet like structures appear (FIG. 29A), which corresponded with the expression of several differentiation markers for β cell progenitors (Ngn3), β cells (Insulin), glucagon (α cells) and somatostatin (δ cells) appear (FIGS. 29B and 29C). Moreover, differentiation markers, such as Glucokinase, Pax6 and Chromogranin A were upregulated starting 10 days after exposure to the DM medium. Therefore, DM optimally consisted of at least EGF and R-Spondin and did not have any FGF7 or 10 present. The sustained expression of Lgr5, a stem cell marker, under differentiation conditions can be explained by the presence of R-spondin, a Wnt agonist, in DM, since Lgr5 is a Wnt responsive gene. When cells were cultured in presence of Nicotinamide in EM, it was also important to remove this from the medium as well to obtain full differentiation.

Figure 29D:
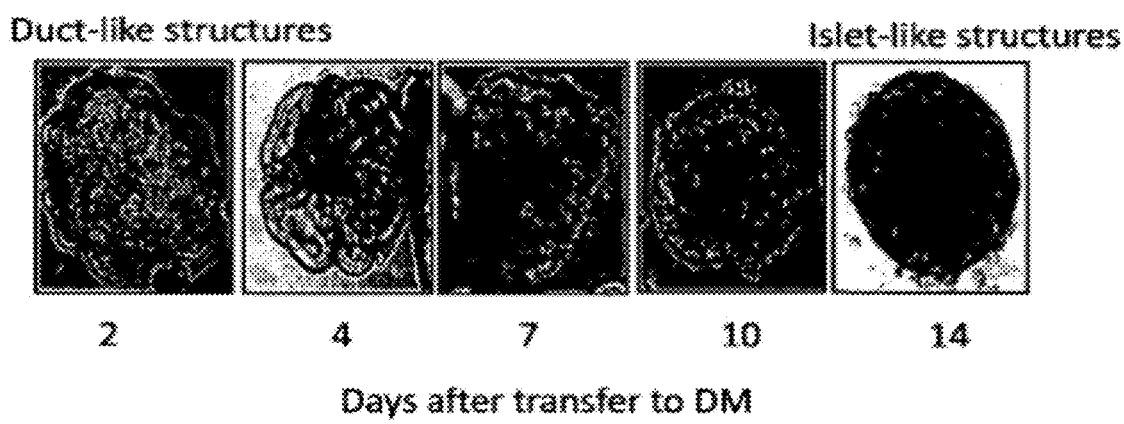

When budding cysts after any period of culture were transferred from EM to DM, the cysts underwent a stereotypic "involution" process: Progressive inward folding of the wall lead to impaction of the cyst into a smaller compact body with morphological resemblance to an islet (FIG. 29D). Islet-like morphology was confirmed by markers for β cell islets such as Insulin and C-peptide (FIG. 29E). To confirm the dependence of this step of the regeneration process on Wnt signaling, pancreatic fragments were cultured in DM in the absence or presence of R-spondin. Importantly, β cell progenitors, as demonstrated by expression of Ngn3, were only detectable in the presence of R-spondin (FIG. 29F).

Example 8: In Vitro Expansion of Human Pancreas Fragments

During embryonic pancreas development, neurogenin3+ or insulin expressing cells were seen in the pancreas ductal network, and it was suggested that pancreas duct cells give rise to endocrine progenitors and consequently mature endocrine cells. It has been shown that human pancreas duct cells differentiate into glucose responsive insulin producing cells in vitro (Bonner-Weir, S. et al. 2000 *PNAS*), and this finding made pancreas duct cells attractive source for beta cells replace therapy. However, it has been difficult to expand duct cells without losing endocrine differentiation capacity. In the previously reported culture system, human pancreas duct cells lost epithelial property or underwent senescence after 2 weeks up to 5 weeks (Trautmann B. et al., *Pancreas* vol. 8 248-254). Therefore, there is no robust culture system to expand human pancreas duct cells, which retain endocrine differentiation ability. Taking advantage of establishment of mouse pancreas organoid culture system, here, we attempted to establish human pancreas organoid culture system.

Growth of Human Pancreatic Progenitors in Vitro

Human pancreas was obtained from Leiden University Medical Center, The Netherlands. Importantly, under the same conditions as described for mouse pancreas fragments above (example 7), human freshly isolated pancreas fragments can also be grown in vitro (FIG. 30).

Under these expansion conditions, the culture efficiency of the pancreatic fragments was appr. 80%, meaning that 80% of the freshly isolated pancreatic fragments were efficiently expanded in vitro for a longer period of time. As compared with mouse pancreas, acinar tissue more easily forms cyst structures, however, these structures ceased to proliferate within 4 weeks. Pancreas duct cells from larger ductular network more efficiently produce cyst structures and eventually form organoids with bud. The pancreas organoids were splitted 1:5 ratio once per week and maintained in vitro at least 5 weeks without losing proliferation ability.

In summary, we established human pancreas organoids culture system and succeeded in expansion of pancreas duct cells at least 3000 times from original volume. We are optimizing endocrine differentiation culture condition for human pancreas duct cells, and this in vitro approach, once optimized, might be important implications for making beta cell replacement therapy available to a larger number of people with type 1 and 2 diabetes mellitus.

REFERENCES

Abe K., Watanabe S. (1995) Apoptosis of mouse pancreatic acinar cells after duct ligation. *Arch. Histol. Cytol.* 58:221-9

Apelqvist A., Li H., Sommer L., Beatus P., Anderson D. J., Honjo T., Hrabe de Angelis M., Lendahl U., Edlund H. (1999) Notch signaling controls pancreatic cell differentiation. *Nature* 400:877-81.

Barker N., van Es J. H., Kuipers J., Kujala P., van den Born M., Cozijnsen M., Haegebarth A., Korving J., Begthel H., Peters P. J., Clevers H. (2007) Identification of stem cells in small intestine and colon by marker gene Lgr5. *Nature* 449:1003-7.

Bonner-Weir, S., and Weir, G. C. (2005). New sources of pancreatic beta-cells. *Nat. Biotechnol.* 23, 857-861.

Bonner-Weir, S., Taneja, M., Weir, G. C., Tatarkiewicz, K., Song, K. H., Sharma, A., and O'Neil, J. J. (2000). In vitro cultivation of human islets from expanded ductal tissue. *Proc. Natl. Acad. Sci. USA* 97, 7999-8004.

Bouwens, L., and Rooman, I. (2005). Regulation of pancreatic beta-cell mass. *Physiol. Rev.* 85, 1255-1270.

Dor, Y., Brown, J., Martinez, O. I., and Melton, D. A. (2004). Adult pancreatic beta-cells are formed by self-duplication rather than stem-cell differentiation. *Nature* 429, 41-46.

Githens S., Schexnayder J. A., Desai K., Patke C. L. (1989) Rat pancreatic interlobular duct epithelium: isolation and culture in collagen gel. *In Vitro Cell Dev. Biol.* 25:679-88.

Gradwohl, G., Dierich, A., LeMeur, M., and Guillemot, F. (2000). neurogenin3 is required for the development of the four endocrine cell lineages of the pancreas. *Proc. Natl. Acad. Sci. U.S.A.* 97, 1607-1611.

Gu, G., Dubauskaite, J., and Melton, D. A. (2002). Direct evidence for the pancreatic lineage: NGN3+ cells are islet progenitors and are distinct from duct progenitors. *Development* 129, 2447-2457.

Hao, E., Tyrberg, B., Itkin-Ansari, P., Lakey, J. R., Geron, I., Monosov, E. Z., Barcova, M., Mercola, M., and Levine, F. (2006). Beta-cell differentiation from nonendocrine epithelial cells of the adult human pancreas. *Nat. Med.* 12, 310-316.

Jaks V., Barker N., Kasper M., van Es J. H., Snippert H. J., Clevers H., Toftgård R. (2008) Lgr5 marks cycling, yet long-lived, hair follicle stem cells. *Nat. Genet.* 40:1291-9.

Lefebvre V. H., Otonkoski T., Ustinov J., Huotari M. A., Pipeleers D. G., Bouwens L. (1998) Culture of adult human islet preparations with hepatocyte growth factor and 804G matrix is mitogenic for duct cells but not for beta-cells. *Diabetes* 47:134-7

Lustig B., Jerchow B., Sachs M., Weiler S., Pietsch T., Karsten U., van de Wetering M., Clevers H., Schlag P. M., Birchmeier W., Behrens J. (2002) Negative feedback loop of Wnt signaling through upregulation of conductin/axin2 in colorectal and liver tumors.

Lustig B., Jerchow B., Sachs M., Weiler S., Pietsch T., Karsten U., van de Wetering M., Clevers H., Schlag P. M., Birchmeier W., Behrens J. *Mol. Cell. Biol.* 1184-93.

Miralles F., Czernichow P., Ozaki K., Itoh N., Scharfmann R. (1999) Signaling through fibroblast growth factor receptor 2b plays a key role in the development of the exocrine pancreas. *Proc. Natl. Acad. Sci. U.S.A.* 96:6267-72.

Ramiya, V. K., Maraist, M., Arfors, K. E., Schatz, D. A., Peck, A. B., and Cornelius, J. G. (2000). Reversal of insulin-dependent diabetes using islets generated in vitro from pancreatic stem cells. *Nat. Med.* 6, 278-282.

Rooman I., Heremans Y., Heimberg H., Bouwens L. (2000) Modulation of rat pancreatic acinoductal transdifferentiation and expression of PDX-1 in vitro. *Diabetologia* 2000 July; 43(7):907-14.

Rooman I., Lardon J., Flamez D., Schuit F., Bouwens L. (2001) Mitogenic effect of gastrin and expression of gastrin receptors in duct-like cells of rat pancreas. *Gastroenterology* 121:940-9.

Sato T., Vries R. G., Snippert H. J., van de Wetering M., Barker N., Stange D. E., van Es J. H., Abo A., Kujala P., Peters P. J., Clevers H. (2009) Single Lgr5 stem cells build crypt-villus structures in vitro without a mesenchymal niche. *Nature* 459:262-5.

Schwitzgebel, V. M., Scheel, D. W., Conners, J. R., Kalamaras, J., Lee, J. E., Anderson, D. J., Sussel, L., Johnson, J. D., and German, M. S. (2000). Expression of neurogenin3 reveals an islet cell precursor population in the pancreas. *Development* 127, 3533-3542.

Seaberg, R. M., Smukler, S. R., Kieffer, T. J., Enikolopov, G., Asghar, Z., Wheeler, M. B., Korbutt, G., and van der Kooy, D. (2004). Clonal identification of multipotent precursors from adult mouse pancreas that generate neural and pancreatic lineages. *Nat. Biotechnol.* 22, 1115-1124.

Suzuki, A., Nakauchi, H., and Taniguchi, H. (2004). Prospective isolation of multipotent pancreatic progenitors using flow-cytometric cell sorting. *Diabetes* 53, 2143-2152.

Teta, M., Rankin, M. M., Long, S. Y., Stein, G. M., and Kushner, J. A. (2007). Growth and regeneration of adult beta cells does not involve specialized progenitors. *Dev. Cell.* 12, 817-826.

Trautmann B., Schlitt H. J., Hahn E. G., Lohr M. (1993) Isolation, culture, and characterization of human pancreatic duct cells. *Pancreas* 8:248-54.

Wang, R. N., Kloppel, G., and Bouwens, L. (1995). Duct- to islet-cell differentiation and islet growth in the pancreas of duct-ligated adult rats. *Diabetologia* 38, 1405-1411.

Xu X., D'Hoker J., Stangé G., Bonne S., De Leu N., Xiao X., Van de Casteele M., Mellitzer G., Ling Z., Pipeleers D., Bouwens L., Scharfmann R., Gradwohl G., Heimberg H. (2008) Beta cells can be generated from endogenous progenitors in injured adult mouse pancreas. *Cell* 132(2):197-207.

Example 9: Culturing of Human Small Intestinal or Colon Crypts In Vitro

As described in examples 1 and 2 it is now for the first time possible to generate long time culture conditions for mouse small intestine and colon epithelium. Crypt-villus organoids grow through the supplementation of a set of divined growth factors and an extracellular matrix. The organoids contain intestinal stem cells that actively divide and giving rise to all major differentiated cell lineages present in the intestine. In this example we show that these culture conditions are not unique to the mouse intestinal epithelium but can also be used to grow human intestinal epithelium.

Material and Methods

Mouse Colon Organoid Cultures

Mouse organoid cultures were cultured as described in example 1. Inhibitor of Wnt production (IWP-2) was used to inhibit Wnt secretion (Chen et al., *Nat. Chem. Biol.* 2009 February; 5(2):100-7).

Human Colon Organoid Cultures

Human colon crypts were isolated from resected normal colonic specimen and cultured as organoid structures for 7 days using the established organoid culture system (Sato et al., 2009 *Nature* May 14; 459(7244):262-5). Since this protocol was optimized for mouse derived organoid cultures, we made a small change by the addition of Wnt3a conditioned medium, in order to ensure optimal growth of the human colon organoids. To obtain this conditioned medium, Wnt3a is expressed in a cell line by transfecting a suitable expression construct encoding the ligand. the cell line is cultured and the culture medium comprising the secreted ligand is harvested at suitable time intervals. For example, cells start the production of Wnt3a at the moment they reach confluency and stop growing. Culture medium from cells that were not transfected or infected with the empty expression construct was used as a negative control. The conditioned medium was harvested and tested, for example in an assay wherein luciferase expression in controlled by TCF responsive elements to quantitate the presence of a Wnt agonist such as Wnt3a (Korinek et al., 1997, *Science* 275:1784-1787).

Results

Figure 31A:
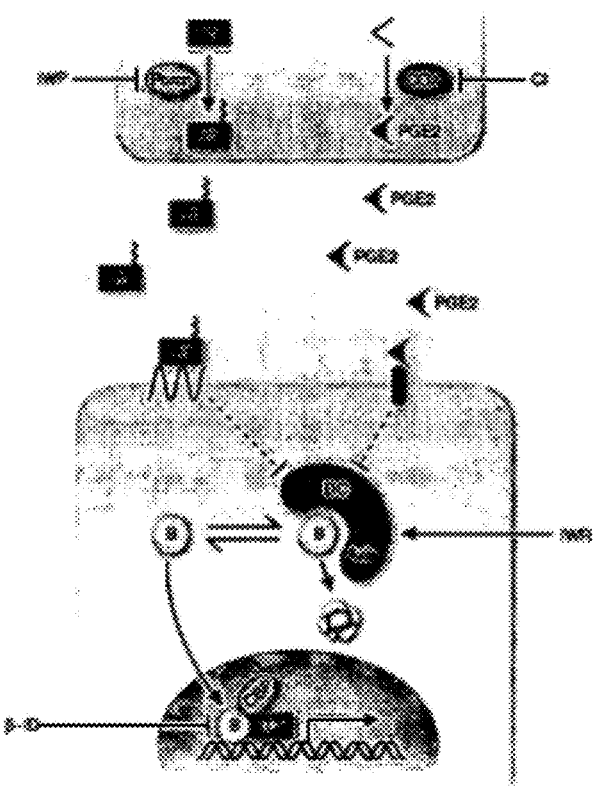
FIG. 31. In vitro crypt cultures produce Wnt ligand(s). (A) Schematic representation of the Wnt pathway. When Wnt ligands are secreted, they can autocrine or paracrine activate the Wnt signaling pathway. Porcupine is important for proper Wnt ligands secretion. IWP inhibitors result in a inhibition of Wnt ligand secretion. (B) Mouse organoids cultured under normal conditions as indicated in example 1. (C) Incubation of mouse organoid cultures with 1 µM IWP results in cell death of organoid cultures. (D) Addition of Wnt3a conditioned medium enhances the mouse organoid cultures. (E) IWP induced organoid death is rescued by the addition of Wnt3a conditioned medium. A magnification of 10× is shown (B-E).
Figure 31:
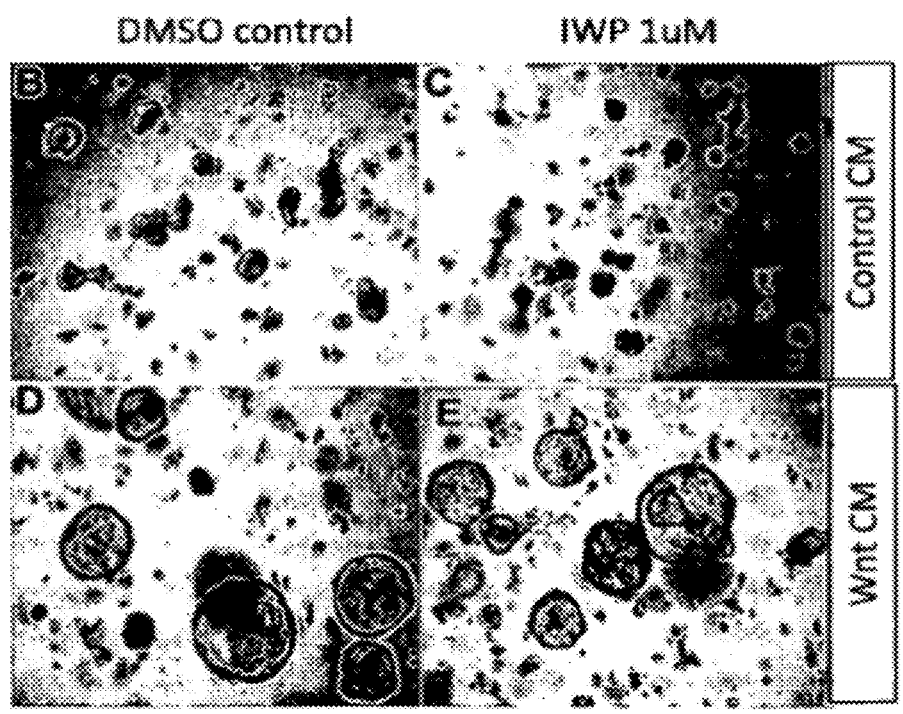

The proliferation of the intestinal epithelium is dependent on the Wnt signaling pathway. The exact location of the Wnt source is however unclear (Gregorieff and Clevers, 2005, *Genes Dev*. April 15; 19(8):877-90). Since the mouse intestinal organoids grew in a niche independent fashion (Sato et al., 2009 *Nature May* 14; 459(7244):262-5) we assumed that these organoids may produce their own Wnt ligands. To test this we inhibited Wnt secretion through incubation with a porcupine inhibitor. Porcupine is important for the Wnt secretion (schematic FIG. 31A). Incubation with 1 µM IWP (Chen et al., *Nat. Chem. Biol.* 2009 February; 5(2):100-7) resulted in death of the organoids (FIGS. 31B and 31C). The organoids could be rescued by addition of Wnt3a conditioned medium, indicating that the organoids indeed produce Wnt ligands (FIGS. 31D and 31E).

Figure 32:
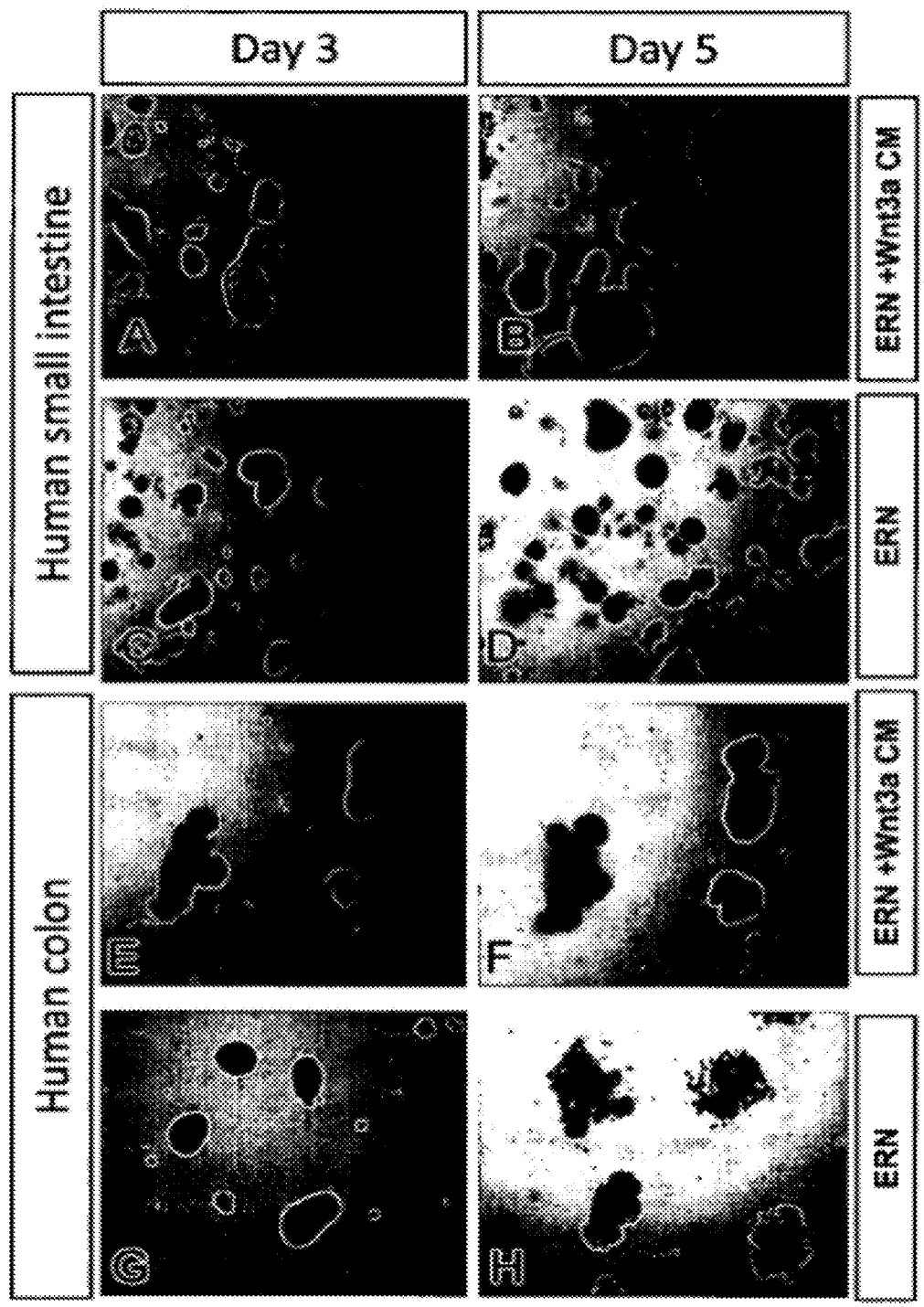
FIG. 32. Establishment of human intestinal crypt culture. Human organoids cultured out of small intestine (A-D) and colon (E-H) after 3 (A, C, E, G) and 5 (B, D F, H) days in medium supplemented with EGF, Noggin and Rspondin with (A, B, E, F) and without (C, D, G, H) Wnt3a conditioned medium.

We next tried to culture human intestinal organoids. It turned out that the addition of Wnt3a to the medium was necessary because without, crypt organoids never formed budding structures and died within 5-10 days for the small intestine and in 3-4 days for the colon (FIG. 32). Overall the human intestinal crypt organoids grew in a comparable fashion to the mouse organoids cultures. Typically, we obtained up to 80% culture efficiency depending on activity of Wnt-3a conditioned medium. The human intestinal cultures have been in culture for up to 3 months. The effect of Wnt-3a in human colon was expected, as it was observed also to enhance the effects in mouse colon organoid culture. The requirement of Wnt-3a in human small intestine and colon may come from lower production of endogenous Wnt ligands by the human organoids, due to the lower numbers of Paneth cells present in the human gut as compared with mouse intestine. So far, there was no reproducible long term human intestinal culture system, and our culture system is useful not only to understand human intestinal stem cell biology but also to apply clinic orientated test, such as drug screening.

Example 10: Optimized Culture Conditions for the Growth of Stomach Organoids

As described in example 5a culture medium has been identified which can be used to culture stomach epithelium for long periods. Here we describe the optimized conditions for these stomach organoid cultures.

Materials and Methods

Gastric Unit Isolation, Single Cell Dissociation and EGFP$^{+ve}$ Cell Sorting

Gastric glands were isolated from mouse pylorus regions as previously described with some modifications (Bjerknes and Cheng, 2002, *Am. J. Gastrointest. Liver Physiol*. September; 283(3):G767-77). Briefly, under the microscope, the stomach was opened along the greater curvature, washed with saline solution and the pylorus isolated. The muscular layer of the stomach was removed and the remaining epithelia was divided into 5 mm pieces and incubated for 3-5 h in a buffered saline solution (Na2HPO4 28 mM, KH2PO4 40 mM, NaCl 480 mM, KCl 8 mM, Sucrose 220 mM, D-Sorbitol 274 mM, DL-Dithiotreitol 2.6 mM) containing 10 mM EDTA (for culturing or staining) or 5 mM EGTA (for RNA isolation) at 4° C. After removal of the chelating agent, the tissue fragments were vigorously suspended in the buffered solution using a 10 ml pipette. After suspension and centrifugation, the sediment was enriched in gastric glands. After gland isolation, cells were collected and resuspended in calcium-free SMEM medium (Invitrogen), supplemented with 10 mg/ml Trypsine and 0.8 Units/µl DNAse I (for microarray analysis) or resuspended in TrypleExpress (GIBCO) supplemented with 0.8 Units/ul DNAase (for culturing purposes). In both cases, after incubation at 37° C. for 20-25 minutes, cells were spun down, and filtered through a 40 µM mesh. EGFPhi and EGFPlo cells were sorted by flow cytometry (MoFlo, Beckman Coulter). Single viable epithelial cells were gated by forward scatter and pulse-width parameter. Where stated, cells were either gated for negative staining of propidium iodide, collected in Trizol LS (Invitrogen) and RNA isolated according manufacturers' protocol or collected in gastric culture medium, embedded in Matrigel (BD Bioscience) and cultured according to the protocol detailed below.

Gastric Culture

For culturing, isolated gastric glands were counted and a total of 100 glands mixed with 50 ul of Matrigel (BD Bioscience) and plated in 24-well plates. After polymerization of Matrigel, gastric culture medium (Advanced DMEM/F12 supplemented with B27, N2 and nAcetylcistein (Invitrogen) containing growth factors (50 ng/m EGF (Peprotech), 1 ug/ml R-spondin 1, 100 ng/ml Noggin (Peprotech), 100 ng/ml FGF10 (Preprotech) and Wnt3A conditioned media) was overlaid. For the single cell culture, a total of 100 sorted EGFP$_{hi}$ cells/well were collected in gastric culture medium and embedded in Matrigel (BD Bioscience). After polymerization of Matrigel, gastric culture media was overlaid. For the first 2 days after seeding, the media was also supplemented with 10 µM ROCK inhibitor Y-27632 (Sigma Aldrich), to avoid anoikis. Growth factors were added every second day and the entire medium was changed every 4 days. For passage, gastric organoids were removed from Matrigel, mechanically dissociated and transferred to fresh Matrigel. Passage was performed every 1-2 weeks with a 1:5-1:8 split ratio. To confirm the Wnt3A requirement, mouse Wnt3A recombinant protein (Stem cell technologies) was supplemented instead of the Wnt3A conditioned media. For the in-vitro tracing experiments, 2-week old gastric organoids were incubated with 100 nM of 4-hydroxytamoxifen in gastric culture medium for 20 h to activate Lgr5-CreERT2. YFP was subsequently visualized and recorded in live organoids using confocal microscopy (Leica, SP5).

Wnt3a Conditioned Media

The Wnt3a media was prepared following protocol described elsewhere (Willert et al., 2003, *Nature*, May 22; 423(6938):448-52). The TOP/FOP assay was used to test the Wnt activity of the Wnt3a conditioned media and the Control conditioned media, as described by van de Wetering and colleagues (van de Wetering et al., 2001 *Cancer Res*. January 1; 61(1):278-84). A TOP/FOP ratio ≥50 was considered high Wnt media and diluted 1:1 with the gastric organoid culture media. A 1:10 dilution of this high Wnt3a media (TOP/FOP ratio ~5) was considered low Wnt media and used for differentiation purposes.

Gastric Organoid Immunohistochemistry

For immunohistochemistry gastric organoids were washed once with PBS and immediately fixed with Paraformaldehyde 4% for 15-20 min at RT. When stated gastric organoids were embedded in paraffin and processed using standard techniques. For whole mount staining, samples were permeabilized with PBS 0.5% Triton-X100-1% BSA and incubated o/n with the primary antibodies. Following several washes in PBS 0.3% Triton X100, samples were incubated with the secondary antibody. EdU staining was performed following manufacturer's instructions (Click-IT; Invitrogen). Nuclei were stained with TOPRO3 iodine or Hoescht33342. The images of gastric glands and gastric organoids were acquired using confocal microscopy (Leica, SP5). Three-dimensional reconstruction was performed using Volocity Software (Improvision).

RT-PCR

RNA was extracted from gastric cell cultures or freshly isolated tissue using the RNeasy Mini RNA Extraction Kit (Qiagen) and reverse-transcribed using Moloney Murine Leukemia Virus reverse transcriptase (Promega). cDNA was amplified in a thermal cycler (GeneAmp PCR System 9700; Applied Biosystems, London, UK) as previously described (Huch et al., 2009). Primers used are shown below (Gene symbol followed by Forward (5'-3') and Reverse (5'-3') primers).

```
Lgr5:
GGAAATGCTTTGACACACATTC,      (SEQ ID NO: 24)

GGAAGTCATCAAGGTTATTATAA      (SEQ ID NO: 25)

Gif:
TGAATCCTCGGCCTTCTATG,        (SEQ ID NO: 26)

CAGTTAAAGTTGGTGGCACTTC       (SEQ ID NO: 27)

Pgc:
CCAACCTGTGGGTGTCTTCT,        (SEQ ID NO: 28)

TTAGGGACCTGGATGCTTTG         (SEQ ID NO: 29)

Muc6:
TGCATGCTCAATGGTATGGT,        (SEQ ID NO: 30)

TGTGGGCTCTGGAGAAGAGT         (SEQ ID NO: 31)

Muc5ac:
CCATGAAGTGGGAGTGTGTG,        (SEQ ID NO: 32)

TTGGGATAGCATCCTTCCAG         (SEQ ID NO: 33)

Ghrl:
GCCCAGCAGAGAAAGGAATCCA,      (SEQ ID NO: 34)

GCGCCTCTTTGACCTCTTCC         (SEQ ID NO: 35)

Gast:
GCCAACTATTCCCCAGCTCT,        (SEQ ID NO: 36)

GGCTCTGGAAGAGTGTTGCT         (SEQ ID NO: 37)

Stt:
GAGGCAAGGAAGATGCTGTC,        (SEQ ID NO: 38)

GGGCATCATTCTCTGTCTGG         (SEQ ID NO: 39)

Muc2:
GAACGGGGCCATGGTCAGCA,        (SEQ ID NO: 40)

CATAATTGGTCTTGCATGCC         (SEQ ID NO: 41)

Cdx2:
CTTGCTGCAGACGCTCAAC,         (SEQ ID NO: 42)

TCTGTGTACACCACCCGGTA         (SEQ ID NO: 43)

Hprt:
AAGCTTGCTGGTGAAAAGGA,        (SEQ ID NO: 44)

TTGCGCTCATCTTAGGCTTT         (SEQ ID NO: 45)
```

Results

Figure 33A:
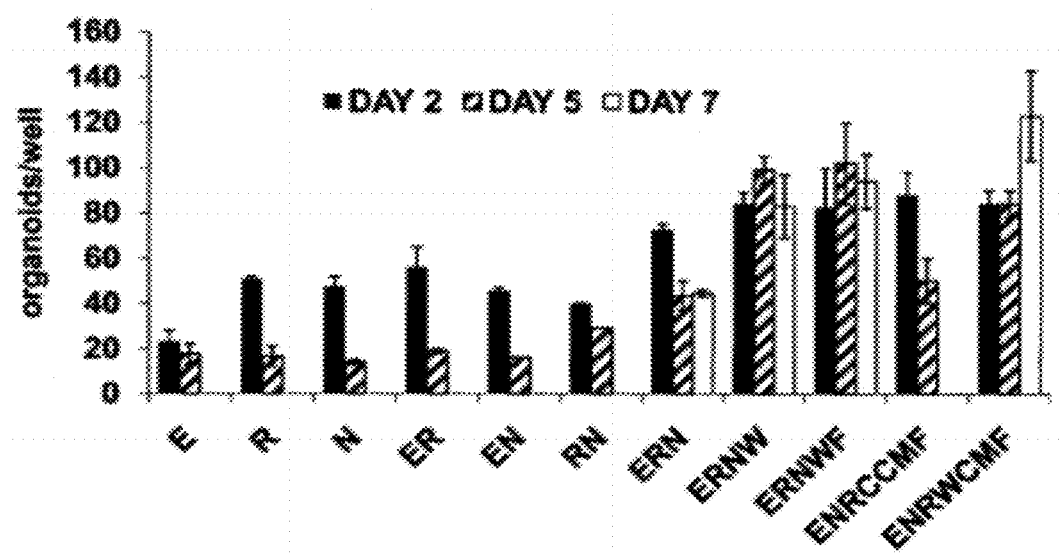
FIG. 33. Establishment of the gastric organoid culture. (A) A total of 100 gastric glands/well were seeded in duplicate with EGF (E); R-spondin 1 (R); Noggin (N); EGF+R-spondin 1 (ER); EGF+Noggin (EN); EGF+R-spondin 1+Noggin (ERN); EGF+R-spondin 1+Noggin+Wnt3A (ERNW); EGF+R-spondin 1+Noggin+Wnt3A+FGF10 (ER-NWF); EGF+R-spondin 1+Noggin+control conditioned media+FGF10 (ERNCCMF) or EGF+R-spondin 1+Noggin+Wnt3A conditioned media+FGF10 (ERNWCMF). The number of gastric organoids was counted 2, 5 and 7 days later. Results are shown as mean±SEM of 2 independent experiments. (B) A total of 100 gastric glands/well were seeded in duplicate with Wnt3A conditioned media (ENRWCM) or Wnt3A conditioned media supplemented with FGF10 (ENRWCMF). The number of budding organoids was counted after 7, 15 (passage 2) and 60 days (passage 10) in culture. (C) A total of 100 gastric glands/well were seeded in Wnt3A conditioned media (WCM)+EGF+Noggin and R-spondin supplemented with either FGF7/KGF (K) or FGF10 (F) both 100 and 1000 ng/ml has been tested. The number of budding organoids was counted after 4 days (passage 7) in culture. A representative experiment has been shown. (D) Isolated gastric glands developing into organoids. Differential-interference contrast images from days 1, 2, 3, 4, 7 after seeding. After one week, cultures required splitting 1:5 or 1:6. Subculturing and maintenance has been performed as described in the supplementary materials and methods section. Representative images of the cultures after 15 days, 3 months, 4.5 and 6 months in culture; (10× magnification). (E) Example of a 5 day-old culture grown in control conditioned media. Note that the culture is not growing and has failed to form gland domains. Under these conditions the culture survived no longer than 7 days. (F) Whole-mount E-Cadherin staining in a 3 month-old gastric organoid.
Figure 33B:
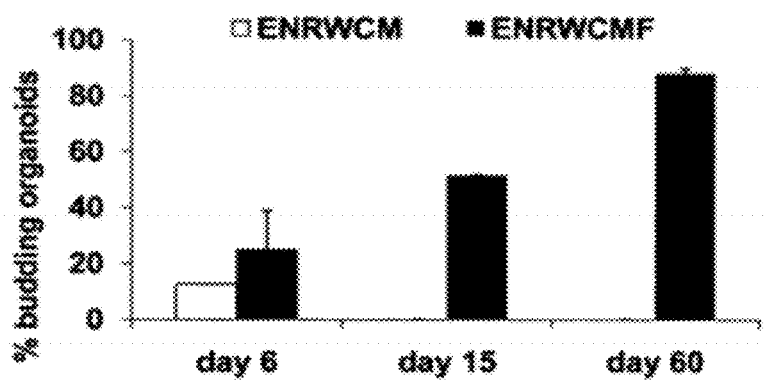
Figure 33C:
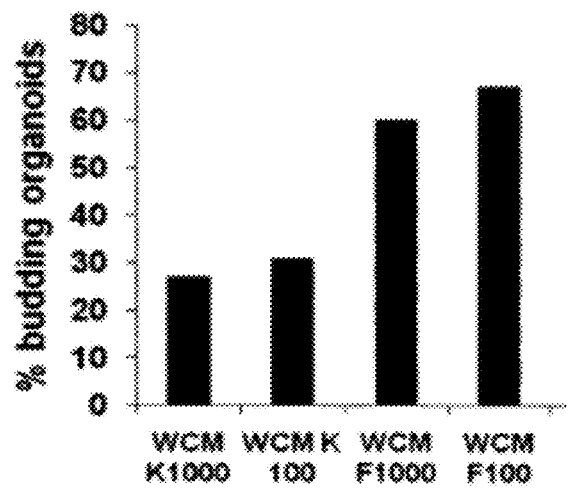
Figure 33D:
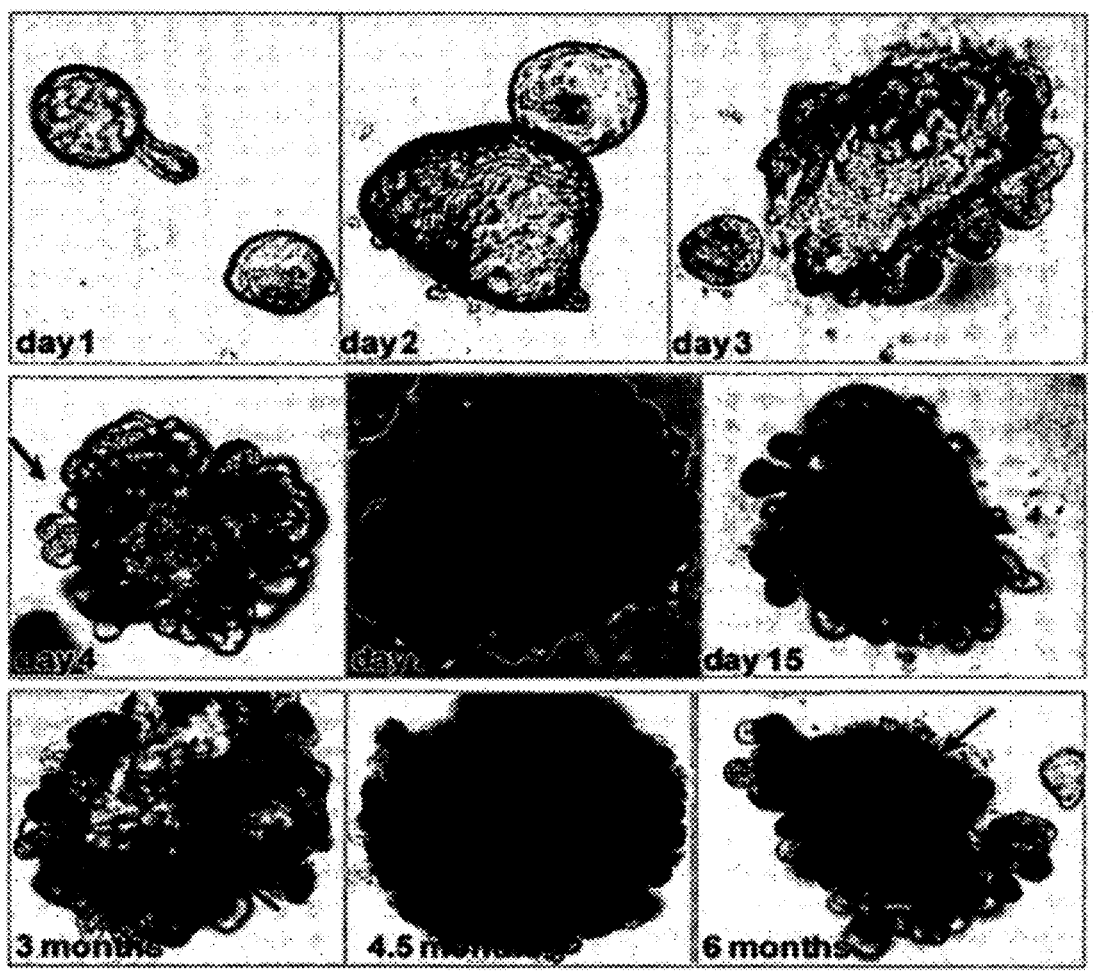
Figure 33E:
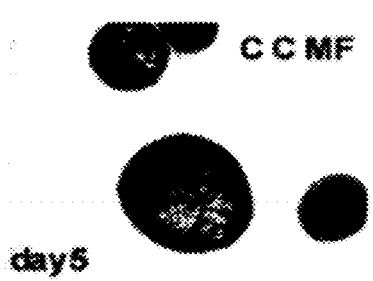
Figure 33F:
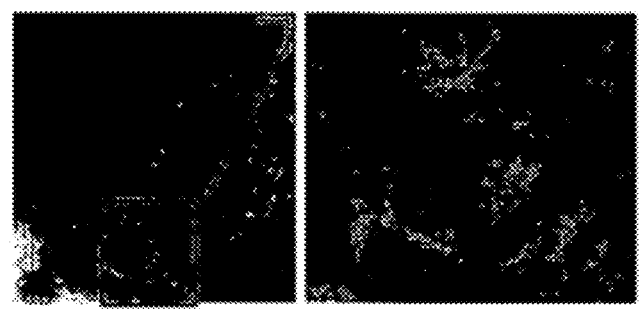

To determine optimal growth of gastic units in vitro we isolated gastric gland units which were suspended in Matrigel and cultured under different conditions. Gastric culture growth conditions were similar to those of the small intestine cultures (including EGF, Noggin and R-spondin 1), except for a strict dependence on Wnt3A in the form of conditioned media. This requirement was confirmed using purified Wnt3a protein (FIG. 33A). Furthermore, FGF10 proved to be an essential component for driving budding events and for the expansion of the cultures into multi-unit organoids (FIG. 33B). FGF10 can be used to replace FGF7 (KGF), which has been used in Example 5, and even results in a 2-fold increase of % of budding organoids 4 days after the start of the culture (FIG. 33C). The newly-formed gastric organoids underwent continuous budding events, whilst maintaining their polarity, with gastric gland-domain buds distributed around a central lumen (FIG. 33D). In the absence of Wnt3A conditioned medium, the gastric organoids rapidly deteriorated (FIG. 33E). Each week, organoids were mechanically dissociated and split to one-fifth of their pre-plating density. Cultured pyloric units were single-layered epithelial structures, as evidenced by E-Cad staining (FIG. 33F). We have successfully cultured gastric organoids for at least 8 months without any detectable loss of the properties described above.

Figure 34G:
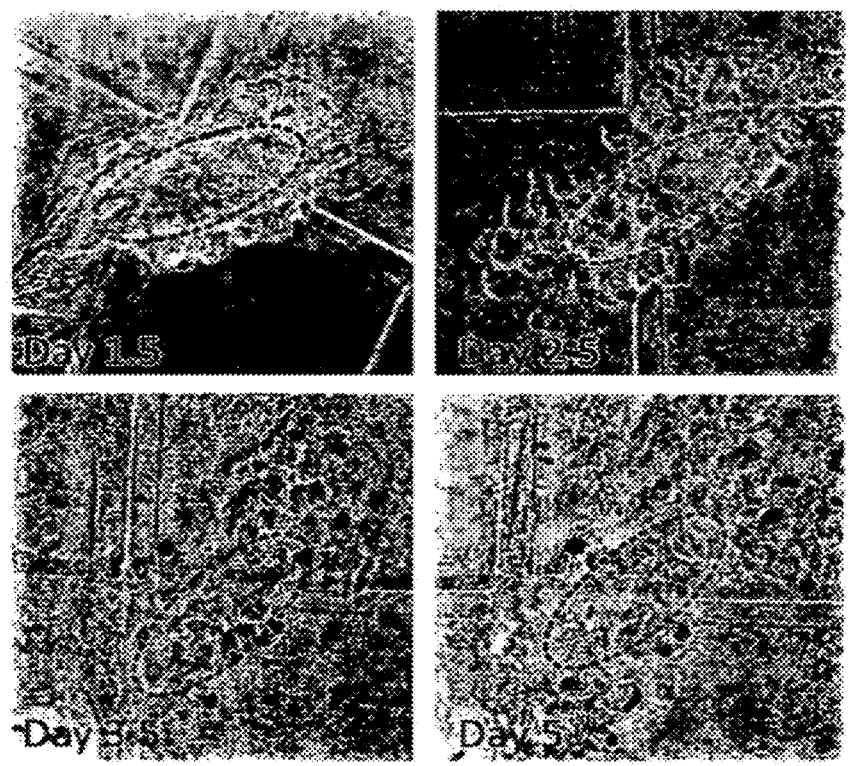
FIG. 34. Single Lgr5+ve cells build long-lived gastric organoids in-vitro. (A) Confocal analysis of a freshly isolated pyloric gastric unit from an Lgr5-EGFP-ires-CreERT2 mouse stomach. Arrows showing GFPhi (grey), GFPlo (black) and GFP-ve (white) distinct populations. (B) Lgr5-EGFP+ve cells are discriminated from the GFPlo and GFP-ve populations according to their GFP expression level. FSC, forward scatter. (C) Representative example of a growing organoid originating from a single Lgr5+ve cell. Arrows showing the formation of gland-like domain buds at day 7. Original magnifications: days 1-4; 40× magnification, days 5-6; 20× magnification, days 7-8; 10× magnification and day 9; 5× magnification. (D) Organoids derived from single Lgr5+ve cells have been dissociated and split every 5-7 days. Representative images of a 3 months-old culture. Original magnifications: left panel; 4× magnification, right panel; 10× magnification. (E) Confocal analysis of Lgr5 EGFP-expressing cells in a 14 day-old gastric culture grown from a single GFPhi cell. Note that Lgr5-GFP+ve cells are located at the bottom of the gland domains (white arrow; 10× magnification). (F) Organoids cultured with the thymidine analogue EdU (red) for 1.5 h. Only gland domains incorporate EdU (white arrows; 20× magnification). Counterstain, 4,6-diamidino-2-phenylindole (DAPI; nuclear). (G) A 2-week old culture from a single-cell culture of Lgr5-EGFP-ires-CreERT2/Rosa26-YFP reporter mouse was stimulated with tamoxifen in-vitro for 20 hrs, and imaged on the indicated days. YFP fluorescence (yellow) shows that scattered single yellow cells (day 1.5) generate multiple offspring in-vitro. Note that YFP+ve cells migrate towards the central lumen (white dotted circle). (H) Expression analysis of gastric-specific genes from 2 month-old cultures derived from Lgr5+ve single cells. Cultures maintained in high (left panel) or low (middle panel) Wnt3A medium. Note that gastric-derived cultures are negative for intestine specific genes (right panel). (I) Cultures maintained in low Wnt3A media for at least 10 days. Upper panel: confocal image of ECad staining (red, epithelium derived organoids). Counterstain, Hoescht 33345 (blue). Lower panels: paraffin sections stained for Tff2 (brown, mucus neck cells), periodic acid-Schiff (red, pit cells), MUC5AC (brown, pit cells) and chromogranin A (brown, enteroendocrine cells).
Figure 34H:
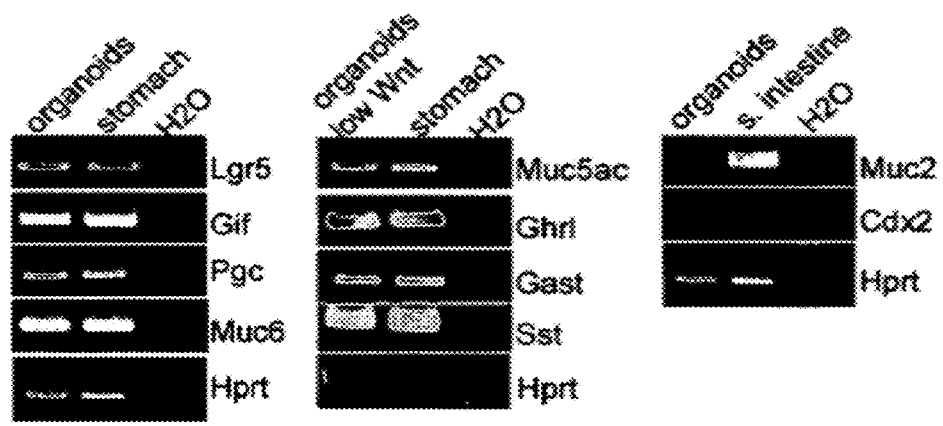
Figure 34I:
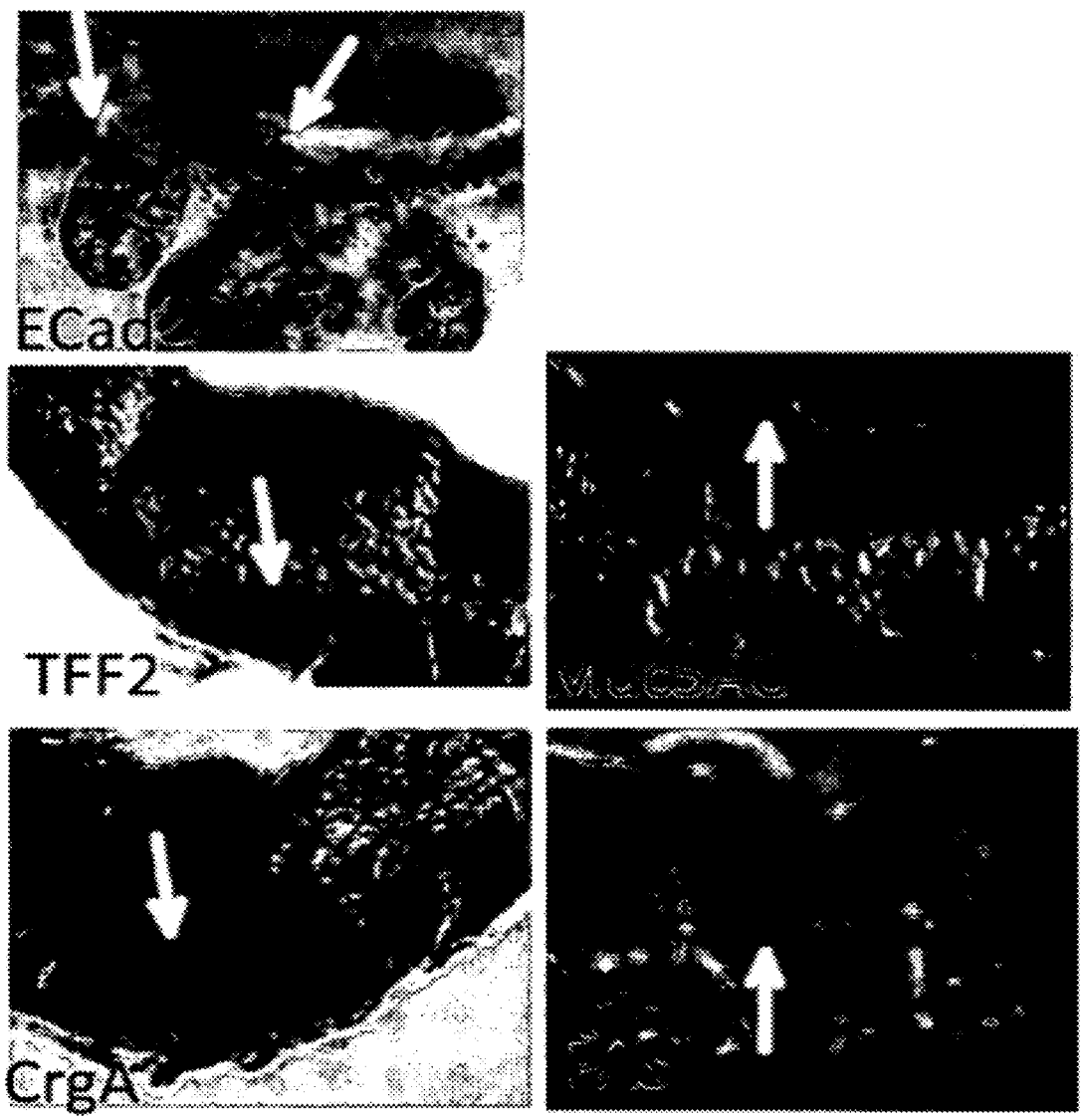

To determine whether gastric Lgr5$^{+ve}$ cells (FIG. 34A) were capable of generating and maintaining pyloric gastric glands units in vitro we sorted Lgr5-EGFP high cells (FIG. 34B). When single Lgr5-EGFP high cells were sorted, an average of 8% of the cells grew into organoids, whereas the remaining cells died within the first 24 h. The sorted Lgr5-EGFPhi cells rapidly began dividing and small cyst-like structures were already visible after 5 days. During the following days, the newly-formed (cyst-like) structures started to generate gland-like domains (FIG. 34C). After 9-11 days in culture, gastric organoids were dissociated manually and split to generate new organoids. Gastric organoids derived from single cells have been successfully re-plated on a weekly basis for at least 3 months, without losing the properties described (FIG. 34D). From day 7 onwards, Lgr5-EGFP expression was restricted to the base of the gland-like domains (FIG. 34E). As evidenced by EdU staining, proliferating cells were located at the base of these gland-like domains (FIG. 34F), while apoptotic caspase 3-positive cells were found extruded into the lumen (data not shown). Lineage tracing was studied in established organoids derived from single Lgr5+ve cells isolated from an Lgr5-EGFP-ires-CreERT2/Rosa26-YFP reporter mouse. Following tamoxifen induction, the YFP+ve reporter gene was rapidly activated in single Lgr5+ve cells within the gland-like domains. Over the next few days, the YFP expression domain expanded considerably within the growing organoids, confirming the contribution of the Lgr5+ve stem cells to organoid growth in-vitro (FIG. 34G). The organoids derived from single-cell cultures were single-layered epithelial structures, as evidenced by E-cadherin staining (FIG. 34I). In addition to Lgr5, the cultures expressed the gastric epithelial markers Gastric intrinsic Factor, Mucin 6 and Pepsinogen C. No differentiation to the pit or enteroendocrine lineages was observed under these culture conditions (This is different from example 5 were the pit cell lineage was observed. However in that example Wnt3a protein was used instead of Wnt conditioned medium which is less active. Lowering the Wnt conditioned medium concentration results in differentiation into the pit cell lineage, see below). Reduction of the Wnt3A concentration in the culture media resulted in the formation of comparable gastric structures harbouring polarized pit cells, as evidenced by the expression of the gastric mucin 5AC (MUC5AC) and Periodic acid-Schiff (PAS), mucus neck cells, as demonstrated by Tff2 expression and some scattered immature enteroendocrine cells (Chromogranin A) (FIGS. 34H, 34I). Addition of additional growth factors like: RA, IGF and exendin4 may result into more mature differentiation of stomach cultures towards the various cell lineages. Taken together, these in-vivo and in-vitro observations demonstrate that Lgr5 is marking a previously unappreciated population of self-renewing, multipotent adult stem cells in the pyloric stomach.

Example 11

To address the need for improved culture media and methods for human epithelial stem cells, the inventors investigated signaling pathways that are known to be subverted in certain cancers, e.g., colorectal cancer. It was hypothesized that these pathways, which affect cell fate in cancer, may also play a role in determining cell fate under in vitro cell culture conditions.

In a first screening experiment, a series of vitamins, hormones and growth factors were tested in combination with standard stem cell culture media. Gastrin and nicotinamide were identified as resulting in significantly improved culture conditions. Incorporating these factors into the standard culture conditions, a second screening experiment was performed, in which certain small molecule inhibitors related to relevant signaling pathways, such as ERK, p38, JNK, PTEN, ROCK, and Hedgehog, were tested. Whilst there is reasonable basis for choosing to test these compounds, as described above, it is to be emphasized that in the present state of the art, there would be no reasonable way to predict what the outcome of each of these additional compounds would be on the culture medium properties.

TABLE 1

List of reagents used for optimization of human intestinal organoids culture

| | Description | Source | Concentration | Activity* |
|---|---|---|---|---|
| *First screening (WENR**)* | | | | |
| *Hormones, vitamins etc* | | | | |
| Hydrocortison | | Sigma | 500 nM | 0 |
| Gastrin\*\*\* | | Sigma | 1 uM | 1+ |
| Exendin4 | GLP1 analog | Sigma | 100 nM | 0 |
| Nicotinamide | Vitamin B derivative | Sigma | 10 mM | 3+ |
| L-Ascorbic acid | Vitamin C | Sigma | 10 uM | 0 |
| anti-oxidant mixture | | Sigma | 1x | 0 |
| Lipid mixture | | Sigma | 1x | 0 |
| PGE2 | | Sigma | 10 uM | 1+ (Cystic) |
| Cholera Toxin | | Sigma | 100 nM | 1+ (Cystic) |
| *Growth factors* | | | | |
| BDNF | | Peprotech | 100 ng/ml | 0 |
| GDNF | | Peprotech | 100 ng/ml | 0 |
| FGF2 | | Peprotech | 100 ng/ml | 0 |
| FGF10 | | Peprotech | 100 ng/ml | 0 |
| Follistatin | | Peprotech | 100 ng/ml | 0 |
| Cyr61 | | Peprotech | 1 ug/ml | 0 |
| LIF | | Millipore | 1000 U/ml | 0 |
| *Second screening (WENR + gastrin + Nicotinamide)* | | | | |
| *Small molecule inhibitors* | | | | |
| PD98059 | ERK inhibitor | Sigma | 10 uM | 1− |
| SB203580 | p38 inhibitor | Sigma | 1-10 uM | 2+ |
| SB202190 | p38 inhibitor | Sigma | 1-10 uM | 2+ |
| SP600125 | JNK inhibitor | Sigma | 10 uM | 0 |
| PS48 | PDK1 activator | Sigma | 5 uM | 0 |
| Y27632 | ROCK inihibitor | Sigma | 10 uM | 1+ cystic |
| Cyclopamine | Hedgehog inhibitor | Sigma | 100 nM | 1− |
| 5 Azacytidin | DNA methylase inhibitor | Stemolecule | | 1− |
| Dorsomorphin | BMP inhibitor | Stemolecule | | 0 |
| A83-01 | ALK4,5,7 inhibitor | Tocris | 50 n-1 uM | 3+ |
| VO-OHpic trihydrate | PTEN inhibitor | Sigma | 500 nM | 3− |
| Pifithrin-α | p53 inhibitor | Sigma | | 0 |
| BIX01294 | G9a HMTase inhibitor | Stemolecule | | 1− |

*Activity scale (plating efficiency was compared with control after 4 days culture): 0 = no change; 1+ = <50% increase; 2+ = 50-100% increase; 3+ = >100% increase; 1− = 0-50%; 2− = 50-100% decrease; 3− = >100% decrease.

**WENR comprises EGF + Noggin + R-spondin + Wnt-3a

***Highlighted in bold are the compounds which showed the greatest improvement to the culture medium.

In summary, the inventors have established long-term culture conditions under which single crypts or stem cells derived from murine small intestine (SI) expand over long periods of time. Growing crypts undergo multiple crypt fission events, whilst simultaneously generating villus-like epithelial domains in which all differentiated cell types are present. The inventors have now adapted the culture conditions to grow similar epithelial organoids from mouse colon and human SI and colon. Based on the murine small intestinal culture system, the inventors optimized the murine and human colon culture system. They found that addition of Wnt3A to the growth factor cocktail allowed mouse colon crypts to expand indefinitely. Further addition of nicotinamide, a small molecule Alk inhibitor and a p38 inhibitor was preferable for long-term human SI and colon culture. The culture system also allowed growth of murine Apc$^{min}$ adenomas, human colorectal cancer and human esophageal metaplastic Barrett's epithelium. The culture technology should be widely applicable as a research tool for infectious, inflammatory and neoplastic pathologies of the human gastrointestinal tract. Moreover, regenerative applications may become feasible with ex vivo expanded intestinal epithelia. Self-renewal of the small intestinal and colonic epithelium is driven by the proliferation of stem cells and their progenitors located in crypts. Although multiple culture systems have been described (Evans G S et al. *J. Cell Sci.* 1992; 101 (Pt 1):219-31; Fukamachi H., *J. Cell Sci.* 1992; 103 (Pt 2):511-9; Perreault N & Jean-Francois B., *Exp. Cell. Res.* 1996; 224:354-64; Whitehead R. H. et al., *Gastroenterology* 1999; 117:858-65), only recently have long-term culture systems become available that maintain basic crypt physiology. Two different protocols were published which allow long-term expansion of murine small intestinal epithelium. Kuo and colleagues demonstrated long-term growth of small fragments containing epithelial as well as stromal elements in a growth factor-independent fashion (Ootani A et al. *Nat. Med.* 2009; 15:701-6). The inventors designed a culture system for single stem cells by combining previously defined insights in the growth requirements of intestinal epithelium. Wnt signaling is a pivotal requirement for crypt proliferation (Korinek V. et al. *Nat. Genet.* 1998; 19:379-83; Pinto D. et al., *Genes Dev.* 2003; 17:1709-13; Kuhnert F. et al., *Proc. Natl. Acad. Sci. U.S.A.* 2004; 101:266-71) and the Wnt agonist R-spondin1 induces dramatic crypt hyperplasia in vivo (Kim K. A. et al., *Science* 2005; 309:1256-9). Second, EGF signaling is associated with intestinal proliferation (Dignass AU & Sturm A., *Eur. J. Gastroenterol. Hepatol* 2001; 13:763-70). Third, transgenic expression of Noggin induces expansion of crypt numbers (Haramis A. P. et al. *Science* 2004; 303:1684-6). Fourth, isolated intestinal cells undergo anoikis outside the normal tissue context (Hofmann C. et al., *Gastroenterology* 2007; 132:587-600). Since laminin ($\alpha$1 and $\alpha$2) is enriched at the crypt base (Sasaki T. et al., *Exp. Cell Res.* 2002; 275:185-), the inventors explored laminin-rich Matrigel to support intestinal epithelial growth. Matrigel-based cultures have successfully been used for growth of mammary epithelium (Stingl J. et al., *Breast Cancer Res. Treat.* 2001; 67:93-109). Under this culture condition (R-spondin1, EGF, and Noggin in Matrigel), the inventors obtained ever-expanding small intestinal organoids, which displayed all hallmarks of the small intestinal epithelium in terms of architecture, cell type composition and self-renewal dynamics.

Despite extensive efforts, long-term adult human intestinal epithelial cell culture has remained difficult. There have been some long-term culture models, but these techniques and cell lines have not gained wide acceptance, possibly as a result of inherent technical difficulties in extracting and maintaining viable cells (Rogler G. et al., *Scandinavian Journal of Gastroenterology*, 2001; 36:389-98; Buset M. et al., In vitro cellular & developmental biology: journal of the Tissue Culture Association 1987; 23:403-12; Whitehead R. H. et al., In vitro cellular & developmental biology: journal of the Tissue Culture Association 1987; 23:436-42; Deveney C. W. et al., The Journal of surgical research 1996; 64:161-9; Pang G. et al., *Gastroenterology* 1996; 111:8-18; Latella G. et al., *International Journal of Colorectal Disease* 1996; 11:76-83; Panja A. Laboratory investigation; a journal of technical methods and pathology 2000; 80:1473-5; Grossmann J. et al., *European Journal of Cell Biology* 2003; 82:262-70). Encouraged by the establishment of murine small intestinal culture, the inventors aimed to adapt the culture condition to mouse and human colonic epithelium. The inventors now report the establishment of long-term culture protocols for murine and human colonic epithelium, which can be adapted to primary colonic adenoma/adenocarcinoma and Barrett's esophagus.

Results

Establishment of a Mouse Colon Culture System

In an attempt to establish a mouse colon culture system, the inventors explored our small intestinal culture condition (here termed ENR: EGF+Noggin+R-spondin). In our experience, initial growth of colon epithelium is often observed under the ENR culture condition, but is invariably abortive. Organoid formation was studied using epithelium isolated from the distal part of the mouse colon. Under ENR conditions, the plating efficiency of single distal colonic crypts was much lower than that of small intestine (1-3% vs >90%) and these organoids could not be passaged. Recently, the inventors have shown that Paneth cells produce several Wnt ligands (Gregorieff A. et al. *Gastroenterology* 2005; 129: 626-38), and that the production of Wnt by these Paneth cells is essential to maintain intestinal stem cells (Sato T. et al., *Nature* 469:415-8). To determine the Wnt signaling status in colon organoids, the inventors cultured colon crypts from Axin2-lacZ mice, (a faithful Wnt reporter) (Lustig B. et al., *Mol. Cell. Biol.* 2002; 22:1184-93) or Lgr5-GFP knock-in mice (Lgr5 being a Wnt-dependent stem cell marker)(Barker N. et al. *Nature* 2007; 449:1003-7).

Figure 35B:
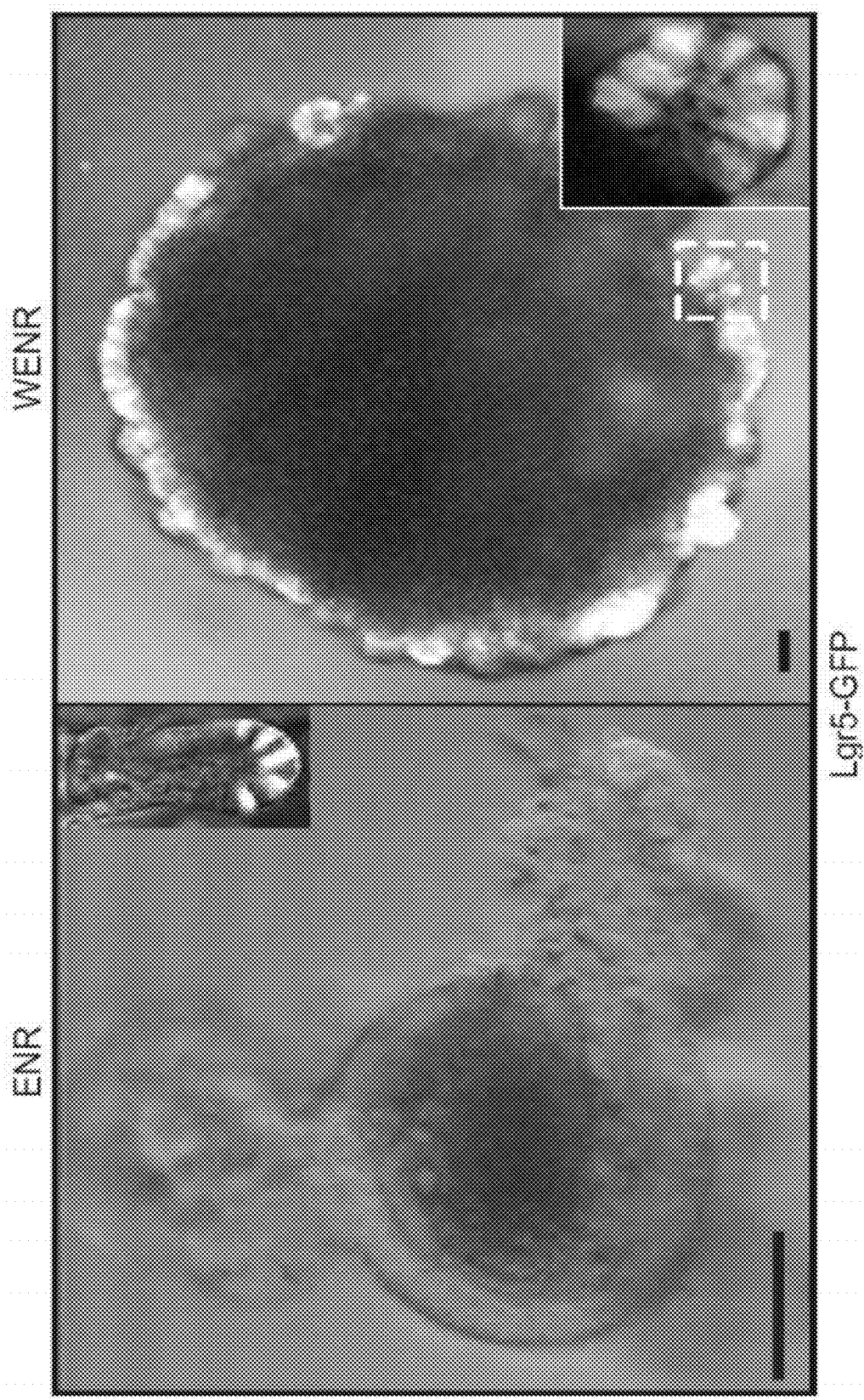
FIG. 35. Mouse colon culture. a. left: Axin2 expression is under the control of the Wnt signaling pathway. Colon crypt organoids of Axin2-LacZ reporter mice cultured with EGF, Noggin, and R-spondin (ENR) for 3 days. Absence of LacZ stain indicates that no active Wnt signal is present in the colon organoids under ENR growth condition. Inset shows active Wnt signaling visualized by LacZ expression (dark stain) in freshly isolated colon crypts from the Axin2-LacZ reporter mice. right: Axin2-LacZ mice derived colon crypts cultured with ENR+Wnt3A (WENR) for 10 days. Dark stain indicates LacZ expression in these organoids. b. left: Lgr5-GFP-ires-CreER colon crypts cultured with ENR for 3 days. Absence of GFP fluorescence indicates loss of Lgr5 expression in the colon organoids under ENR growth condition. Inset shows Lgr5-GFP expression in freshly isolated colon crypts from Lgr5-GFP-ires-CreER mice. right: Lgr5-GFP-ires-CreER colon crypt cultured with WENR for 10 days demonstrates the presence of Lgr5 stem cells. c. Culture efficiency is determined under three different conditions: ENR, WENR full crypts, and WENR crypts after mild enzymatic digestion (WENR digested). Colon crypts were isolated from proximal colon (black columns) or distal colon (white columns). *:p<0.05. d, e: 4 days after removal of Wnt3A from the WENR culture medium results in organoid differentiation. d. Chromogranin A (ChA) in enteroendocrine cells; Mucin2 (muc2) in Goblet cells and the counter stain with DAPI can be seen. e. Mature enterocytes are visualized by Alkaline phosphatase staining. f. Relative mRNA expression of mature epithelial cell markers (Vil1 (Villin1), Alpi (Alkalin phosphatase), Chga (Chromogranin A), Muc2 (Mucin2)) are shown. WENR cultured colon crypt organoids are cultured for 4 days in WENR (hatched pattern) or ENR (black) condition. Freshly isolated colon crypts (white) are used for control. Scale bar in a, b, d, e: 50 µm. Error bars indicate s.e.m. n=3.
Figure 35C:
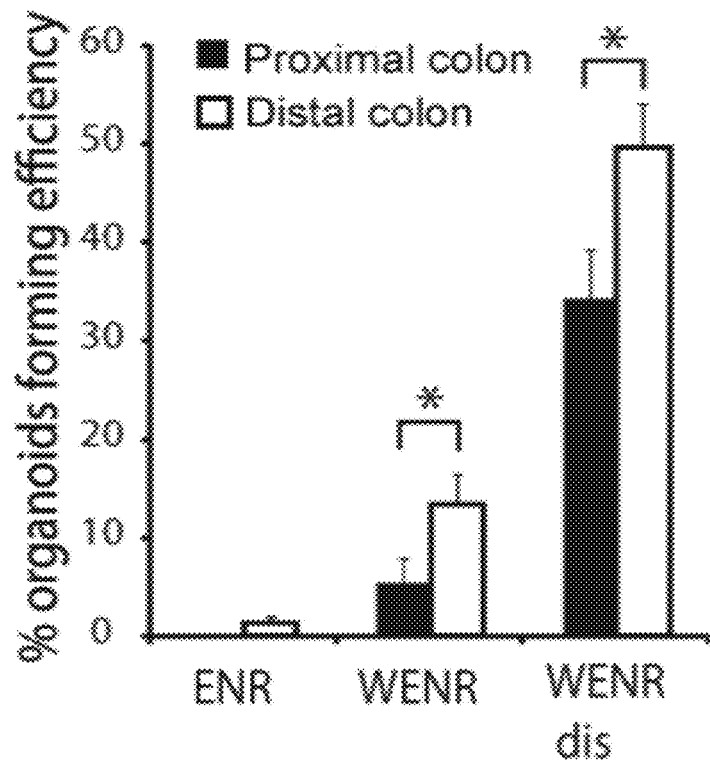
Figure 40:
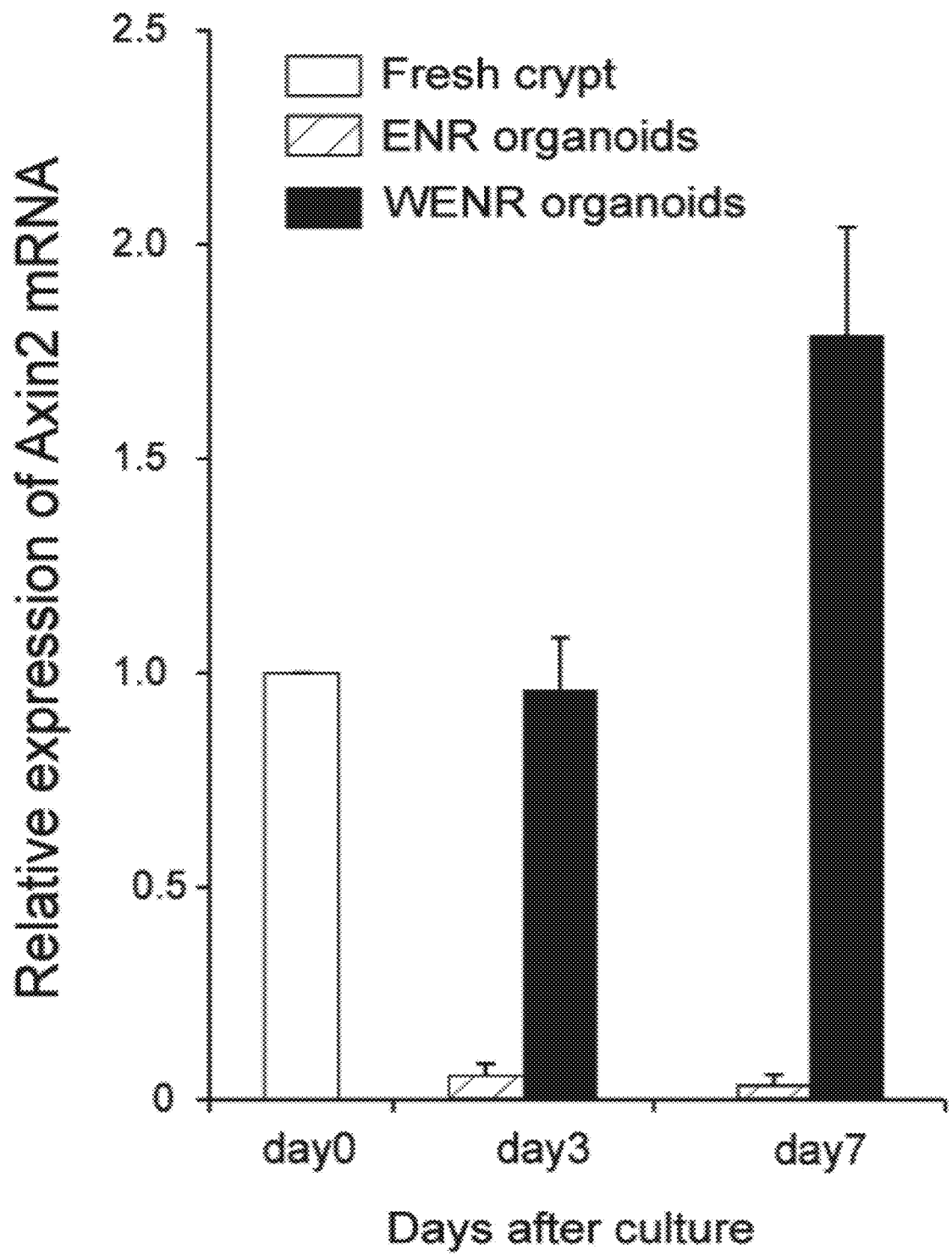
FIG. 40. Axin2 mRNA expression is recovered in mouse colon organoids under the presence of Wnt-3A. Isolated colonic crypts are analyzed for Axin2 mRNA expression after 3 days or 7 days culture with ENR (hatched) or WENR (black). Freshly isolated colon crypts were used as control. Error bars indicate s.e.m. n=3

Freshly isolated colon crypts readily expressed Axin2-LacZ or Lgr5-GFP at their bottoms, but they lost expression of the Wnt reporters shortly after initiation of culture (FIGS. 35*a*, 35*b* and FIG. 40). By contrast, small intestinal organoids constitutively expressed the Wnt reporters at their budding structures (Sato T. et al., *Nature* 469:415-8; Sato T. et al., *Nature* 2009; 459:262-5). These findings suggested that colon organoids produce insufficient amounts of Wnt ligands to maintain colon stem cells. To overcome this, the inventors added recombinant Wnt3a or Wnt3a-conditioned medium to ENR culture medium (WENR medium). This increased plating efficiency of crypts in the order of 10-fold. Colon crypts formed organoids structures with numerous Axin2-LacZ (FIG. 35*a*) or Lgr5-GFP+ (FIG. 35*b*) buds, implying that Wnt activation was restored. Freshly isolated colon crypts contain fully mature cells in their upper parts, and the inventors reasoned that these mature cells may interfere with organoid growth. When the inventors mildly digested colon crypts into small clusters of cells, thus physically separating proliferative crypt bottoms from differentiated upper crypt regions, most of fragments derived from crypt top died, yet cell clusters from colon crypt base efficiently formed organoids (FIG. 35*c*).

Figure 35F:
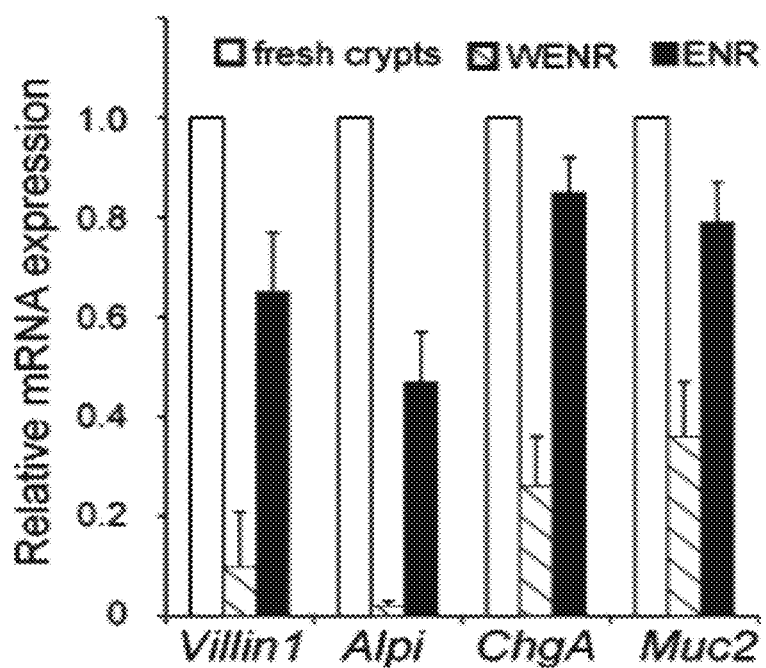
Figure 35D:
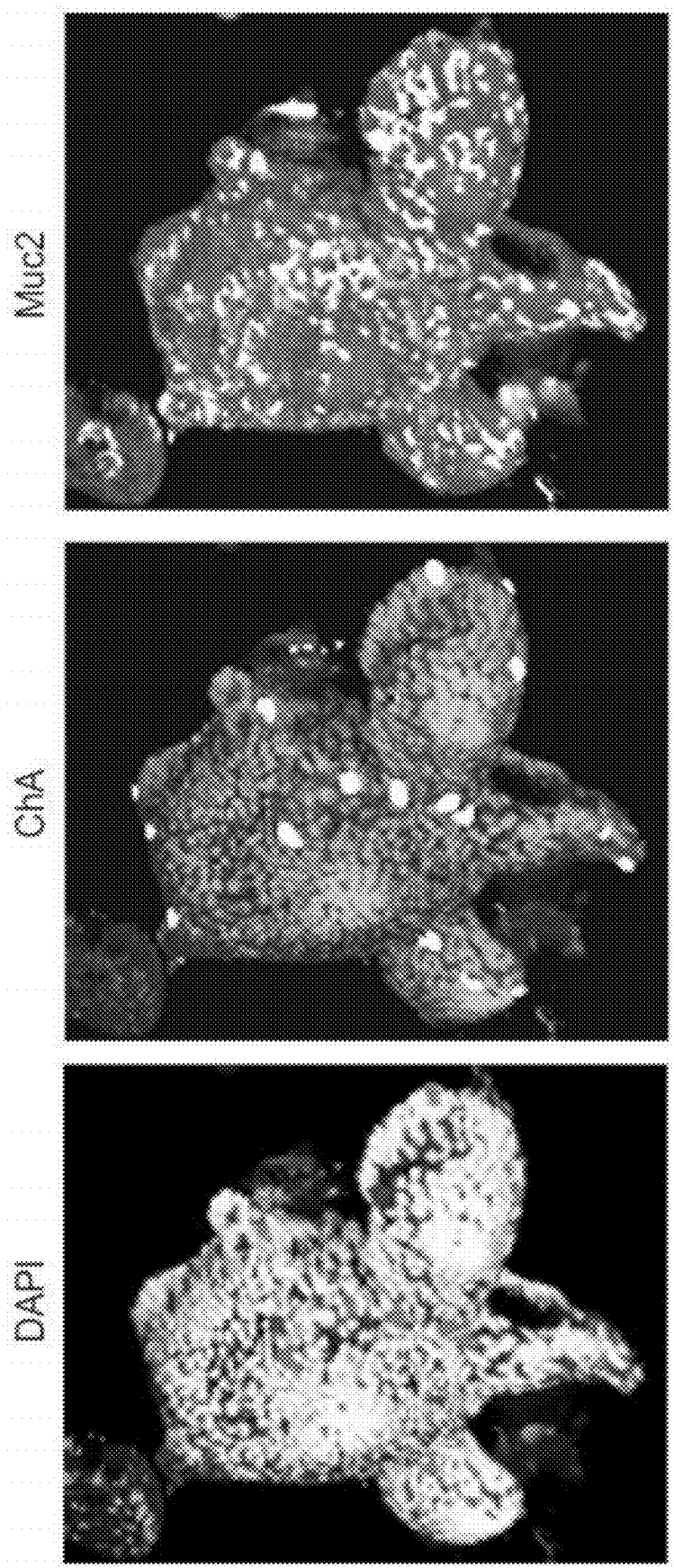
Figure 35E:
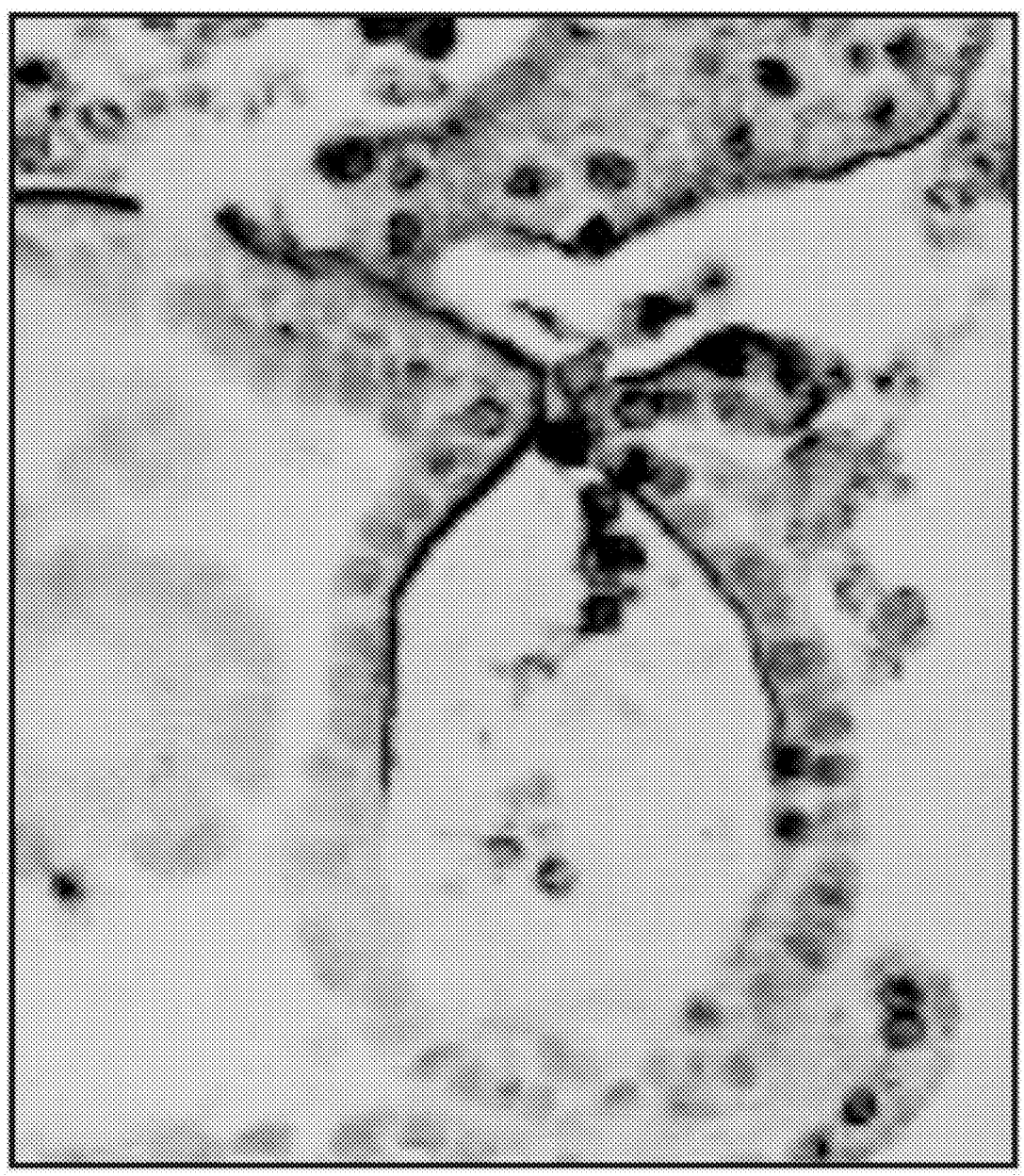

Mouse small intestinal epithelium grown under ENR conditions generates all differentiated epithelial cell types concomitant with stem cell self-renewal. The inventors have shown previously that the addition of Wnt3A to these cultures interferes with intestinal differentiation and yields organoids that largely consist of undifferentiated progenitors (Sato T. et al., *Nature* 469:415-8). This is not unexpected given the central role of Wnt signaling in the maintenance of the undifferentiated crypt progenitor state (van de Wetering M. et al. *Cell* 2002; 111:241-50). Consistent with this observation, colonic organoids in WENR condition failed to differentiate properly. Upon withdrawal of Wnt-3A, the inventors observed differentiation along all epithelial lineages (FIGS. 35d-35f). Of note, single sorted Lgr5+ colonic epithelial stem cells can form organoids when cultured in the presence of Y-27632 for the first two days.

Establishment of Human Colon Culture System

Encouraged by the success of the improved mouse colon crypt culture, the inventors applied the culture condition to human colon crypts. Although these crypts initially survived, most subsequently disintegrated within 7 days. To increase the plating efficiency of human colon crypts, the inventors screened candidate growth factors, hormones and vitamins (list in FIG. 46). Among these, the inventors found that gastrin and nicotinamide (Precursor of $NAD^+$, and found to suppress Sirtuin activity (Denu J. M. *Trends Biochem. Sci.* 2005; 30:479-83)) improved culture efficiency (FIG. 46). The effect of gastrin on plating efficiency was marginal. However, the hormone did not interfere with intestinal differentiation and we decided to include gastrin (hereafter shortened to 'g') in all human intestinal culture conditions. Importantly, nicotinamide (10 mM) was essential for prolongation of culture period beyond the initial 7 days (FIG. 36a). Under this culture condition, human colonic organoids could be expanded for at least 1 month. From 1 month onward, the colonic organoids changed their morphology from budding organoids structure into cystic structures FIG. 36b left). Coinciding with the morphological conversion, proliferation progressively decreased. Occasionally, cystic organoids regained their proliferative potential. However, all organoids eventually arrested growth within 3 months. A two-phase growth arrest has been observed in other primary culture systems, such as mammary epithelial cells or keratinocytes, and has been referred to as mortality stage 1 (M1; senescence) and mortality stage 2 (M2; crisis) (Shay et al., 2006). Multi-lineage differentiation was not observed in the human intestinal organoids cultured in this condition even after the withdrawal of Wnt (data not shown).

Figure 36C:
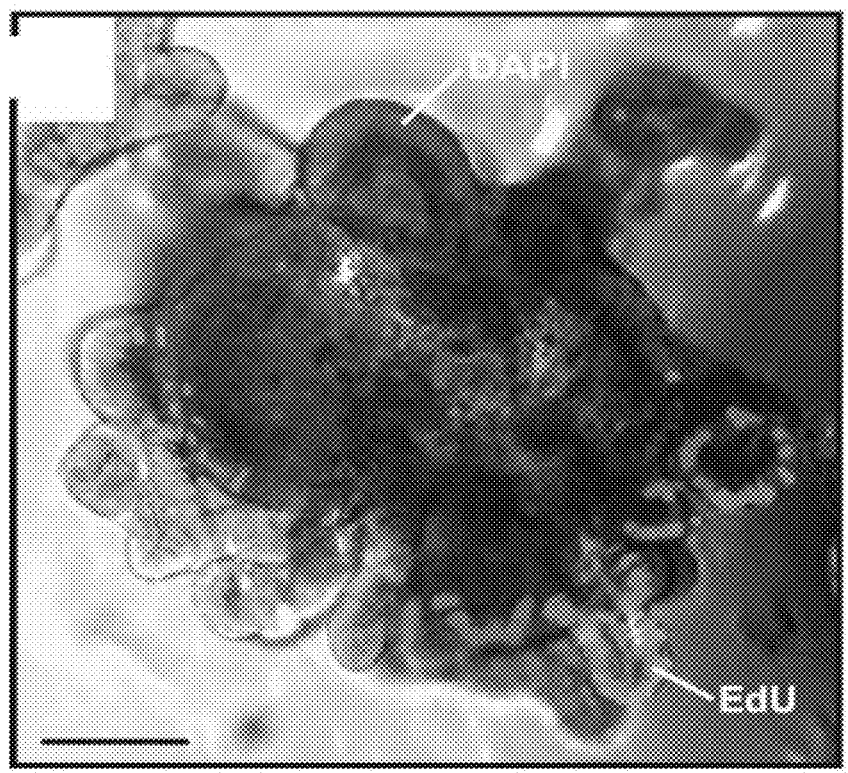
FIG. 36. Human colon culture. a. The effect of nicotinamide on human colon crypt organoids. The majority of human colon crypt organoids die within a few days in WENR+gastrin (WENRg) condition (left panel). Addition of nicotinamide (middle panel: WENRg+nic) improves culture efficiency and lifespan of human colon organoids. * p<0.001. nic: nicotinamide. b. The effect of small molecule inhibitor for Alk4/5/7 (A83-01) and for the MAP kinase p38 (SB202190) on human colon crypt organoids. Left panel: Human colon organoids cultured in WENRg+nicotinamide containing medium form cystic structures 3-4 weeks after culture. Middle panel: Human colon organoids retain their characteristic budding structure under the Human Intestinal Stem Cell Culture ("HISC") condition (WENRg+nicotinamide+A83-01+SB202190). Right panel: A83-01 and SB202190 synergistically increase number of passages of the human colon organoids. * p<0.001. N.S.=statistically not significant. Error bars indicate s.e.m. n=5. c. Proliferating cells visualized by the incorporation of EdU are confined to the budding structures. DAPI is used as a counterstain d. Representative picture of a karyotype from a 3-month-old human colon crypt organoid. Scale: 100 µm. e. Heat-map of the expression profile of cultured human intestinal organoids. The heat-map is a comparison of human small intestinal crypts and human small intestinal villi. Genes more highly expressed in the crypt are dark grey (top-half of heat-map), genes more highly expressed in the villus are light grey (bottom-half of the heat-map). Organoids cultured in-vitro clearly exhibit a similar expression profile to freshly isolated small intestinal crypts and express known stem cell markers. (lane 1: human small intestinal organoids #1, lane 2: human small intestinal organoids #2, lane 3: human colon organoids, lane 4: freshly isolated human small intestinal crypts. The four samples are compared to human smallintestinal villus).
Figure 36D:
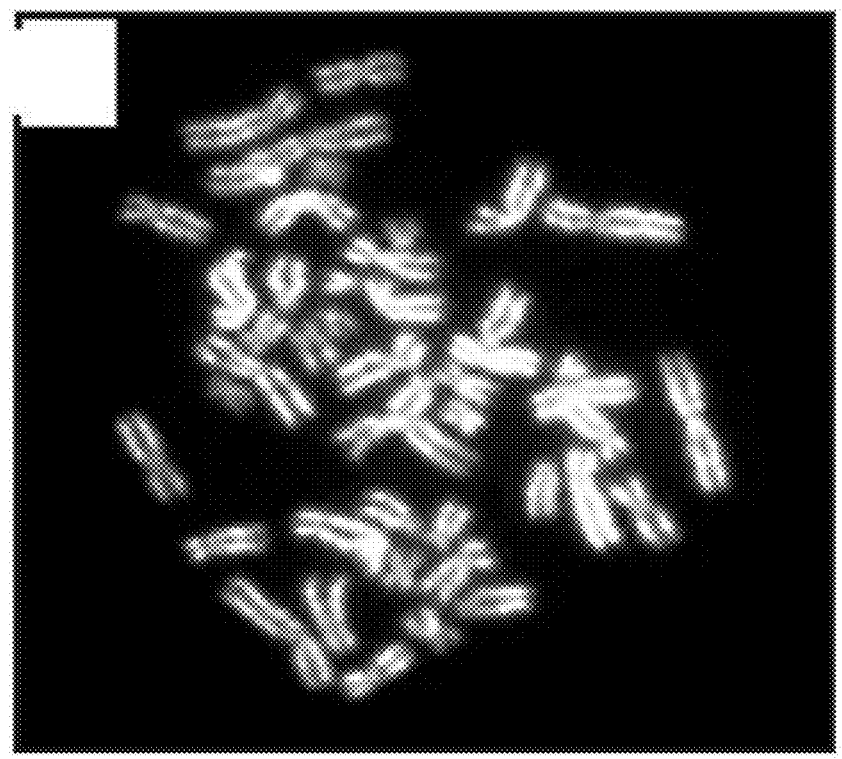
Figure 36E:
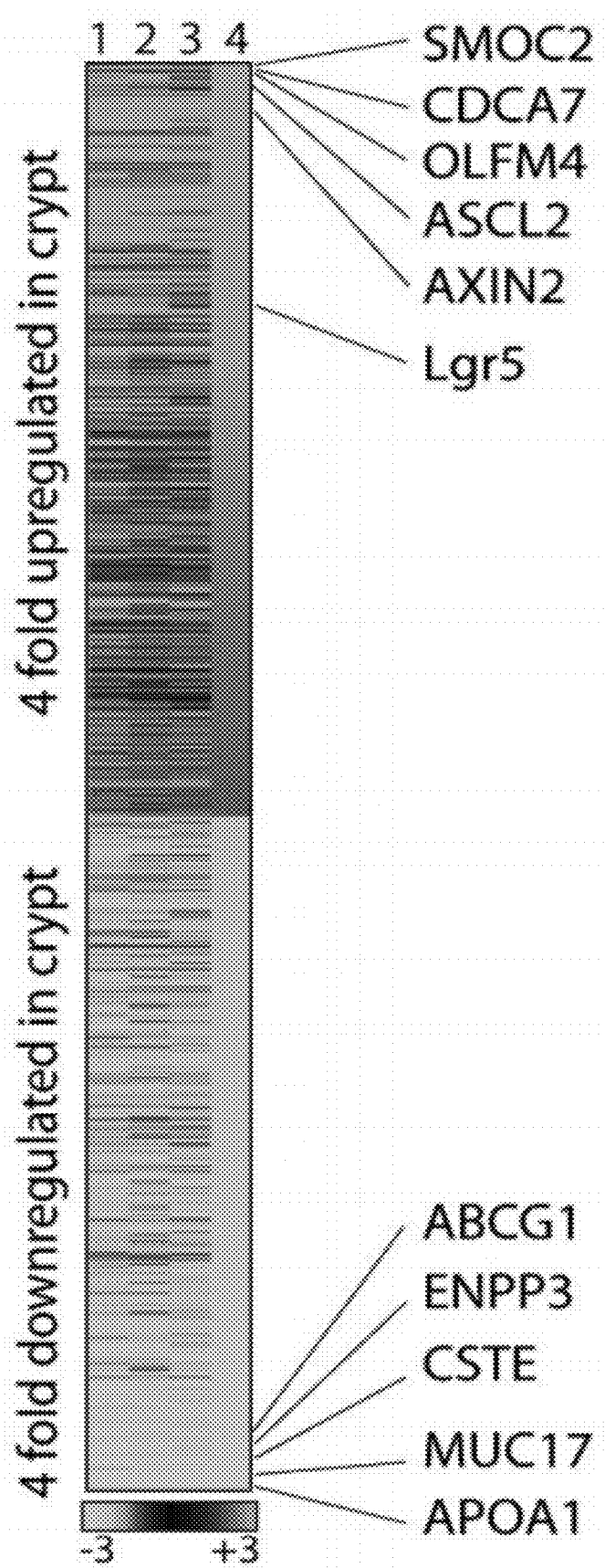

The inventors assumed that growth arrest occurred because of inadequate culture conditions rather than a cell-intrinsic property of senescence/replicative aging. The inventors therefore extended our attempts to optimized the culture condition. The inventors screened various small molecule modulators of MAP kinases, of signaling molecules mutated in colon cancer, and of histone modifiers (FIG. 46) under the WENR+gastrin+nicotinamide culture condition. The inventors found that two small molecule inhibitors, A83-01 (Alk4/5/7 inhibitor; nM) and SB202190 (p38 inhibitor; 10 uM) significantly improved the plating efficiency. Other TGF-beta receptor 1 (ALK 5) inhibitors that were also tested and showed the same results as A83-01 were LY364943, SB431542, SB505124. It would be expected that other ALK inhibitors would also work in the same way. Furthermore, the combination of the two compounds synergistically prolonged the culture period. The inventors demonstrated that all of ten tested samples expanded for at least 6 months with weekly 1:5 split. Under this culture condition, the human colonic organoids displayed budding organoid structures, rather than the cystic structures seen under the previous culture condition (FIG. 36b). The proliferating cells were confined to the buds (FIG. 36c). Metaphase spreads of organoids more than 3 months old consistently revealed 46 chromosomes in each cell (20 cells each from three different donors; FIG. 36d). The inventors sequenced the whole exome (all exons) of the colon organoids after two months in culture. The number of mutations in the organoids was extremely low. In fact in four parallel organoid cultures originating from one clone, only one mutation was found which was present in all cultures and therefore likely originated from the parental tissue.

These results implied that Alk receptor and p38 signaling negatively regulate long-term maintenance of human intestinal epithelial cells. The inventors refer to the optimized culture condition as the HISC (Human intestinal stem cell culture) condition.

Human Intestinal Organoids Mimic in Vivo Differentiation

Figure 37A:
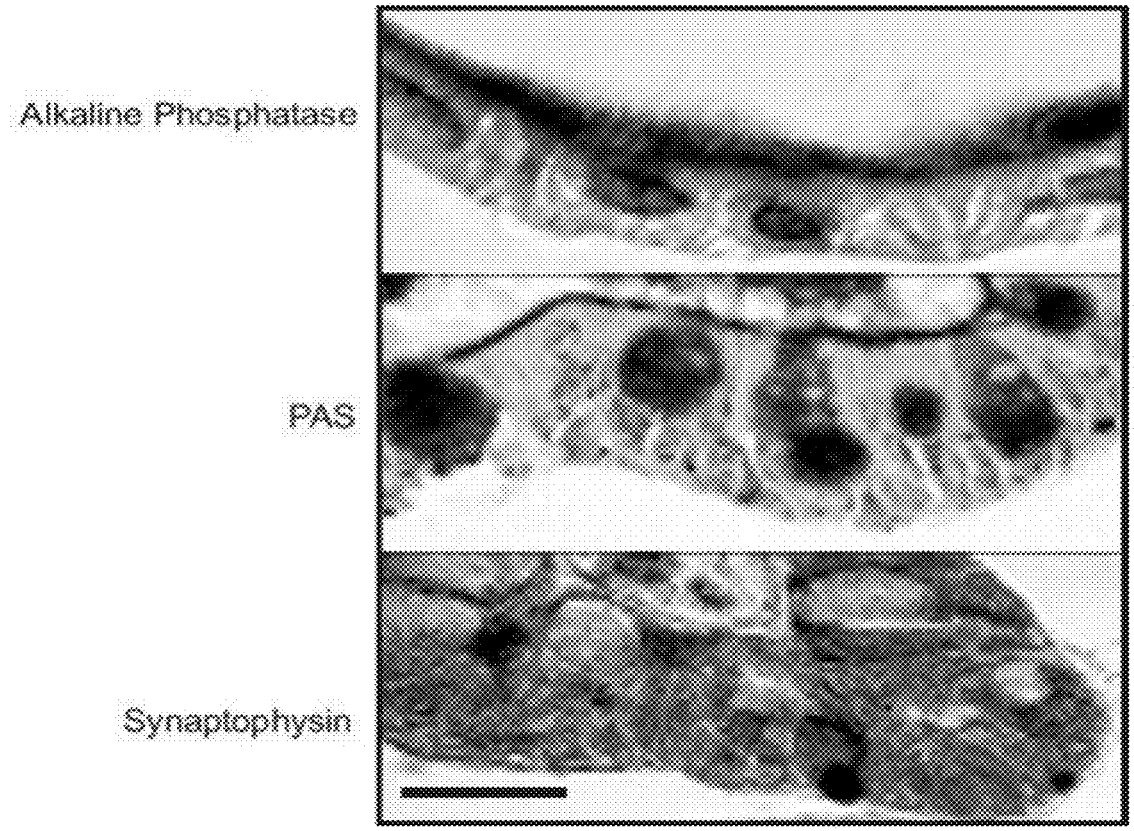
FIG. 37. Human intestinal organoid cell type composition. (a-c) Human organoids differentiate into the different cell types of the intestine after withdrawal of Nicotinamide and SB202190. Markers of the different cell types were used to demonstrate differentiation. (a) Top panel: Alkaline phosphatase staining for mature enterocytes, Middle panel: PAS staining for goblet cells, Bottom panel: Synaptophysin staining for enteroendocrine cells. (b) In each case, the light areas indicate staining. Mucin2 (Muc2) staining in the middle panel represents goblet cells and Chromogranin A (ChgA) in the left-hand panel represents enteroendocrine cells (see arrow and inset). DAPI is used as a counterstain (right panel). (c) Lysozyme (Lysz) is stained in the left-hand panel to show Paneth cells. DAPI is used as a counterstain (right panel). (d-f) Goblet cell differentiation (Muc2) is blocked by SB202190 treatment of organoids (d), while the Notch inhibitor DBZ increases goblet cell number in the human organoids (f). Proliferating cells are represented by EdU incorporation (middle panel) are increased in SB202190 treated organoids (d) or decreased in DBZ treated organoids (f). Organoids are cultured under the following conditions for 5 days: a) top: ENRg+A83-01+SB202190+Nicotinamide, a) middle and bottom, b), c) WENRg+A83-01, d) WENRg+A83-01+SB202190, e) WENRg+A83-01, f) WENRg+A83-01+DBZ. Scale bar: 20 µm (a), 50 µm (b-f). a, b, d-f: human colon crypt organoids, c: human small intestinal organoids.
Figure 37B:
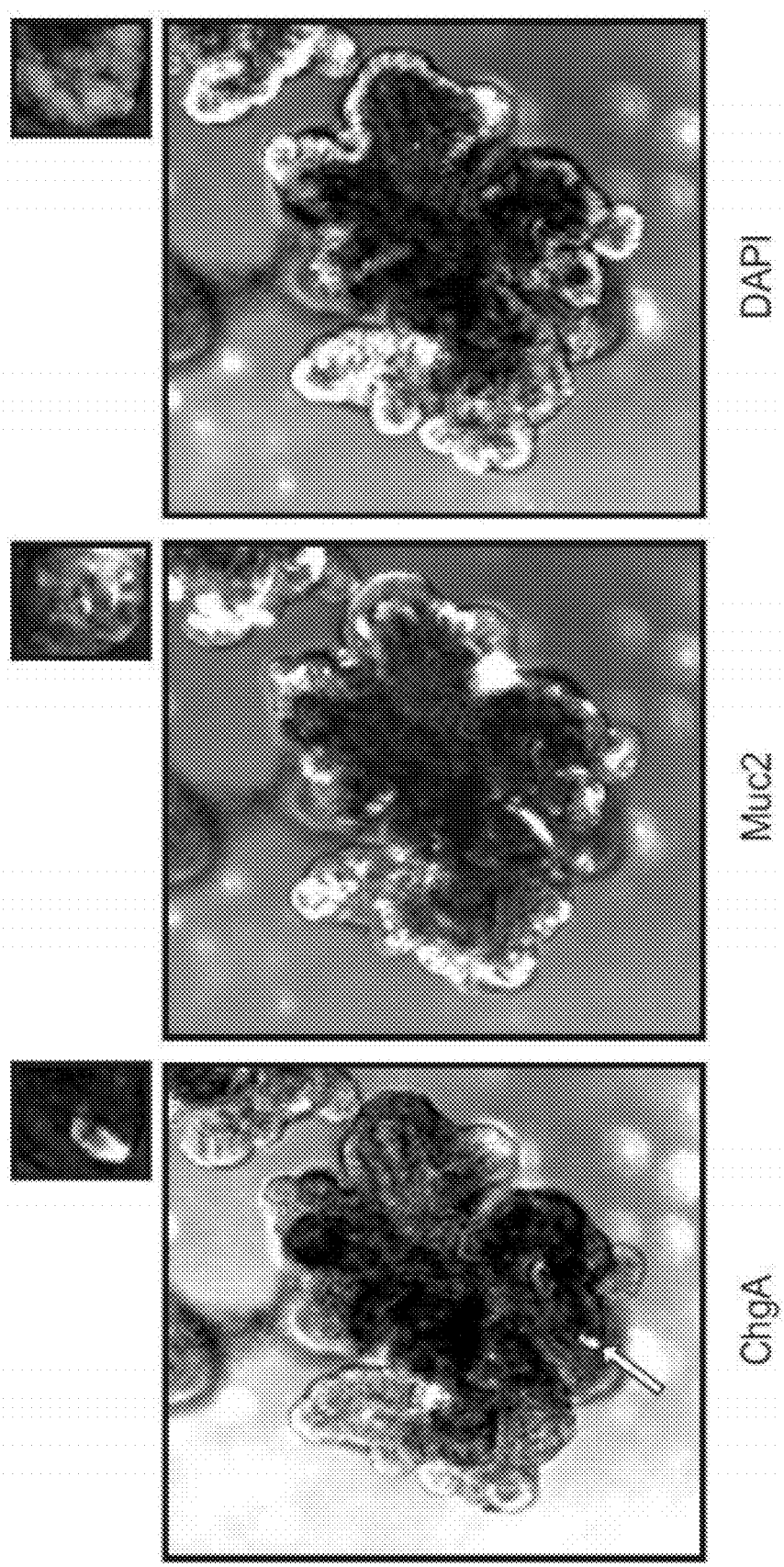
Figure 41:
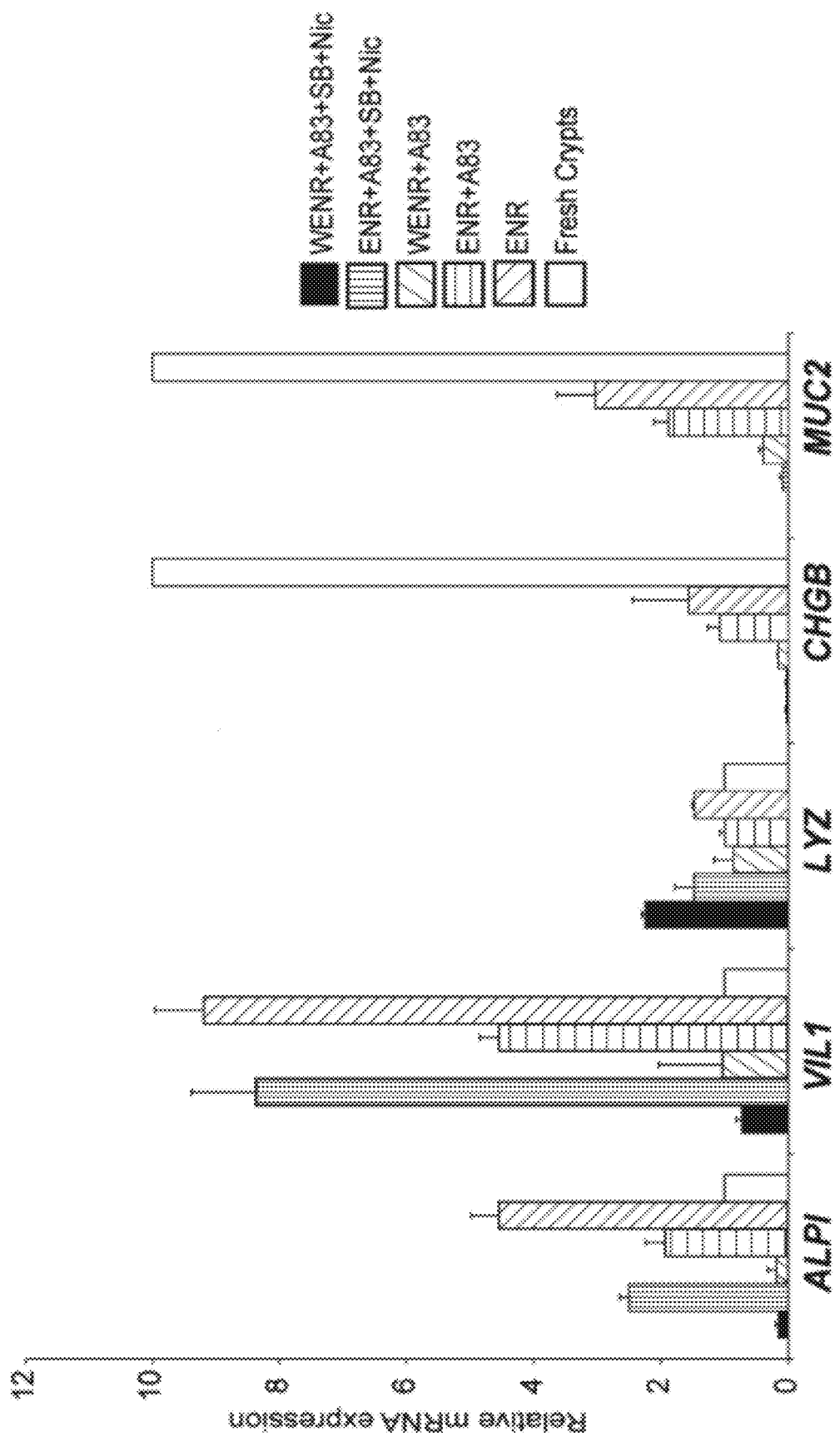
FIG. 41. Relative mRNA expression of mature epithelial cell markers. Freshly isolated small intestinal crypts (white) are cultured in HISC condition for 14 days, followed by a culture with the indicated culture condition for 4 days. mRNA expression of ALPI (Alkaline phosphatase), VIL1 (Villin 1), LYZ (Lysozyme), CHGB (ChromograninB) and MUC2 (Mucin2) was analyzed. Culture condition: RISC (black), ENRg+A83-01+SB202190+Nicotinamide, WENRg+A83-01, ENRg+A83-01, ENRg. Freshly isolated small intestinal crypts were used as control (set as 1.0 for ALPI, VIL1 and LYZ, as 5.0 for CHGB and MUC2. Error bars indicate s.e.m. n=3.
Figure 42A:
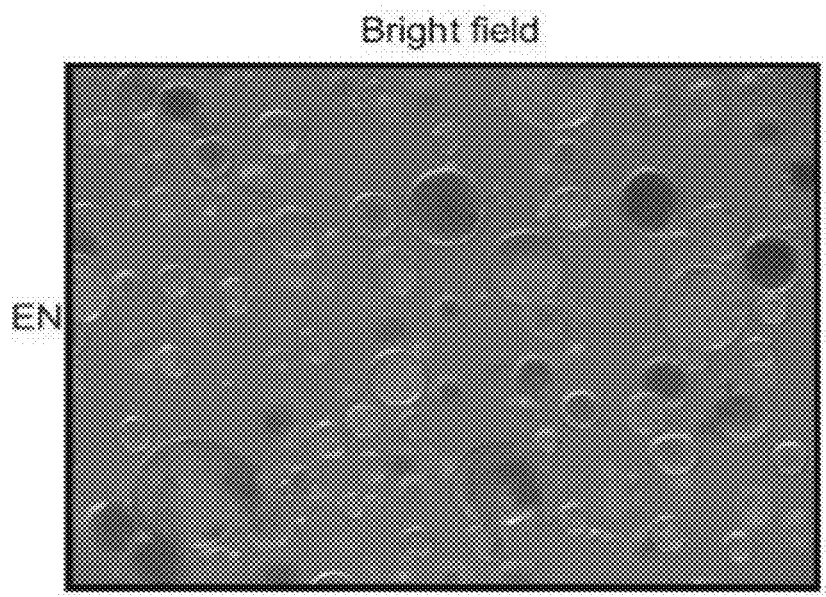
FIG. 42. Sorted Lgr5-GFP− cells form Lgr5-GFP+ organoids. Single sorted Lgr5-GFP-APCf1/f1 adenoma cells are cultured with EGF+Noggin (EN) or EGF (E) for 7 days. Adenoma organoids derived from Lgr5-GFP− cells recovered Lgr5-GFP expression under EN condition but not under E condition (a, c: bright, b, d: GFP autofluorescence).
Figure 42B:
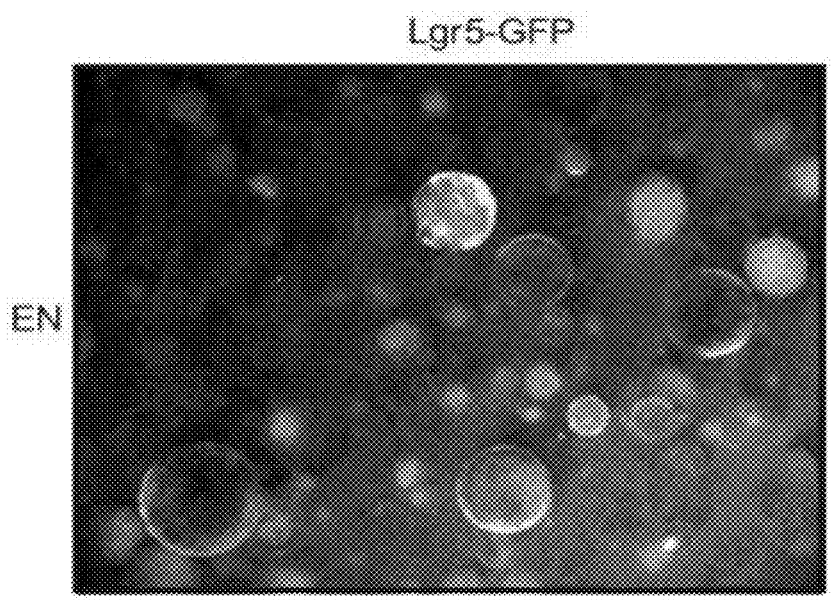
Figure 42C:
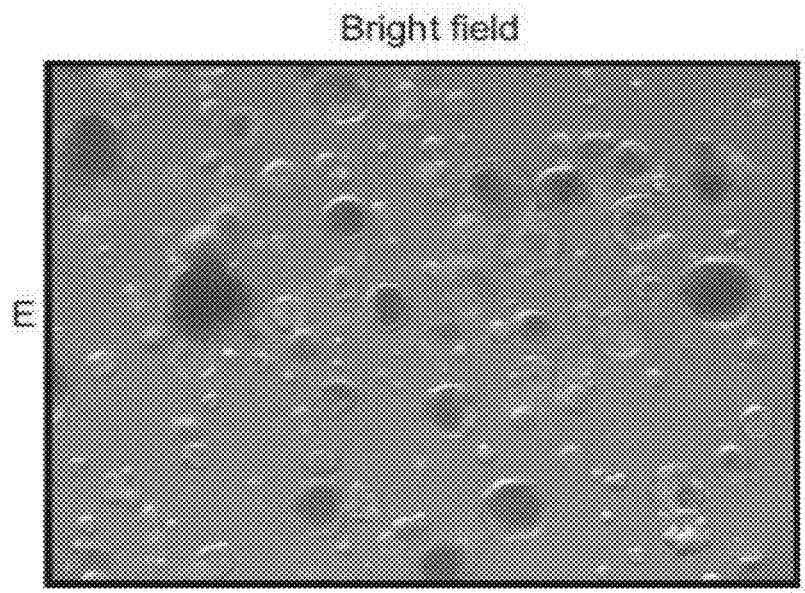
Figure 42D:
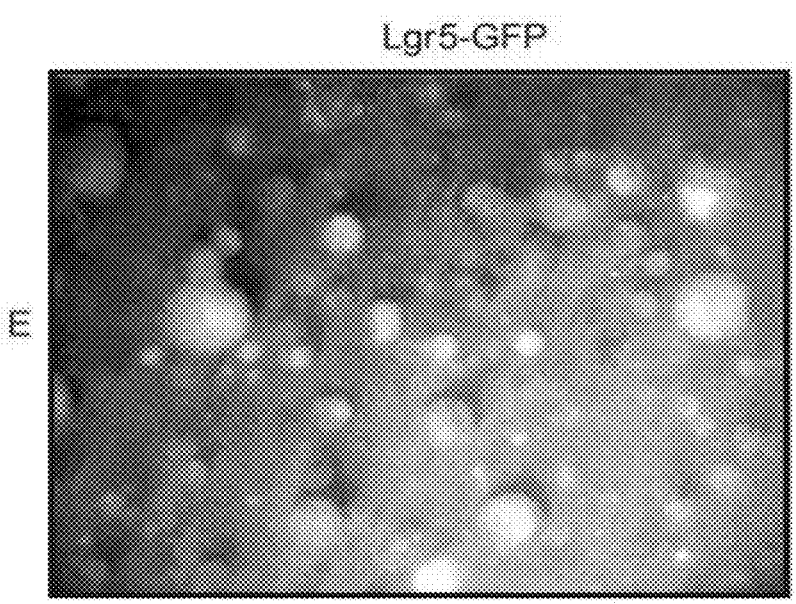

Under the HISC condition, the inventors failed to observe differentiated cells. As was seen in the mouse colon organoids, withdrawal of Wnt was required for mature enterocyte differentiation in human organoids (FIG. 37a top panel and FIG. 41). However, goblet and enteroendocrine cell differentiation remained blocked. We found that Nicotinamide and SB202190 strongly inhibited this differentiation, while withdrawal of the two reagents enabled the organoids to produce mature goblet and enteroendocrine cells (FIGS. 37a (middle and bottom panel), 37b and FIG. 41.

Figure 37D:
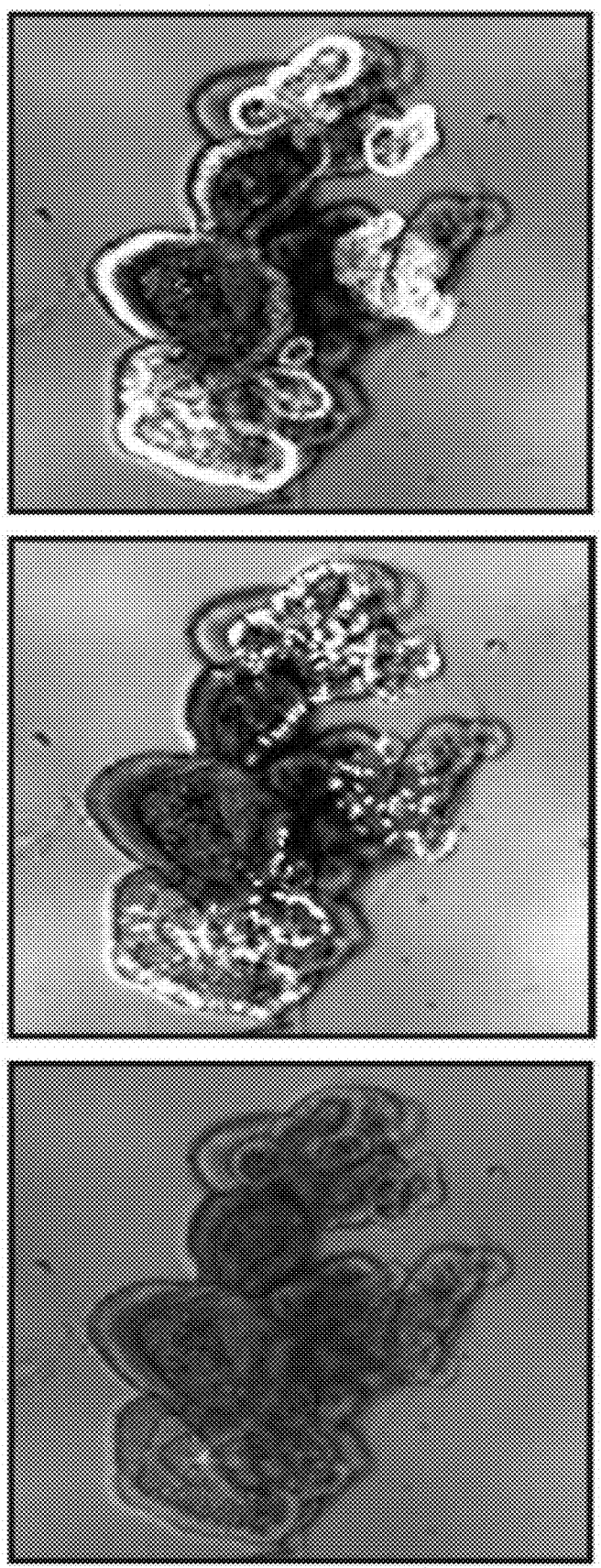
Figure 37E:
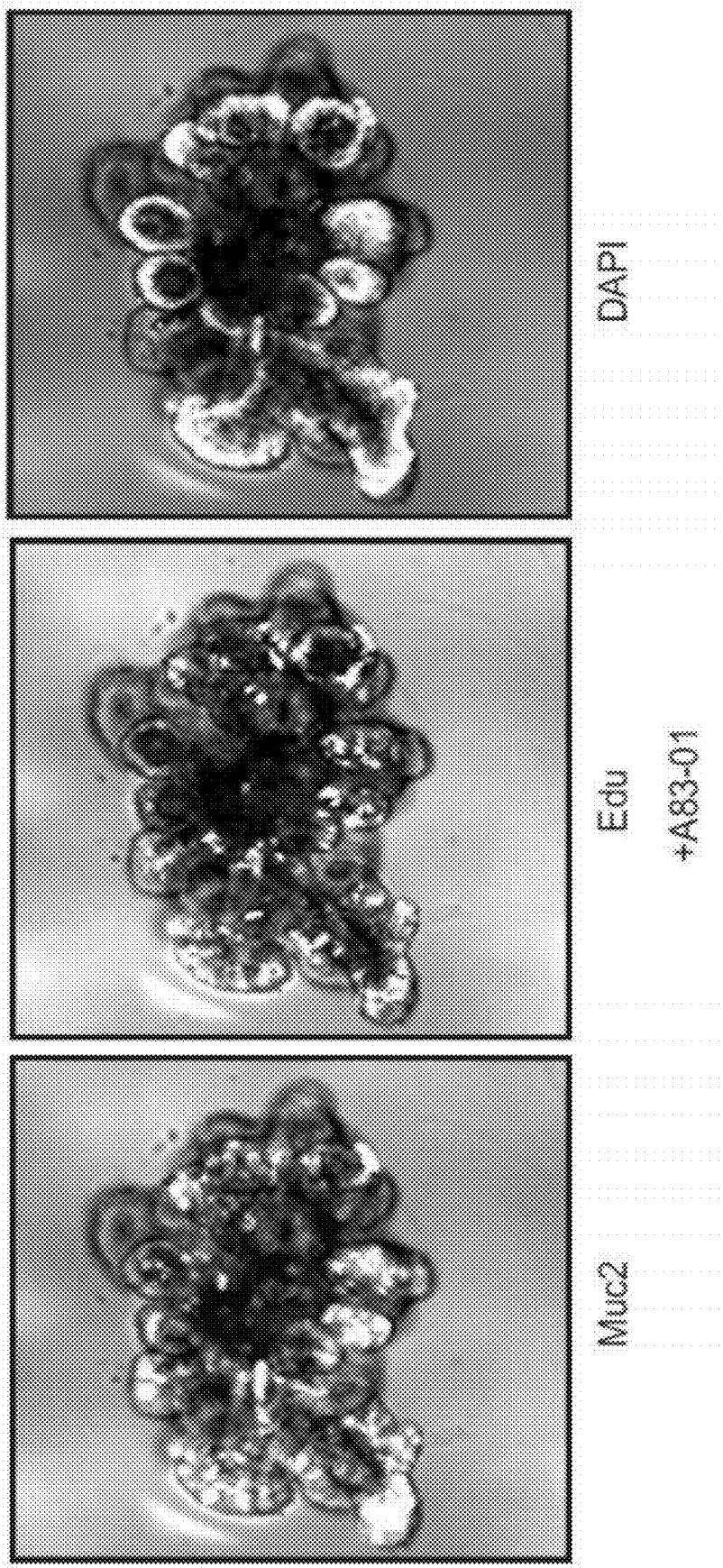
Figure 37F:
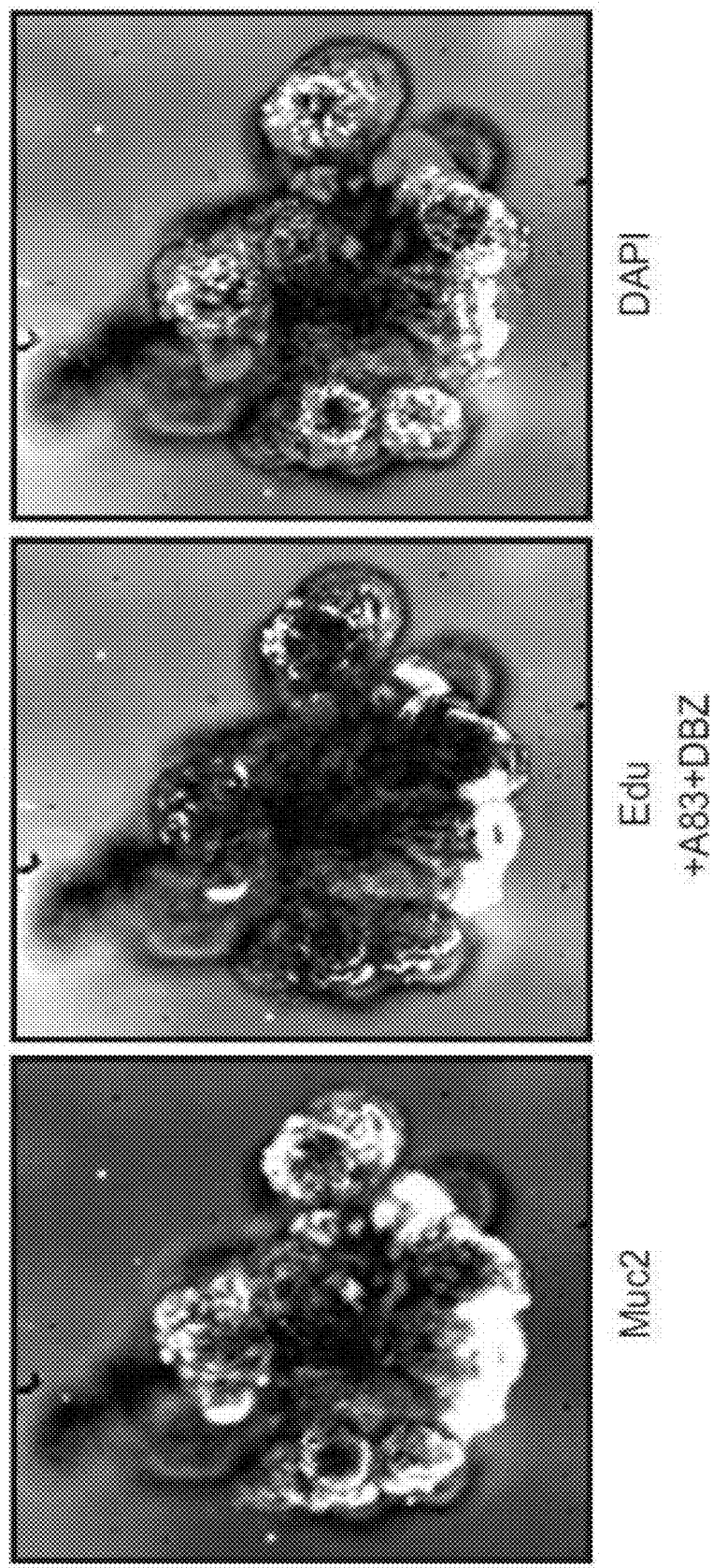

The same differentiation inhibitory effects of Wnt, Nicotinamide and SB202190 were observed in human small intestinal organoids. Lysozyme+Paneth cells were observed in small intestinal organoids, but not in colonic organoids (FIG. 37d). It has been reported that p38 inhibitor treatment in vivo inhibits goblet cell differentiation and increases intestinal epithelial proliferation (Otsuka M. *Gastroenterology* 2010; 138:1255-65, 1265 e1-9). Indeed, the inventors observed the same phenotype in the p38 inhibitor treated intestinal organoids (FIG. 37d vs. 37e).

The inventors further examined the response of human intestinal organoids to Notch-inhibition. The inventors have previously shown that Notch inhibition with either γ-secretase inhibitors (dibenzazepine; DBZ) or by conditional targeting of the Notch pathway transcription factor CSL depleted intestinal stem cells, terminated intestinal epithelial proliferation and induced goblet cell hyperplasia in vivo (van Es J. H. et al., *Nature* 2005; 435:959-63). Indeed, upon treatment with DBZ, the intestinal organoids ceased their proliferation and most cells converted into goblet cells within 3 days (FIG. 37g vs 37f).

Establishment of APC-Deficient Adenoma and Colon Adenocarcinoma

Figure 38A:
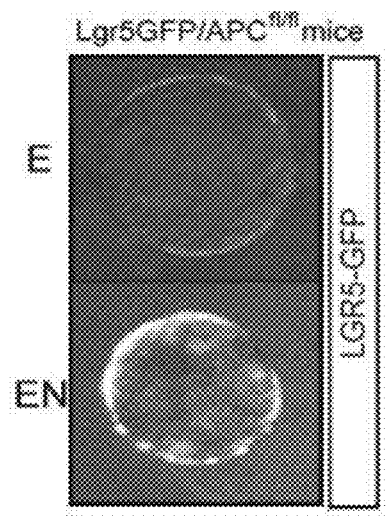
FIG. 38. Adeno(carcino)ma cultures. a. Lgr5-GFP-ires-CreER/APCfl/fl crypts cultured with EGF (E) (top) or EGF+Noggin (EN) (bottom) for 10 days. b. Relative mRNA expression of Lgr5 and Axin2. Freshly isolated adenoma cells (white) were cultured with EGF (hatched) or EGF+Noggin (black). c. Culture efficiency of organoids from sorted Lgr5-GFPhi, Lgr5-GFPlo, Lgr5-GFP-ve cells. *p<0.01. one way ANOVA. Error bars indicate s.e.m. n=3 d. Time course culture of human colon adenocarcinoma cells.
Figure 38B:
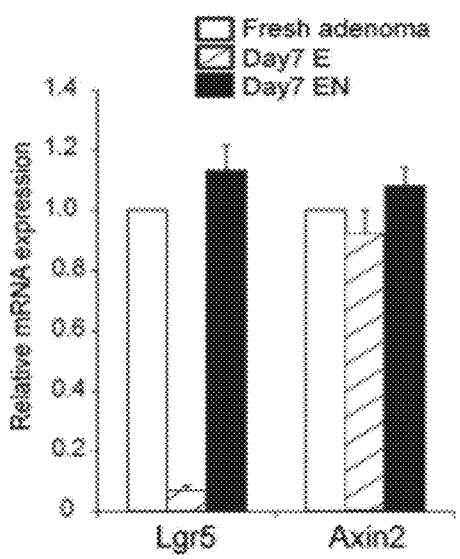
Figure 38C:
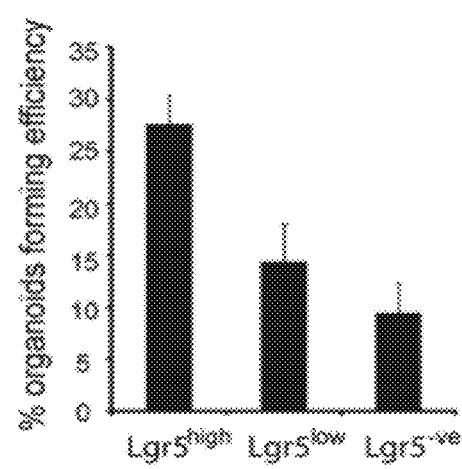

Recently, the inventors reported efficient mouse intestinal adenoma formation from Lgr5 stem cells in Lgr5-GFP-ires-CreERT2×APC$^{flox/flow}$ mice upon Tamoxifen-induced Cre activation_ENREF_32 (Barker N. et al., *Genes Dev.* 2008; 22:1856-64). The inventors isolated the intestinal adenomas 10 days after induction and optimized the culture condition. The adenomas efficiently formed cystic organoid structure without budding. Since APC loss constitutively activates the Wnt pathway, the inventors expected that R-spondin1 would become dispensable for adenoma organoid growth. This was indeed observed. Furthermore, Noggin, which is essential for long-term culture of normal small intestine, was dispensable in adenoma organoids. Interestingly, the inventors observed a loss of Lgr5-GFP but not Axin2-LacZ in adenomatous organoids 7 days after withdrawal of Noggin (FIGS. 38a, 38b and data not shown). Similar observations were made for normal intestinal organoids when grown in ER-medium_ENREF_27 (Sato T. et al., Nature 2009; 459: 262-5). This indicated that Noggin, most likely through inhibition of BMP signals, is required to maintain Lgr5 expression, but is not required for expansion of adenoma organoids. Freshly isolated Lgr5$^{hi}$ (but not Lgr5$^{low}$) cells isolated from intestinal crypts can initiate organoid growth in vitro (Sato T. et al., Nature 2009; 459:262-5). To determine the existence of a similar Lgr5-hierarchy within adenomas, the inventors isolated Lgr5-GFP$^{hi}$, GFP$^{low}$ and GFP$^{-ve}$ cells from EN-cultured organoids and examined their organoid formation ability. After a 7 day culture, Lgr5-GFP$^{hi}$ showed the highest organoid-forming efficiency. Yet, Lgr5-GFP$^{low}$ or $^{-ve}$ also formed organoids with considerable efficiency (FIG. 38c). Of note, sorted GFP$^{-ve}$ adenoma cells could give rise to Lgr5-GFP$^{hi}$ organoids (FIG. 42).

Figure 38D:
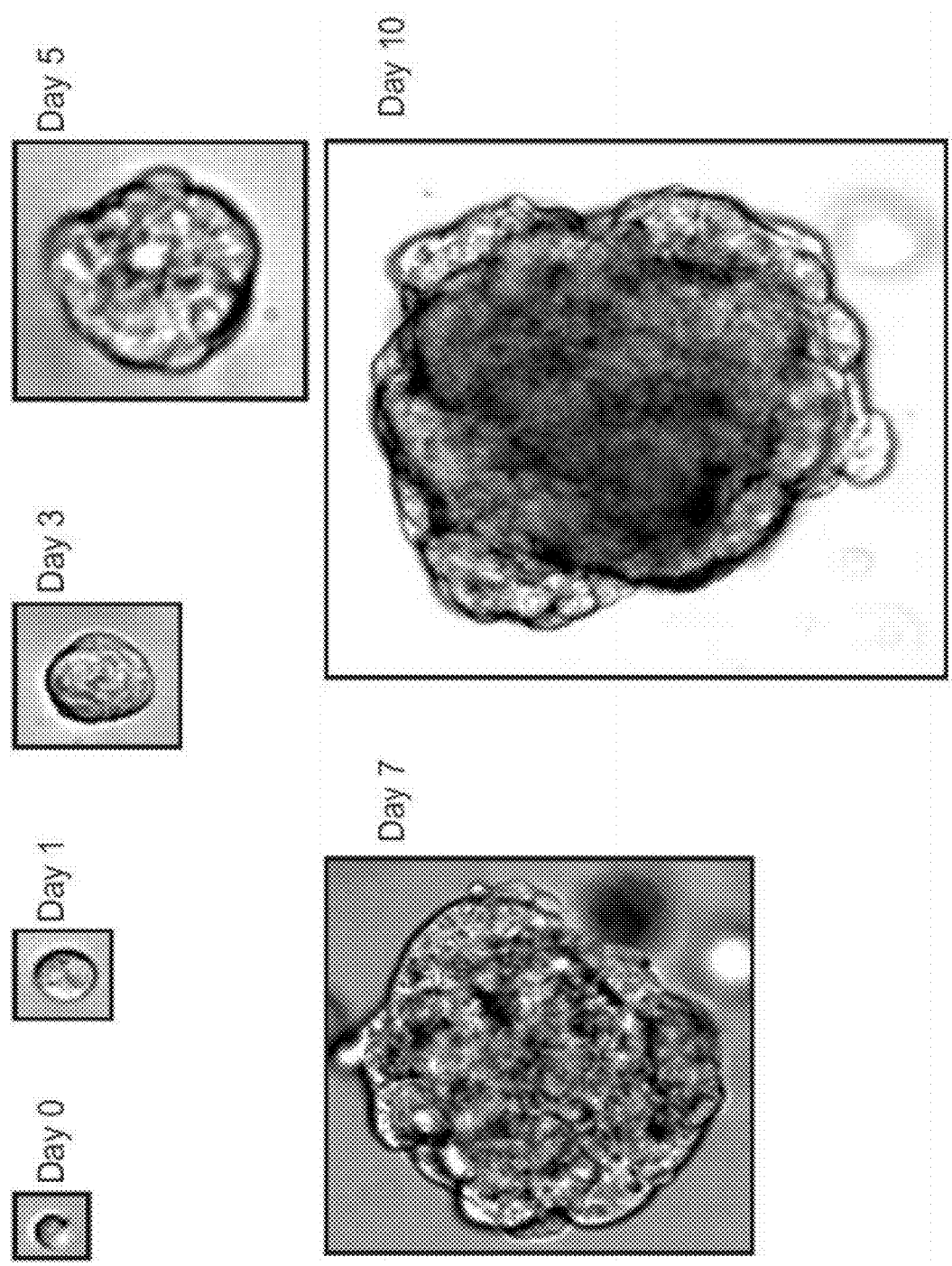

Many colorectal cancer cell lines have been isolated over the past four decades. Typically, such cell lines emerge as rare, clonal outgrowths after primary cultures of colon tumors enter tissue-culture crisis. Currently, no robust culture system exists which allows the consistent culture of primary human colon cancer samples without culture crisis and the consequent clonal outgrowth of culture-adapted cells. As an obvious next step, the inventors applied intestinal adenoma culture conditions to human colorectal cancer samples. As expected, colon cancer cells required neither R-spondin nor Noggin. EGF was dispensable in most colon cancer organoids, while some colon cancer organoids decelerated their proliferation after withdrawal of EGF. Distinct from mouse intestinal adenoma, colorectal cancer organoids in the culture condition grew as irregular compact structures rather than as simple cystic structures (FIG. 38d).

Figure 43:
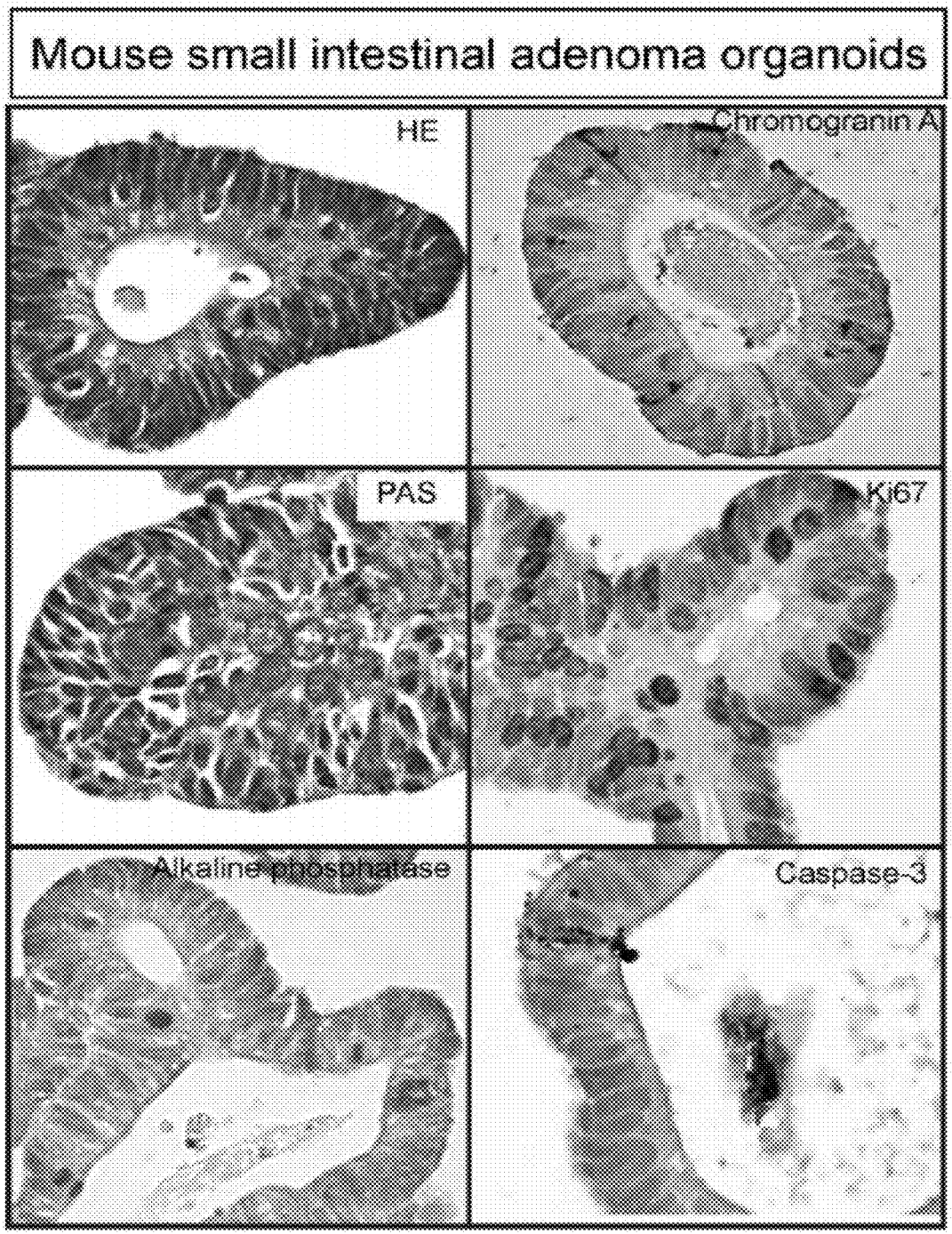
FIG. 43. Histochemical analysis of adenoma/colon cancer organoids. Mouse small intestinal adenoma organoids (Left panel) and human colon cancer organoids (Right panel) were analyzed with indicated histochemical (HE, PAS and Alkaline phosphatase) or immunohistochemical (Chromogaranin A, Ki67 and Caspase3) stainings.
Figure 43:
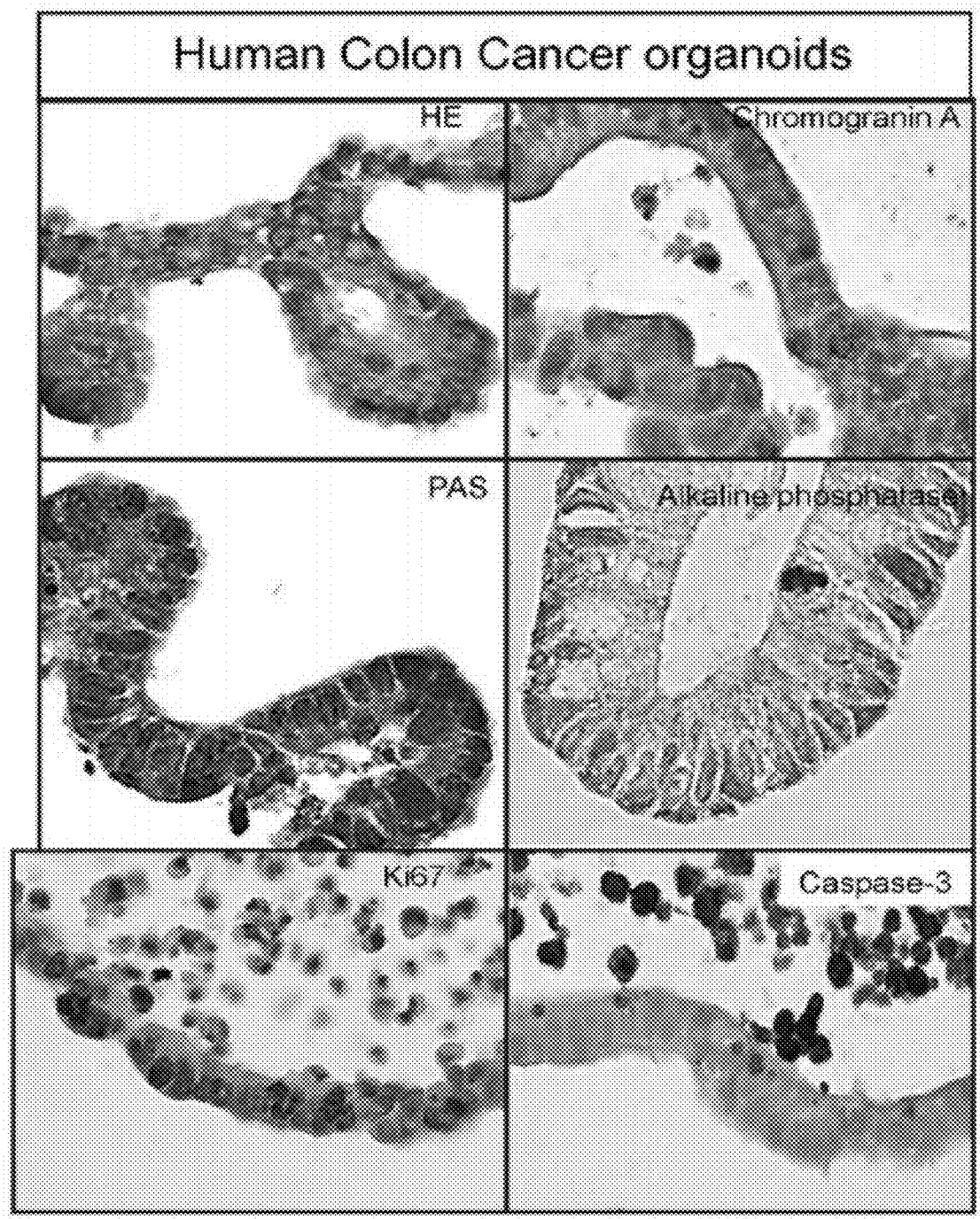

The inventors examined the proliferation/differentiation status of adenoma and colon cancer organoids. As expected, most of cells were Ki67+. Consistent with the strong inhibitory effect of Wnt on enterocyte differentiation (FIG. 35f and FIG. 41), alkaline phosphatase staining was not observed in both types of organoids (FIG. 43). In contrast, we occasionally observed PAS+ goblet cells and chromogranin A+ endocrine cells in adenoma organoids and in some colon cancer organoids (FIG. 43).

Culturing Human Metaplastic Barrett's Epithelium

Figure 39A:
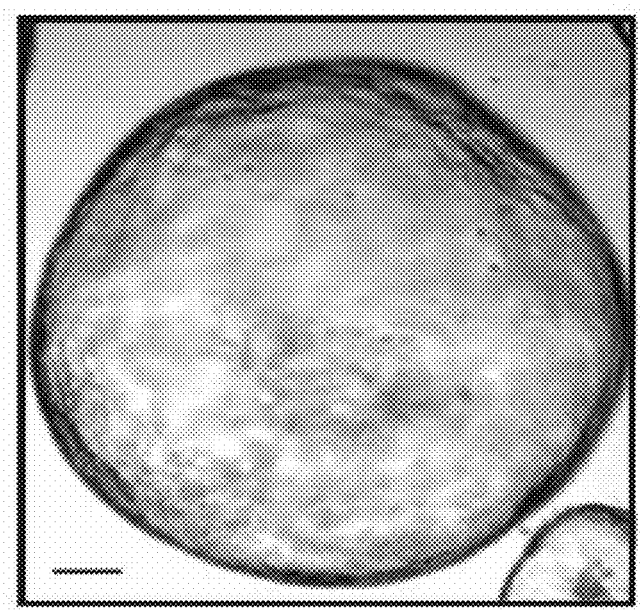
FIG. 39. Culture of Barrett's esophagus and treatment with Notch inhibitor. a. Isolated epithelium from Barrett's esophagus (BE) cultured with HISC condition for 7 days forms cystic structures. b. Addition of FGF10 significantly increases the number of passages for BE organoids. Error bars indicate s.e.m. n=3 c. Representative time course of a BE organoid. d. Paraffin sections from BE organoids. Nicotinamide and SB202190 are withdrawn for 4 days with (right) or without (left) the Notch inhibitor DBZ added to the medium. Proliferating cells (Ki67 stain) disappear and PAS+ goblet cells increase with DBZ treatment.
Figure 39B:
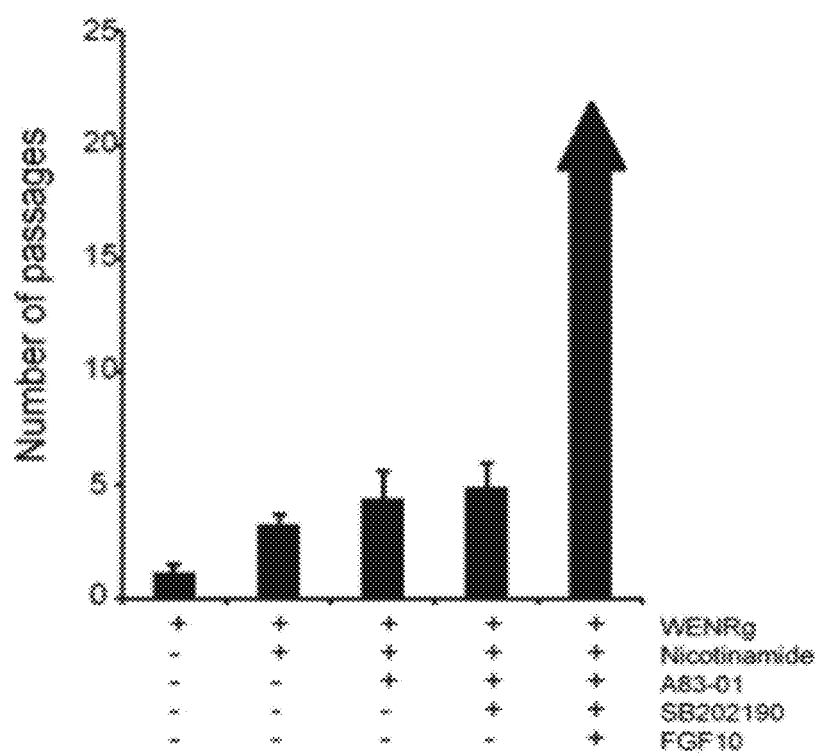
Figure 39C:
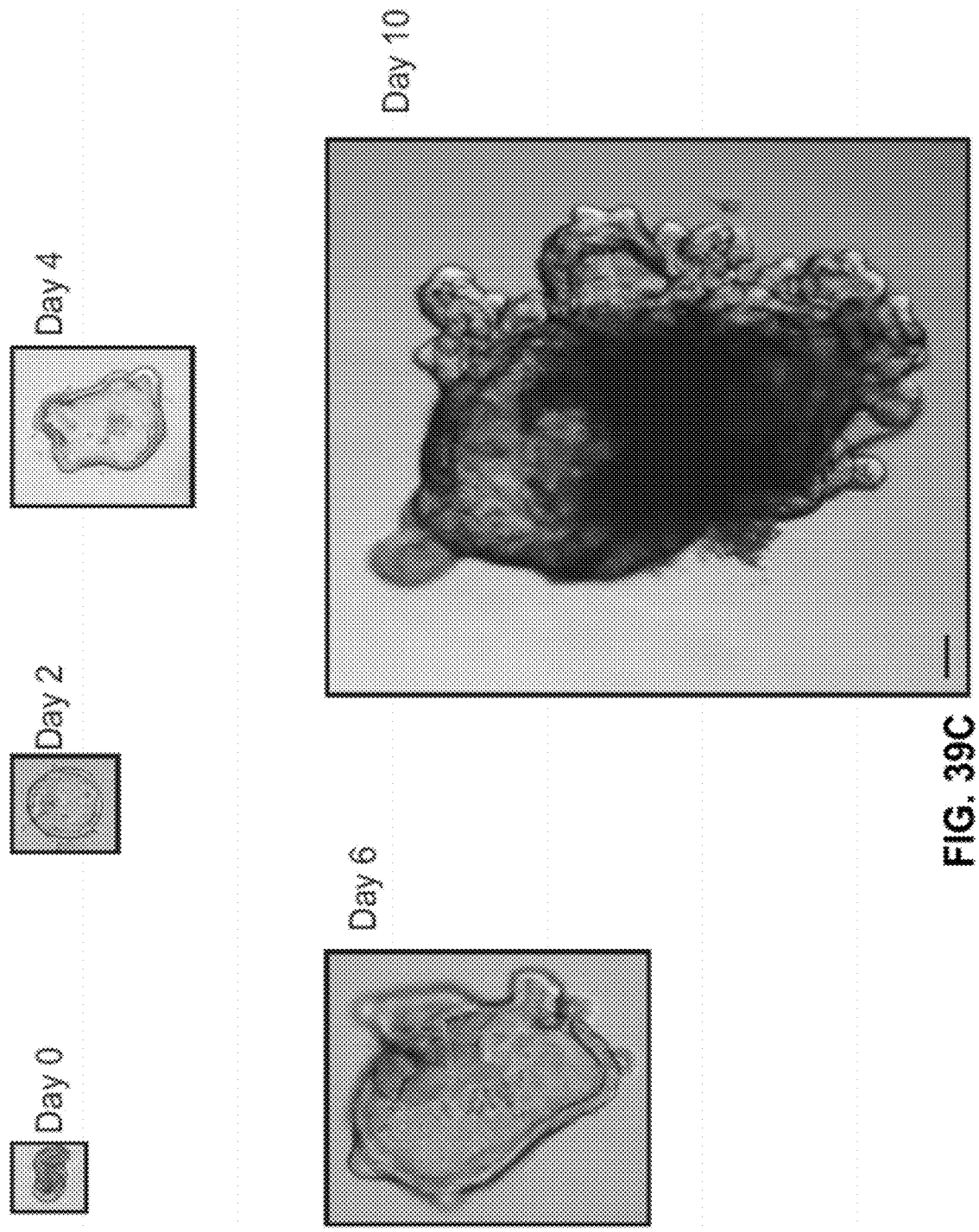
Figure 39D:
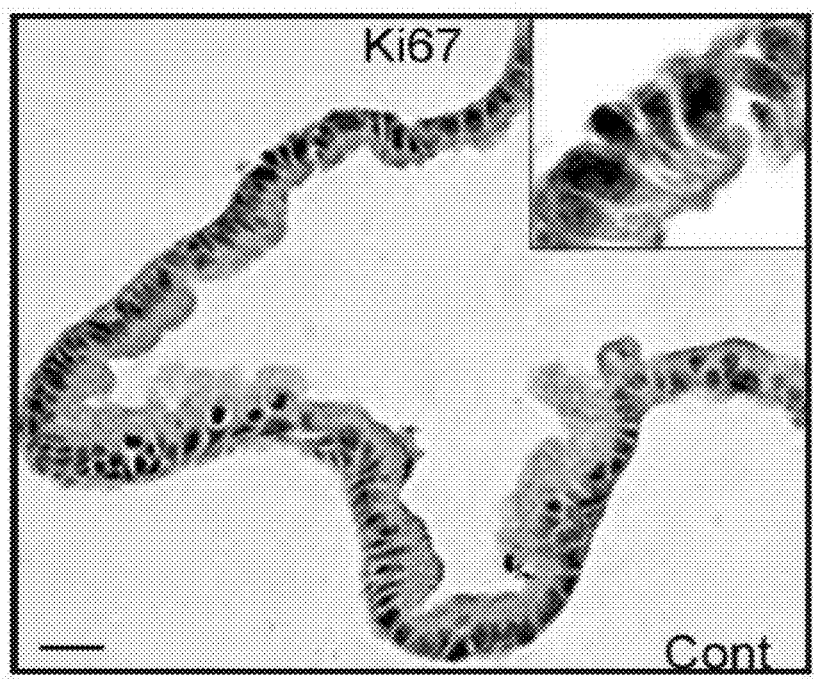
Figure 39E:
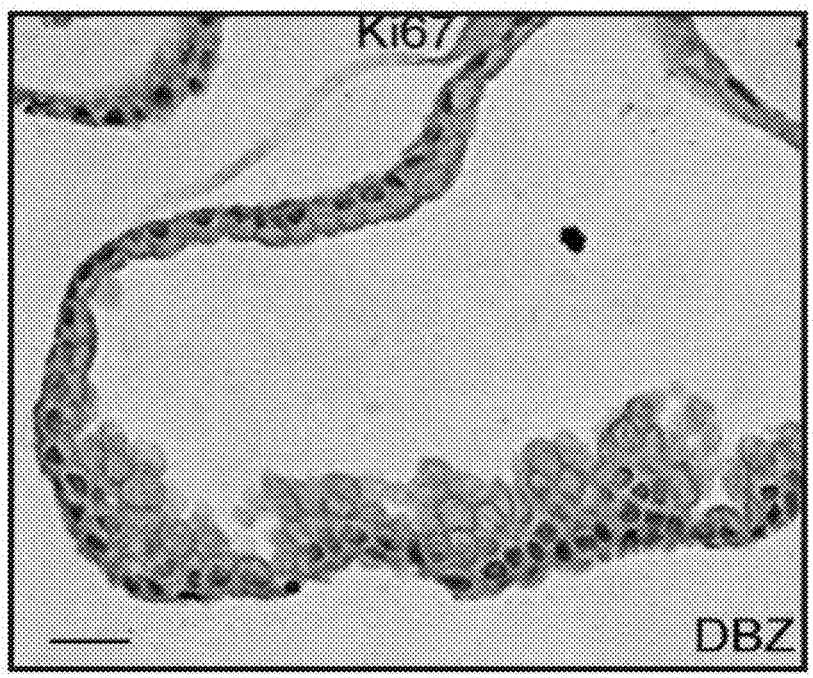
Figure 39F:
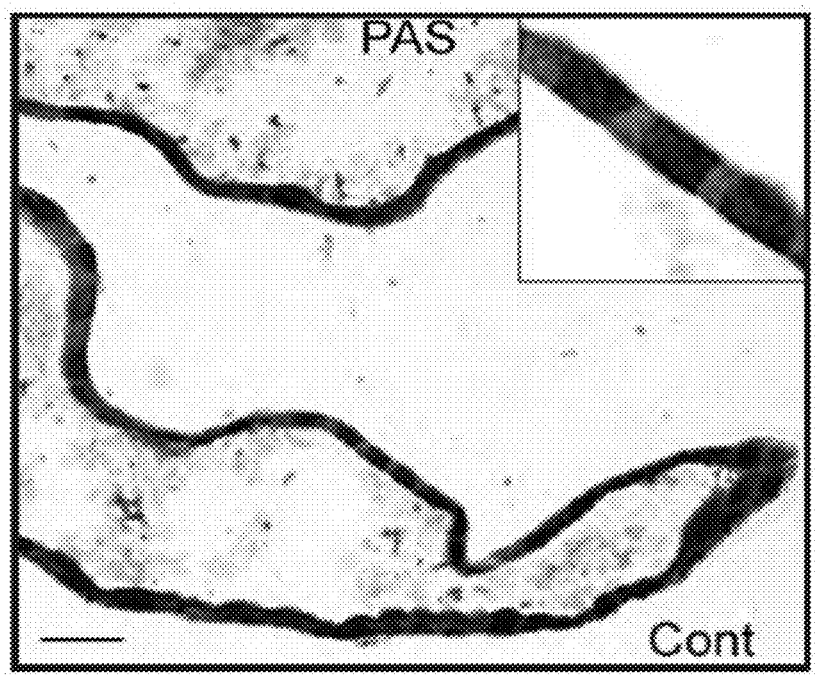
Figure 39G:
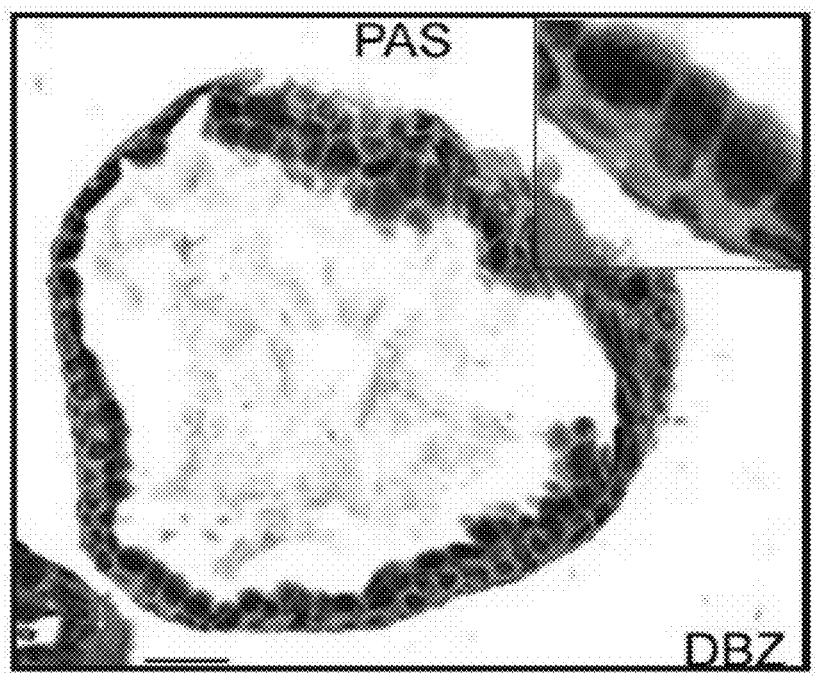
Figure 44:
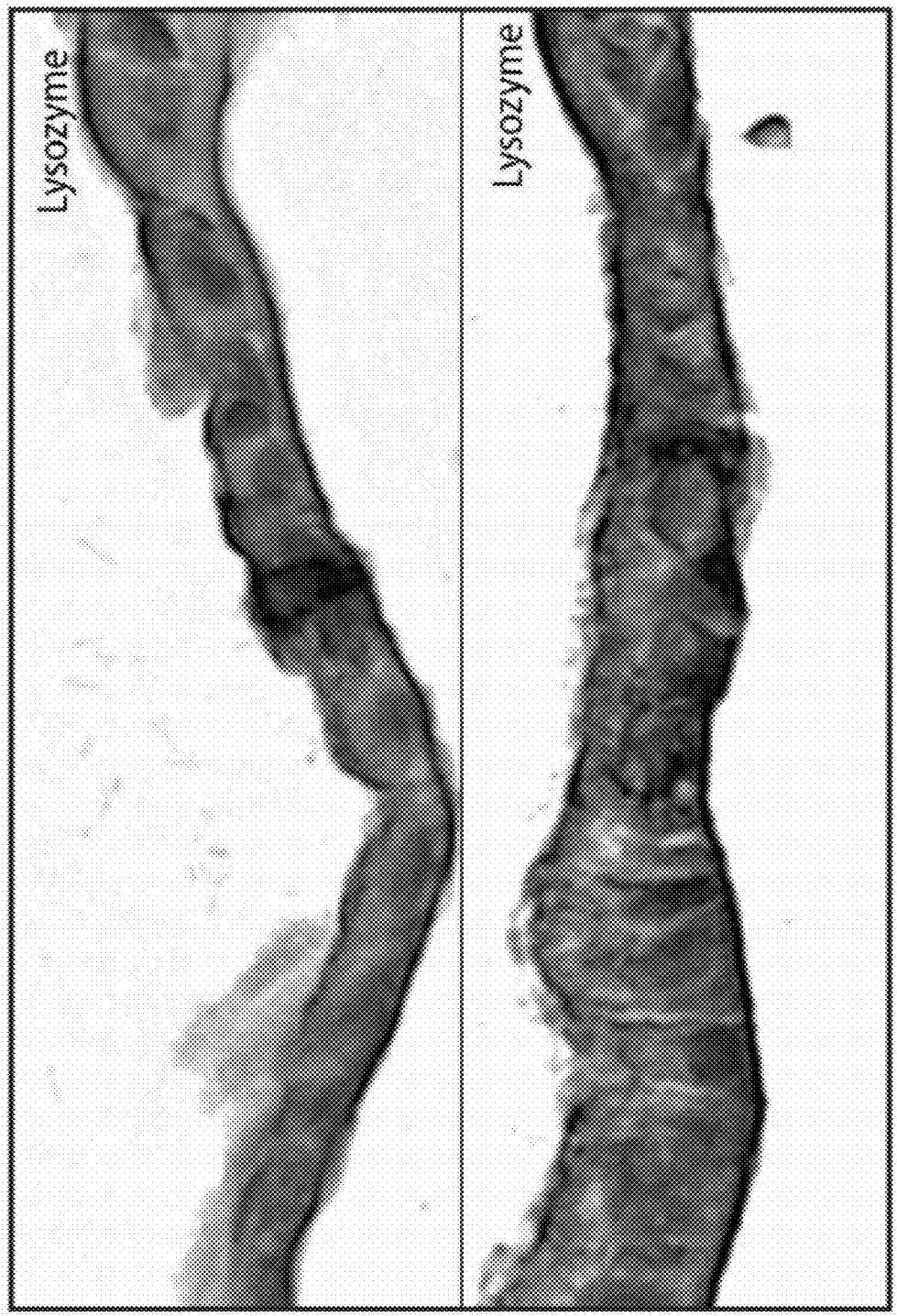
FIG. 44. Paneth cells in BE organoids. Lysozyme+ Paneth cells were observed in differentiated BE organoids.

Barrett's Esophagus is marked by the presence of columnar epithelium in the lower esophagus, replacing the normal squamous cell epithelium as a result of metaplasia (Odze R. D. Nat. Rev. Gastroenterol. Hepatol. 2009; 6:478-90). The histological hallmark of Barrett's Esophagus is the presence of intestinal goblet cells in the esophagus. Exploiting the similarity between Barrett and intestinal epithelium, the inventors subjected small Barrett's epithelium (BE) biopsies to the human colon culture condition. Under these culture conditions, normal esophageal squamous cells transiently proliferated for 1 week, but the organoids could not be passaged. Barrett's Esophagus epithelium could be maintained for up to 1 month under HISC conditions (FIG. 39a). The BE organoids formed cystic organoid structures indistinguishable from that of senescent human colon organoids, and typically underwent growth arrest 1 month after the culture. Addition of FGF10 to the HISC condition enabled the BE organoids to form budding structures and significantly prolonged the culture duration (>3 months) (FIGS. 39b, 39c). In contrast to human intestinal organoids, BE organoids remained Ki67+ with a minimal number of PAS+ and Mucin+ cells 4 days after withdrawal of Nicotinamide and SB202190. Treatment with the γ-secretase inhibitor DBZ (10 uM) for 4 days after the withdrawal blocked proliferation and induced goblet cell differentiation (FIGS. 39d-39g). This supported our previous suggestion that local delivery of such inhibitors may represent a useful therapeutic strategy for the removal of Barrett's Esophagus lesions by differentiation therapy (Menke V. et al., Disease Models and Mechanisms 2010; 3:104-10). Of note, we occasionally observed Lysozyme+ Paneth cells (FIG. 44), which indicates that BE organoids preserve multilineage differentiation.

Discussion

The protocols developed here allow robust and long-term culture of primary human epithelial cells isolated from small intestine, colon, adeno(carcino)mas and Barrett's Esophagus (table 2).

TABLE 2

List of components of the organoid culture systems

| Reagent name | Supplier | Cat No. | Solvent | Stock solution | Final conc. |
|---|---|---|---|---|---|
| Matrigel, GFR, phenol free | BD bioscience | 356231 | | | |
| Advanced DMEM/F12 | Invitrogen | 12634-028 | | | |
| GlutaMAX-I | Invitrogen | 35050-079 | | 200 mM | 2 mM |
| HEPES 1M | Invitrogen | 15630-056 | | | 10 mM |
| Penicillin/Streptomycin | Invitrogen | 15140-122 | | 10000/10000 U/ml | 100/100 U/ml |
| N2 supplement | Invitrogen | 17502-048 | | 100x | 1x |
| B27 supplement | Invitrogen | 17504-044 | | 50x | 1x |
| N-Acetylcysteine | Sigma-Aldrich | A9165-5G | DW | 500 mM = 81.5 mg/ml | 1 mM |
| EDTA | Sigma-Aldrich | 431788-25g | DW | 500 mM = 14.6 g/100 ml | 2 mM |
| Mouse recombinant noggin | Peprotech | 250-38 100 ug | PBS/BSA | 100 mg/ml | 100 ng/ml |
| mouse recombinant EGF | Invitrogen | PMG8043 | PBS/BSA | 500 mg/ml | 50 ng/ml |
| human recombinant R-spondin | Nuvelo | | PBS/BSA | 1 mg/ml | 1 mg/ml |
| human recombinant FGF10 | Peprotech | 100-26 | PBS/BSA | 100 mg/ml | 100 ng/ml |
| mouse recombinant Wnt-3A | Millipore | GF-160 | PBS | 10 mg/ml | 100 ng/ml |
| Y-27632 | Sigma-Aldrich | Y0503 | PBS | 10 mM = 1 g/338 ml | 10 mM |
| A-83-01 | Tocris | 2939 | DMSO | 500 mM | 500 nM |
| SB202190 | Sigma-Aldrich | S7067 | DMSO | 30 mM | 10 mM |

TABLE 2-continued

List of components of the organoid culture systems

| Reagent name | Supplier | Cat No. | Solvent | Stock solution | Final conc. |
|---|---|---|---|---|---|
| Nicotinamide | Sigma-Aldrich | | DW | 1M | 10 mM |
| [Leu15]-Gastrin I | Sigma-Aldrich | G9145 | PBS/BSA | 100 mM | 10 nM |
| DNase | Sigma-Aldrich | DN25-1g | PBS | 200000 U/ml | 2000 U/ml |
| TrypLE express | Invitrogen | 12605-036 | | | |
| Collagenase type XI | Sigma-Aldrich | C9407 | | | |
| Dispase | Invitrogen | 17105-041 | | | |
| 70 um Cell strainer | BD falcon | 352350 | | | |

All stock solutions and aliquoted Matrigel are stored in −20° C.

In contrast to murine small intestine, murine colonic epithelial cells require Wnt ligand in the culture medium. The inventors have previously reported that CD24$^{hi}$ Paneth cells produce Wnt-3/11, which are essential for stem cell maintenance in small intestine (Sato T., et al., *Nature* 2011; 469:415-8). Wnt-6 and -9b mRNA are expresses at the bottom of colon crypts (Gregorieff A., et al. *Gastroenterology* 2005; 129:626-38.). It remains undetermined whether this local Wnt production by colon crypt base cells is sufficient to activate canonical Wnt signal in vivo or there is another source of Wnt ligand in colon mucosa. The difference between human and mouse intestinal organoid culture conditions was unexpectedly large. A83-01 inhibits ALK4/5/7, receptors that are detected in both murine and human crypts by microarray. The inventors are currently investigating the mechanism by which ALK signal regulates human organoid growth. The inventors have not observed cellular transformation in long-term cultures and no chromosomal changes become obvious under the optimized culture conditions. Furthermore, the organoids can undergo a considerably higher number of cell division than reported for other adult human epithelial culture system (Dey D. et al., *PloS one*, 2009; 4:e5329; Garraway I. P. et al., *The Prostate* 2010; 70:491-501). It is generally believed that somatic cells are inherently limited in their proliferative capacity, a phenomenon called replicative aging (Walen K. H., *In vitro cellular & developmental biology, Animal* 2004; 40:150-8). Most normal human cells are believed to count the number of times they have divided, eventually undergoing a growth arrest termed cellular senescence. This process may be triggered by the shortening of telomeres, and the consequent activation of DNA damage signals (M1), or telomere attrition (M2). In the absence of the two small molecule kinase inhibitors, human intestinal organoids underwent growth arrest after 10-20 population doublings. By contrast, the replicative capacity in the optimized culture condition was extended at least up to 100 population doublings upon addition of the inhibitors, which exceeded the Hayflick limit (Hayflick L. The *Journal of Investigative Dermatology* 1979; 73:8-14). This result clearly indicates that the senescent phenotype seen in the first culture system reflects inadequate growth conditions, rather than inherent replicative aging.

The culture techniques can be used to study basic aspects of stem cell biology and the control of differentiation, exemplified by depletion of stem cells and goblet cell differentiation upon Notch inhibitor treatment. Moreover, the organoid culture platform may be used for pharmacological, toxicological or microbiological studies on pathologies of the intestinal tract, as the organoids represent more closely the intestinal epithelium than often-used colon cancer cell lines such as CaCo2 or DLD1. Lastly, since small biopsies taken from adult donors can be expanded without any apparent limit or genetic harm, the technology may serve to generate transplantable epithelium for regenerative purposes.

Example 12: Culturing Mouse Pancreatic Organoids

The use of a TGF-beta inhibitor was also tested in a culture medium for mouse pancreatic organoids. The expansion medium that was used was DMEM/F12 media (supplemented with P/S, Glutamax, 10 mM Hepes, B27, N2 and N-Acetylcysteine), EGF (50 ng/ml), R-spondin (10%), Noggin (100 ng/ml), FGF10 (100 ng/ml), A8301 (TGF-beta inhibitor, 500 nM) and Gastrin (10 µM). This differs slightly from that of the HISC culture used in Example 16 in that there is no Wnt agonist (other than Rspondin) or Nicotinamide and FGF10 is added. However, these culture media share a number of key components (ENR+gastrin+TGF-beta inhibitor), the addition of the TGF-beta inhibitor being advantageous in both cases. Pancreas organoids grown in these conditions could be expanded for >3 months and passaged at least 5 times.

Figure 50A:
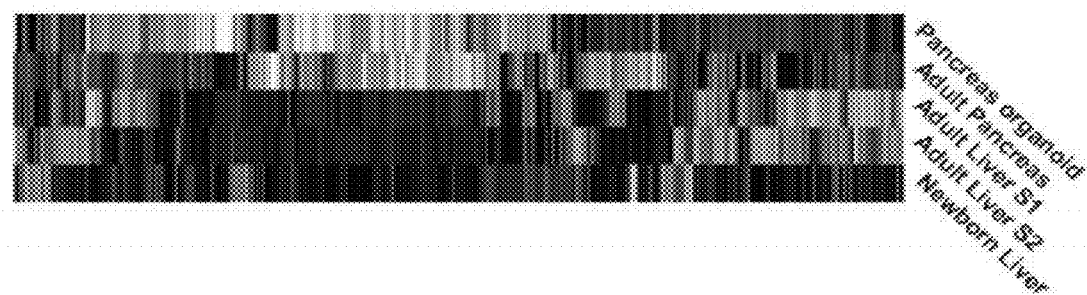
FIG. 50. Microarray comparison of mouse pancreatic organoids. A—Microarray clustering analysis, comparing RNA from the pancreas organoids (cultured in the conditions described in Example 2) with adult pancreas, adult liver and newborn liver. From left to right: i) pancreas organoid; ii) adult pancreas; iii) adult liver (sample 1 [S1] and sample 2 [2]); iv) adult liver S2; and v) newborn liver. B—Raw signal data from the microarray analysis, comparing the expression levels of selected ductal markers, transcription factors necessary for Ngn3 expression and endocrine markers in adult liver, adult pancreas, pancreas organoids and liver organoids in expansion media.

Microarray experiments were carried out for the pancreas organoids grown in the above-described expansion medium and the results were compared to the adult pancreas, adult liver and newborn liver (see FIG. 50A). The pancreas organoid clearly clusters with the adult pancreas, rather than with the liver samples, demonstrating a good phenotypic similarity with the adult pancreas.

Figure 50B:
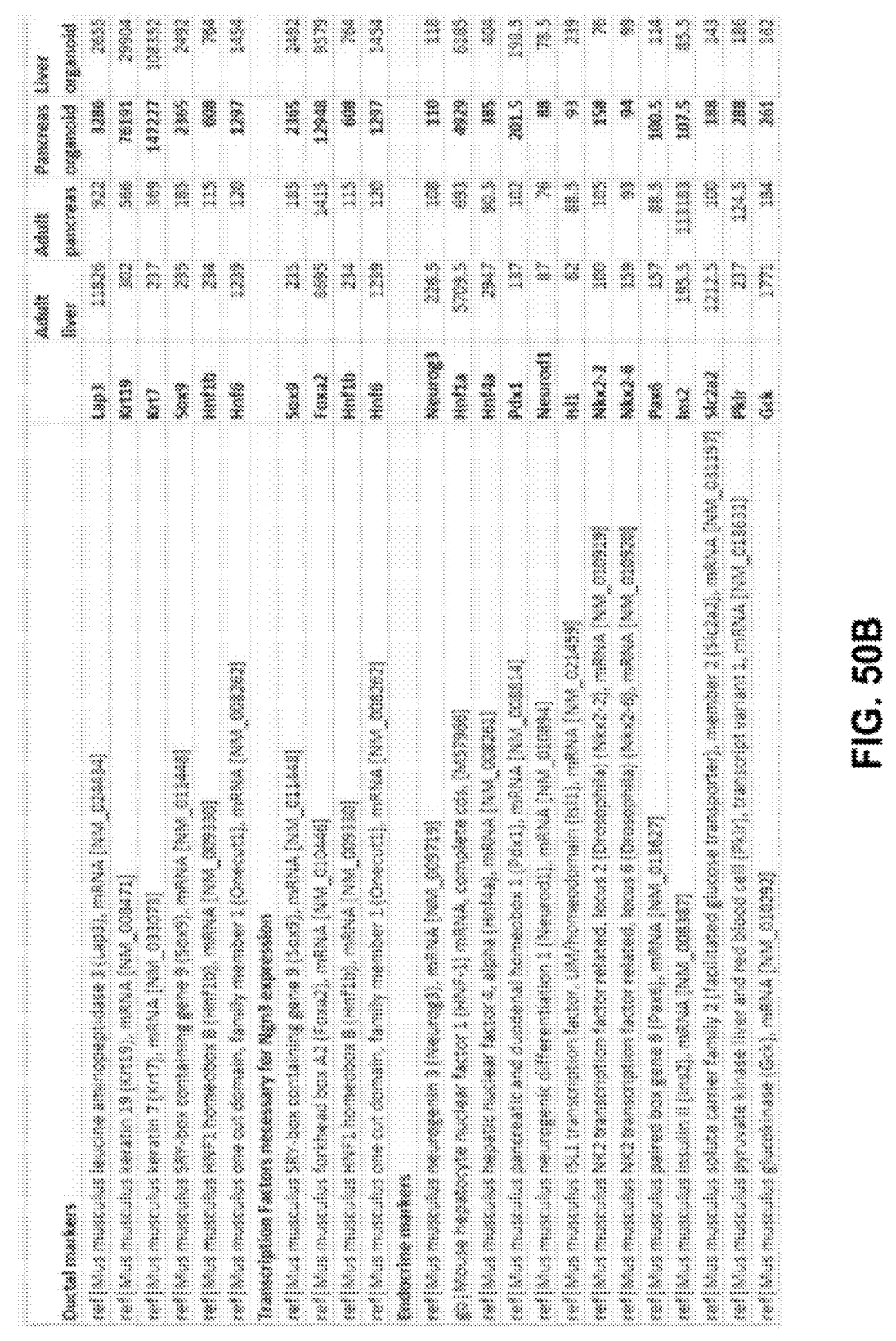

FIG. 50B shows the raw signal from the microarray experiment comparing expression levels in pancreas organoids, adult pancreas, adult liver and liver organoids for ductal markers, endocrine markers and transcription factors necessary for Ngn3 expression (Ngn3 is a transcription factor that is associated with the specification of endocrine lineages). The high levels of expression of Krt19, Krt7 and other ductal markers in the pancreas organoids, show that the pancreas organoids clearly have a ductal phenotype. These pancreatic organoids were originally grown from ductal preparations. The essential transcription factors for Ngn3 expression (Foxa2, Hnf6, Hnf1b, Sox9) were all also expressed in the pancreas organoids, although expression of Ngn3 itself was not detected under expansion conditions.

The expression levels of genes important for the generation of insulin-producing cells are low. However, it is clear that in the expansion medium, proliferation and expression patterns of the pancreatic organoids closely resemble those seen in early progenitor endocrine cells.

The pancreas is mainly formed by three different cell types: acinar cells, ductal cells and endocrine cells. In a total RNA sample of adult pancreas, 90% of the RNA comes from acinar cells, so the expression levels of endocrine markers are very diluted in a total pancreas sample. Therefore, further experiments are planned for each specific cell type. For example, the inventors plan to carry out a microarray comparison between pancreas organoids, enriched acinar cell preparation, enriched ductal cell preparation and enriched endocrine cell preparation, to have a better estimation of the mRNA levels of the important genes in our pancreas organoids compared with the levels present in insulin producing cells. For example, in an enriched endocrine cell sample, 75-85% of the cells present would be insulin-secreting cells).

Example 13: The Effect of Noggin on the Expansion Medium

Figure 51A:
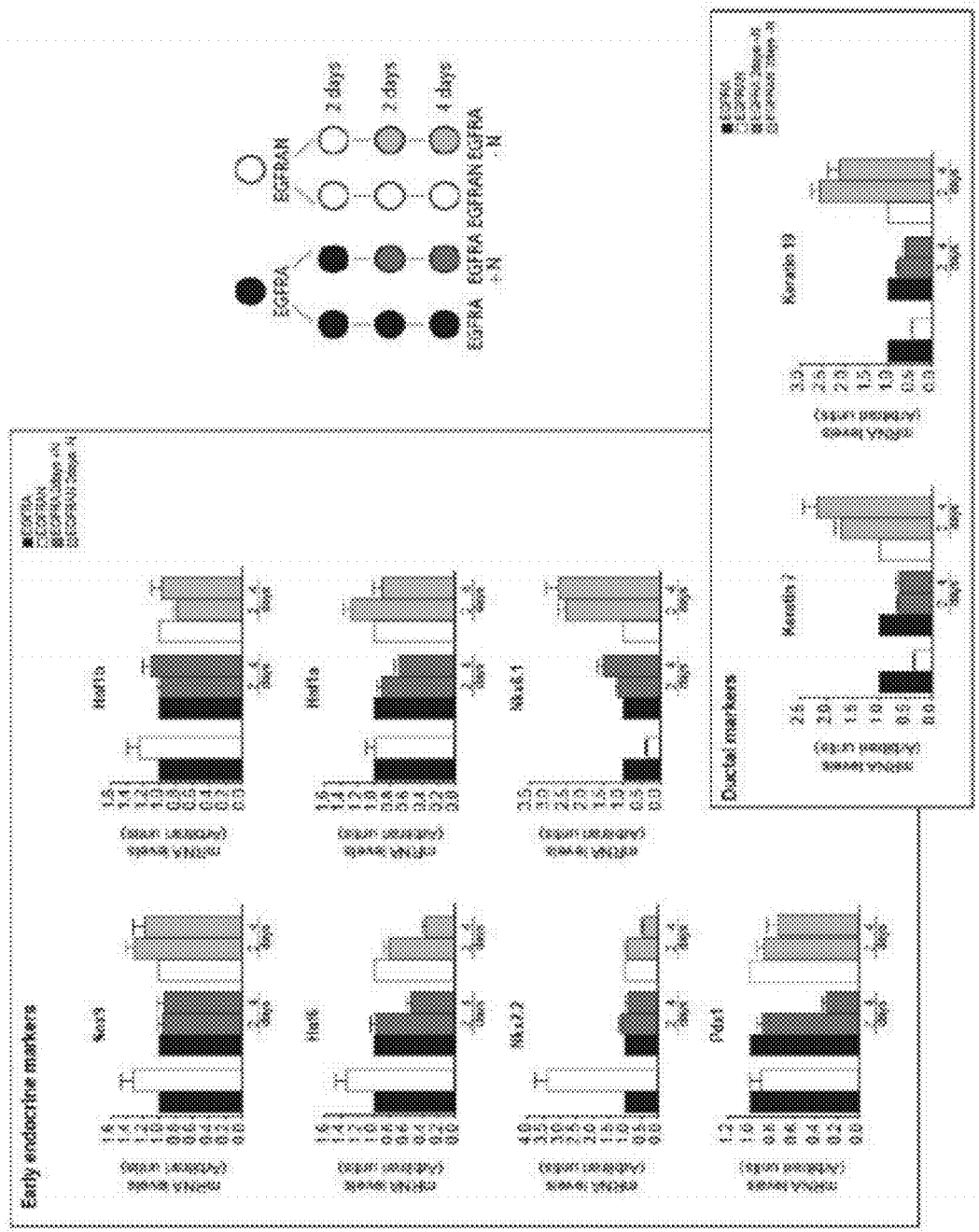
FIG. 51. The effect of Noggin on the expansion of pancreatic organoids A—Bar charts showing gene expression analysis of pancreatic organoids cultured in EGFRA so, that have never been cultured with Noggin (black) with organoids cultured in EGFRAN, so have always been cultured with Noggin (white). The effect of culturing the pancreatic organoids in EGFRA for 2 days and then withdrawing Noggin and culturing for a further 2 or 4 days (light grey) and the effect of culturing the pancreatic organoids in EGFRA for 2 days and then adding Noggin and culturing for a further 2 or 4 days (dark grey) on gene expression is also shown. mRNA levels (arbitrary units) are presented on the Y axis. mRNA of the following early endocrine markers is analyzed in the main figure: Sox9, Hnf1b, Hnf6, Hnf1a, NRx2.2, NRx6.1 and Pdx1. mRNA of the following ductal markers is analyzed in the inset part: keratin 7 (Krt7) and keratin 19 (Krt19). B—Bar chart showing the effect of Noggin on the expression of Lgr5 in pancreatic organoids in the expansion culture medium. Data are provided for pancreatic organoids cultured in EGFRA that have never been cultured with Noggin (black) with organoids cultured in EGFRAN and so have always been cultured with Noggin (white). The effect of culturing the pancreatic organoids in EGFRAN and then withdrawing Noggin and culturing for a further 6 days (light grey) and the effect of culturing the pancreatic organoids in EGFRA and then adding Noggin and culturing for a further 6 days (dark grey) on Lgr5 gene expression is also shown. mRNA levels (arbitrary units) are presented on the Y axis.

To investigate the role of the BMP inhibitor, Noggin, in the expansion medium, the inventors compared mRNA levels of early endocrine markers and ductal markers in pancreatic organoids that have always been cultured in EGFRA medium so have never been cultured in the presence of Noggin with the level of expression of the same markers in organoids that have always been cultured in EGFRAN medium (i.e., always in the presence of Noggin). The inventors also compared mRNA levels of these markers in pancreatic organoids from which Noggin was added or removed from the cultures respectively. Specifically, one sample of pancreatic organoids was cultured in EGFRA medium and then Noggin was added and the organoids were cultured for a further 2 or 4 days. Another sample of pancreatic organoids was cultured in EGFRAN medium and then Noggin was removed and the organoids were cultured for a further 2 or 4 days. The gene expression was compared and the results are shown in FIG. 51A. It was found that Noggin reduces the expression of keratin 7 and keratin 19 (ductal markers) showing that Noggin blocks the differentiation towards the ductal phenotype (the keratin levels in white and dark grey samples are lower than in the black samples). Expression levels of some transcription factors essential for the generation of insulin producing cells (i.e., Sox9, Hnf6, Hnf1a, Pdx1, NRx2.2, NRx6.1 and Hnf1b) were unaffected by Noggin. Although Noggin prevents the cultures from acquiring a full ductal phenotype, which will likely prevent future differentiation to insulin producing cells, the inventors include Noggin in the expansion medium because it allows the cells to expand whilst maintaining some ductal features in combination with features of insulin-producing precursor cells.

Figure 51B:
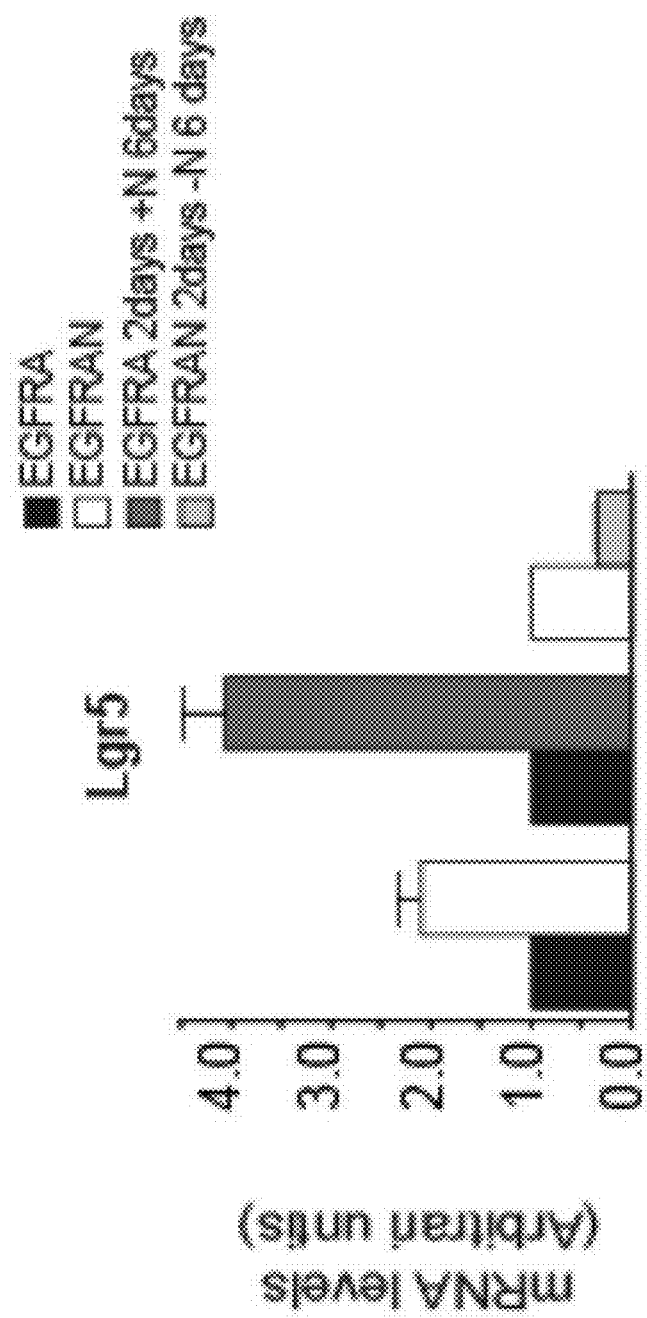

The effect of the presence or absence of Noggin, or its addition or withdrawal to EGFRA medium on Lgr5 gene expression was assessed using pancreatic organoids obtained from pancreatic ducts. The results in FIG. 51B show that pancreas organoids cultured with Noggin express 2 fold more Lgr5 than pancreas organoids cultured without Noggin (compare white bar second from left with black bar on left). Addition (dark grey) or withdrawal (light grey) of Noggin was also shown to affect Lgr5 levels. It is unclear whether the increase in Lgr5 gene expression in the presence of Noggin is due to an increased number of Lgr5+ cells or due to an increased level of Lgr5 expression per cell. However, the present inventors show here that BMP inhibitors, such as Noggin, promote expression of Lgr5 and, therefore, result in more proliferative organoids. Thus, BMP inhibitors are shown to be an advantageous component of the expansion media.

This is surprising, because in the literature it is described that BMP activity is useful for culture of pancreatic cells. This conclusion is based on the observations that BMP signaling is required for the differentiation into both the ductal (see keratin7 and 19 expression) and endocrine cells. Thus, the skilled person would expect the inclusion of a BMP inhibitor, such as Noggin, to be disadvantageous. However, the inventors surprisingly found that the use of a BMP inhibitor was advantageous because it resulted in more proliferative organoids and higher expression of Lgr5.

Figure 52A:
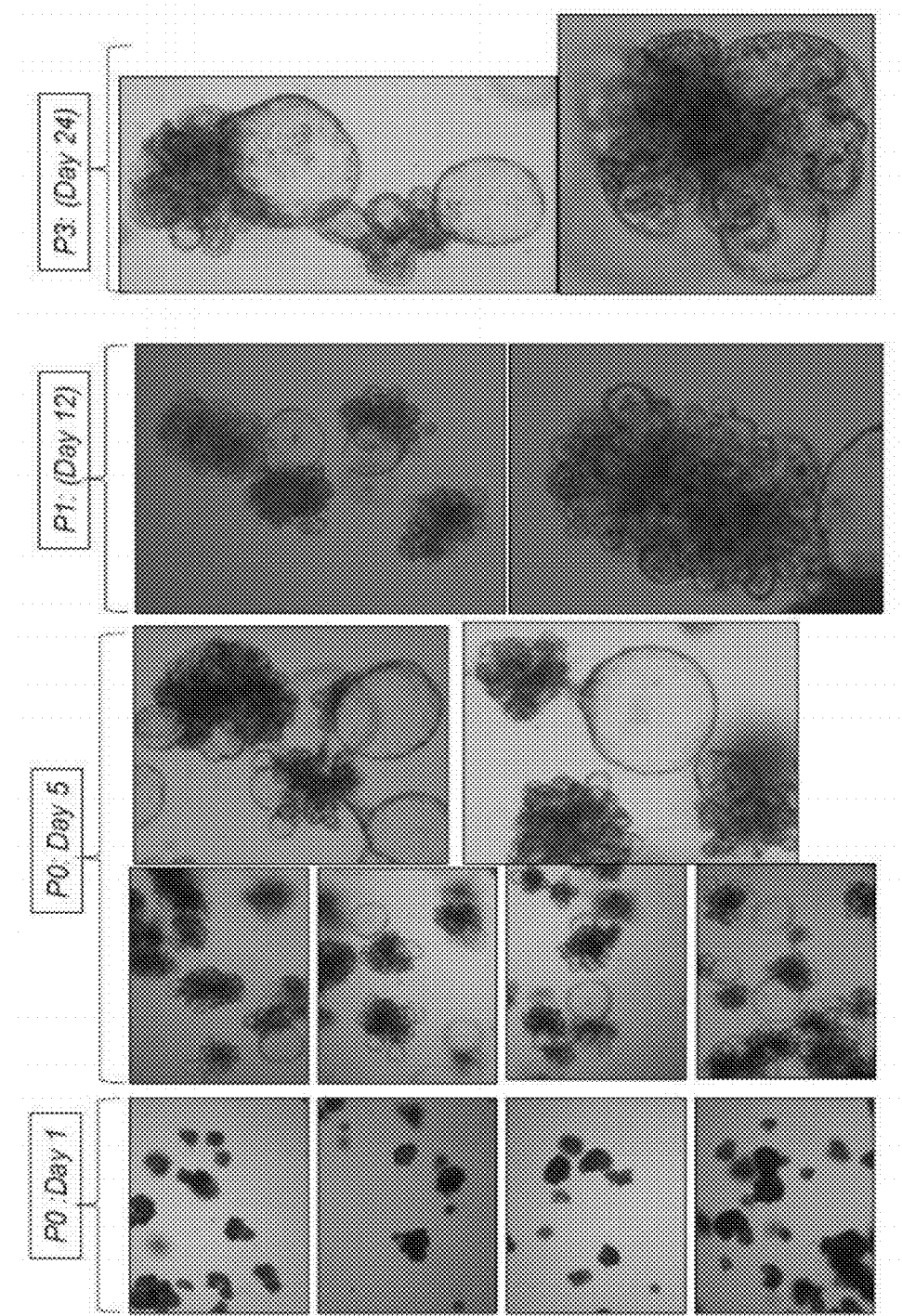
FIG. 52. Human insulin producing cells develop from ex vivo expanded, in vivo transplanted progenitor cells A—Growth of human pancreas tissue from progenitor cells (pancreas stem cells) at P0: (Day 1); P0: (Day 5); P1: (Day 12) and P3: (Day 24), where "P" refers to the number of passages.
FIGS. 52B and C show transplantation of human pancreatic organoids under the murine peri-renal capsule. B—3 hours after transplantation of the pancreatic organoid cells into the recipient mice: DAPI (nuclear marker) staining in the upper picture indicates all cells; K19 (ductal marker) staining in the lower picture shows all transplanted cells and insulin (beta cell marker) in the lower picture indicates insulin-producing cells. C—1 month after transplantation of the pancreatic organoid cells into the recipient mice: DAPI (nuclear marker) staining in the upper picture (in blue) indicates all cells; CK19 (ductal marker) expression in the middle picture (in green) indicates all transplanted cells and insulin (beta cell marker) in the lower picture (in red) indicates insulin-producing cells. A selection of the insulin-producing cells are encircled but all clearly stained cells are thought to be insulin positive.

Example 14: Transplantation of Human Pancreatic Organoids Under the Kidney Capsule in Mice Pancreatic organoids, that had been expanded using the protocol described in example 11 (see FIG. 52A), were transplanted under the renal capsule of immunodeficient mice.

Just before transplantation, organoids were treated with cell recovery solution (BD#354253, BD Biosciences) to get rid of matrigel residues. Organoids were washed several times with PBS and pelleted.

Transplantation of these organoids under the renal capsule of immunodeficient recipients was carried out using an NIH recommended procedure for islet transplantation under the kidney capsule ("Purified Human Pancreatic Islets, In Vivo Islets Function," Document No. 3104, A04, Effective Date 7 Jul. 2008, DAIT, NIAID, NIH). A week before the transplantation, hyperglycemia was chemically induced in the recipient mice (NOD/SCID/IL2RgammaKO a.k.a. NSG) with a high dose 130 mg/kg streptozotocin injection. Blood glucose levels were monitored and mice having a blood glucose above 18 mmol/l were considered hyperglycaemic.

For transplantation, the hyperglycemic recipient was anesthetized and a small incision was made in the left flank to expose the left kidney. Approximately 2.5-3.0 mm$^3$ of organoids were collected in a siliconized PESO transplantation tube and transplanted under the kidney capsule using a Hamilton syringe. After cauterizing the damaged capsule the kidney was placed back into the abdominal cavity. The peritoneum and the skin were then closed with 5-0 silk sutures.

Figure 52B:
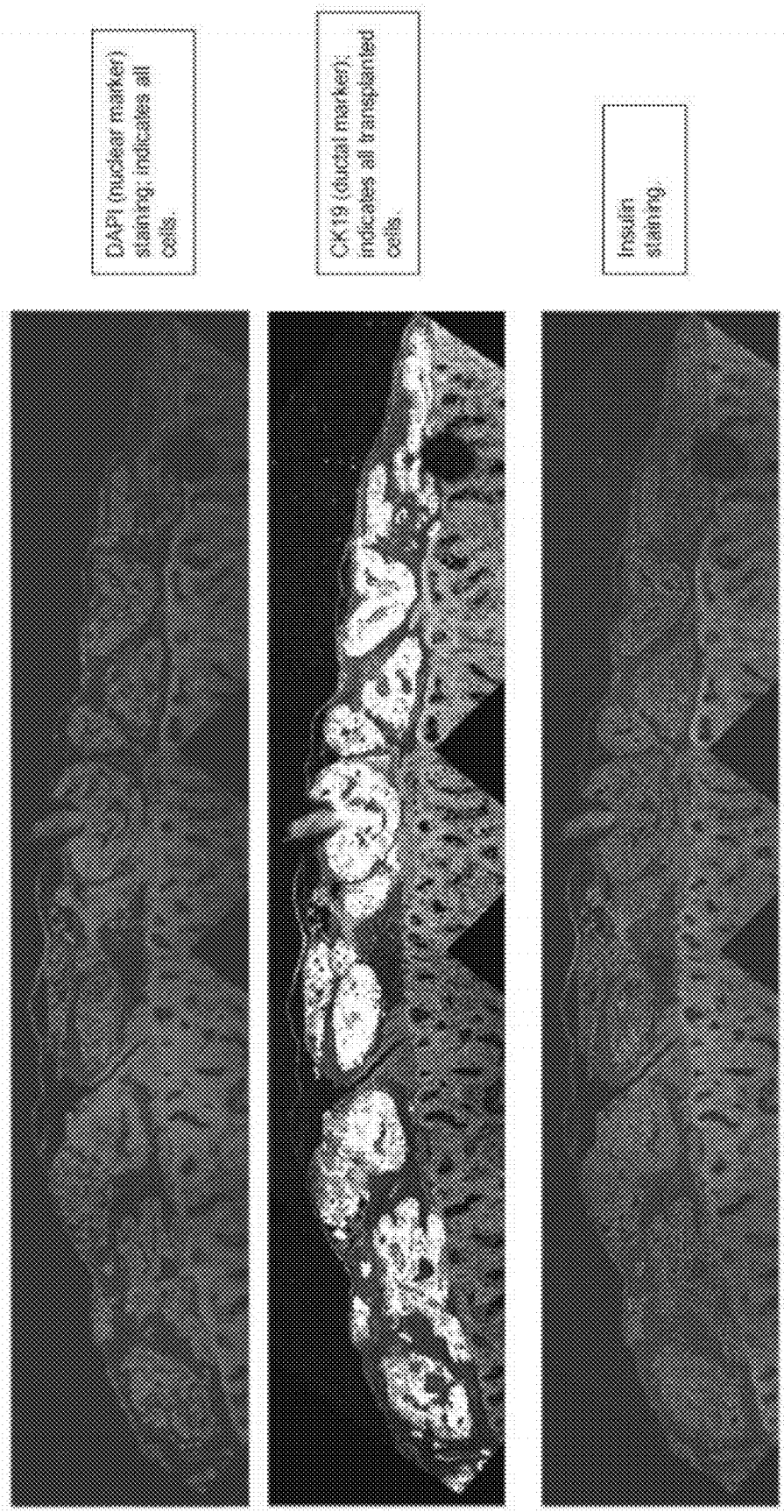

One mouse was sacrificed three hours post-transplantation and the graft was analyzed for mature beta cell and progenitor markers. In this mouse, no insulin-producing cells could be seen in the murine peri-renal capsule (FIG. 52B).

A further mouse was allowed to recover in the cage with a heat pad, under close supervision. Bodyweights and blood glucose levels of the transplanted mouse were monitored for 1 month. After one month the mouse was sacrificed and the graft was analyzed for mature beta cell and progenitor markers.

Figure 52C:
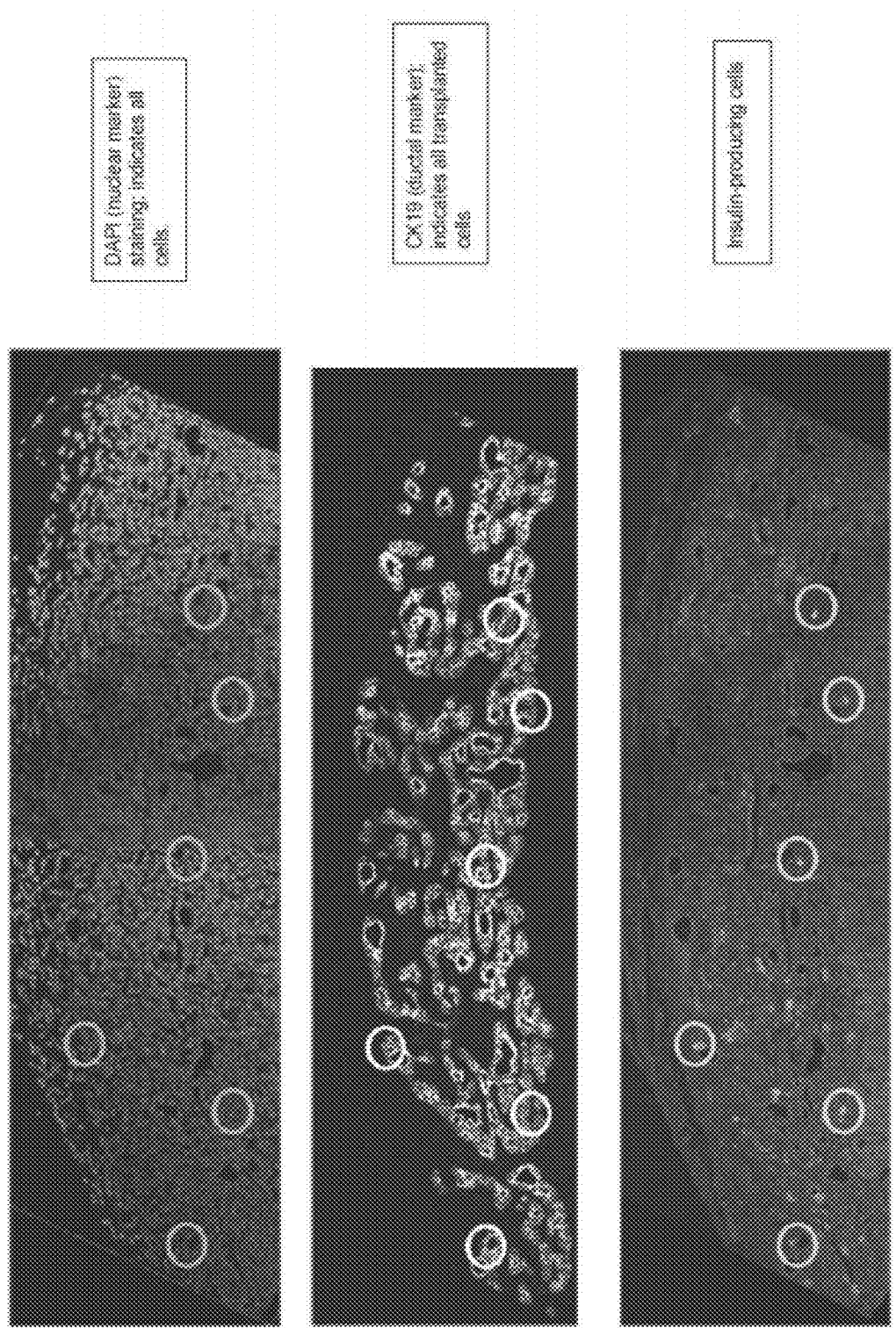

1 month after transplantation, a number of insulin-producing cells could be identified. These insulin-producing cells are all the stained cells in FIG. 52C, a selection of which are circled for enhanced clarity. In particular, insulin-positive cells appeared from the ductal lining, whereas no insulin-positive cells were seen in initial preparations.

The finding that the insulin producing cells are present 1 month after transplantation but are not present 3 hours after transplantation demonstrates that the insulin producing cells largely or only arise after transplantation.

These results show that cells taken from pancreatic organoids of the present invention, cultured with the media and methods of the present invention, can be transplanted into mice and can promote the growth of insulin-producing cells in the pancreas. Excitingly, human pancreatic organoids could be transplanted. This opens a number of exciting possibilities for using transplanted organoid cells to promote insulin production, e.g., for treatment of diabetes.

Example 15: An Expansion Medium for Liver Organoid Growth and Expansion

Figure 54A:
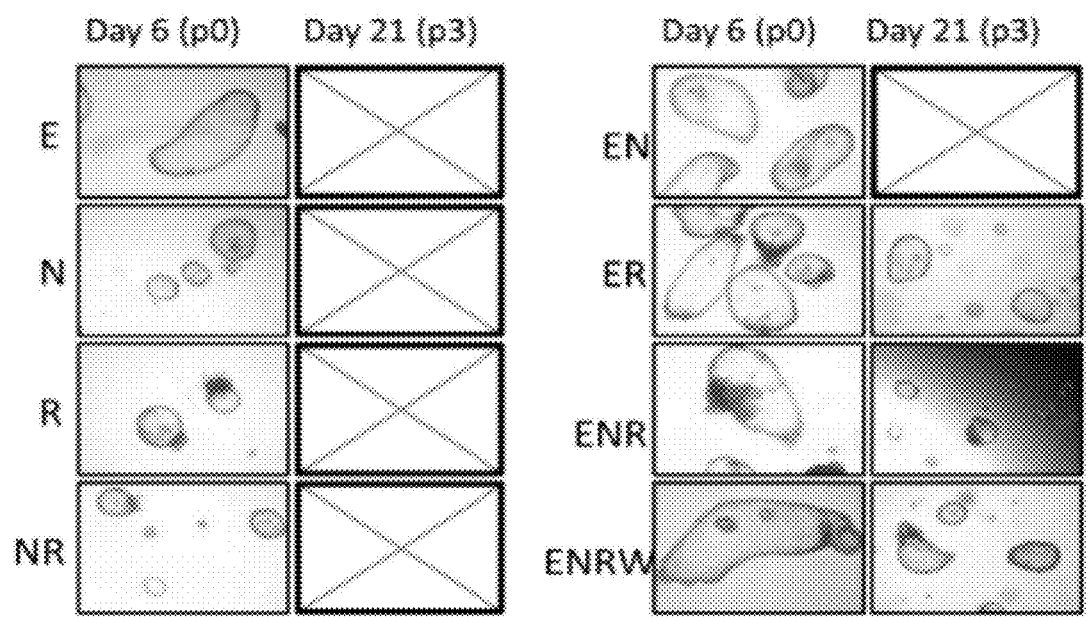
FIG. 54. Liver organoids growth factor requirement. (A) DIC images of liver organoids maintained with EGF (E), R-spondin 1 (R), Noggin (N), Wnt3A conditioned media (W) or the combination of them, supplemented with FGF10, HGF and Nicotinamide. (B) The number of organoids was counted weekly and passaged when required. Results are shown as mean±SEM of 3 independent experiments. (C) gene expression analysis by RTPCR of Lgr5, Keratin 7 (K7) and Albumin (Alb) genes. (D) Isolated bibliary ducts growing into organoids. Differential interference contrast images from the corresponding days after seeding. Magnification 10× (days 0, 1, 3 and 5). Days 15 on magnification 4×. Cultures were passage every 4-7 days by mechanical dissociation. Cultures have been grown at least for 8 months.
Figure 54B:
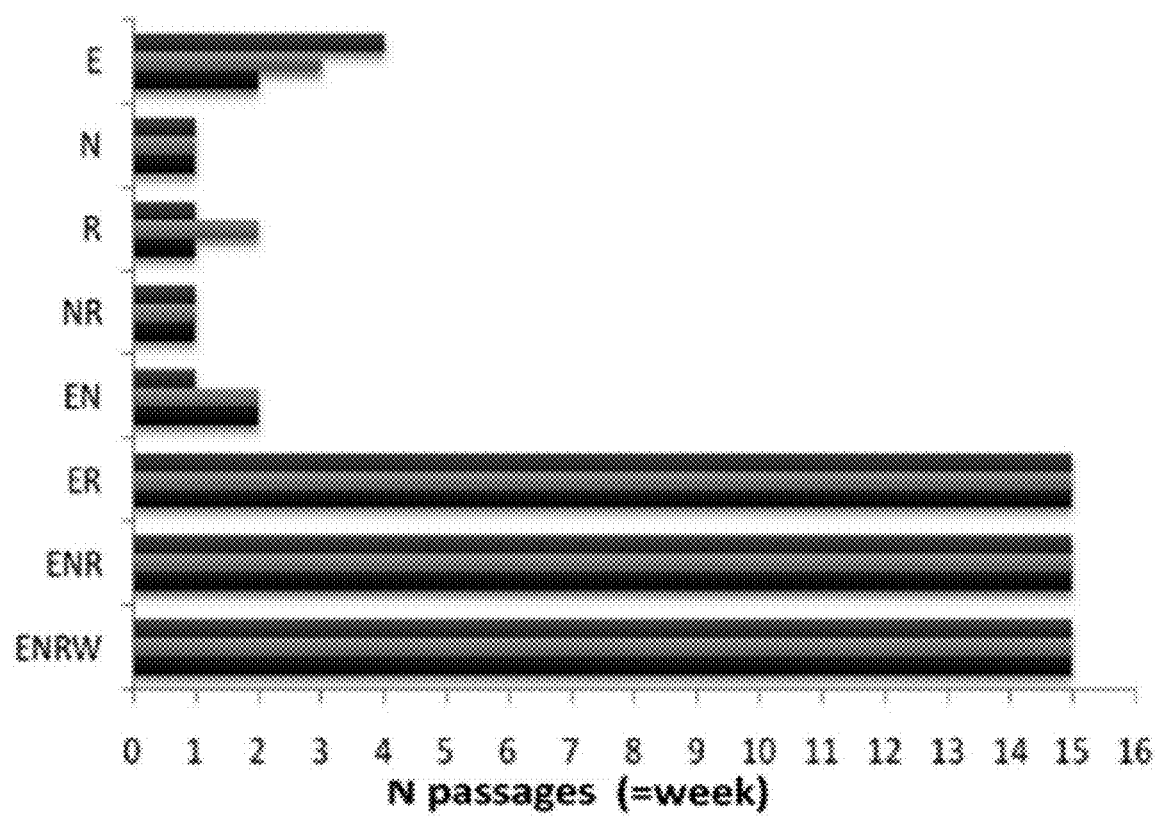
Figure 54C:
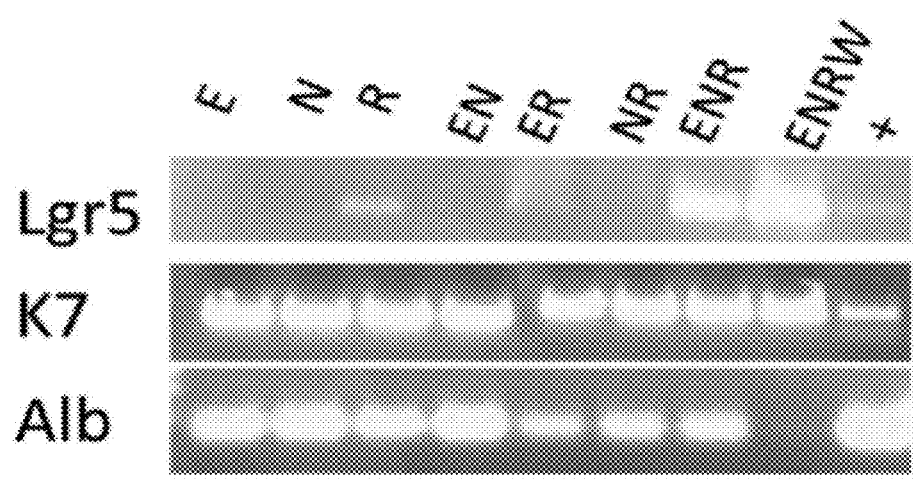
Figure 54D:
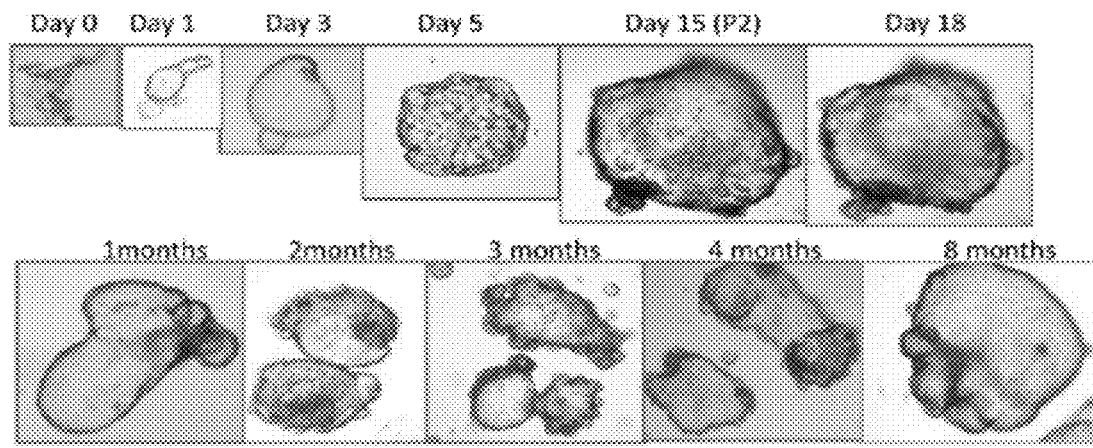
Figure 55A:
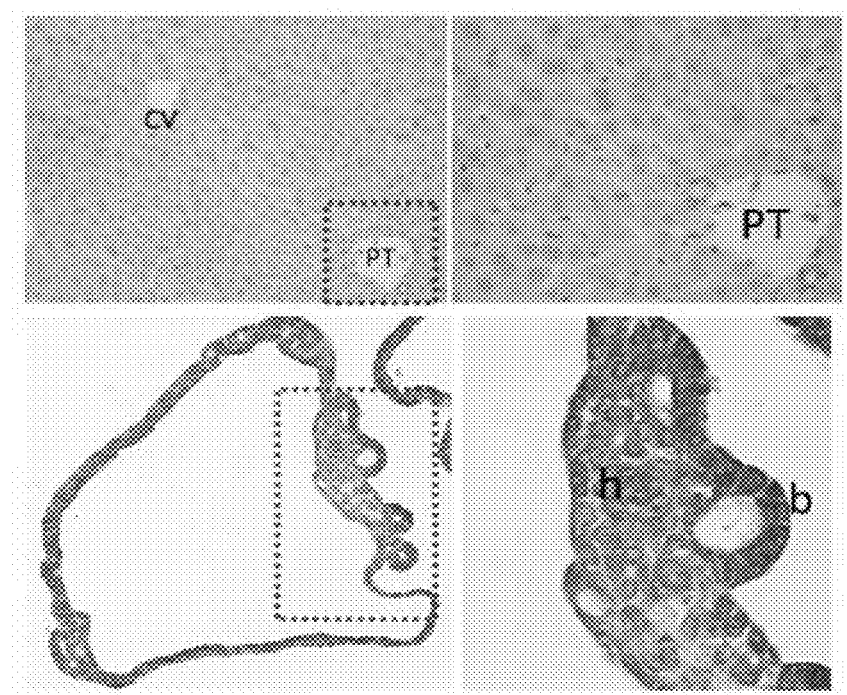
FIG. 55. Morphology of liver organoids. (A) Upper panels: paraffin section of a mouse liver showing the different domains (PT=portal triad, CV=central vein). Lower panels: Paraffin section of a liver organoid showing different domains b (single layered epithelia) and h (stratified epithelia) (B) Right pannel: Ecadherin staining in the liver organoids. Two different domains can be identified. Domain b, formed by a single layered epithelia that resembles the bile duct structures in the liver. This bile duct domain is formed by highly polarized cells that shows positive staining for pancytokeratin (PCK) (lower panel). Left panels show the presence of a second domain within the liver organoids. This h domain is formed by a stratified epithelia with non-polarized cells. The cells are organized around a central lumen and express the hepatocyte marker Alb. Magnification 10×.
Figure 55B:
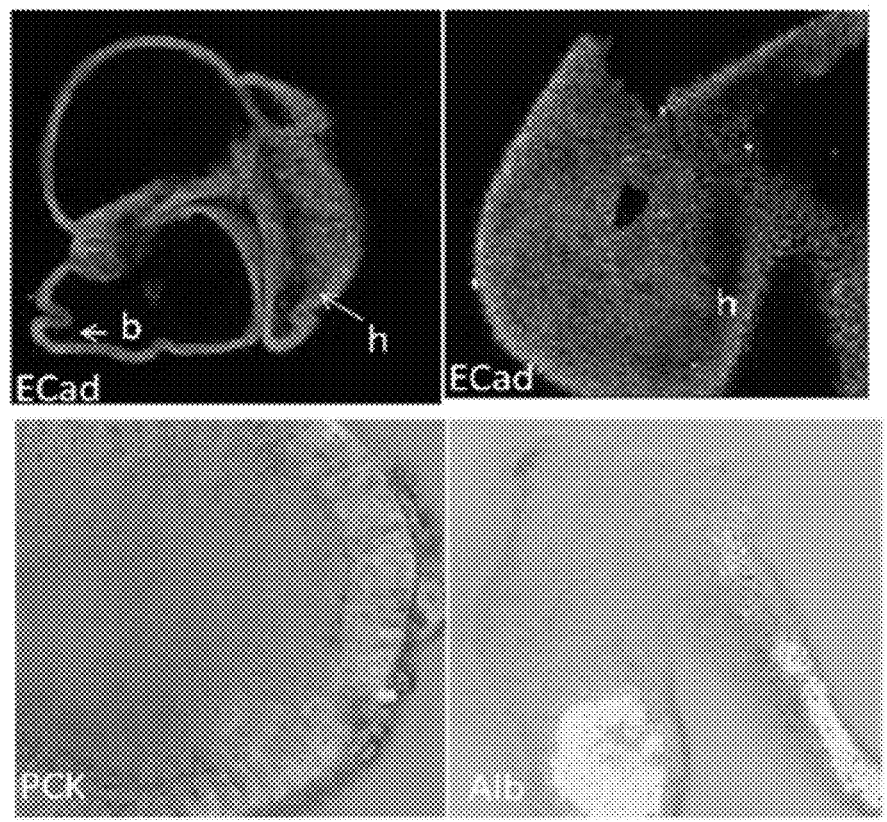

After isolation, biliary ducts (see FIG. 54) were suspended in Matrigel and cultured in different growth factor conditions. The combination of EGF (50 ng/ml) and R-spondin 1 (1 ug/ml) supplemented with FGF10 (100 ng/ml), HGF (25-50 ng/ml) and Nicotinamide (1-10 mM), (ERFHNic) were essential for the long term maintenance of the cultures, indicating that Wnt signaling and EGF signaling are strictly required to maintain adult liver progenitor proliferation in vitro. The addition of Noggin (100 ng/ml) and Wnt conditioned media (50%) also showed long term maintenance of the cultures (see FIGS. 54A and 54B). Under these conditions that supported long-term maintenance, Lgr5 expression as well as hepatocyte markers (Albumin) and cholangiocyte markers (K7) were detected by RT-PCR (see FIG. 54C). Under these conditions liver organoids have been weekly passaged by mechanical or enzymatic dissociation, at 1:8 dilution, and have been grown for many months (FIG. 54D).

Figure 56:
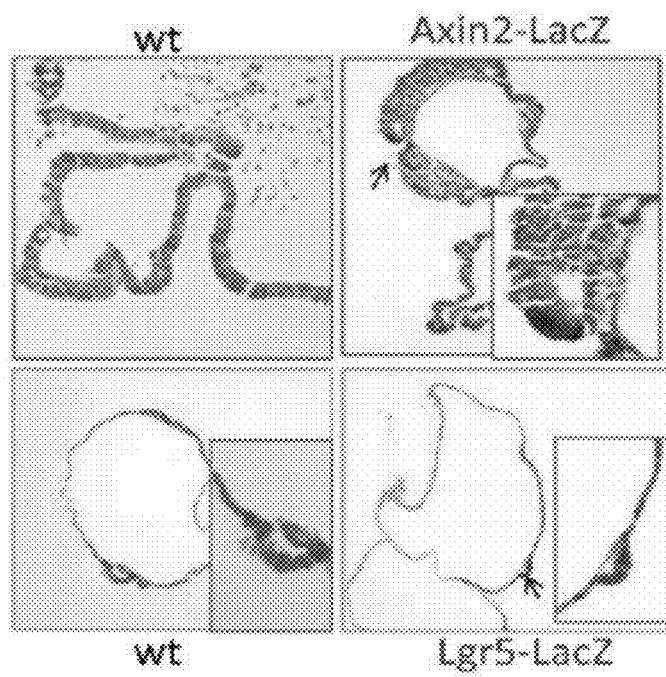
FIG. 56. Wnt signaling in the liver cultures. Lac Z expression was detected in cultures derived from Lgr5-LacZ or Axin2 LacZ mice. No positive staining was detected in liver cultures derived from a B16 mice. Magnification 4×, inset 20×.
Figure 57A:
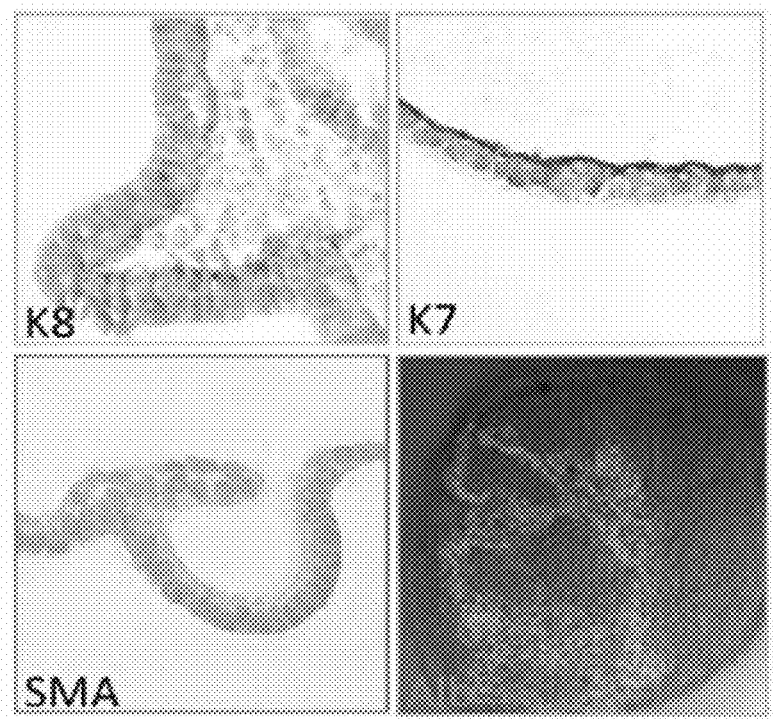
FIG. 57. Expression of liver differentiating markers. (A) immunohistochemical and immunofluorescence analysis of the expression of the cholangiocyte marker keratin 7 (K7) and the hepatocyte markers keratin 8 (K8) and albumin (Alb). (B) analysis of the gene expression of hepatocyte markers: Albumin (Alb), transthyretrin (Ttr), Glutamine synthetase (Glu1), glucose 6 phosphatase (G6P) and Cytocrome p450 isoform 3A11 (CYP3A11); and cholangiocyte markers keratin 7 (K7) and Keratin 19 (K19).
Figure 57B:
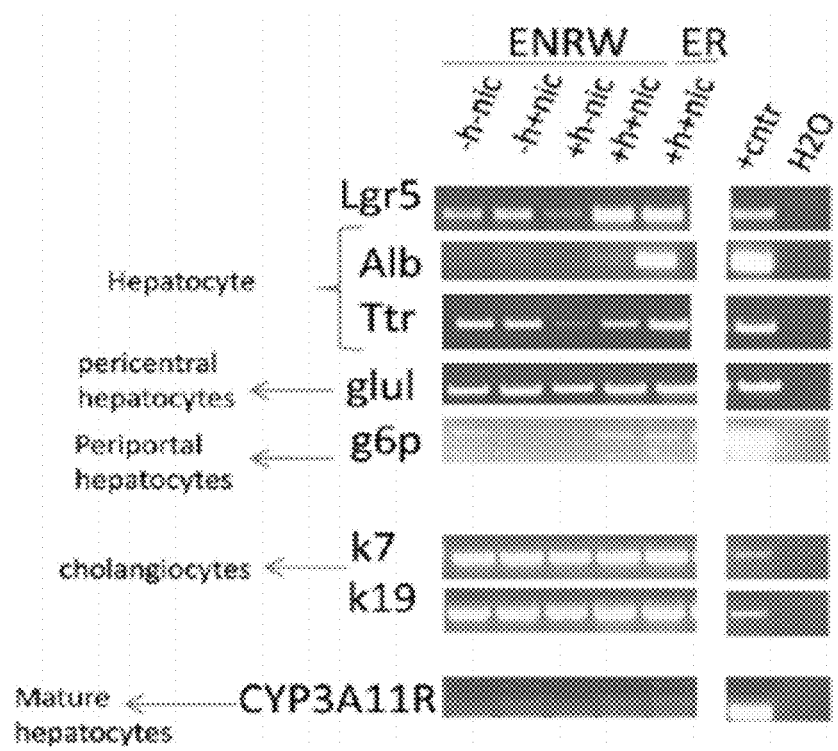

We analyzed the expression of the Wnt target genes Axin2 and Lgr5 in the cultures. Cultures of both Axin2LacZ and Lgr5-LacZ livers revealed the presence of Axin2- and Lgr5-positive cells in the liver organoids 1 month after seeding, thus confirming that the Wnt signaling is active and required for culture growth (FIG. 56). The liver cultures also express hepatocyte markers (e.g., albumin, transthyretrin, Glutamine synthetase) and cholangiocyte makers (Keratin 7 and 19) (see FIG. 57).

Figure 58C:
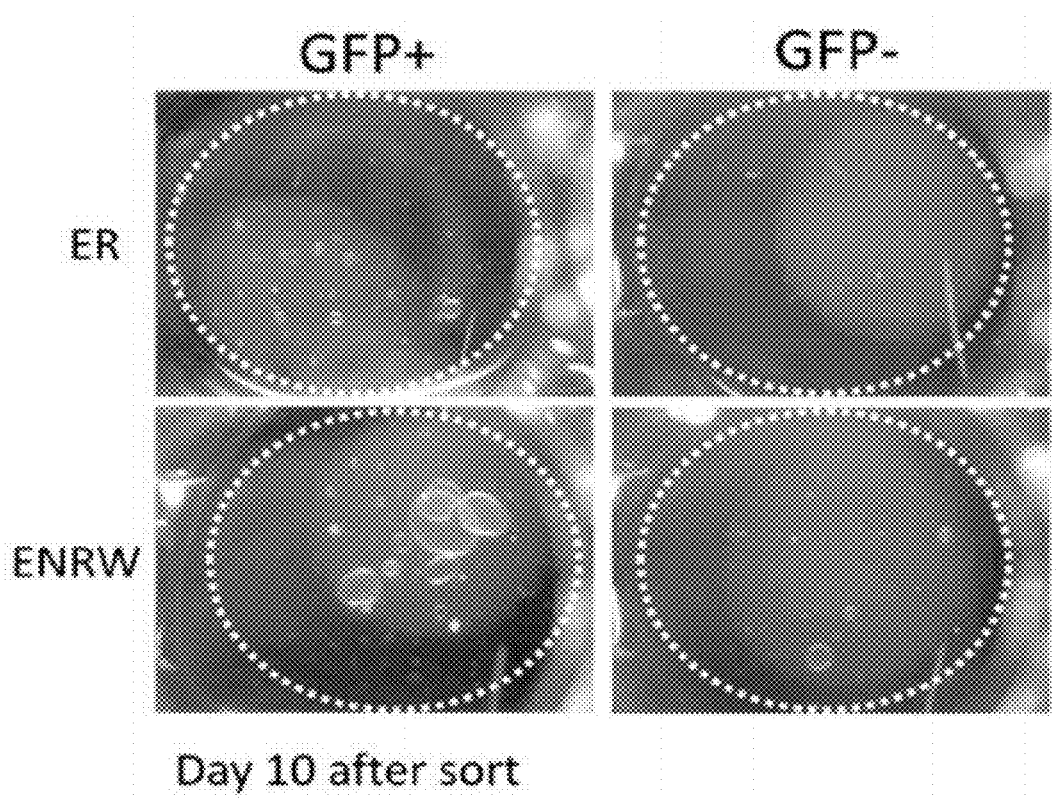
FIG. 58. Liver single cell cultures. (A) flow cytometry plot indicating the area of the sorted cells. (B) single cell growing into organoids at the time points indicated. Magnification 40× (day 1-3), 10× (day 16), 4× (day 21-on). (C & D) representative image of the colony formation efficiency of a Lgr5GFP single sorted cells. 100 cells were seeded in triplicate and colonies were counted 10 days later.
Figure 58D:
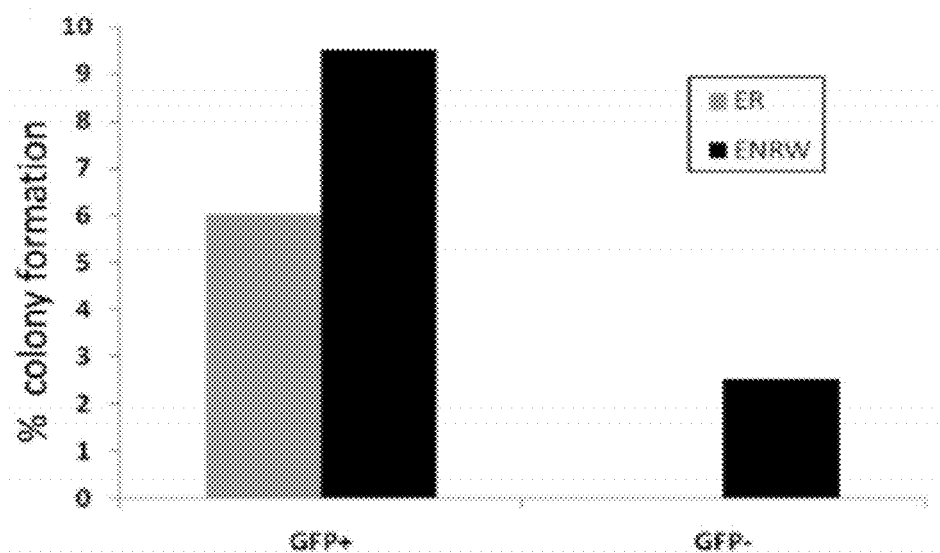

When single Lgr5 cells from a Lgr5LacZ or LgrSGFP mouse were sorted, single colonies grew into organoids. These cultures also express markers of cholangiocyte and hepatocyte lineages and have been maintained and regularly split into 1:6-1:8 for more than 4 months (see FIGS. 58A & 58B). Interestingly, only the cultures derived from Lgr5 positive cells grew into organoids FIGS. 58C & 58D). These data indicate that Lgr5 cells are progenitor cells of these cultures and able to propagate progeny of the 2 different liver lineages.

Figures 59A, 59B:
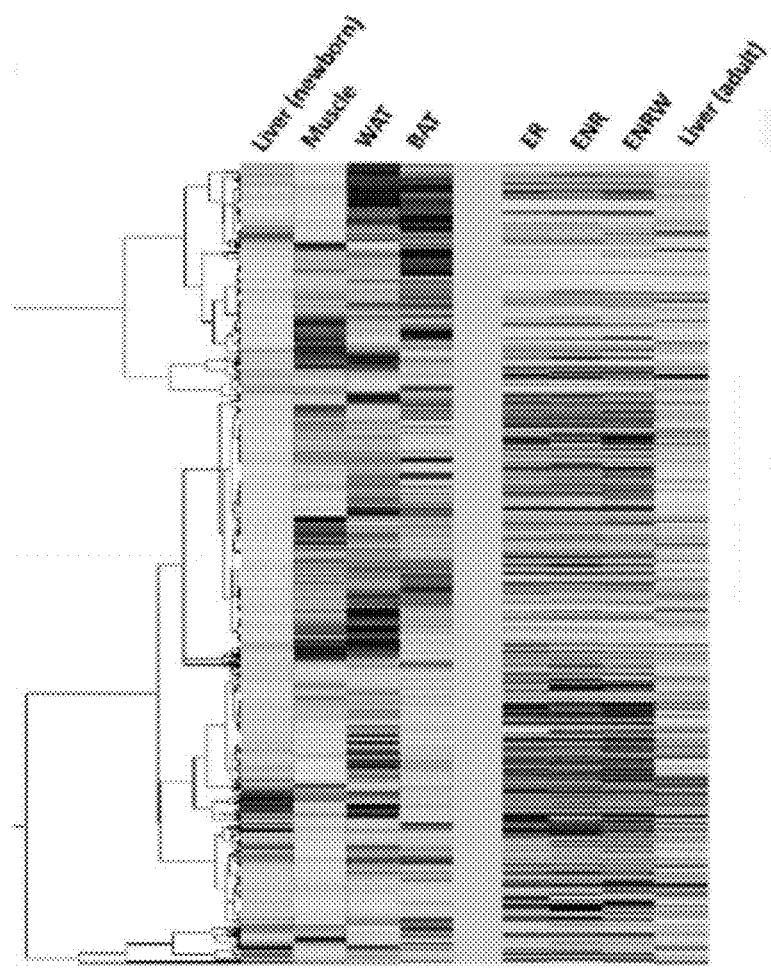
FIG. 59. Microarray analysis of the liver cultures. Analysis of the gene expression profile of adult liver tissue and liver organoid cultures maintained for 1 month in the ER or ER media supplemented with Noggin (ENR) or with noggin and Wnt (ENRW). The genetic profile was compared between the different samples and the genetic profile of Brow adipose tissue (BAT) white adipose tissue (WAT), muscle and new born liver. (A) hit map analysis showing that the cultures present a similar profile to the adult liver but a different profile to non-liver related tissues as muscle and BAT and WAT, (B) List of hepatocyte markers and cholangyocyte markers in the different conditions.

Having established that the liver organoids are derived from Lgr5+ve cells we set out to determine their individual gene signature as compared to the adult liver signature. RNA was isolated from adult liver and from liver organoids grown in ER or ENRW media supplemented with FGF10, Nicotinamide and Hepatocyte Growth Factor. The genetic signature of the adult liver and the 2 liver culture conditions was subsequently derived via comparative gene expression profiling in respect to the expression of a Universal RNA reference. The use of the same reference RNA for the hybridization to all the samples allowed us to compare the 3 independent samples among them (adult liver, ER and ENRW). The heat map analysis revealed that the expression profile of both culture conditions highly resemble the adult liver tissue expression profile, whereas they do not share the same profile when compared to muscle or adipose tissue profile (see FIG. 59). Among the similar gene expression profile between the adult liver and the liver cultures, liver specific genes as HNF1a, HNF1b, HNF4, Alb, Glu1, Met, G6P, Fand1, Fand2a, CYP4B1, K7 and K19 are detected. The heat map analysis reveals that both culture conditions present similar expression pattern among each other and when compared to the adult liver sample. However, when analyzing the data in detail, we can observe that the condition without Wnt and without noggin shows a more differentiated pattern that the condition including both growth factors. This is in agreement with the data shown in FIG. 54C where hepatocyte differentiation (by means of albumin expression) is almost absent in the presence of Wnt. This result would indicate that Wnt is favouring the self-renewal of the culture in detriment of the differentiation.

Also, in both culture conditions as well as in the adult liver, non-specific adult liver genes as AFP, and non-liver transcription factors as Pdx1 or NeuroD can be detected.

It is remarkable that, in both culture conditions but not in the adult liver, the stem cell marker Lgr5 was one of the most highly enriched genes in the liver culture signature. Also, cell markers of progenitor populations in small intestine and stomach as Cd44 and Sox9 (Barker & Huch et al., *Cell stem cell* 2010) were highly expressed in both culture conditions but not in adult liver, indicating again the self-renewal capacity of the liver cultures as well as the quiescent status of the normal adult liver.

Additionally, apart from Lgr5, multiple Wnt target genes were also highly upregulated in the liver cultures compared to the adult liver including MMP7, Sp5 and Tnfrs19, among others, providing strong evidence of the requirement of an active and robust canonical Wnt signaling activity to maintain the self renewing capacity of the cultures.

Example 16: An Improved Differentiation Medium

Under ER or ENRW conditions the liver cultures self-renew, and can be maintained and expanded in a weekly basis, for up to 1 year (FIG. 60A). The karyotypic analysis after 1 year shows no evidence of chromosomal aberrations. More than 66% of the cells analyzed presented normal chromosomal counts and 13% of them also showed polyploidy, a characteristic trait of hepatocytes (FIG. 60B).

Figure 61A:
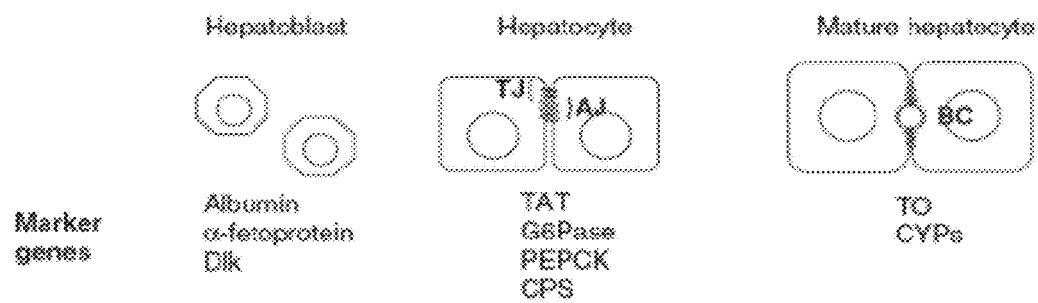
FIG. 61. Supplemental factors FGF10, HGF and Nicotinamide; effect on growth and differentiation. A—Diagram depicting the genes differentially expressed during the 3 stages of liver development, from hepatoblast to mature hepatocyte. B—Scheme showing the protocol used. Cultures were seeded in expansion medium EM2 (ERFHNic: EGF (E) and R-spondin 1 (R), supplemented with FGF10, HGF and Nicotinamide; ERFHNic is indicated as 'ER' in FIG. 8B) 2 days prior the experiment. Two days later, culture media was changed to either EGF (E) alone or EGF supplemented with R-spondin 1 (ER) with or without additional supplements chosen from FGF10 (F) or HGF (H) or Nicotinamide (Nic) or a combination of these at the concentrations stated in the text. Five days later cultures were split and replated at 1:4 ratio for each condition. Under these conditions, cultures have been split and replated every 7 days for a total period of 10 weeks. C—First day after first split in each of the culture conditions tested. Results shows that EGF and R-spondin 1 combined with FGF10 or HGF or Nicotinamide or a combination of these are essential to achieve at least 1 passage. D—After long-term culture, the combination of ER supplemented with FNic or ER supplemented with FHNic, both result in high passage numbers. After passage 10, the growth rate is better for the culture condition including the 3 supplemental factors; ERFHNic (FIG. 68 A, B). E—RT-PCR analysis showing the expression of different hepatocyte markers (CYP3A11, Alb, FAH) and cholangiocyte marker (K19) and stem cell marker IGR5 5 days after the withdrawal of certain factors (starting point was ERFHNic). Note that only the condition EF showed expression of all hepatocyte markers tested. HPRT was used as a housekeeping gene to normalize for gene expression.

The combination of EGF (50 ng/ml) and R-spondin 1 (1 ug/ml) supplemented with FGF10 (100 ng/ml), HGF (25-50 ng/ml) and Nicotinamide (1-10 mM), were preferable for the long term maintenance of the cultures. Under these conditions, we obtained long-lived cell cultures that express biliary duct and some hepatoblast or immature-hepatocyte markers (Glu1, Albumine). However, the number of cells positive for these hepatocyte markers was very low. Under these culture conditions, no mature hepatocyte markers (e.g., p450 Cytochromes) were detected. These results suggest that the culture conditions described here facilitate the expansion of liver progenitors able to generate hepatocyte-like cells, albeit at lower numbers, but not fully mature hepatocytes (FIG. 61A).

Figure 61B:
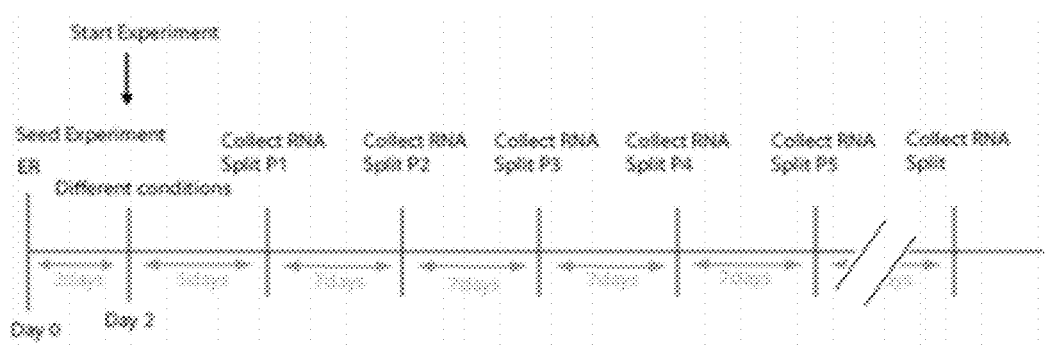

To enhance the hepatocytic nature of the cultures and obtain mature hepatocytes in vitro, we first determined whether the three supplemental factors (FGF10, HGF and Nicotinamide) added to EGF and R-spondin 1 were exerting either a positive or negative effect on the hepatocyte expression, as well as on the self-renewal of the culture. We generated liver organoid cultures and cultured them either with EGF or EGF and R-spondin 1 plus FGF10 or HGF or Nicotinamide or the combination of these, and we split the cultures once a week for a total period of 10 weeks. At each time-point we also analyzed the expression of several mature hepatocyte markers (FAH, CYP3A11) and hepatoblast markers (albumin) (FIG. 61B).

Figure 61C:
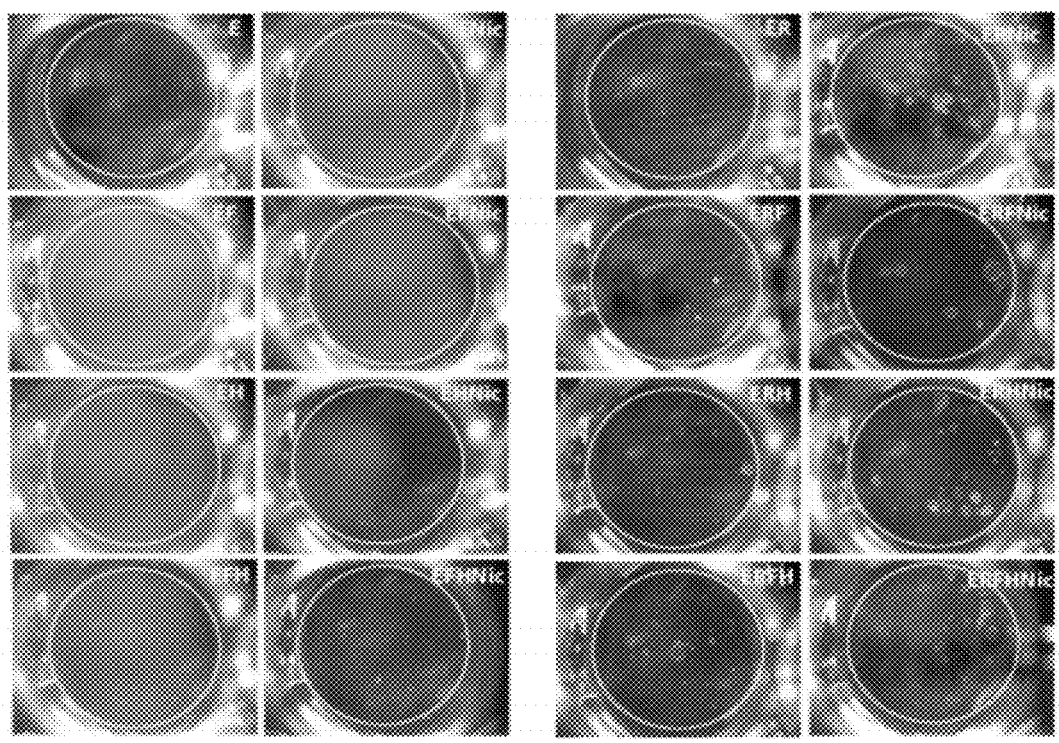
Figure 61D:
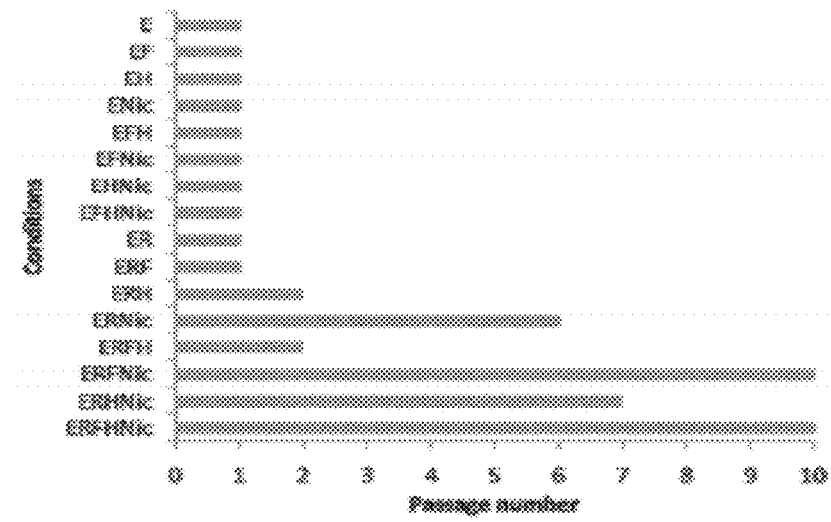
Figure 61E:
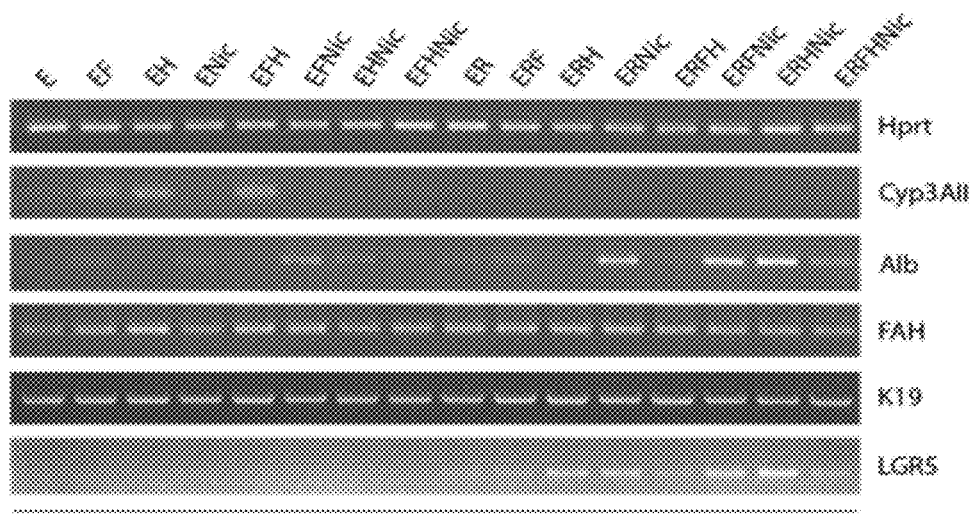

In agreement with the data in FIG. 54 (see Example 15), we observed that R-spondin1 and Nicotinamide combined with FGF10 are essential for the growth and self-renewal of the liver cultures (FIGS. 61C & 61D). R-spondin 1 and Nicotinamide both inhibit the expression of the mature marker CYP3A11 and yet promote the expression of the hepatoblast marker albumin. The addition of either FGF10 or HGF to media containing only EGF (without R-spondin1 and without nicotinamide), facilitated the expression of the mature marker CYP3A11, albeit at very low levels (FIG. 61E). To identify additional compounds that might facilitate hepatocyte differentiation, we used two different approaches, both based upon base conditions of: EGF+HGF and/or FGF10.

The first approach involved testing a series of compounds in addition to the EGF+FGF10 or HGF condition. A complete list of the compounds analyzed is shown in Table 3.

TABLE 3

| Compounds | Signal | | Concentration | Result Alb | CYP3AII |
|---|---|---|---|---|---|
| Exendin4 | Glucagon like peptide 2 analog | Sigma E7144 | 0.1-1 uM | | |
| Retinoic Acid | RAR-RXR receptor ligand | Sigma | 25 nM | | |
| Retinoic Acid + Exendin 4 | | | | | |
| Sonic Hedgehog | | Invitrogen C25II | 500-100 ng/ml | | |
| BMP4 | BMP signaling | Peprotech 120-05 | 20 ng/ml | | |
| DAPT | Gamma-secretase inhibitor | Sigma D5942 | 10 nM | | |
| A8301 | Alk5/4/7 inhibitor | Tocris Bioscience 2939 | 50 nM | | |
| DAPT + A8301 | | | | +++ | +++ |
| FGF4 | FGFR1,2 ligand | Peprotech | 50 ng/ml | | |
| FGF1 | FGFR1,2,3,4 ligand | Peprotech 450-33A | 100 ng/ml | | |
| Dexamethasone | | Sigma D4902 25MG | 10 μM-1 mM | | |
| Oncostatin M (OSM) | | R&D systems 495-MO-025 | 10-1000 ng/ml | | |
| FGF4 + OSM + Dexa | | | | | |
| IGF | | peprotech | 100 ng/ml | | |
| Valproic acid | histone deacetylase inhibitor and regulator of ERK, PKC Wnt/β-catenin pathways | Stemgent 04-0007 | 250 μM | | |
| Sodium Butyrate | histone deacetylase inhibitor | Stemgent 04-0005 | 250 μM | | |
| BIX01294 | G9a HMTase inhibitor | Stemgent 04-0002 | 1 μM | | |
| RG 108 | DNA methyltransferase inhibitor | Stemgent 04-0001 | 1 μM | | |
| TSA | | | 100 nM | + | − |
| Hydrocortisone | glucocorticoid | Sigma H6909 | 5 nM | | |
| Oncostatin M (OSM) | | R&D systems 495-MO-025 | 10-1000 ng/ml | | |
| ARA | | Sigma A 0937 | 500 nM | | |
| R 59022 | Diacylglycerol kinase inhibitor | Sigma D 5919 | 500 nM-50 nM | + | + |
| Arterenol bitrartre: ---- | andrenoreceptor agonist | sigma A 0937 | 500 nM-50 nM-5 nM | | |
| LIF | | | $10^3$ | | |
| PD 035901 | MEK1 inhibitor | Axon Medchem cat n 1386 | 500 nM | | |
| CHIR99021 | GSK3 inhibitor | Axon Medchem cat n 1408 | 3 uM | | |
| DMSO | | | 1% | | |
| L-Ascobic acid | | Sigma 077K13021 | 1 mM | | |
| VEGF | | Peprotech | | | |
| Matrigel 50% | | | | | |
| Matrigel 20% | | | | | |
| VEGF + DEXA | | | | | |

The second approach took into account knowledge from published developmental studies regarding the expression of the transcription factors essential to achieve biliary and hepatocyte differentiation in vivo. A comparative analysis of the expression of transcription factors in the organoids under E or ER or ENRW conditions supplemented with FGF10, HGF and Nicotinamide is shown in FIG. 61. All the transcription factors required for Hepatocyte specification were present, besides tbx3 and prox1. However, we also noticed that the expression of specific biliary transcription factors was highly upregulated in the cultures containing R-spondin1 (R), indicating that the culture gene expression was unbalanced towards a more biliary cell fate.

Figure 63A:
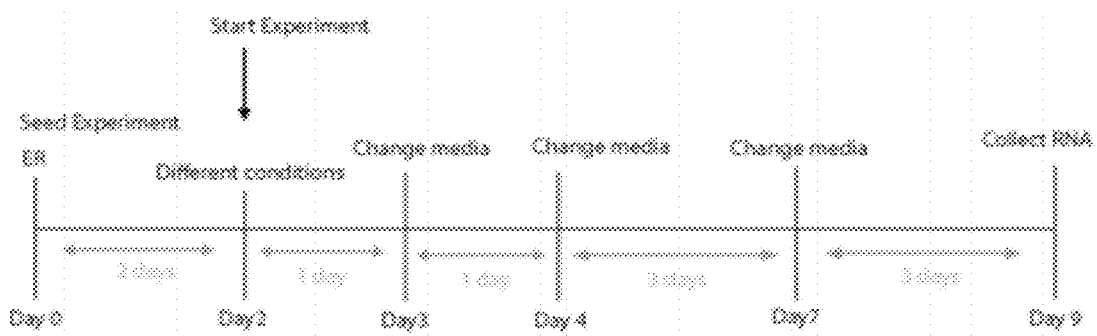
FIG. 63. Differentiation protocol A—Scheme showing the protocol used. Cultures were seeded in expansion medium (ERFHNic: EGF (E) and R-spondin 1 (R), supplemented with FGF10, HGF and Nicotinamide; ERFHNic is indicated as 'ER' in FIG. 10A) 2 days prior to the experiment. Two days later, culture media was changed to EGF (E) supplemented with either A8301 (A), or DAPT (D), or FGF10 (F) or HGF (H) or Nicotinamide (Nic) or R-spondin 1 (R) or Wnt3A or Noggin (N) or a combination of these at the concentrations shown. RNA was isolated at several time points. Mouse liver tissue was taken as positive control (+) whereas water was taken as negative control (−). B—RT-PCR analysis showing the expression of the hepatocyte markers CYP3A11, Alb, FAH, tbx3, TAT and Gck 7 days after differentiation conditions. Note that only the condition EADF showed an expression of all hepatocyte markers tested. HPRT was used as a housekeeping gene to normalize for gene expression. C—Time course expression analysis after differentiation conditions. At days 2, 5 and 8 days after differentiation, the expression of the hepatocyte markers CYP3A11, Alb, FAH, and the cholangyocyte marker K19, was analyzed by RTPCR. Note that the expression of the liver markers CYP3A11 and FAH starts at day 5 and peaks at day 8 after. HPRT was used as a housekeeping gene to normalize for gene expression. A; A8301, D; DAPT, F; FGF10, H; HGF, De; Dexamethasone. D—Titration experiment showing the expression of the hepatocyte markers CYP3A11, Alb, FAH, tbx3, TAT, G6P and Gck 7 days after different concentrations of the differentiation compounds A and D. HPRT was used as a housekeeping gene to normalize for gene expression. E—Immunofluorescent staining for the liver markers K19, Albumin and hepatocyte surface marker. Hoeschst was use to stain nuclei. F—Xgal staining on Albcreert2LacZ mice liver-derived organoids. Albumin positive cells (arrows) were detected after EADF differentiation in tamoxifen induced Albcreert2LacZ derived cultures.

Notch and TGF-beta signaling pathways have been implicated in biliary cell fate in vivo. In fact, deletion of Rbpj (essential to achieve active Notch signaling) results in abnormal tubulogenesis (Zong Y., *Development* 2009) and the addition of TGF-beta to liver explants facilitates the biliary differentiation in vitro (Clotman F., *Genes and Development* 2005). Since both Notch and TGF-beta signaling pathways were highly upregulated in the liver cultures (FIG. 62) we reasoned that inhibition of biliary duct cell-fate might trigger the differentiation of the cells towards a more hepatocytic phenotype. A8301 was selected as an inhibitor of TGF-beta receptor ALK5, 4, and 7 and DAPT as inhibitor of the gamma-secretase, the active protease essential to activate the Notch pathway. We first cultured the cells for 2 days in the expansion conditions (ER media) and at day 2 (FIG. 63A) we started the differentiation conditions by adding the combination of the different compounds. Media was changed every other day, and the expression of differentiated markers was analyzed 8-9 days later. The ER and ENRW conditions were used as negative control.

Figure 63B:
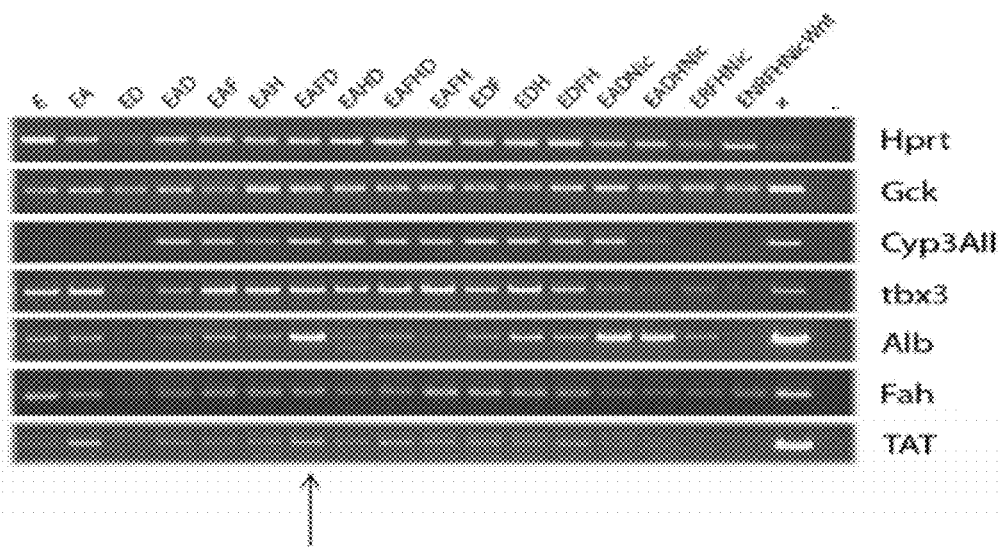
Figure 63C:
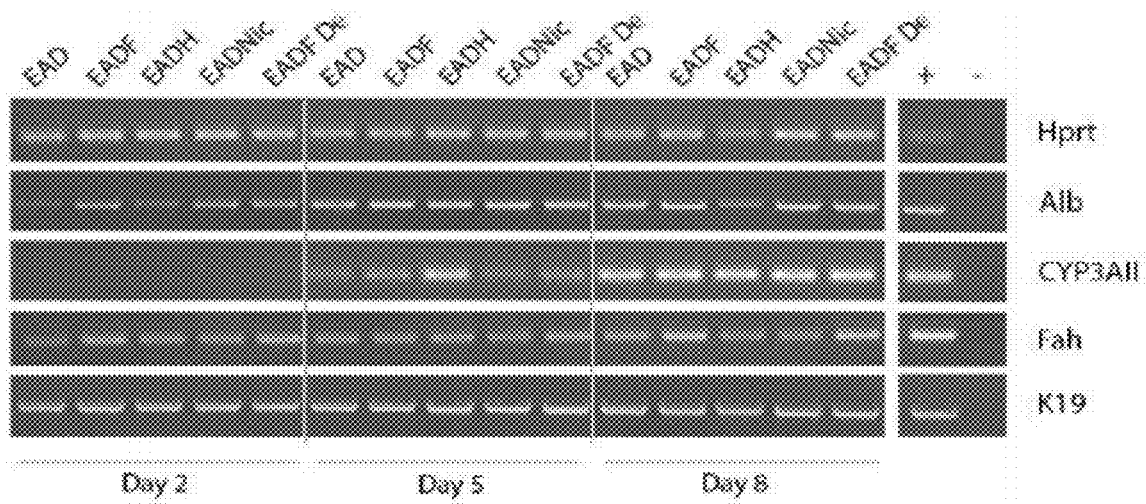
Figure 63D:
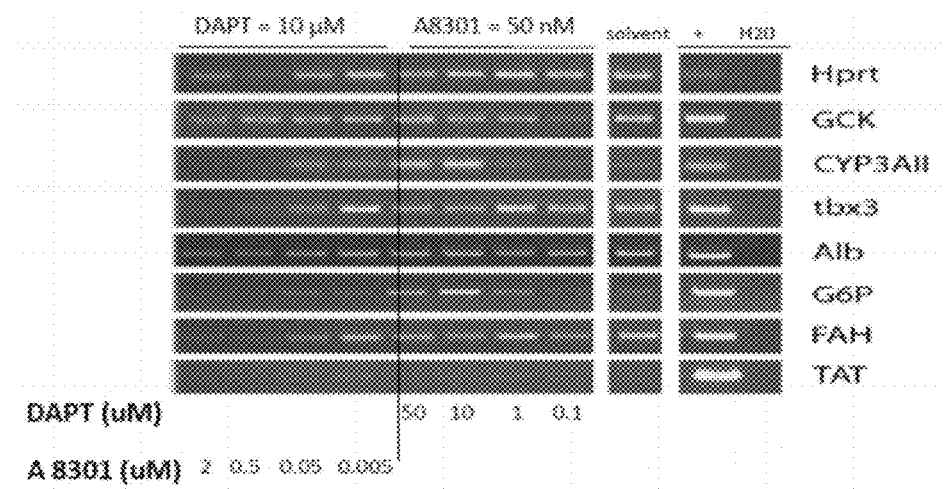
Figure 63E:
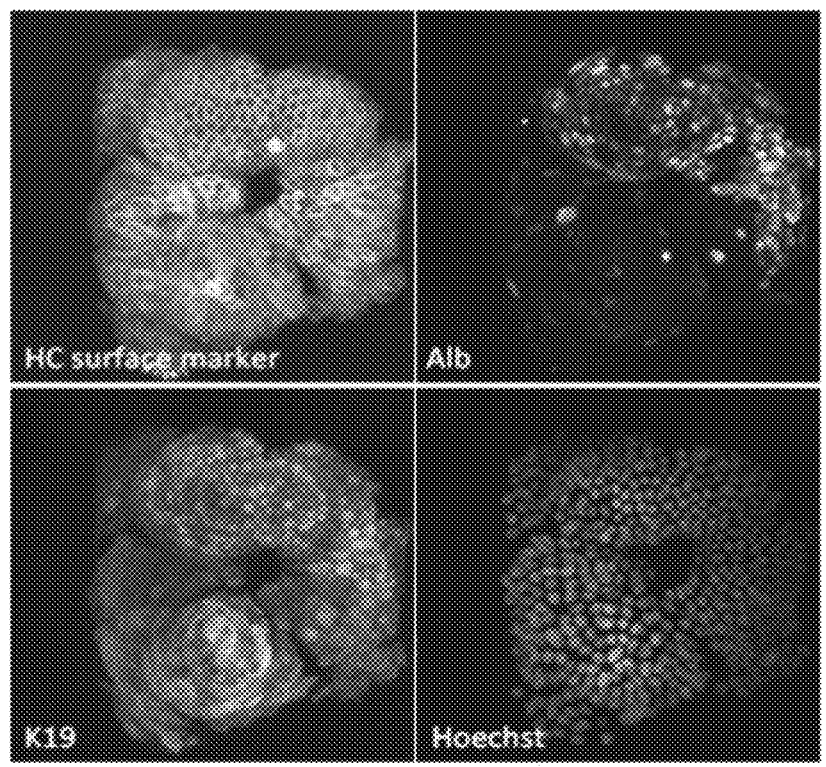
Figure 63F:
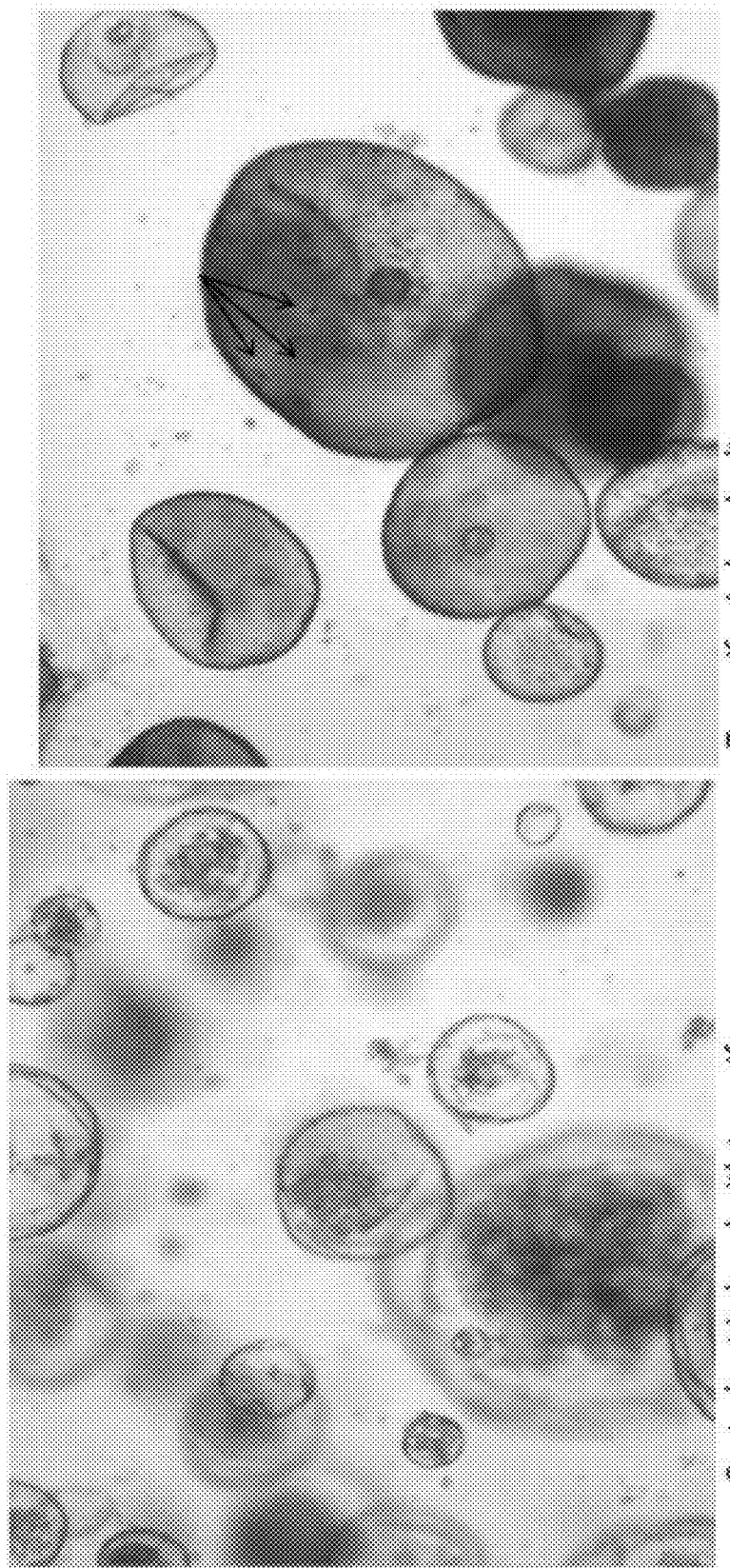

The combination of EGF+FGF10 with DAPT and A8301 resulted in surprisingly large enhancement of expression of the hepatocyte markers analyzed (CYP3A11, TAT, Albumin) (FIG. 63B). The effect was already detectable by day 5 and peaked at days 8-9 (FIG. 63C). The maximal concentration efficiency was achieved at 10 uM (DAPT) and 50 nM (A8301) (FIG. 63D), respectively. The addition of dexamethasone (a known hepatocyte differentiation molecule) did not result in any improvement in gene expression. The combination of EGF, FGF10, A8301 and DAPT not only enhances the expression but also increases the number of hepatocyte-like cells, as assessed by immunofluorescent against the hepatocyte markers albumin and 2F8, and Xgal staining on AlbCreLacZ derived organoids (FIGS. 63E & 63F). Therefore, we can conclude that the aforementioned differentiation protocol facilitates the generation of hepatocyte-like cells in vitro from liver stem cell cultures.

Example 17: Human Liver Organoids

Using these expansion conditions (ERFHNic and ENRW-FHNic) we have also been able to expand human biliary-derived cultures (FIG. 64) with the addition of 500 uM TGF beta inhibitor (A83-01) to the expansion medium.
Material and Methods (For Examples 15-17)
Liver Culture-Biliary Duct Isolation Isolated adult liver tissue was washed in cold Advanced-DMEM/F12 (Invitrogen) and then, the tissue was chopped into pieces of around 5 mm animals and further washed with cold dissociation buffer (collagenase, dispase, FBS in DMEM media). The tissue fragments were incubated with the dissociation buffer for 2 h at 37° C. Then, the tissue fragments were vigorously suspended in 10 ml of cold isolation buffer with a 10 ml pipette. The first supernatant containing death cells was discarded and the sediment was suspended with 10-15 ml of dissociation buffer. After further vigorous suspension of the tissue fragments the supernatant is enriched in biliary ducts. This procedure is repeated until enough biliary ducts are obtained.

Isolated biliary ducts are pelleted and mixed with 50 µl of Matrigel (BD Bioscience), seeded on 24-well tissue culture plates and incubated for 5-10 min at 37° C. until complete polymerization of the Matrigel. After polymerization, 500 µl of tissue culture media are overloaded.
Media Composition:

Advanced-DMEM/F12 supplemented with B27, N2, 200 ng/ml N-Acetylcysteine, 50 ng/ml EGF, 1 µg/ml R-spondin1, gastrin: 10 nM, FGF10 100 ng/ml, Nicotinamide 10 mM and HGF: 50 ng/ml and 50% Wnt conditioned media.

The entire medium was changed every 2 days. After 1 week, Wnt conditioned media is withdrawal and the formed organoids removed from the Matrigel using a 1000 µl pipette and were dissociated mechanically into small fragments and transferred to fresh Matrigel. Passage was performed in 1:4 split ratio once or twice per week. Under these conditions cultures have been maintained for at least 6 month.
Reagents Human Hepatocyte Growth Factor (HGF) was purchased from Peprotech, EGF invitrogen, R-Spondin Nuvelo, Noggin peprotech, FGF10 Peprotech, gastrin Sigma Aldrich, nicotinamide Sigma.
Microarray For the expression analysis of Lgr5-derived liver cultures, RNA was isolated using a Qiagen RNAase kit, from adult liver or from liver cultures cultured in media without Wntcm and Noggin (ER) or with Wntcm and Noggin (ENRW). 150 ng of total RNA was labelled with low RNA Input Linear Amp kit (Agilent Technologies, Palo Alto, Calif.). Universal mouse Reference RNA (Agilent) was differentially labelled and hybridized to either adult liver tissue or ER or ENRW treated cultures. A 4×44K Agilent Whole Mouse Genome dual colour Microarrays (G4122F) was used. Labelling, hybridization, and washing were performed according to Agilent guidelines.

Example 18: Lgr5 Expression is Upregulated Following Liver Injury

Figure 65:
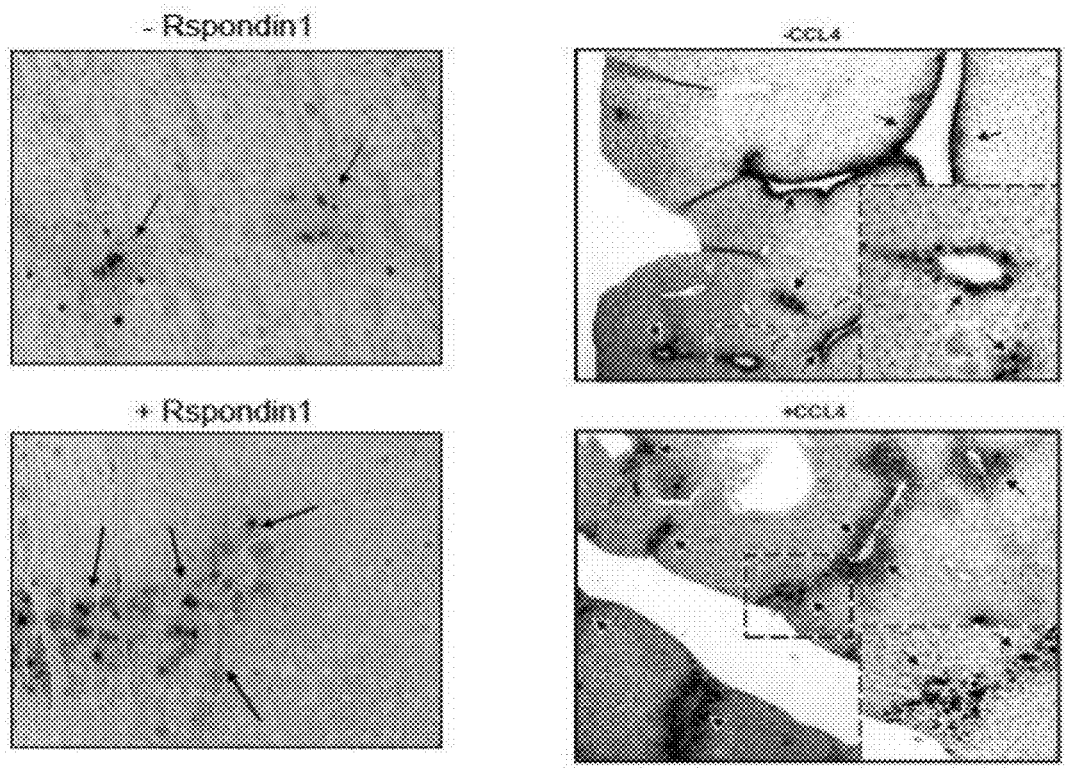
FIG. 65. Liver response to Wnt signaling stimulation under physiological conditions or during regeneration after injury A: Injection of Lgr5 ligand R-spondin1 in Axin2 LacZ mice shows that liver cells are responsive to Wnt stimulation (arrows pointing X-gal positive cells). There was no Lgr5 expression so the inventors hypothesise that Lgr4 was used to initiate the response. B: CCL4 injection in Axin2 LAcZ mice shows that during the regeneration response Wnt signaling is activated.

In the liver, Wnt signaling is active in central vein areas. We have recently observed that Wnt signaling plays a key role in liver metabolism (Boj et al. personal communication). In the liver duct cells, Wnt signaling is activated following liver injury (Hu et al. 2007, *Gastroenterology* 133(5): 1579-91). Similarly, using the Axin2-LacZ allele, which represents a faithful, general reporter for Wnt signaling we also have observed upregulation of Wnt signaling in the whole liver parenquima after injection of the Wnt agonist Rspo1 (see FIG. 65A) or following liver injury by the hepatotoxic compound carbon tetrachloride (CCl4) (see FIG. 65B).

Figure 66A:
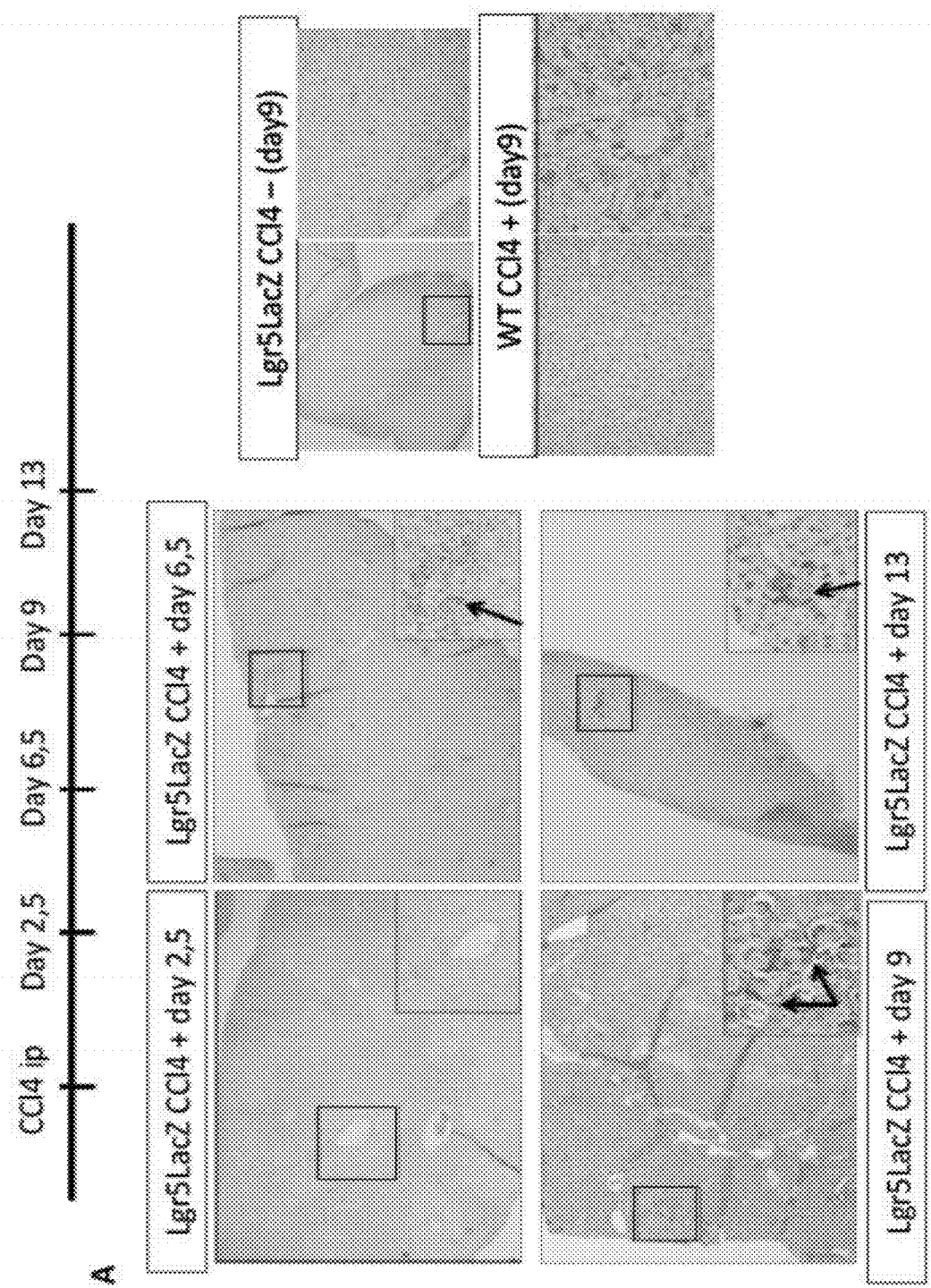
FIG. 66. Lgr5 upregulation following liver injury-regeneration model. Adult Lgr5-LacZ KI mice were injected with 0.8 ml/kg of the hepatotoxic compound CCL4. The pictures show that in non injected (undamaged) livers the Wnt pathway is active only in cells lining the ducts. After damage by CCl4 cells also cells not lining duct have an activated Wnt pathway. A—Time course experiment showing upregulation of Lgr5 in CCL4 damaged livers (arrows showing x-gal positive cells). Control CCL4 injected WT mice and placebo-injected Lgr5LacZ Ki mice did not show any staining (right-hand panel). B—Lgr5 co-staining with liver markers.

The Wnt target gene Lgr5 marks stem cells in several actively self-renewing tissues, but has not previously been reported to be expressed upon injury. Our previously described Lgr5-LacZ knockin mice (Barker et al, 2007, *Nature* 449 (7165): 1003-7) show that Lgr5 is essentially undetectable in healthy liver although a residual mRNA expression is detected by qPCR. Following injection of CCl4 on Lgr5-LacZ knockin mice (see Barker et al, 2007, supra for LacZ mice and Furuyama K. et al., *Nat. Genetics* 43, 34-41, 2001 for description of CCl4 method), we observed a clear expression of the reporter in newly formed bud structures in the liver (see FIG. 66A), peaking at day 6.5 after injury and being maintained up to day 9 to show a clear decay once the liver is completely regenerated at day 13 after injury (see FIG. 66A, top right panel). No expression of the reporter was detected in wild-type littermates undergoing similar injury protocol (see FIG. 66A, bottom right panel).

Figure 66B:
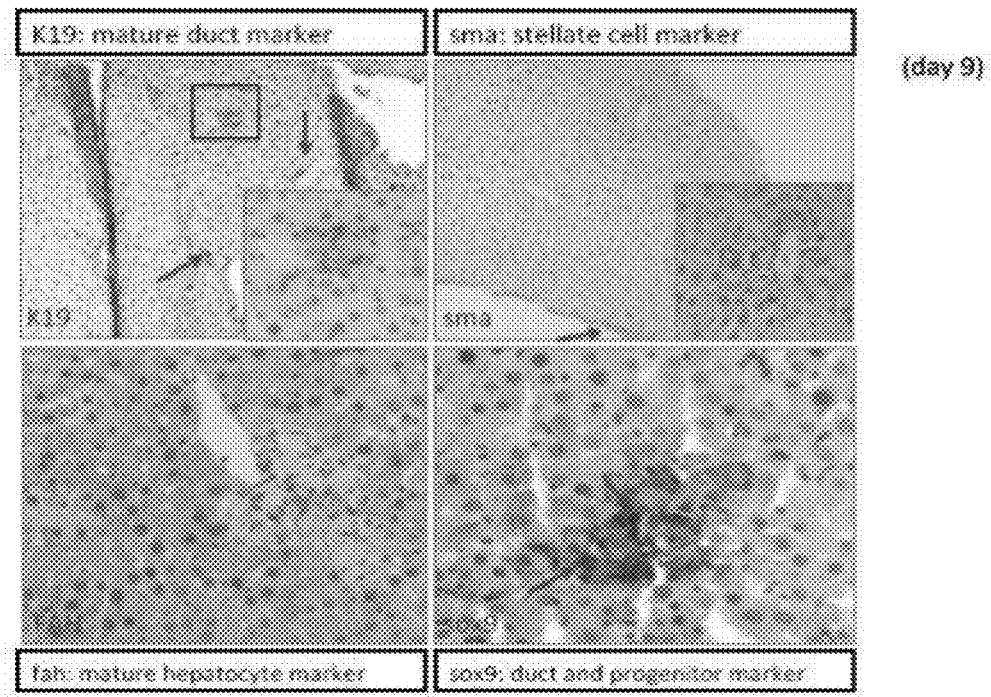

The appearance of Lgr5 expression at sites of active regeneration, suggested that Lgr5 might herald de novo activation by Wnt of regenerative stem cells/progenitors upon injury. Indeed, we found that the novo appearing Lgr5 cells do not express markers of mature liver cells (K19 or FAH) or stellate cells (SMA) but instead, they are positive for the recently described liver progenitor marker Sox9 (FIG. 66B). This means that Lgr5+ cells, which are the starting point for obtaining in vitro organoids, can be obtained from liver fragments by inducing liver injury or by stimulating Wnt signaling with R-spondin. The induction of Lgr5 expression in liver cells by injury or by R-spondin may be carried out in vivo before the cells are obtained, ex vivo in an isolated liver, or in vitro in a liver fragment or population of liver cells.

Example 19: Long-Term Expansion of Liver Organoid Cultures

Figure 68A:
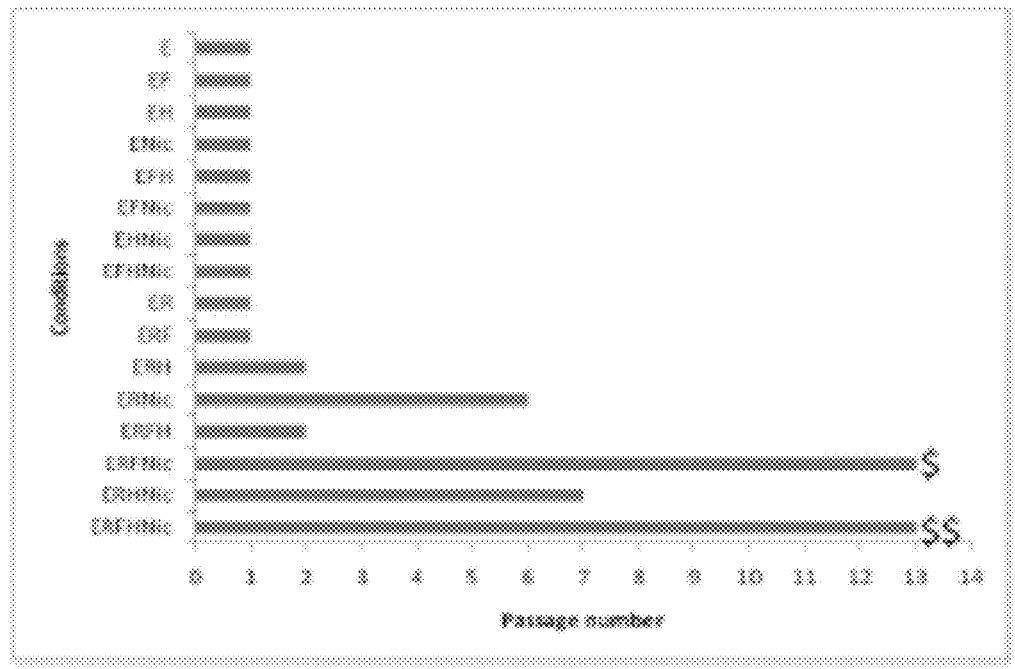
FIG. 68. Growth factor requirement. The 3 supplemental factors (FGF10, HGF and Nicotinamide) are essential for long term self-maintenance of liver cultures. After long-term culture, the combination of ER including FNic ($) or ERFH-Nic ($$), both result in high passage numbers. After passage 10, the growth rate is better for the culture condition including the 3 supplemental factors; ERFHNic (see FIG. 69B).
Figure 68B:
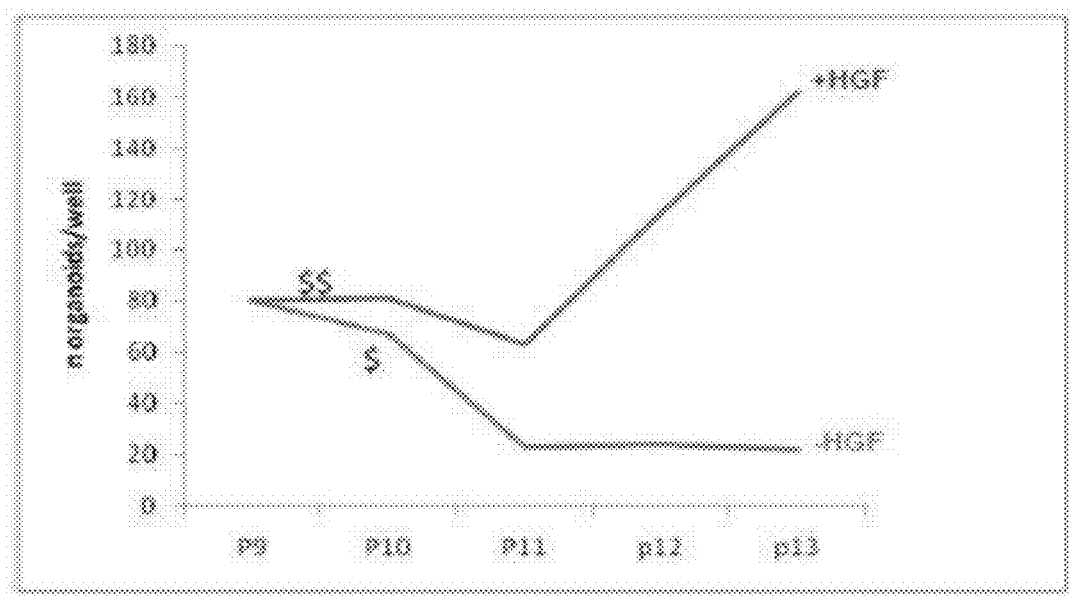

In example 15, it was found that the combination of EGF (50 ng/ml) and R-spondin 1 (1 ug/ml) supplemented with FGF10 (100 ng/ml), HGF (25-50 ng/ml) and Nicotinamide (1-10 mM), were preferable for the long term maintenance of the cultures. We now also have evidence that the three supplemental factors (FGF10, HGF and Nicotinamide) added to EGF and R-spondin1 are all necessary for the expansion of the cultures for longer than 3 months. To assess that, we isolated biliary ducts from the liver parenquima, as shown in FIG. 67 (K19 staining was used to confirm the identity of the isolated structures), and generated liver organoid cultures by culturing them with: i) EGF; or ii) EGF and R-spondin 1 plus FGF10 or HGF or Nicotinamide; or iii) EGF and R-spondin1 plus FGF10 and HGF and Nicotinamide (ERFHNic). We have split the cultures once a week for a total period of 14 weeks. Results confirmed, as reported in examples 15 and 16, that EGF, R-spondin1 and Nicotinamide combined with FGF10 are essential for the growth and self-renewal of the liver cultures. After 10 passages, the cultures lacking HGF showed a growth disadvantage compared to the cultures supplemented with HGF. Although still viable, the proliferation ratio decreased to 1:2-1:4 compared to the 1:6-1:8 of the cultures supplemented with the complete combination (FGF10, HGF, and Nicotinamide). After 15 passages, the cultures with ERFNic not supplemented with HGF were no longer viable. Therefore, these results suggest that HGF is essential for maintaining a good proliferating rate after long-term maintenance (FIG. 68).

Example 20: Markers Expressed in Liver Organoids Under Differentiation Conditions Using the differentiation protocol described in example 16, we were able to detect a hepatoblast marker (albumin) and a hepatocyte surface marker in the liver organoids. To quantify the number of these hepatocyte-like cells, we performed flow cytometry analysis of the cultures using a hepatocyte surface marker. We observed that, whereas in the expansion culture condition almost no hepatocyte surface marker-positive cells were detected, after differentiation, up to 35% of the cells were positive for this hepatocyte surface marker (see FIGS. 70B & 70C).

Figure 69A:
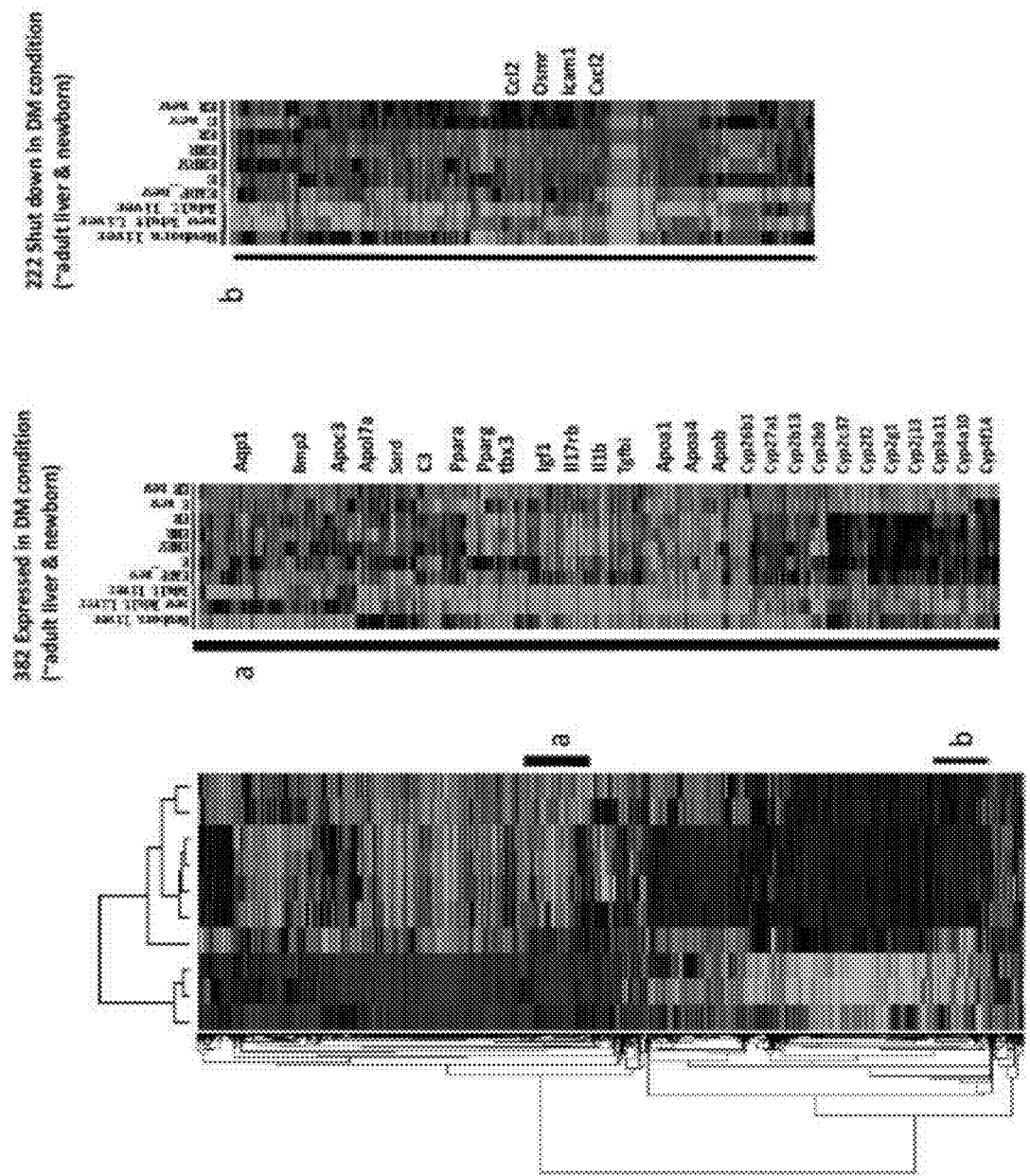
FIG. 69. Gene expression profile of mouse liver organoids under differentiation conditions resemble the adult and newborn liver profile A—Gene clusters showing the genes similarly expressed (a) or similarly shut down (b) between the differentiation condition EADF and adult or newborn liver. B—Gene clusters showing the genes differentially expressed between the liver organoids and adult or newborn liver (a) and the genes similarly expressed between EADF and newborn liver (b). C—Raw signal data from a microarray analysis, comparing the expression levels of selected ductal markers, transcription factors necessary for Ngn3 expression and endocrine markers in adult liver, adult pancreas, pancreas organoids and liver organoids in expansion media.
Figure 69B:
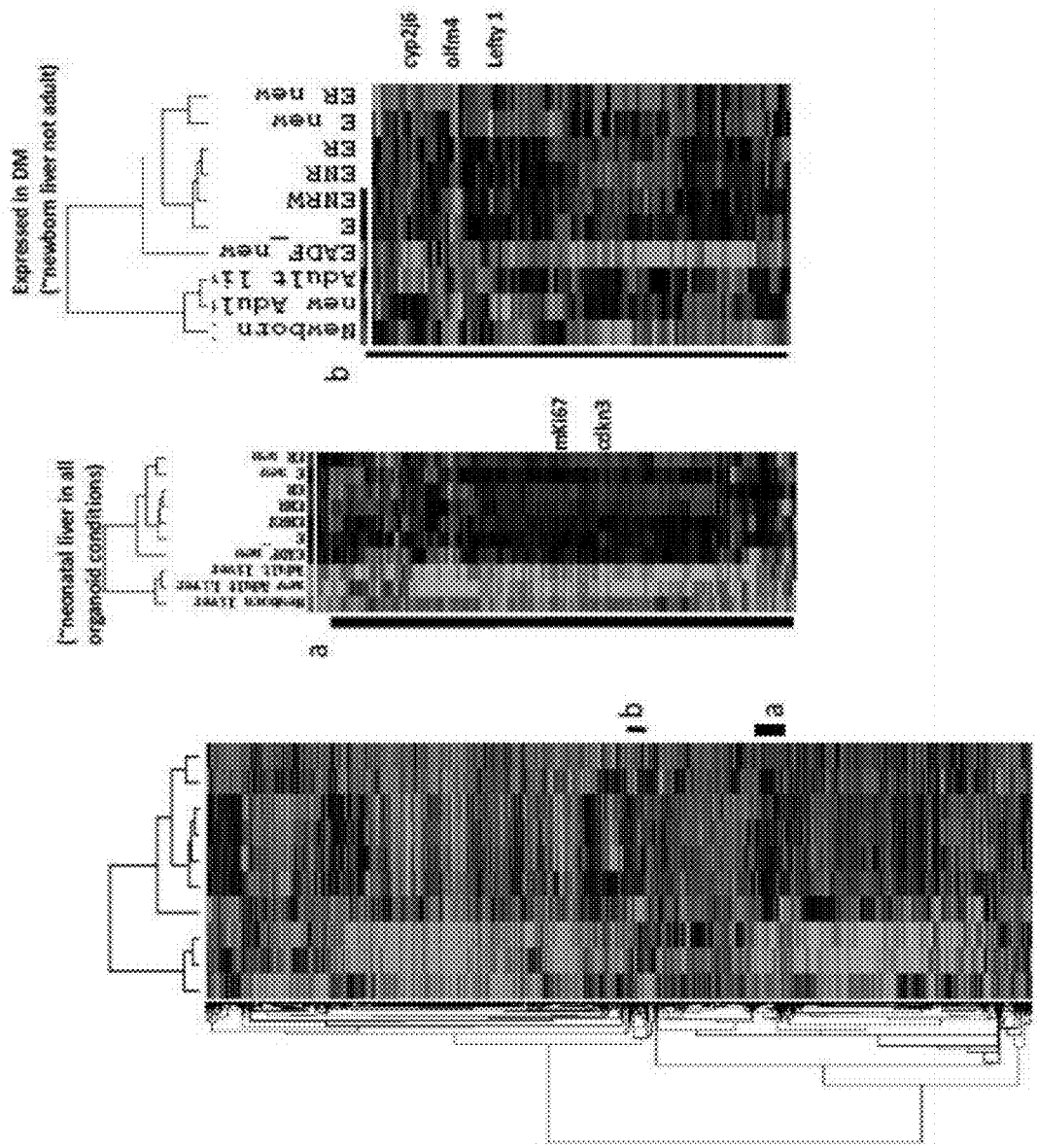

We then analyzed the gene expression profile of the mouse liver organoids under these differentiation conditions (FIG. 69 and FIG. 54, we see strong upregulation of, e.g., Alb, FAH, and TAT and the Cyp3 genes). We found that the gene expression of the mouse liver organoids after differentiation resemble that of mature mouse hepatocytes and/or mouse liver.

Example 21: Transplantation of Liver Organoids into Mice

Figure 70A:
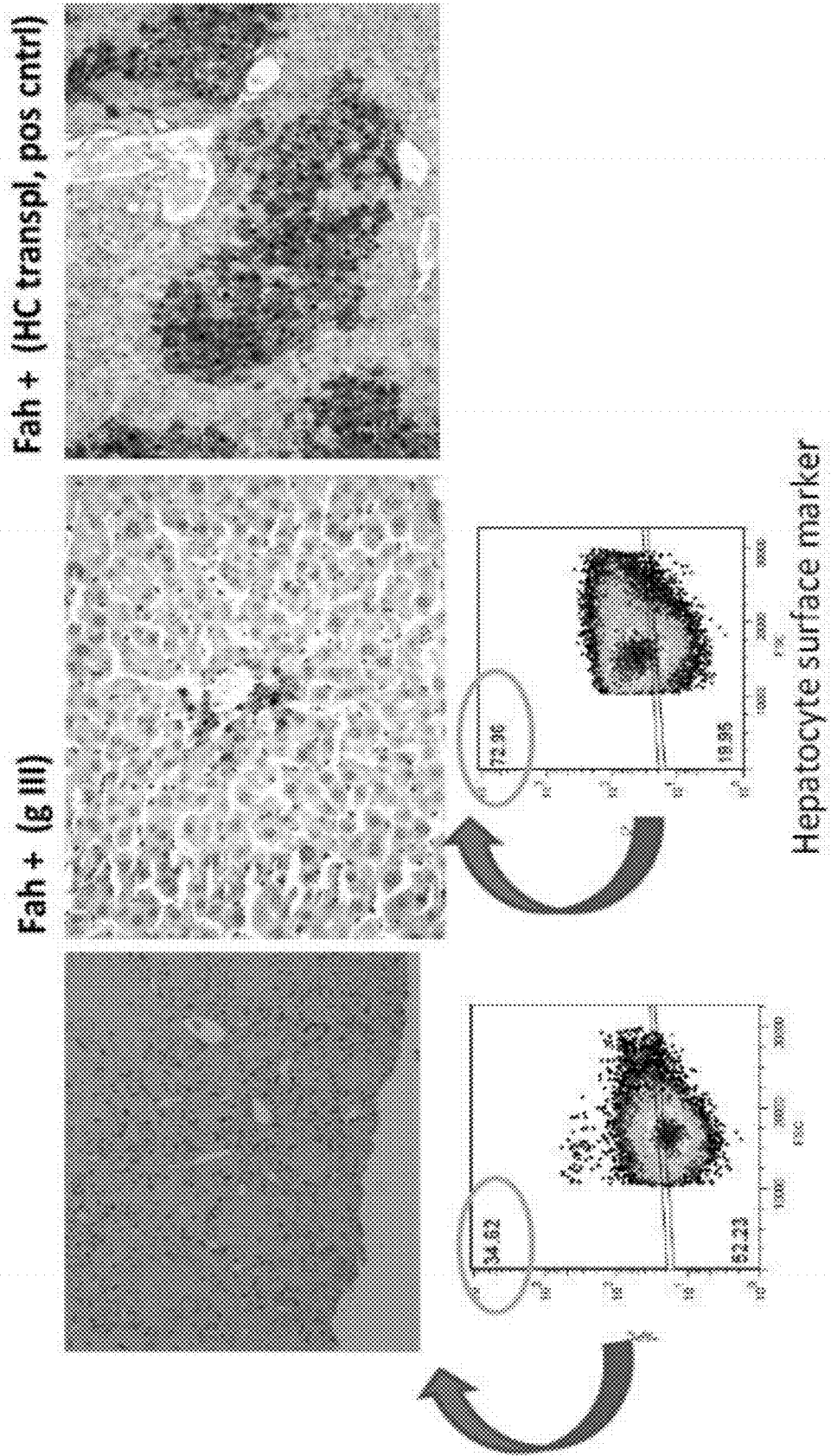
FIG. 70. Transplantation of the cells into mouse model of liver disease. Organoids were transplanted into the mouse model: adult FGR mice (FAH−/−RAG−/−IL2R−/−). Hepatocytes were transplanted into the mice as a control. A—K19 positive cells (left top panel) and Fah positive cells (middle panel) derived from the liver organoids transplanted into FAH knock out mice. Hepatocyte transplanted control (top right panel). Lower flow Cytometry plots show that the % of hepatocyte positive cells was higher in the group that resulted in positive FAH engrafted hepatocytes. C & D—Flow Cytometry analyses of cells transplanted. (C) Clone 1, obtained from Lgr5-GFP mouse, and (D) clone 2, obtained from Lgr5-lacZ mouse. The hepatocyte surface marker shows a positive subpopulation that comprises large cells and highly granular cells, i.e., cells that represent the phenotype of mature hepatocytes. E—Transplantation schedule.
Figure 70B:
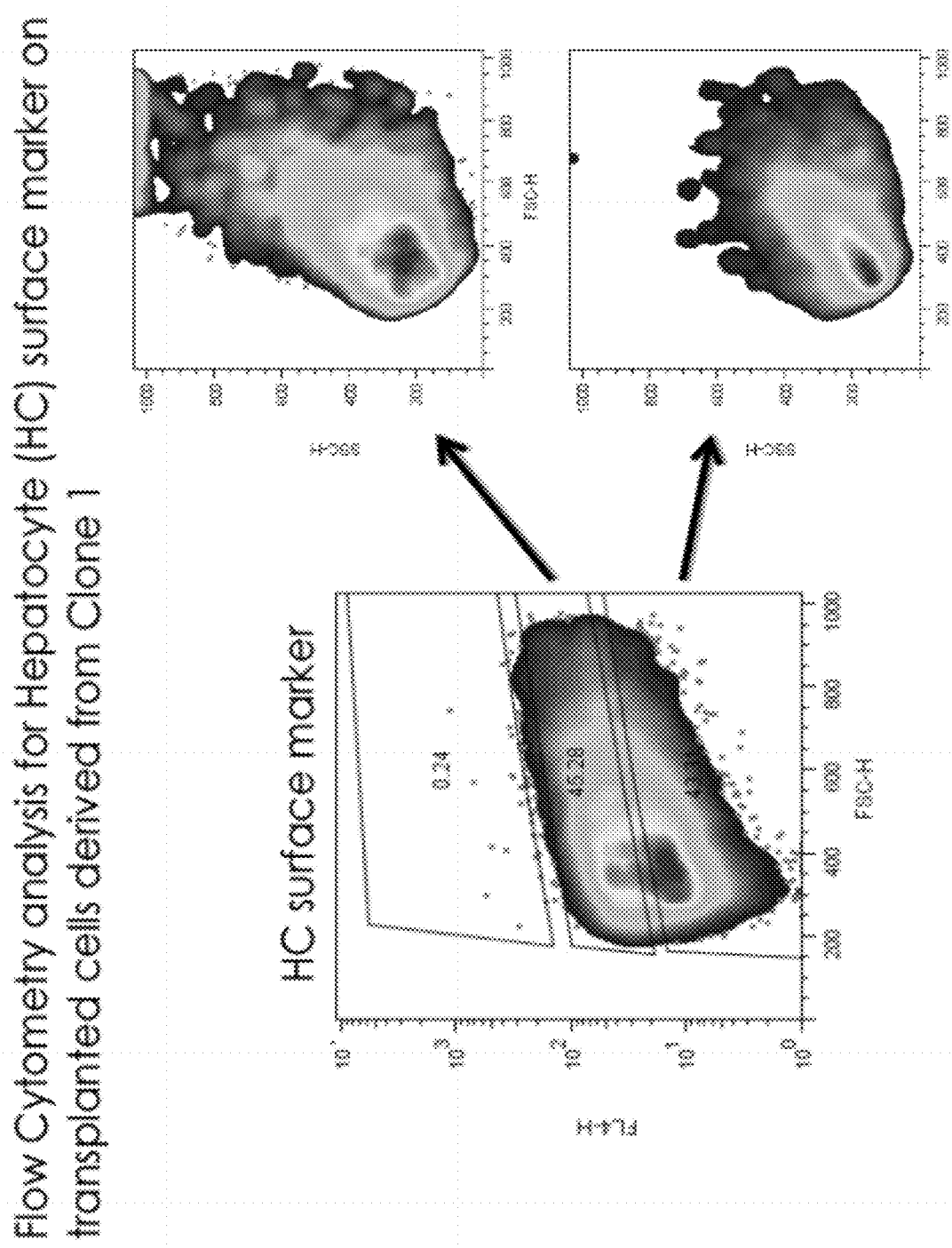
Figure 70C:
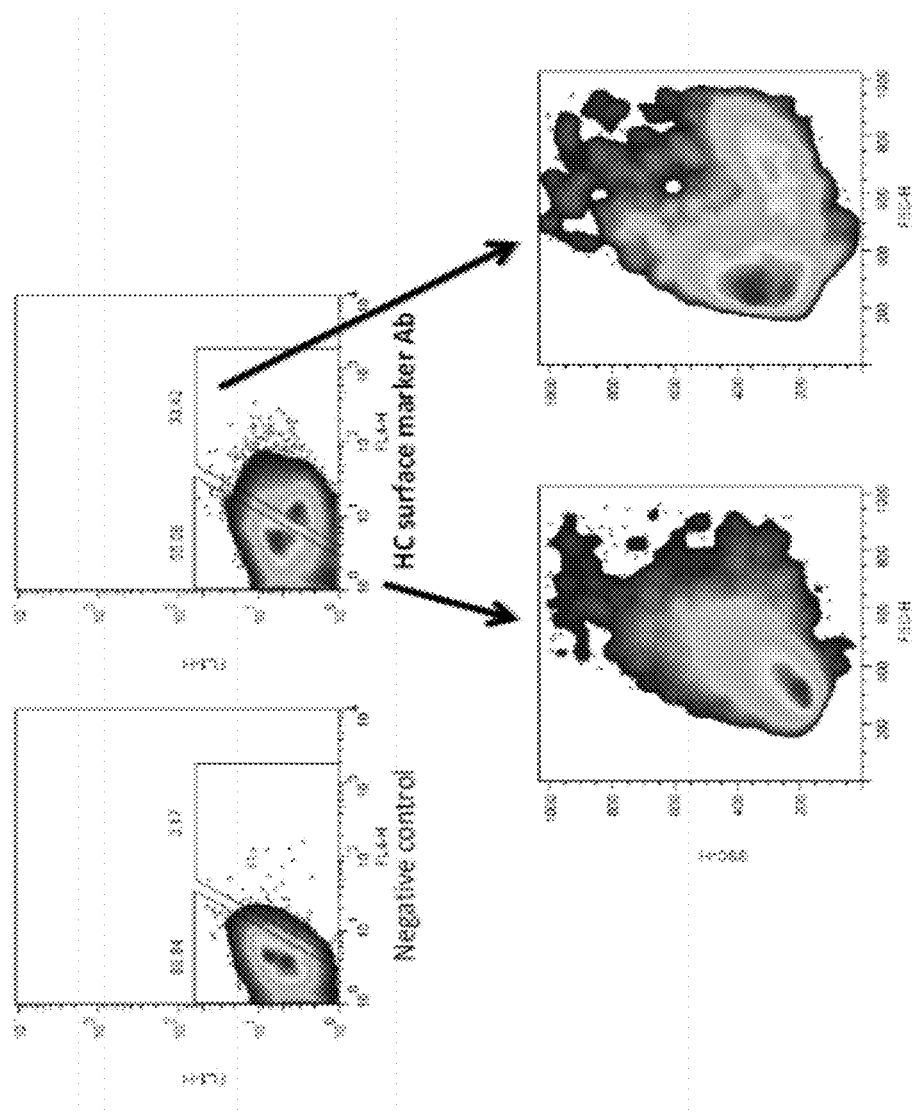
Figure 70D:
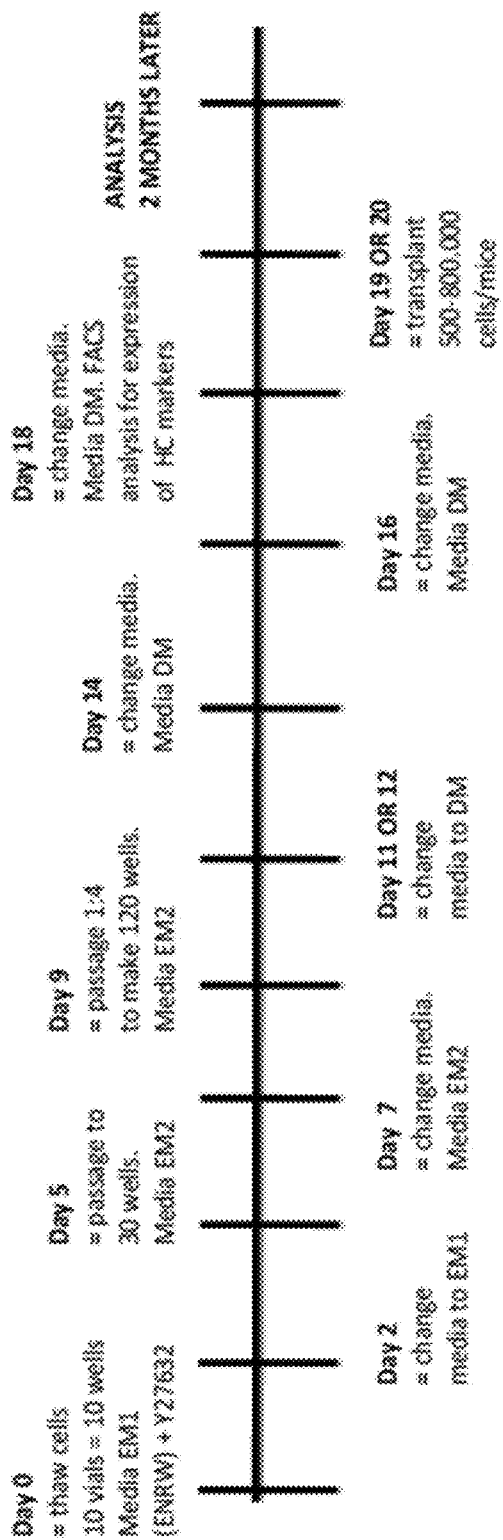

Cells were taken from the organoids that had been grown using ERFHNic expansion conditions and EAFD differentiation conditions and were transplanted into immunodeficient strain of mice deficient in the tyrosine catabolic enzyme fumarylacetoacetate hydrolase (FAH), a mouse model for Tyrosinemia type I human disease (Azuma et al. 2007, Nature Biotech. 25(8), 903-910). The transplantation schedule is shown in FIG. 70D. Preliminary results show that scattered FAH positive cells can be found in the liver parenquima of the FAH deficient mice, indicating that liver cells derived from the organoid cultures have engrafted into the recipient livers (see FIG. 70A, right-hand side). Furthermore, significantly increased numbers of K19 positive cells were also detected in the livers of the recipient mice. This suggests that the organoid-derived transplanted cells are able to generate both lineages in vivo: hepatocytes (as demonstrated by the FAH marker) and cholangyocytes (as demonstrated by the K19 marker) (see FIG. 70A, left top panel). This was further supported by flow cytometry analysis of transplanted cells that had come from two separate clones from two separate cultures (FIGS. 70B and 70C, respectively). The Lgr5+ cells were transduced with a virus containing GFP and flow cytometry analysis was carried out after differentiation. Cells that were positive for the hepatocyte surface marker show a larger scatter indicating larger cells, which represent granularity and maturity i.e., mature hepatocyte cells. The cells that were negative for the hepatocyte surface marker resulted in less scattering indicating smaller cells, i.e., less mature progenitors. Therefore, all cell types are present (mature and immature cells) in a differentiating culture. The rest of the differentiated cells, so the cells not used for FACS analysis were used for the transplantation experiments.

Example 22

Organoids from mouse liver cultured in accordance with a method of the invention were analyzed using microarray analysis to determine which genes are expressed and which genes are not expressed.

Example 23

Organoids from human liver cultured using the EM1, EM2 and DM media of the invention and human liver were analyzed using oligonucleotide microarray analysis to determine which genes are expressed and which genes are not expressed. A significantly different gene expression profile was noticeable between the genes expressed in expansion media, the genes expressed in differentiation medium and the genes expressed in adult liver. The trend for hepatocyte gene expression is roughly the same as for in the mouse but the differentiation of the organoids was less than in the mouse liver organoids. This may be due to use of the human cell used.

As often happens in an analysis using an oligonucleotide microarray, Lgr5 and Tnfrsf19 were not detected. However, they were found to be present in organoids cultured in the expansion medium.

Materials & Methods (for Examples 18 to 23)

Animal Treatment

Two-Eight month old Lgr5LacZ or Axin2-LacZ or WT littermates BL6/Balbc F1 mice received an intraperitoneal injection of 0.8 ml/kg of CCL4 dissolved in corn oil (n=) or corn oil alone (n=). Mice were sacrificed 2 or 5 or 9 or 13 days later and the liver was isolated and further processed for RNA or bgalactosidase staining.

β-Galactosidase (lacZ) Staining

Liver tissues were isolated and immediately incubated for 2 hours in a 20-fold volume of ice-cold fixative (1% Formaldehyde; 0.2% Gluteraldehyde; 0.02% NP40 in PBS0) at 4° C. on a rolling platform. The fixative was removed and the tissues washed twice in washing buffer (PBS0; 2 mM $MgCl_2$; 0.02% NP40; 0.1% NaDeoxycholate) for 20 minutes at room temperature on a rolling platform. The β-galactosidase substrate (5 mM $K_3FE(CN)_6$; 5 mM $K_4Fe(CN)_6.3H_2O$; 2 mM $MgCl_2$; 0.02% NP40; 0.1% NaDeoxycholate; 1 mg/ml X-gal in PBS0) was then added and the tissues incubated in the dark at 37° C. for 2 h and overnight at room temperature. The substrate was removed and the tissues washed twice PBS0 for 20 minutes at room temperature on a rolling platform. The tissues were then fixed overnight in a 20-fold volume of 4% Paraformaldehyde (PFA) in PBS0 at 4° C. in the dark on a rolling platform. The PFA was removed and the tissues washed twice in PBS0 for 20 minutes at room temperature on a rolling platform.

The stained tissues were transferred to tissue cassettes and paraffin blocks prepared using standard methods. Tissue sections (4 μM) were prepared and counterstained with neutral red.

R-spondin1 Treatment

Axin2-lacZ mice aged 6-8 weeks were injected IP with 100 μg of purified human R-spondin1 and sacrificed 48 hours later for LacZ expression analysis in the liver.

RT-PCR

RNA was extracted from gastric cell cultures or freshly isolated tissue using the RNeasy Mini RNA Extraction Kit (Qiagen) and reverse-transcribed using Moloney Murine Leukemia Virus reverse transcriptase (Promega). cDNA was amplified in a thermal cycler (GeneAmp PCR System 9700; Applied Biosystems, London, UK) as previously described (Huch et al., 2009). Primers used are shown in Table 4 below.

TABLE 4

Primers for RT-PCR

| Gene name | Gene Symbol | | Sequence | PCR product bp) |
|---|---|---|---|---|
| cytochrome P450, family 3, | CYP3A11 | w | TGGTCAAACGCCTCTCCTTGCTG (SEQ ID NO: 46) | 100 |
| subfamily a, polypeptide 11 | | v | ACTGGGCCAAAATCCCGCCG (SEQ ID NO: 47) | |
| Glucose-6-phoshatase | G6P | w | GAATTACCAAGACTCCAGG (SEQ ID NO: 48) | 581 |
| | | v | TGAGACAATACTTCCGGAGG (SEQ ID NO: 49) | |
| Keratin 19 | Krt19 | w | GTCCTACAGATTGACAATGC (SEQ ID NO: 50) | 549 |
| | | v | CACGCTCTGGATCTGTGACA (SEQ ID NO: 51) | |
| Albumin | Alb | w | GCGCAGATGACAGGGCGGAA (SEQ ID NO: 52) | 358 |
| | | v | GTGCCGTAGCATGCGGGAGG (SEQ ID NO: 53) | |
| t-box 3 | Tbx3 | w | AGCGATCACGCAACGTGGCA (SEQ ID NO: 54) | 441 |
| | | v | GGCTTCGCTGGGACACAGATCTT (SEQ ID NO: 55) | |
| Prospero-related homeobox | Prox1 | w | TTCAACAGATGCATTACC (SEQ ID NO: 56) | 270 |
| protein 1 | | v | TCTTTGCCCGCGATGATG (SEQ ID NO: 57) | |
| Fumarylacetoacetate- | Fah | w | ACGACTGGAGCGCCGAGAC (SEQ ID NO: 58) | 183 |

TABLE 4-continued

Primers for RT-PCR

| Gene name | Gene Symbol | | Sequence | PCR product bp) |
|---|---|---|---|---|
| hydrolase | | v | AGGGCTGGCTGTGGCAGAGA (SEQ ID NO: 59) | |
| Tyrosine aminotransferase | Tat | w | TTTGGCAGTGGCTGAAAGGCA (SEQ ID NO: 60) | 258 |
| | | v | GGGCCCAGGATCCGCTGACT (SEQ ID NO: 61) | |
| Trytophane2,3-dioxygenase | Tdo2 | w | ACTCCCCGTAGAAGGCAGCGA (SEQ ID NO: 62) | 583 |
| | | v | TCTTTCCAGCCATGCCTCCACT (SEQ ID NO: 63) | |
| Leucine-rich repeat-containing G-protein coupled receptor 5 | Lgr5 | w | GGAAATGCTTTGACACACATTC (SEQ ID NO: 64) | 413 |
| | | v | GGAAGTCATCAAGGTTATTATA (SEQ ID NO: 65) | |
| Transthyretin | TTR | w | ATGGTCAAAGTCTGGATGC (SEQ ID NO: 66) | 220 |
| | | v | AATTCATGGAACGGGGAAAT (SEQ ID NO: 67) | |
| Glucokinase | Gck | w | AAGATCATTGGCGGAAAG (SEQ ID NO: 68) | 193 |
| | | v | GAGTGCTCAGGATGTTAAG (SEQ ID NO: 69) | |
| hypoxanthine phosphoribosyltransferase | Hprt | w | AAGCTTGCTGGTGAAAAGGA (SEQ ID NO: 70) | 186 |
| | | v | TTGCGCTCATCTTAGGCTTT (SEQ ID NO: 71) | |

Immunohistochemistry

Immunostaining procedure used here was previously described in Huch et al. 2009. Briefly, five-micrometer sections were deparaffinized, rehydrated, and tissue sections were permeabilized using PBS-T (PBS; Tween 20 0.1%). When required, sections were treated with 10 mMcitrate buffer (pH 6.0) for antigen retrieval, blocked using Universal blocking buffer (BioGenex)) and incubated with the primary antibody. Then, sections were washed twice with PBS and incubated with peroxidase conjugated secondary antibodies. DAB+ (DAKO) was used as a chromogen substrate. Sections were counterstained with Mayer's hematoxylin and visualized on a Leica DMR microscope. The primary antibodies used were rabbit anti-Sox9 (1:600; 1 h at RT, Millipore), mouse anti-SMA (1:1000, overnight at 4° C., Sigma), rabbit anti-FAH (1:5000; overnight 37° C., gift from M. Grompe), rabbit anti-K19 (1:500; overnight 4° C., gift from M. Grompe). The peroxidase conjugated secondary antibodies used were Mouse or Rabbit Brightvision (Immunologic).

Immunofluorescence

For whole mount staining, organoids or isolated biliary ducts were fixed with acetone (organoids) or PFA4% (biliary ducts) for 30 min, washed once with PBS, permeabilized with PBS 0.3% Triton-X100 for 5 min, blocked using Universal blocking solution (Power block HK085-5KE BioGenex) and incubated overnight with the primary antibodies diluted in PBS1% FBS. Following several washes in PBS, samples were incubated with the secondary antibody. Nuclei were stained with Hoescht33342. Images were acquired using confocal microscopy (Leica, SP5). Three-dimensional reconstruction was performed using Volocity Software (Improvision). The primary antibodies used were rabbit anti-K19 (1:500; gift from M. Grompe), rat anti-hepatocyte surface marker (1:50, gift M. Grompe), goat anti-albumin (1:50, santa Cruz). The secondary antibodies used were all raised in donkey and conjugated to different Alexa fluorofores (donkey anti-goat 568, donkey anti rat-488, donkey anti rabbit-647, Molecular probes).

Flow Cytometry

Dissociated cells were resuspended at $1 \times 10^4$ cells per milliliter in 1 ml of DMEM+2% FBS prior to the addition of MIC1-1C3 hybridoma supernatant at a 1:20 dilution or OC2-2F8 hybridoma supernatant at a 1:50 dilution, and incubated for 30 min at 4° C. After a wash with cold Dulbecco's Phosphate Buffered Saline (DPBS), cells were resuspended in DMEM+2% FBS containing a 1:200 dilution of APC-conjugated goat anti-rat secondary antibody adsorbed against mouse serum proteins (Jackson Immunoresearch). Propidium iodide staining was used to label dead cells for exclusion. Cells were analyzed and sorted with a Cytopeia in FluxV-GS (Becton-Dickenson).

Transplantation Assay

The injection of sorted cell populations to the spleen and the withdrawal of NTBC to induce hepatocyte selection were performed as described previously (Overturf et al. 1996). Drug withdrawal was done in periods of 3 wk, followed by readministration until normal weight was restored in the recipient animals.

REFERENCES

1. Barker, N. et al. Identification of stem cells in small intestine and colon by marker gene Lgr5. *Nature* 449, 1003-7 (2007).
2. Bjerknes, M. & Cheng, H. Intestinal epithelial stem cells and progenitors. *Methods Enzymol.* 419, 337-83 (2006).
3. Barker, N., van de Wetering, M. & Clevers, H. The intestinal stem cell. *Genes Dev.* 22, 1856-64 (2008).
4. Evans, G. S., Flint, N., Somers, A. S., Eyden, B. & Potten, C. S. The development of a method for the preparation of rat intestinal epithelial cell primary cultures. *J. Cell. Sci.* 101 (Pt 1), 219-31 (1992).
5. Whitehead, R. H., Demmler, K., Rockman, S. P. & Watson, N. K. Clonogenic growth of epithelial cells from normal colonic mucosa from both mice and humans. *Gastroenterology* 117, 858-65 (1999).
6. Fukamachi, H. Proliferation and differentiation of fetal rat intestinal epithelial cells in primary serum-free culture. *J. Cell. Sci.* 103 (Pt 2), 511-9 (1992).
7. Perreault, N. & Jean-Francois, B. Use of the dissociating enzyme thermolysin to generate viable human normal intestinal epithelial cell cultures. *Exp. Cell. Res.* 224, 354-64 (1996).
8. Korinek, V. et al. Depletion of epithelial stem-cell compartments in the small intestine of mice lacking Tcf-4. *Nat. Genet.* 19, 379-83 (1998).
9. Pinto, D., Gregorieff, A., Begthel, H. & Clevers, H. Canonical Wnt signals are essential for homeostasis of the intestinal epithelium. *Genes Dev.* 17, 1709-13 (2003).
10. Kuhnert, F. et al. Essential requirement for Wnt signaling in proliferation of adult small intestine and colon revealed by adenoviral expression of Dickkopf-1. *Proc. Natl. Acad. Sci. U.S.A.* 101, 266-71 (2004).
11. Kim, K. A. et al. Mitogenic influence of human R-spondin1 on the intestinal epithelium. *Science* 309, 1256-9 (2005).
12. Dignass, A. U. & Sturm, A. Peptide growth factors in the intestine. *Eur. J. Gastroenterol. Hepatol.* 13, 763-70 (2001).
13. Haramis, A. P. et al. De novo crypt formation and juvenile polyposis on BMP inhibition in mouse intestine. *Science* 303, 1684-6 (2004).
14. Hofmann, C. et al. Cell-cell contacts prevent anoikis in primary human colonic epithelial cells. *Gastroenterology* 132, 587-600 (2007).
15. Sasaki, T., Giltay, R., Talts, U., Timpl, R. & Talts, J. F. Expression and distribution of laminin alpha1 and alpha2 chains in embryonic and adult mouse tissues: an immunochemical approach. *Exp. Cell Res.* 275, 185-99 (2002).
16. Stingl, J., Eaves, C. J., Zandieh, I. & Emerman, J. T. Characterization of bipotent mammary epithelial progenitor cells in normal adult human breast tissue. *Breast Cancer Res. Treat.* 67, 93-109 (2001).
17. St Clair, W. H. & Osborne, J. W. Crypt fission and crypt number in the small and large bowel of postnatal rats. *Cell Tissue Kinet.* 18, 255-62 (1985).
18. Batlle, E. et al. Beta-catenin and TCF mediate cell positioning in the intestinal epithelium by controlling the expression of EphB/ephrinB. *Cell* 111, 251-63 (2002).
19. Srinivas, S. et al. Cre reporter strains produced by targeted insertion of EYFP and ECFP into the ROSA26 locus. *BMC Dev. Biol.* 1, 4 (2001).
20. Soriano, P. Generalized lacZ expression with the ROSA26 Cre reporter strain. *Nat. Genet.* 21, 70-1 (1999).
21. Stingl, J. et al. Purification and unique properties of mammary epithelial stem cells. *Nature* 439, 993-7 (2006).
22. Watanabe, K. et al. A ROCK inhibitor permits survival of dissociated human embryonic stem cells. *Nat. Biotechnol.* 25, 681-6 (2007).
23. van Es, J. H. et al. Notch/gamma-secretase inhibition turns proliferative cells in intestinal crypts and adenomas into goblet cells. *Nature* 435, 959-63 (2005).
24. Li, L. et al. The human homolog of rat Jagged1 expressed by marrow stroma inhibits differentiation of 32D cells through interaction with Notch1. *Immunity* 8, 43-55 (1998).
25. Cheng, H. & Leblond, C. P. Origin, differentiation and renewal of the four main epithelial cell types in the mouse small intestine. I. Columnar cell. *Am. J. Anat.* 141, 461-79 (1974).
26. Powell, D. W. et al. Myofibroblasts. II. Intestinal subepithelial myofibroblasts. *Am. J. Physiol.* 277, C183-201 (1999).
27. Yen, T. H. & Wright, N. A. The gastrointestinal tract stem cell niche. *Stem Cell Rev.* 2, 203-12 (2006).
28. Kedinger, M. et al. Intestinal epithelial-mesenchymal cell interactions. *Ann. N.Y. Acad. Sci.* 859, 1-17 (1998).
29. Spradling, A., Drummond-Barbosa, D. & Kai, T. Stem cells find their niche. *Nature* 414, 98-104 (2001).
30. Li, L. & Xie, T. Stem cell niche: structure and function. *Annu. Rev. Cell Dev. Biol.* 21, 605-31 (2005).
31. Binnerts M E et al, *PNAS* 104:14700-5 (2007).
32. Sawada et al. *Int. J. Exp. Pathol.* 72:407-21 (1991).

The invention claimed is:

1. A composition comprising a three-dimensional organoid obtained by in vitro expansion of one or more adult adenoma stem cells, wherein the organoid has a sealed central lumen lined by epithelial cells, wherein the organoid comprises adult adenoma stem cells which are capable of expansion for at least three months, and wherein non-epithelial cells are absent from said organoid and said composition.

2. The composition of claim 1, wherein the three-dimensional organoid comprises cells expressing Lgr5.

3. The composition of claim 1, wherein every epithelial cell within the three-dimensional organoid comprises nuclear beta-catenin.

4. The composition of claim 1, wherein the cells lining the central lumen are polarised.

5. The composition of claim 4, wherein the lumen contains apoptotic cell bodies.

6. The composition of claim 1, comprising differentiated cell types.

7. The composition of claim 1, wherein the organoid is derived from human epithelial stem cells.

8. The composition of claim 1, wherein the composition further comprises an exogenous extracellular matrix.

9. The composition of claim 8, wherein the composition further comprises a cell culture medium comprising a Bone Morphogenetic Protein (BMP) inhibitor; between 5 and 500 ngram/ml of a mitogenic growth factor; and a Wnt agonist.

10. The composition of claim 9, wherein the BMP inhibitor is selected from the group consisting of Noggin, DAN, Cerberus and Gremlin.

11. The composition of claim 9, wherein the Wnt agonist is selected from the group consisting of one or more of Wnt, R-spondin 1 through R-spondin 4, Norrin, and a GSK-inhibitor.

12. The composition of claim 9, wherein the BMP inhibitor is Noggin, the mitogenic growth factor is Epidermal Growth Factor, and the Wnt agonist comprises any one of R-spondin 1 through R-spondin 4.

13. The composition of claim 1, wherein the cells lining the lumen are randomly oriented towards either the periphery or the central lumen.

* * * * *